(12) United States Patent
Heo et al.

(10) Patent No.: US 12,727,378 B2
(45) Date of Patent: Sep. 1, 2026

(54) HETEROCYCLIC COMPOUND AND ORGANIC LIGHT EMITTING DEVICE COMPRISING SAME

(71) Applicant: LT MATERIALS CO., LTD., Yongin-si (KR)

(72) Inventors: Yu-Jin Heo, Yongin-si (KR); Nam-Jin Lee, Yongin-si (KR); Won-Jang Jeong, Yongin-si (KR); Dong-Jun Kim, Yongin-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 931 days.

(21) Appl. No.: 17/619,751

(22) PCT Filed: Sep. 16, 2020

(86) PCT No.: PCT/KR2020/012488
§ 371 (c)(1),
(2) Date: Dec. 16, 2021

(87) PCT Pub. No.: WO2021/054714
PCT Pub. Date: Mar. 25, 2021

(65) Prior Publication Data
US 2022/0393108 A1 Dec. 8, 2022

(30) Foreign Application Priority Data
Sep. 17, 2019 (KR) ........................ 10-2019-0114331

(51) Int. Cl.
*H10K 85/60* (2023.01)
*C07C 211/61* (2006.01)
(Continued)

(52) U.S. Cl.
CPC .......... *H10K 85/633* (2023.02); *C07C 211/61* (2013.01); *C07D 209/88* (2013.01);
(Continued)

(58) Field of Classification Search
CPC ... C07C 211/61; C07C 255/58; C07C 13/567; C07C 211/54; C07D 307/91;
(Continued)

(56) References Cited

U.S. PATENT DOCUMENTS

2015/0179940 A1 6/2015 Mujica-Fernaud et al.
2018/0208836 A1* 7/2018 Kuma .................. H10K 50/131
(Continued)

FOREIGN PATENT DOCUMENTS

CN 110511151 A * 11/2019 ........... C07C 211/61
CN 110950762 A * 4/2020 ........... C07C 211/60
(Continued)

OTHER PUBLICATIONS

Machine-generated English-language translation of CN-110950762-A.*
(Continued)

*Primary Examiner* — Vu A Nguyen
(74) *Attorney, Agent, or Firm* — NKL LAW; Jae Youn Kim

(57) ABSTRACT

The present application provides a heterocyclic compound capable of significantly enhancing lifetime, efficiency, electrochemical stability and thermal stability of an organic light emitting device, and an organic light emitting device including the heterocyclic compound in an organic material layer.

9 Claims, 3 Drawing Sheets

(51) Int. Cl.

| | |
|---|---|
| ***C07D 209/88*** | (2006.01) |
| ***C07D 307/91*** | (2006.01) |
| ***C07D 311/96*** | (2006.01) |
| ***C07D 333/76*** | (2006.01) |
| ***C09K 11/06*** | (2006.01) |
| ***H10K 50/11*** | (2023.01) |
| ***H10K 50/15*** | (2023.01) |
| ***H10K 50/19*** | (2023.01) |
| ***H10K 101/00*** | (2023.01) |

(52) U.S. Cl.
CPC .......... *C07D 307/91* (2013.01); *C07D 311/96* (2013.01); *C07D 333/76* (2013.01); *C09K 11/06* (2013.01); *H10K 85/636* (2023.02); *C07C 2603/18* (2017.05); *C07C 2603/26* (2017.05); *C07C 2603/97* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/156* (2023.02); *H10K 50/19* (2023.02); *H10K 85/624* (2023.02); *H10K 85/626* (2023.02); *H10K 85/6572* (2023.02); *H10K 85/6574* (2023.02); *H10K 85/6576* (2023.02); *H10K 2101/90* (2023.02)

(58) Field of Classification Search
CPC .. C07D 333/76; C07D 209/70; C07D 209/86; C07D 219/02; C09K 11/06; H01L 51/006; H01L 51/504; H01L 51/0054; H01L 51/0056; H01L 51/0073; H01L 51/0074; H01L 51/0058; H01L 51/00; H01L 51/50; H10K 50/131; H10K 85/631; H10K 85/633; H10K 85/636
See application file for complete search history.

(56) References Cited

U.S. PATENT DOCUMENTS

| | | | | |
|---|---|---|---|---|
| 2019/0140177 | A1 | 5/2019 | Lee et al. | |
| 2019/0237668 | A1 | 8/2019 | Miyake et al. | |
| 2019/0288218 | A1 | 9/2019 | La et al. | |
| 2020/0235297 | A1* | 7/2020 | Miyake | H10K 85/636 |

FOREIGN PATENT DOCUMENTS

| | | | | |
|---|---|---|---|---|
| JP | 2019-135228 | A | | 8/2019 |
| KR | 10-2015-0036654 | A | | 4/2015 |
| KR | 10-2017-0031614 | A | | 3/2017 |
| KR | 10-2019-0007892 | A | | 1/2019 |
| KR | 10-2019-0050525 | A | * | 5/2019 |
| KR | 10-2019-0052505 | A | | 5/2019 |
| KR | 10-2019-0091410 | A | | 8/2019 |
| KR | 10-20192-0091410 | | * | 8/2019 |
| TW | 201835074 | A | | 10/2018 |

OTHER PUBLICATIONS

Machine-generated English-language translation of CN-110511151-A.*

International Search Report, issued in PCT/KR2020/012488, mailed Jan. 4, 2021.

* cited by examiner

【FIG. 1】
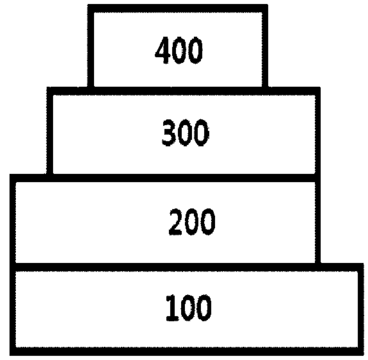
【FIG. 2】
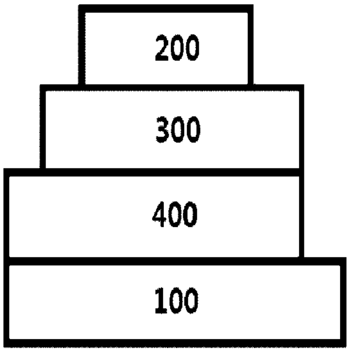

【FIG. 3】
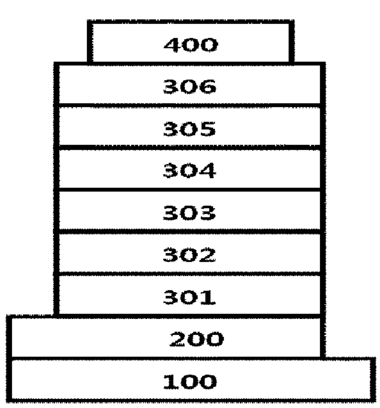

【FIG. 4】
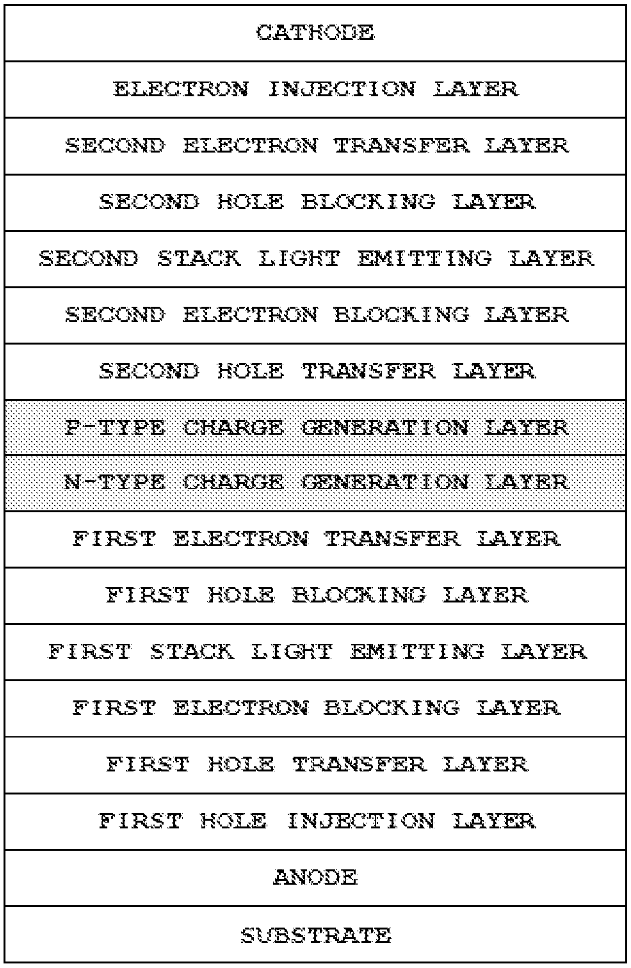

HETEROCYCLIC COMPOUND AND ORGANIC LIGHT EMITTING DEVICE COMPRISING SAME

TECHNICAL FIELD

The present specification claims priority to and the benefits of Korean Patent Application No. 10-2019-0114331, filed with the Korean Intellectual Property Office on Sep. 17, 2019, the entire contents of which are incorporated herein by reference.

The present specification relates to a heterocyclic compound, and an organic light emitting device including the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present specification is directed to providing a heterocyclic compound, and an organic light emitting device including the same.

Technical Solution

One embodiment of the present application provides a heterocyclic compound represented by the following Chemical Formula 1.

[Chemical Formula 1]

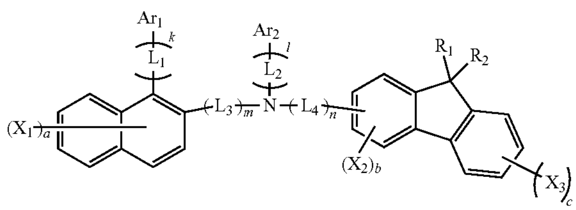

In Chemical Formula 1, $L_1$ to $L_4$ are the same as or different from each other, and each independently a direct bond; a substituted or unsubstituted arylene group having 6 to 60 carbon atoms; or a substituted or unsubstituted heteroarylene group having 2 to 60 carbon atoms, $Ar_1$ and $Ar_2$ are the same as or different from each other, and each independently a substituted or unsubstituted aryl group having 6 to 40 carbon atoms; or a substituted or unsubstituted heteroaryl group having 2 to 40 carbon atoms, $R_1$ and $R_2$ are the same as or different from each other, and each independently a substituted or unsubstituted alkyl group having 1 to 20 carbon atoms; a substituted or unsubstituted aryl group having 6 to 40 carbon atoms; or a substituted or unsubstituted heteroaryl group having 2 to 40 carbon atoms, $X_1$ to $X_3$ are the same as or different from each other, and each independently hydrogen; deuterium; a substituted or unsubstituted aryl group having 6 to 20 carbon atoms; or a substituted or unsubstituted heteroaryl group having 2 to 40 carbon atoms, k, l, m and n are each independently an integer of 1 to 3, a is an integer of 1 to 6, b is an integer of 1 to 3, c is an integer of 1 to 4, and when k, l, m, n, a, b and c are 2 or greater, substituents in the parentheses are the same as or different from each other.

Another embodiment of the present application provides an organic light emitting device including a first electrode; a second electrode; and one or more organic material layers provided between the first electrode and the second electrode, wherein one or more layers of the organic material layers include the heterocyclic compound represented by Chemical Formula 1.

Advantageous Effects

A compound described in the present specification can be used as a material of an organic material layer of an organic light emitting device. In the organic light emitting device, the compound is capable of performing a role of a hole injection material, a hole transfer material, a light emitting material, an electron transfer material, an electron injection material or the like. Particularly, the compound can be used as an electron transfer layer material, a hole blocking layer material or a charge generation layer material of an organic light emitting device.

Specifically, when using the compound represented by Chemical Formula 1 in an organic material layer, a driving voltage of the device can be lowered, light efficiency can be enhanced, and lifetime properties of the device can be enhanced.

DESCRIPTION OF DRAWINGS

FIG. 1 to FIG. 4 are diagrams each illustrating a lamination structure of an organic light emitting device according to one embodiment of the present application.

MODE FOR DISCLOSURE

Hereinafter, the present specification will be described in more detail.

In the present specification, a certain part "including" certain constituents means capable of further including other constituents, and does not exclude other constituents unless particularly stated on the contrary.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of a linear or branched alkyl group having 1 to 60 carbon atoms; a linear or branched alkenyl group having 2 to 60 carbon atoms; a linear or branched alkynyl group having 2 to 60 carbon atoms; a monocyclic or polycyclic cycloalkyl group having 3 to 60 carbon atoms; a monocyclic or polycyclic heterocycloalkyl group having 2 to 60 carbon atoms; a monocyclic or polycyclic aryl group having 6 to 60 carbon atoms; a monocyclic or polycyclic heteroaryl group having 2 to 60 carbon atoms; a silyl group; a phosphine oxide group; and an amine group, or being unsubstituted, or being substituted with a substituent linking two or more substituents selected from among the substituents illustrated above, or being unsubstituted.

More specifically, in the present specification, "substituted or unsubstituted" may mean being substituted with one or more substituents selected from the group consisting of a monocyclic or polycyclic aryl group having 6 to 60 carbon atoms; or a monocyclic or polycyclic heteroaryl group having 2 to 60 carbon atoms, or being unsubstituted.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0%, a hydrogen content being 100% or substituents being all hydrogen.

In one embodiment of the present application, deuterium is one of isotopes of hydrogen, is an element having deuteron formed with one proton and one neutron as a nucleus, and may be expressed as hydrogen-2, and the elemental symbol may also be written as D or 2H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

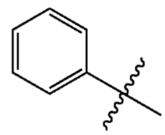 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

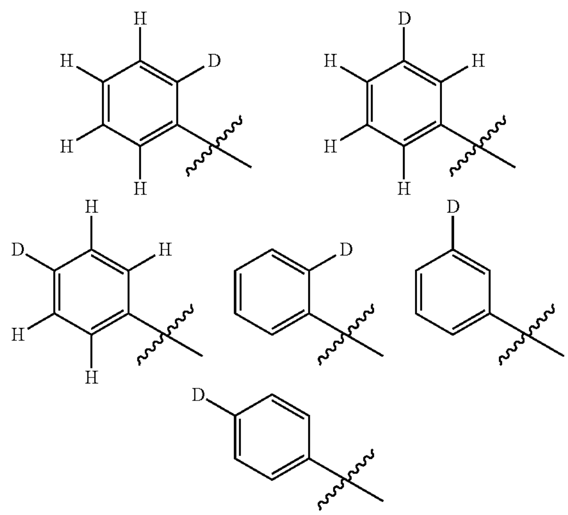

In addition, in one embodiment of the present application, "a phenyl group having a deuterium content of 0%" may mean a phenyl group that does not include a deuterium atom, that is, a phenyl group that has 5 hydrogen atoms.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a terphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P(=O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may include a diphenylphosphine oxide group, a dinaphthylphosphine oxide group and the like, but are not limited thereto.

In the present specification, the silyl group is a substituent including Si, having the Si atom directly linked as a radical, and is represented by $—SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

In the present specification, the spiro group is a group including a spiro structure, and may have 15 to 60 carbon atoms. For example, the spiro group may include structures in which a 2,3-dihydro-1H-indene group or a cyclohexane group spiro bonds to a fluorenyl group. Specifically, the spiro group may include any one of groups of the following structural formulae.

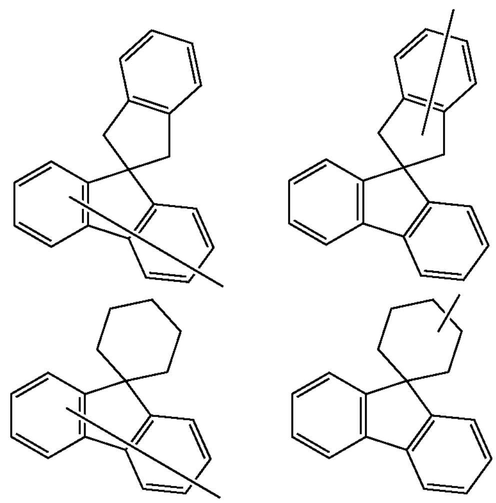

-continued

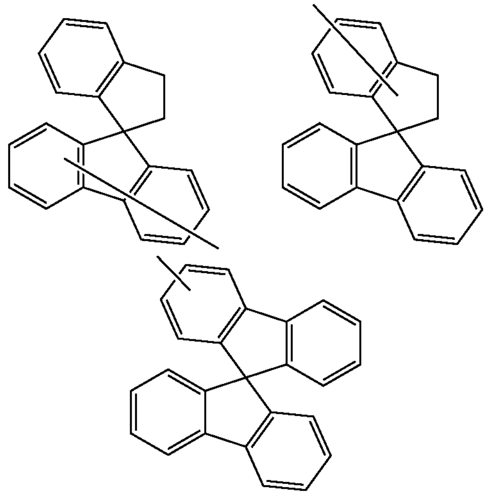

In the present specification, the heteroaryl group includes S, O, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo [2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c] [1,2,5]thiadiazolyl group, a 5,10-dihydrobenzo[b,e][1,4] azasilinyl group, a pyrazolo[1,5-c]quinazolinyl group, a pyrido[1,2-b]indazolyl group, a pyrido[1,2-a]imidazo[1,2-e] indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

One embodiment of the present application provides a heterocyclic compound represented by the following Chemical Formula 1.

[Chemical Formula 1]

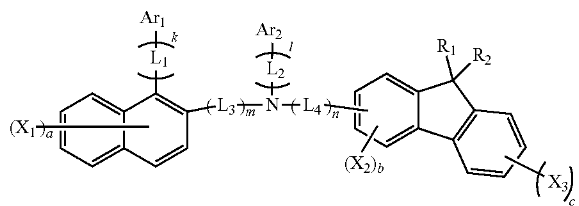

In Chemical Formula 1, $L_1$ to $L_4$ are the same as or different from each other, and each independently a direct bond; a substituted or unsubstituted arylene group having 6 to 60 carbon atoms; or a substituted or unsubstituted heteroarylene group having 2 to 60 carbon atoms, $Ar_1$ and $Ar_2$ are the same as or different from each other, and each independently a substituted or unsubstituted aryl group having 6 to 40 carbon atoms; or a substituted or unsubstituted heteroaryl group having 2 to 40 carbon atoms, $R_1$ and $R_2$ are the same as or different from each other, and each independently a substituted or unsubstituted alkyl group having 1 to 20 carbon atoms; a substituted or unsubstituted aryl group having 6 to 40 carbon atoms; or a substituted or unsubstituted heteroaryl group having 2 to 40 carbon atoms, $X_1$ to $X_3$ are the same as or different from each other, and each independently hydrogen; deuterium; a substituted or unsubstituted aryl group having 6 to 20 carbon atoms; or a substituted or unsubstituted heteroaryl group having 2 to 40 carbon atoms, k, l, m and n are each independently an integer of 1 to 3, a is an integer of 1 to 6, b is an integer of 1 to 3, c is an integer of 1 to 4, and when k, l, m, n, a, b and c are 2 or greater, substituents in the parentheses are the same as or different from each other.

Hole mobility is generally affected by orientation and space size formed by interactions between materials used during a deposition process. When depositing the heterocyclic compound represented by Chemical Formula 1 in an organic light emitting device, uniform orientation and space in which holes may be formed are both obtained, and therefore, a hole transfer ability is superior and a highest occupied molecular orbital (HOMO) energy level may be stabilized. When using the heterocyclic compound represented by Chemical Formula 1 as a material of a hole transfer layer or an electron blocking layer in an organic light emitting device, proper energy level and band gap are formed, and excitons in a light emitting area increase. Excitons increasing in a light emitting area means having effects of increasing driving voltage and efficiency of a device.

In one embodiment of the present application, $X_1$ to $X_3$ of Chemical Formula 1 are the same as or different from each other, and may be each independently hydrogen; deuterium; a substituted or unsubstituted aryl group having 6 to 20 carbon atoms; or a substituted or unsubstituted heteroaryl group having 2 to 40 carbon atoms.

In one embodiment of the present application, $X_1$ to $X_3$ are the same as or different from each other, and each independently hydrogen or deuterium.

In one embodiment of the present application, $X_1$ to $X_3$ are the same as or different from each other, and each independently a substituted or unsubstituted aryl group having 6 to 20 carbon atoms; or a substituted or unsubstituted heteroaryl group having 2 to 40 carbon atoms.

In one embodiment of the present application, $X_1$ is a substituted or unsubstituted aryl group having 6 to 20 carbon atoms; or a substituted or unsubstituted heteroaryl group having 2 to 40 carbon atoms.

In one embodiment of the present application, $X_1$ is hydrogen; or deuterium.

In one embodiment of the present application, $X_1$ is hydrogen.

In one embodiment of the present application, $X_1$ is deuterium.

In one embodiment of the present application, $X_2$ is a substituted or unsubstituted aryl group having 6 to 20 carbon atoms; or a substituted or unsubstituted heteroaryl group having 2 to 40 carbon atoms.

In one embodiment of the present application, $X_2$ is hydrogen; or deuterium.

In one embodiment of the present application, $X_2$ is hydrogen.

In one embodiment of the present application, $X_2$ is deuterium.

In one embodiment of the present application, $X_3$ is a substituted or unsubstituted aryl group having 6 to 20 carbon atoms; or a substituted or unsubstituted heteroaryl group having 2 to 40 carbon atoms.

In one embodiment of the present application, $X_3$ is hydrogen; or deuterium.

In one embodiment of the present application, $X_3$ is hydrogen.

In one embodiment of the present application, $X_3$ is deuterium.

In one embodiment of the present application, $X_1$ to $X_3$ are hydrogen.

In one embodiment of the present application, a of Chemical Formula 1 may be an integer of 1 to 6, b thereof may be an integer of 1 to 3, c thereof may be an integer of 1 to 4, and when a, b and c are 2 or greater, substituents in the parentheses may be the same as or different from each other.

In one embodiment of the present application, a is an integer of 1 to 6.

In one embodiment of the present application, a is 6.

In one embodiment of the present application, a is 5.

In one embodiment of the present application, a is 4.

In one embodiment of the present application, a is 3.

In one embodiment of the present application, a is 2.

In one embodiment of the present application, a is 1.

In one embodiment of the present application, when a is 2 or greater, substituents in the parentheses are the same as or different from each other.

In one embodiment of the present application, b is an integer of 1 to 3.

In one embodiment of the present application, b is 3.

In one embodiment of the present application, b is 2.

In one embodiment of the present application, b is 1.

In one embodiment of the present application, when b is 2 or greater, substituents in the parentheses are the same as or different from each other.

In one embodiment of the present application, c is an integer of 1 to 4.

In one embodiment of the present application, c is 4.

In one embodiment of the present application, c is 3.

In one embodiment of the present application, c is 2.

In one embodiment of the present application, c is 1.

In one embodiment of the present application, when c is 2 or greater, substituents in the parentheses are the same as or different from each other.

In one embodiment of the present application, k, l, m and n of Chemical Formula 1 are each independently an integer of 1 to 3, and when k, l, m and n are 2 or greater, substituents in the parentheses may be the same as or different from each other.

In one embodiment of the present application, m is an integer of 1 to 3.

In one embodiment of the present application, m is 3.

In one embodiment of the present application, m is 2.

In one embodiment of the present application, m is 1.

In one embodiment of the present application, when m is 2 or greater, substituents in the parentheses are the same as or different from each other.

In one embodiment of the present application, n is an integer of 1 to 3.

In one embodiment of the present application, n is 3.

In one embodiment of the present application, n is 2.

In one embodiment of the present application, n is 1.

In one embodiment of the present application, when n is 2 or greater, substituents in the parentheses are the same as or different from each other.

In the heterocyclic compound provided in one embodiment of the present application, Chemical Formula 1 is represented by any one of the following Chemical Formula 2 to Chemical Formula 5.

[Chemical Formula 2]

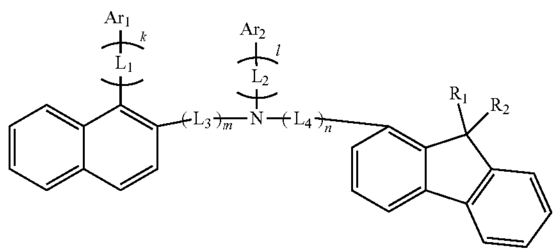

[Chemical Formula 3]

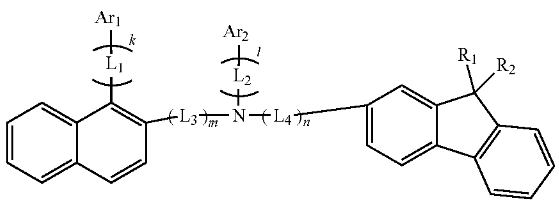

[Chemical Formula 4]

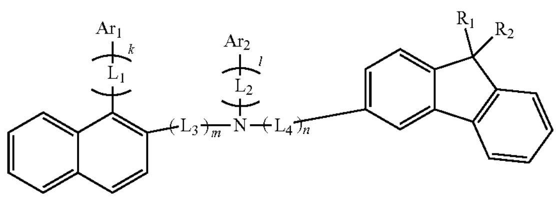

[Chemical Formula 5]

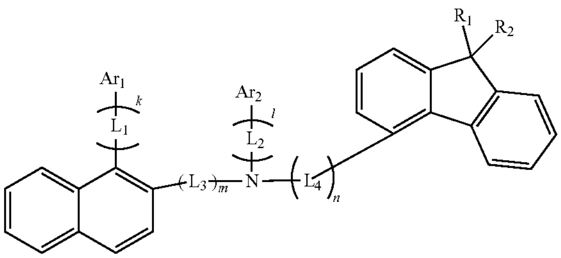

In Chemical Formulae 2 to 5, each substituent has the same definition as in Chemical Formula 1.

In one embodiment of the present application, $L_1$ to $L_4$ are the same as or different from each other, and may be each independently a direct bond; a substituted or unsubstituted arylene group; or a substituted or unsubstituted heteroarylene group.

In another embodiment, $L_1$ to $L_4$ are the same as or different from each other, and may be each independently a direct bond; a substituted or unsubstituted arylene group having 6 to 60 carbon atoms; or a substituted or unsubstituted heteroarylene group having 2 to 60 carbon atoms.

In another embodiment, $L_1$ to $L_4$ are the same as or different from each other, and may be each independently a direct bond; a substituted or unsubstituted arylene group having 6 to 40 carbon atoms; or a substituted or unsubstituted heteroarylene group having 2 to 40 carbon atoms.

In another embodiment, $L_1$ to $L_4$ are the same as or different from each other, and may be each independently a direct bond; a substituted or unsubstituted arylene group having 6 to 20 carbon atoms; or a substituted or unsubstituted heteroarylene group having 2 to 20 carbon atoms.

In another embodiment, $L_1$ to $L_4$ are the same as or different from each other, and may be each independently a direct bond; a substituted or unsubstituted phenylene group; or a substituted or unsubstituted biphenylene group.

In another embodiment, $L_1$ to $L_4$ are the same as or different from each other, and may be each independently a direct bond; a phenylene group; or a biphenylene group.

In one embodiment of the present application, $L_1$ and $L_2$ are the same as or different from each other, and may be each independently a direct bond; a substituted or unsubstituted arylene group; or a substituted or unsubstituted heteroarylene group.

In one embodiment of the present application, $L_1$ and $L_2$ may be different from each other.

In one embodiment of the present application, $L_1$ and $L_2$ may be the same as each other.

In one embodiment of the present application, $L_1$ is a direct bond, and $L_2$ may be a substituted or unsubstituted arylene group having 6 to 60 carbon atoms; or a substituted or unsubstituted heteroarylene group having 2 to 60 carbon atoms.

In one embodiment of the present application, $L_1$ is a direct bond, and $L_2$ may be a substituted or unsubstituted arylene group having 6 to 40 carbon atoms; or a substituted or unsubstituted heteroarylene group having 2 to 40 carbon atoms.

In one embodiment of the present application, $L_1$ is a direct bond, and $L_2$ may be a substituted or unsubstituted arylene group having 6 to 20 carbon atoms; or a substituted or unsubstituted heteroarylene group having 2 to 20 carbon atoms.

In one embodiment of the present application, $L_2$ is a direct bond, and $L_1$ may be a substituted or unsubstituted arylene group having 6 to 60 carbon atoms; or a substituted or unsubstituted heteroarylene group having 2 to 60 carbon atoms.

In one embodiment of the present application, $L_2$ is a direct bond, and $L_1$ may be a substituted or unsubstituted arylene group having 6 to 40 carbon atoms; or a substituted or unsubstituted heteroarylene group having 2 to 40 carbon atoms.

In one embodiment of the present application, $L_2$ is a direct bond, and $L_1$ may be a substituted or unsubstituted arylene group having 6 to 20 carbon atoms; or a substituted or unsubstituted heteroarylene group having 2 to 20 carbon atoms.

In one embodiment of the present application, $L_1$ may be a direct bond; a substituted or unsubstituted arylene group having 6 to 60 carbon atoms; or a substituted or unsubstituted heteroarylene group having 2 to 60 carbon atoms.

In another embodiment, $L_1$ may be a direct bond; a substituted or unsubstituted arylene group having 6 to 40 carbon atoms; or a substituted or unsubstituted heteroarylene group having 2 to 40 carbon atoms.

In another embodiment, $L_1$ may be a direct bond; a substituted or unsubstituted arylene group having 6 to 20 carbon atoms; or a substituted or unsubstituted heteroarylene group having 2 to 20 carbon atoms.

In another embodiment, $L_1$ may be a direct bond; a substituted or unsubstituted phenylene group; or a substituted or unsubstituted biphenylene group.

In another embodiment, $L_1$ may be a direct bond; a phenylene group; or a biphenylene group.

In another embodiment, $L_1$ is a direct bond.

In another embodiment, $L_1$ is a phenylene group.

In another embodiment, $L_1$ is a biphenylene group.

In one embodiment of the present application, $L_2$ may be a direct bond; a substituted or unsubstituted arylene group having 6 to 60 carbon atoms; or a substituted or unsubstituted heteroarylene group having 2 to 60 carbon atoms.

In another embodiment, $L_2$ may be a direct bond; a substituted or unsubstituted arylene group having 6 to 40 carbon atoms; or a substituted or unsubstituted heteroarylene group having 2 to 40 carbon atoms.

In another embodiment, $L_2$ may be a direct bond; a substituted or unsubstituted arylene group having 6 to 20 carbon atoms; or a substituted or unsubstituted heteroarylene group having 2 to 20 carbon atoms.

In another embodiment, $L_2$ may be a direct bond; a substituted or unsubstituted phenylene group; or a substituted or unsubstituted biphenylene group.

In another embodiment, $L_2$ may be a direct bond; a phenylene group; a biphenylene group; or a naphthylene group.

In another embodiment, $L_2$ is a direct bond.

In another embodiment, $L_2$ is a phenylene group.

In another embodiment, $L_2$ is a biphenylene group.

In another embodiment, $L_1$ and $L_2$ are a direct bond.

In one embodiment of the present application, $L_3$ and $L_4$ are the same as or different from each other, and each independently a direct bond; a substituted or unsubstituted arylene group; or a substituted or unsubstituted heteroarylene group.

In another embodiment, $L_3$ and $L_4$ are the same as or different from each other, and may be each independently a direct bond; a substituted or unsubstituted arylene group having 6 to 60 carbon atoms; or a substituted or unsubstituted heteroarylene group having 2 to 60 carbon atoms.

In another embodiment, $L_3$ and $L_4$ are the same as or different from each other, and may be each independently a direct bond; a substituted or unsubstituted arylene group having 6 to 40 carbon atoms; or a substituted or unsubstituted heteroarylene group having 2 to 40 carbon atoms.

In another embodiment, $L_3$ and $L_4$ are the same as or different from each other, and may be each independently a direct bond; a substituted or unsubstituted arylene group having 6 to 20 carbon atoms; or a substituted or unsubstituted heteroarylene group having 2 to 20 carbon atoms.

In another embodiment, $L_3$ and $L_4$ are the same as or different from each other, and may be each independently a direct bond; a substituted or unsubstituted phenylene group; or a substituted or unsubstituted biphenylene group.

In another embodiment, $L_3$ and $L_4$ are the same as or different from each other, and may be each independently a direct bond; a phenylene group; or a biphenylene group.

In one embodiment of the present application, $L_3$ and $L_4$ may be the same as each other.

In one embodiment of the present application, $L_3$ and $L_4$ may be different from each other.

In one embodiment of the present application, $L_3$ is a direct bond, and $L_4$ may be a substituted or unsubstituted arylene group having 6 to 60 carbon atoms; or a substituted or unsubstituted heteroarylene group having 2 to 60 carbon atoms.

In one embodiment of the present application, $L_3$ is a direct bond, and $L_4$ may be a substituted or unsubstituted arylene group having 6 to 40 carbon atoms; or a substituted or unsubstituted heteroarylene group having 2 to 40 carbon atoms.

In one embodiment of the present application, $L_3$ is a direct bond, and $L_4$ may be a substituted or unsubstituted arylene group having 6 to 20 carbon atoms; or a substituted or unsubstituted heteroarylene group having 2 to 20 carbon atoms. In one embodiment of the present application, $L_4$ is a direct bond, and $L_3$ may be a substituted or unsubstituted arylene group having 6 to 60 carbon atoms; or a substituted or unsubstituted heteroarylene group having 2 to 60 carbon atoms.

In one embodiment of the present application, $L_4$ is a direct bond, and $L_3$ may be a substituted or unsubstituted arylene group having 6 to 40 carbon atoms; or a substituted or unsubstituted heteroarylene group having 2 to 40 carbon atoms.

In one embodiment of the present application, $L_4$ is a direct bond, and $L_3$ may be a substituted or unsubstituted arylene group having 6 to 20 carbon atoms; or a substituted or unsubstituted heteroarylene group having 2 to 20 carbon atoms.

In one embodiment of the present application, $L_3$ may be a direct bond; a substituted or unsubstituted arylene group having 6 to 60 carbon atoms; or a substituted or unsubstituted heteroarylene group having 2 to 60 carbon atoms.

In another embodiment, $L_3$ may be a direct bond; a substituted or unsubstituted arylene group having 6 to 40 carbon atoms; or a substituted or unsubstituted heteroarylene group having 2 to 40 carbon atoms.

In another embodiment, $L_3$ may be a direct bond; a substituted or unsubstituted arylene group having 6 to 20 carbon atoms; or a substituted or unsubstituted heteroarylene group having 2 to 20 carbon atoms.

In another embodiment, $L_3$ may be a direct bond; a substituted or unsubstituted phenylene group; or a substituted or unsubstituted biphenylene group.

In another embodiment, $L_3$ may be a direct bond; a phenylene group; or a biphenylene group.

In another embodiment, $L_3$ is a direct bond.

In another embodiment, $L_3$ is a phenylene group.

In another embodiment, $L_3$ is a biphenylene group.

In one embodiment of the present application, $L_4$ may be a direct bond; a substituted or unsubstituted arylene group having 6 to 60 carbon atoms; or a substituted or unsubstituted heteroarylene group having 2 to 60 carbon atoms.

In another embodiment, $L_4$ may be a direct bond; a substituted or unsubstituted arylene group having 6 to 40 carbon atoms; or a substituted or unsubstituted heteroarylene group having 2 to 40 carbon atoms.

In another embodiment, $L_4$ may be a direct bond; a substituted or unsubstituted arylene group having 6 to 20 carbon atoms; or a substituted or unsubstituted heteroarylene group having 2 to 20 carbon atoms.

In another embodiment, $L_4$ may be a direct bond; a substituted or unsubstituted phenylene group; or a substituted or unsubstituted biphenylene group.

In another embodiment, $L_4$ may be a direct bond; a phenylene group; a biphenylene group; or a naphthylene group.

In another embodiment, $L_4$ is a direct bond.

In another embodiment, $L_4$ is a phenylene group.

In another embodiment, $L_4$ is a biphenylene group.

In one embodiment of the present application, $Ar_1$ and $Ar_2$ of Chemical Formula 1 are the same as or different from each other, and may be each independently a substituted or unsubstituted aryl group having 6 to 40 carbon atoms; or a substituted or unsubstituted heteroaryl group having 2 to 40 carbon atoms.

In one embodiment of the present application, $Ar_1$ and $Ar_2$ of Chemical Formula 1 are the same as or different from each other, and may be each independently a substituted or unsubstituted aryl group having 6 to 40 carbon atoms; or a substituted or unsubstituted heteroaryl group having 2 to 40 carbon atoms.

In another embodiment, $Ar_1$ and $Ar_2$ are the same as or different from each other, and may be each independently a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted fluorenyl group; a substituted or unsubstituted carbazole group; a substituted or unsubstituted triphenylenyl group; a substituted or unsubstituted dibenzofuran group; a substituted or unsubstituted dibenzothiophene group; a substituted or unsubstituted spirobifluorenyl group; or a substituted or unsubstituted spiro[fluorene-9,9'-xanthene] group.

In one embodiment of the present application, $Ar_1$ of Chemical Formula 1 may be a substituted or unsubstituted aryl group having 6 to 40 carbon atoms; or a substituted or unsubstituted heteroaryl group having 2 to 40 carbon atoms.

In another embodiment, $Ar_1$ may be a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted fluorenyl group; a substituted or unsubstituted carbazole group; a substituted or unsubstituted triphenylenyl group; a substituted or unsubstituted dibenzofuran group; a substituted or unsubstituted dibenzothiophene group; a substituted or unsubstituted spirobifluorenyl group; or a substituted or unsubstituted spiro[fluorene-9,9'-xanthene]group.

In another embodiment, $Ar_1$ may be a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted dibenzofuran group; a substituted or unsubstituted dibenzothiophene group; or a substituted or unsubstituted spirobifluorenyl group.

In another embodiment, $Ar_1$ may be a phenyl group; a biphenyl group; a terphenyl group; a naphthyl group; a fluorenyl group; a dibenzofuran group; a dibenzothiophene group; or a spirobifluorenyl group.

In the heterocyclic compound provided in one embodiment of the present application, $Ar_1$ of Chemical Formula 1 is represented by any one of the following chemical formulae.

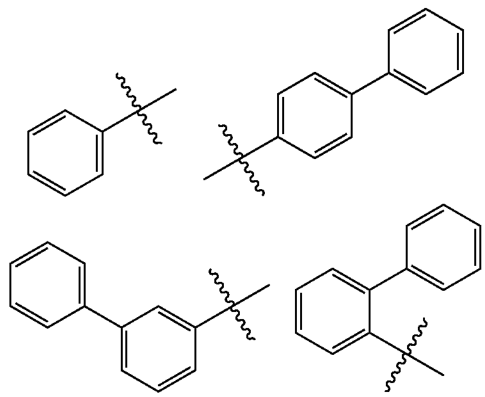

-continued

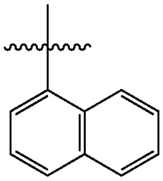
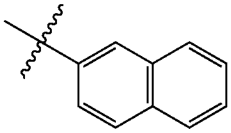
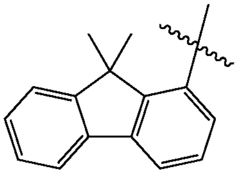
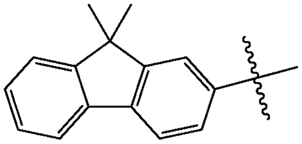
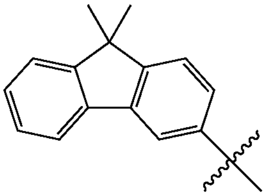
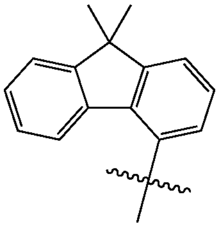
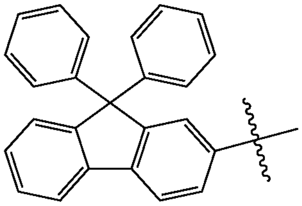
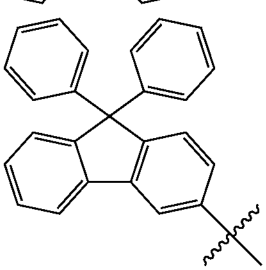
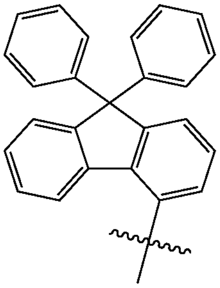
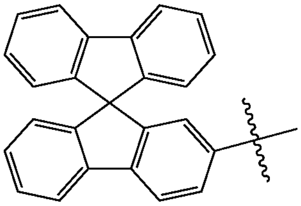
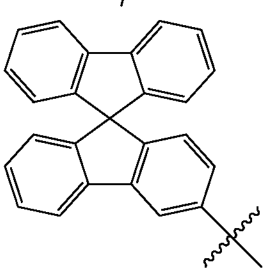
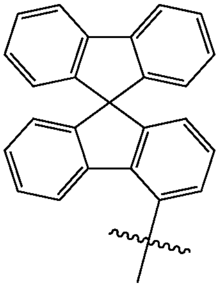

-continued

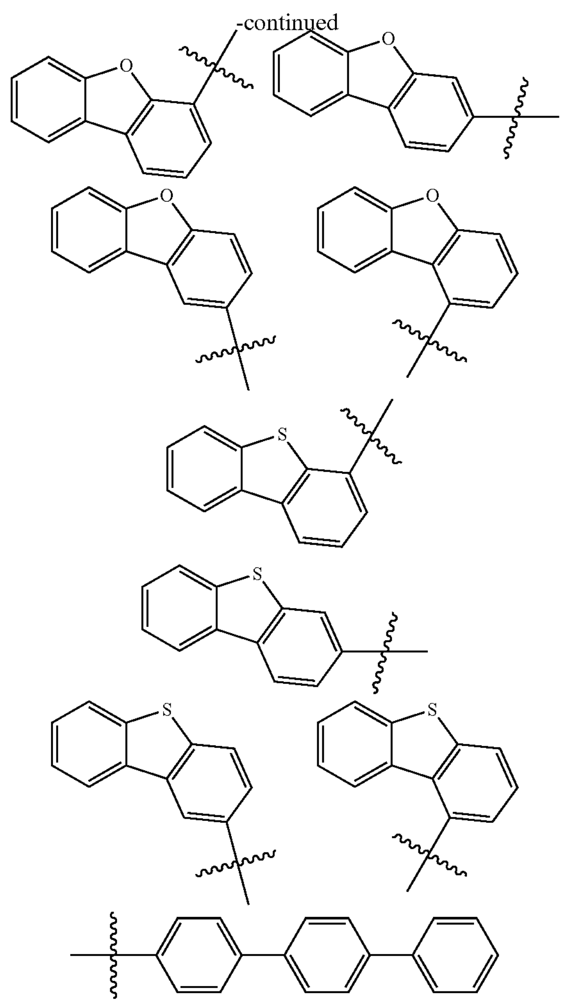

In the chemical formulae that may be expressed as $Ar_1$, hydrogen may be substituted with deuterium, and  means a position at which $Ar_1$ bonds to Chemical Formula 1.

In one embodiment of the present application, $Ar_2$ of Chemical Formula 1 may be a substituted or unsubstituted aryl group having 6 to 40 carbon atoms; or a substituted or unsubstituted heteroaryl group having 2 to 40 carbon atoms.

In another embodiment, $Ar_2$ may be a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted fluorenyl group; a substituted or unsubstituted carbazole group; a substituted or unsubstituted triphenylenyl group; a substituted or unsubstituted dibenzofuran group; a substituted or unsubstituted dibenzothiophene group; a substituted or unsubstituted spirobifluorenyl group; or a substituted or unsubstituted spiro[fluorene-9,9'-xanthene]group.

In another embodiment, $Ar_2$ may be a phenyl group unsubstituted or substituted with a cyano group; a biphenyl group; a terphenyl group; a naphthyl group unsubstituted or substituted with a phenyl group; a phenanthrenyl group unsubstituted or substituted with a phenyl group; a 9,9-dimethyl-9H-fluorenyl group unsubstituted or substituted with a phenyl group; a carbazole group unsubstituted or substituted with a phenyl group or a naphthyl group; a triphenylenyl group; a dibenzofuran group unsubstituted or substituted with a phenyl group; a dibenzothiophene group unsubstituted or substituted with a phenyl group; a spirobifluorenyl group unsubstituted or substituted with a phenyl group; or a spiro[fluorene-9,9'-xanthene] group unsubstituted or substituted with a phenyl group.

In the heterocyclic compound provided in one embodiment of the present application, $Ar_2$ of Chemical Formula 1 is represented by any one of the following chemical formulae.

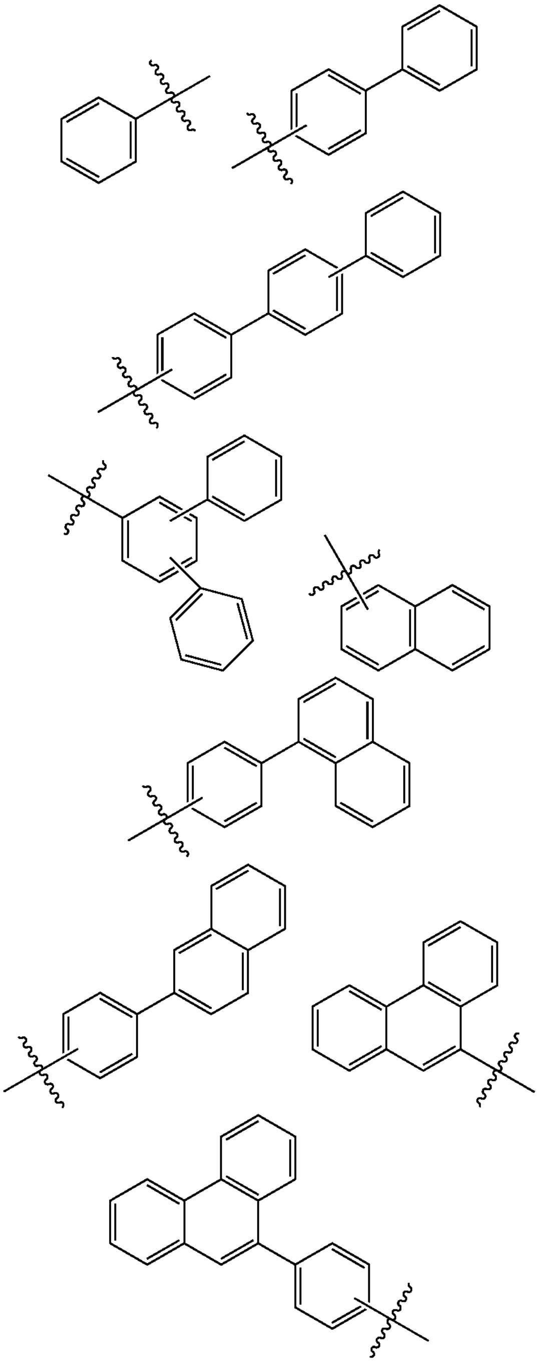

-continued
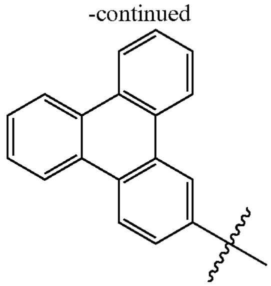
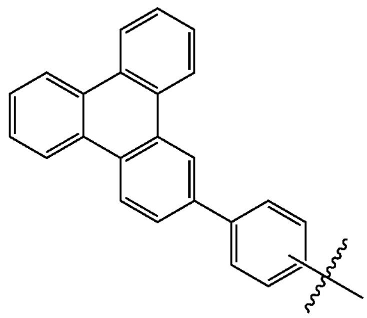
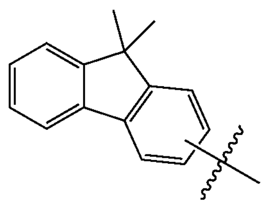
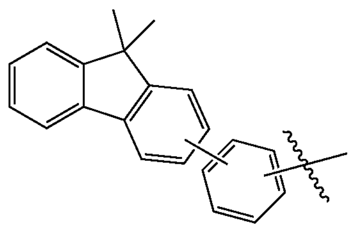
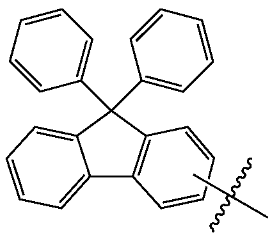
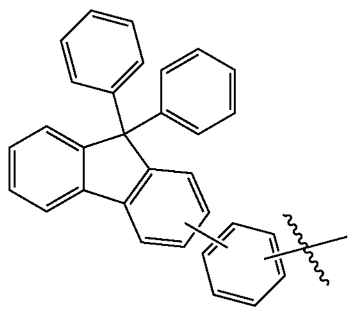
-continued
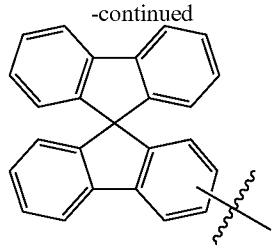
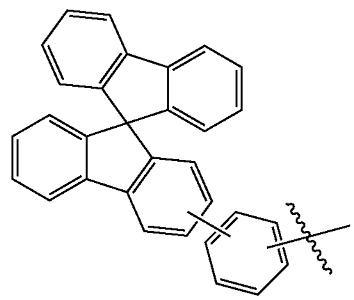
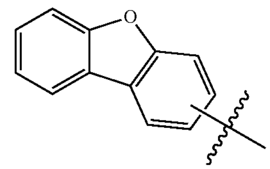
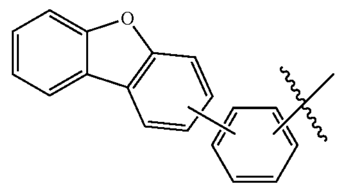
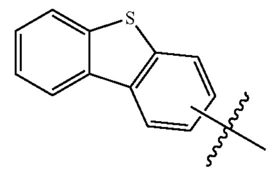
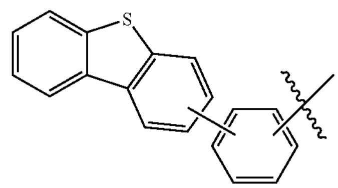
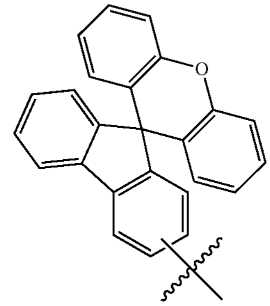

-continued

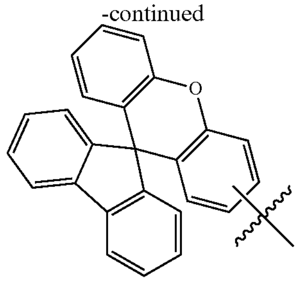

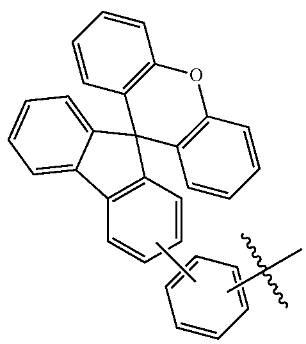

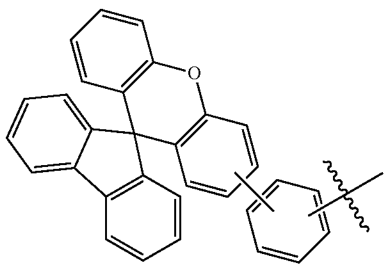

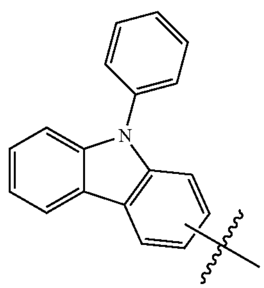

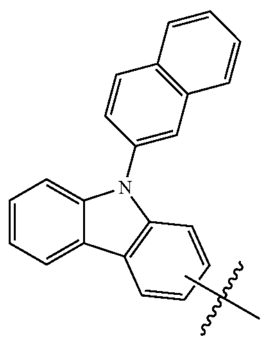

-continued

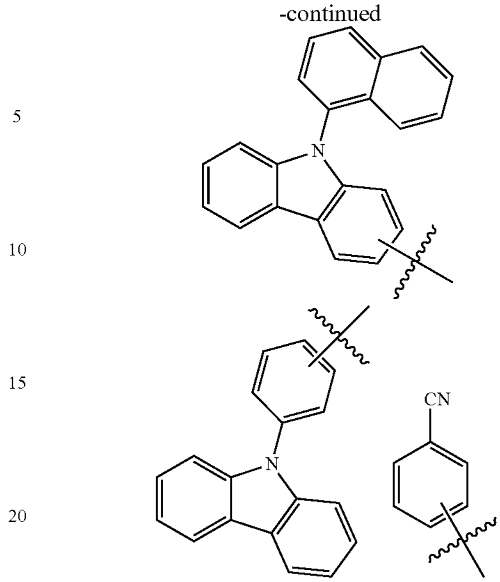

In the chemical formulae that may be expressed as $Ar_2$, hydrogen may be substituted with deuterium, and  means a position at which $Ar_2$ bonds to Chemical Formula 1.

In one embodiment of the present application, $R_1$ and $R_2$ are the same as or different from each other, and may be each independently a substituted or unsubstituted alkyl group having 1 to 20 carbon atoms; a substituted or unsubstituted aryl group having 6 to 40 carbon atoms; or a substituted or unsubstituted heteroaryl group having 2 to 40 carbon atoms.

In another embodiment, $R_1$ and $R_2$ are the same as or different from each other, and may be each independently a substituted or unsubstituted alkyl group having 1 to 10 carbon atoms; a substituted or unsubstituted aryl group having 6 to 20 carbon atoms; or a substituted or unsubstituted heteroaryl group having 2 to 20 carbon atoms.

In another embodiment, $R_1$ and $R_2$ are the same as or different from each other, and may be each independently a substituted or unsubstituted methyl group; a substituted or unsubstituted phenyl group; or a substituted or unsubstituted spirobifluorenyl group.

In another embodiment, $R_1$ and $R_2$ are the same as or different from each other, and may be each independently a methyl group; a phenyl group; or a spirobifluorenyl group.

In one embodiment of the present application, $R_1$ and $R_2$ may be the same as each other.

In one embodiment of the present application, $R_1$ and $R_2$ may be different from each other.

In another embodiment, $R_1$ may be a substituted or unsubstituted alkyl group having 1 to 20 carbon atoms; a substituted or unsubstituted aryl group having 6 to 40 carbon atoms; or a substituted or unsubstituted heteroaryl group having 2 to 40 carbon atoms.

In another embodiment, $R_1$ may be a substituted or unsubstituted alkyl group having 1 to 10 carbon atoms; a substituted or unsubstituted aryl group having 6 to 20 carbon atoms; or a substituted or unsubstituted heteroaryl group having 2 to 20 carbon atoms.

In another embodiment, $R_1$ may be a substituted or unsubstituted methyl group; a substituted or unsubstituted phenyl group; or a substituted or unsubstituted spirobifluorenyl group.

In another embodiment, $R_1$ may be a methyl group; a phenyl group; or a spirobifluorenyl group.

In another embodiment, $R_1$ is a methyl group.

In another embodiment, $R_1$ is a phenyl group.

In another embodiment, $R_1$ is a spirobifluorenyl group.

In another embodiment, $R_2$ may be a substituted or unsubstituted alkyl group having 1 to 20 carbon atoms; a substituted or unsubstituted aryl group having 6 to 40 carbon atoms; or a substituted or unsubstituted heteroaryl group having 2 to 40 carbon atoms.

In another embodiment, $R_2$ may be a substituted or unsubstituted alkyl group having 1 to 10 carbon atoms; a substituted or unsubstituted aryl group having 6 to 20 carbon atoms; or a substituted or unsubstituted heteroaryl group having 2 to 20 carbon atoms.

In another embodiment, $R_2$ may be a substituted or unsubstituted methyl group; a substituted or unsubstituted phenyl group; or a substituted or unsubstituted spirobifluorenyl group.

In another embodiment, $R_2$ may be a methyl group; a phenyl group; or a spirobifluorenyl group.

In another embodiment, $R_2$ is a methyl group.

In another embodiment, $R_2$ is a phenyl group.

In another embodiment, $R_2$ is a spirobifluorenyl group.

In the heterocyclic compound provided in one embodiment of the present application, Chemical Formula 1 is represented by any one of the following compounds.

1

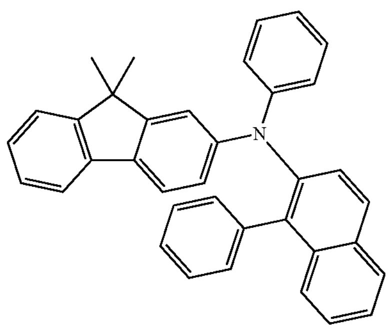

2

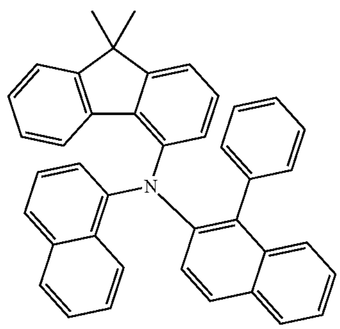

-continued

3

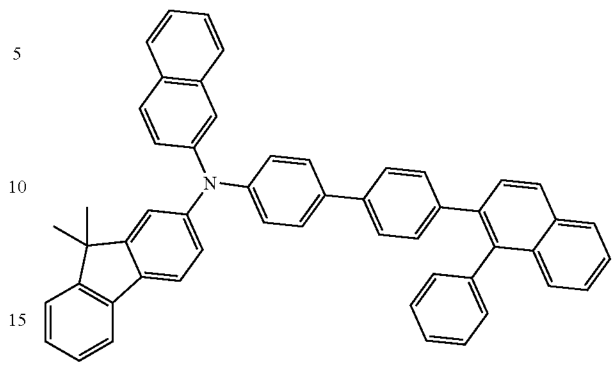

4

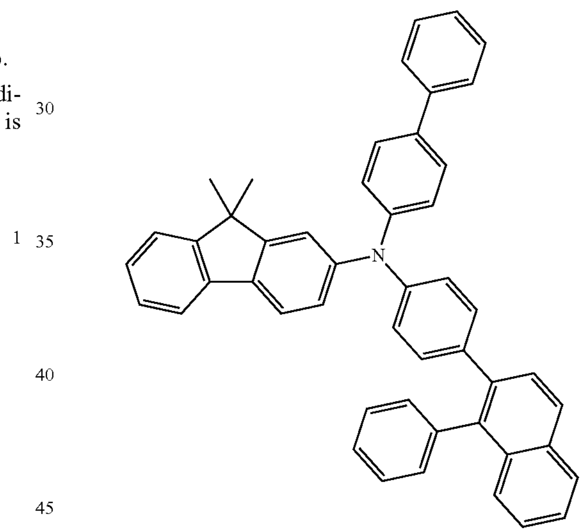

5

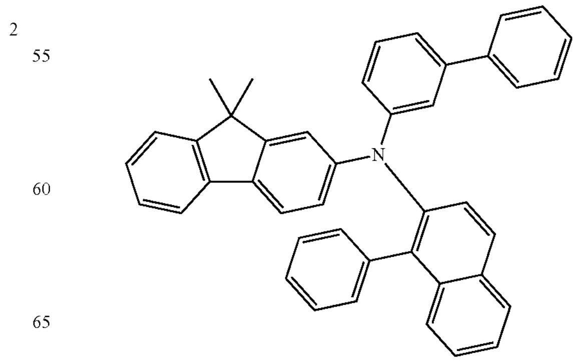

-continued
6
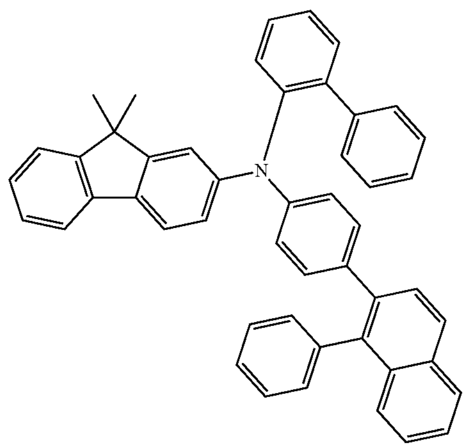
7
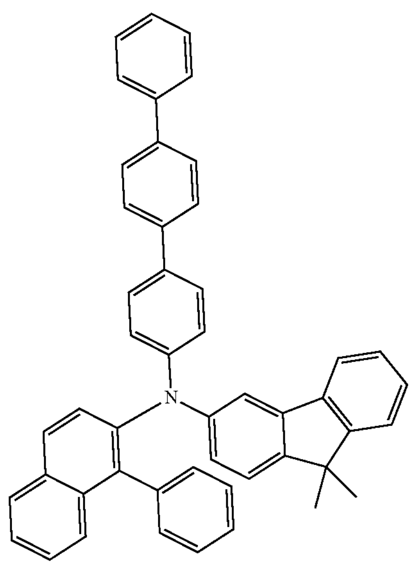
8
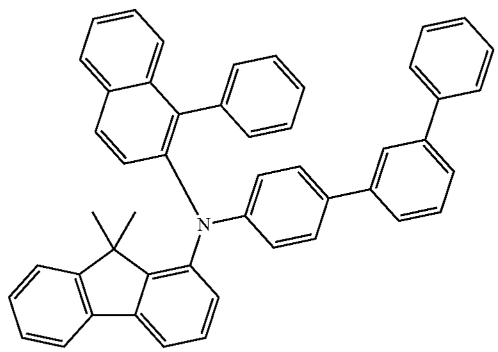
-continued
9
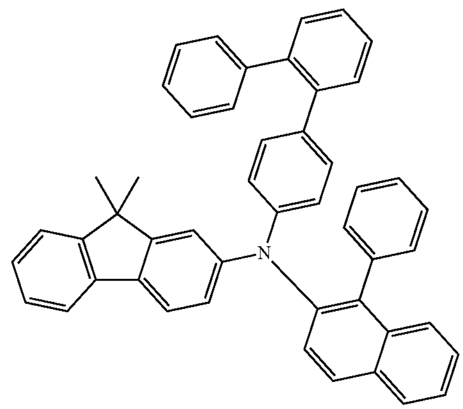
10
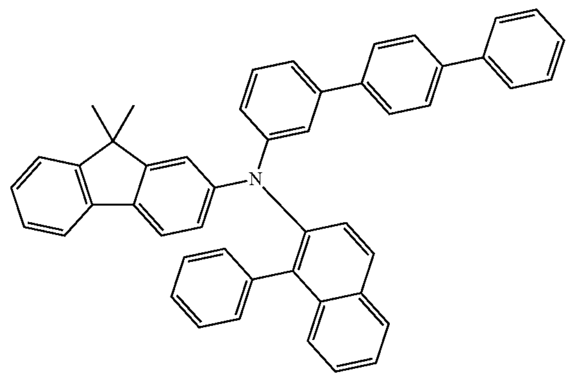
11
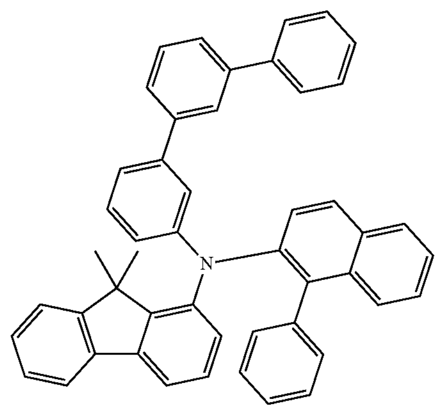

-continued
12
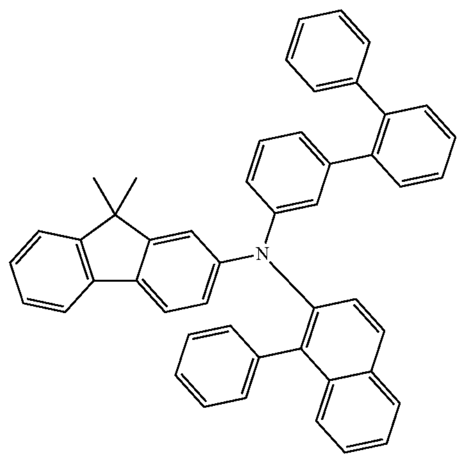
13
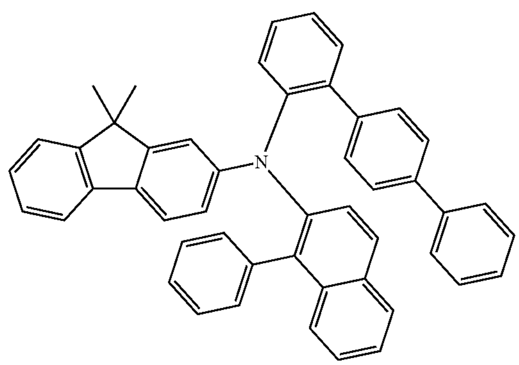
14
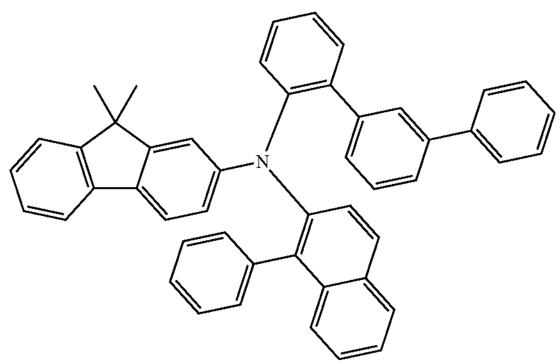
15
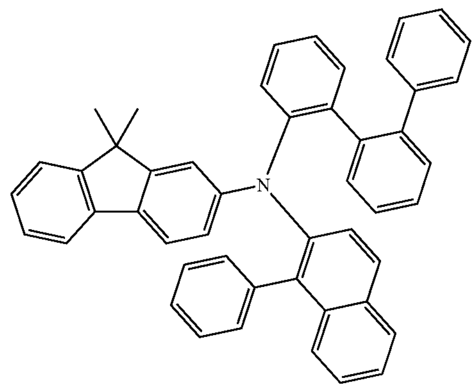
-continued
16
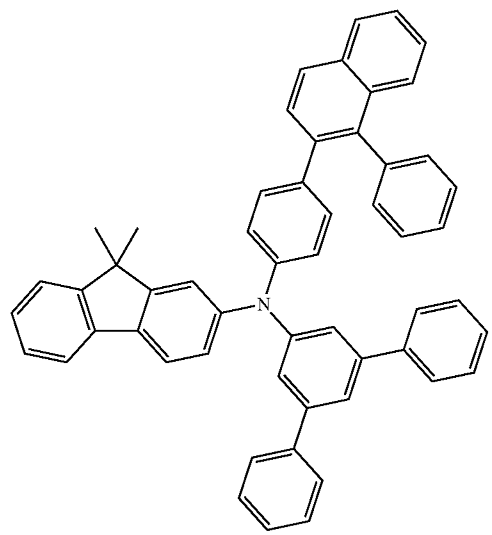
17
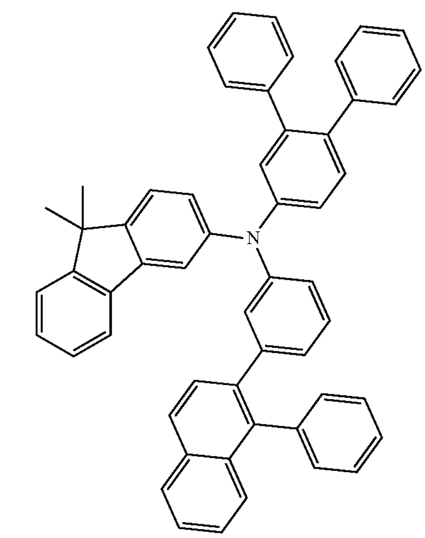
18
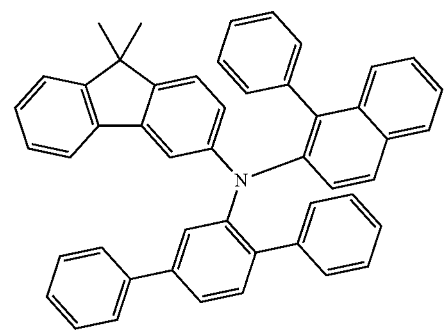

-continued
19
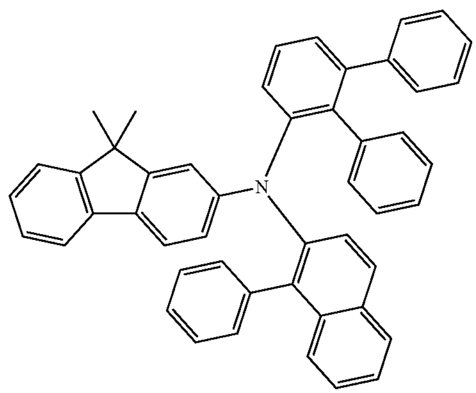
20
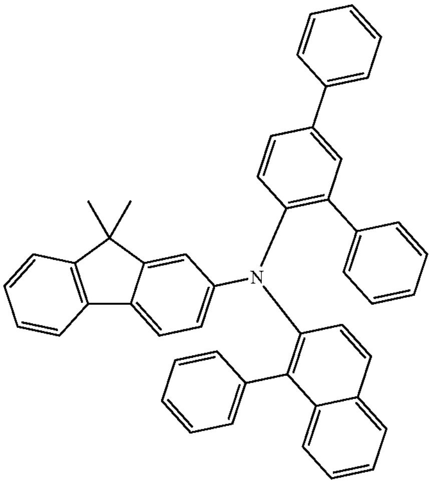
21
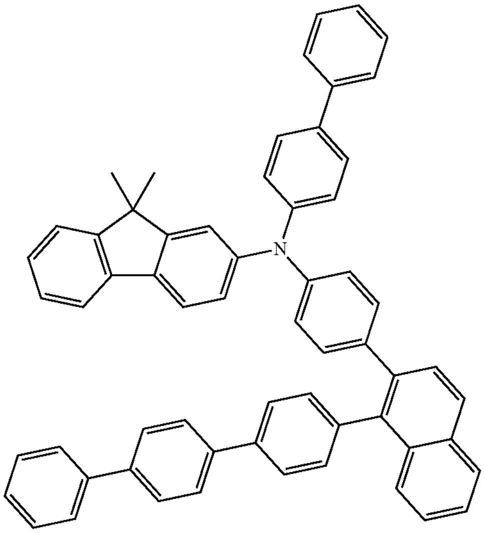
-continued
22
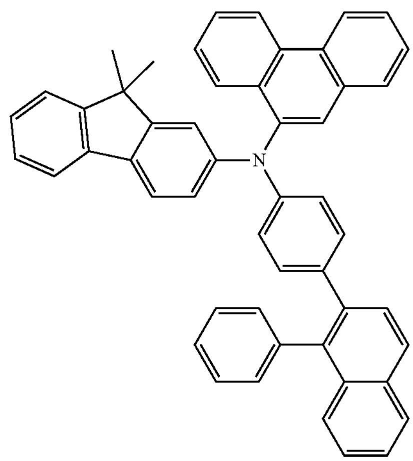
23
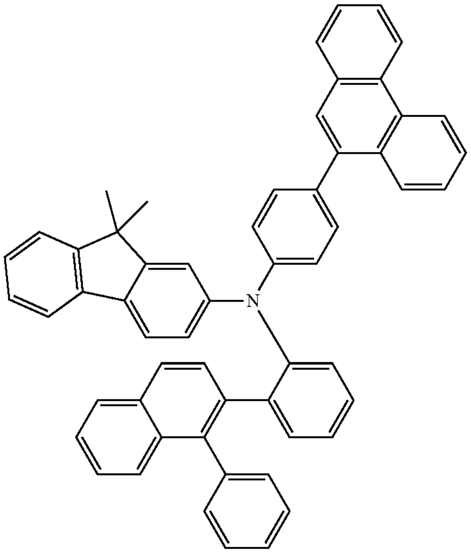
24
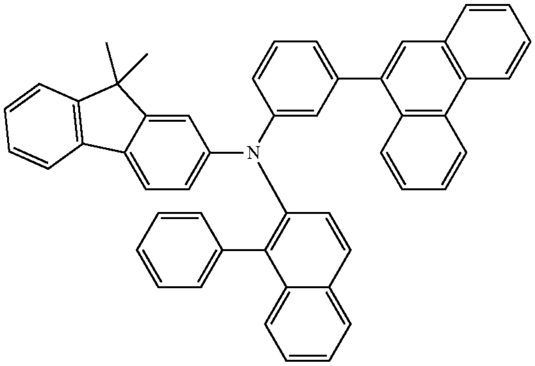

-continued
25
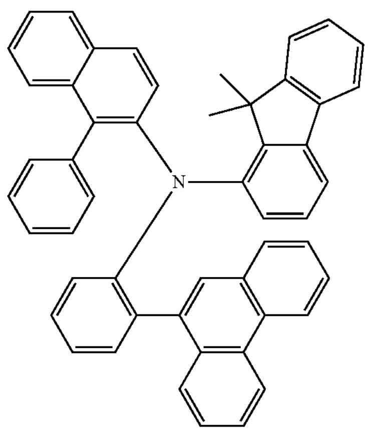
26
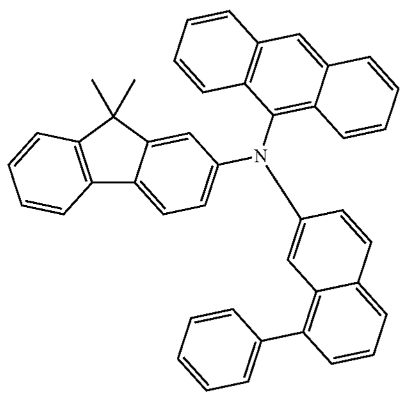
27
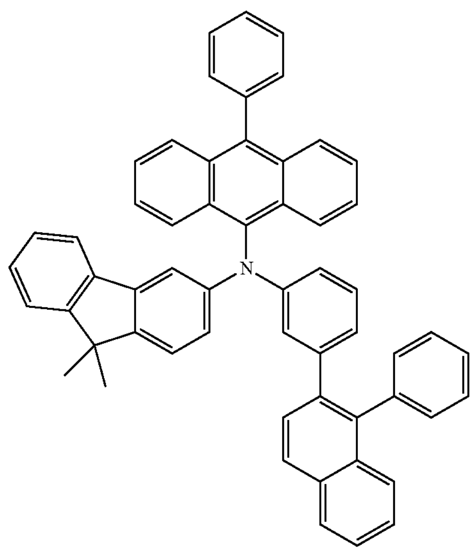
-continued
28
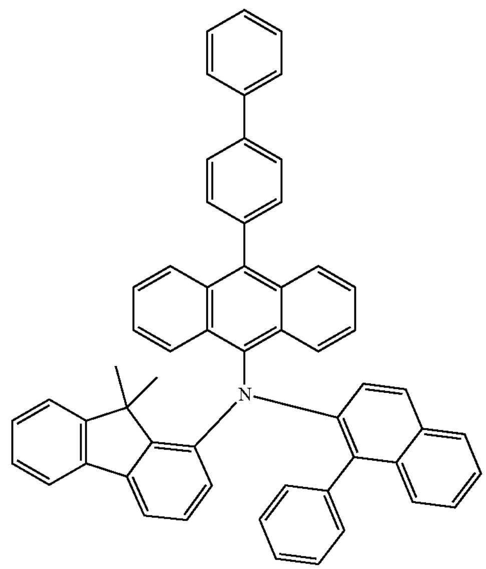
29
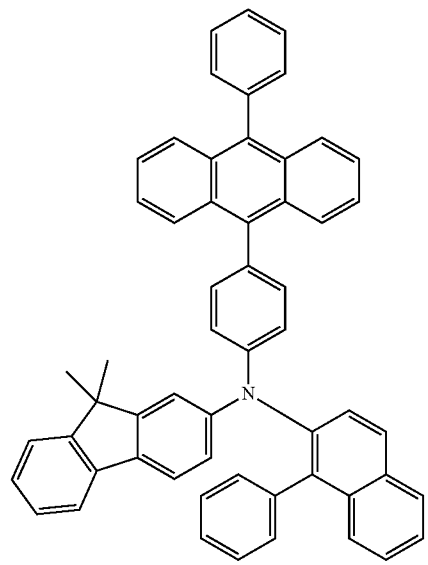
30
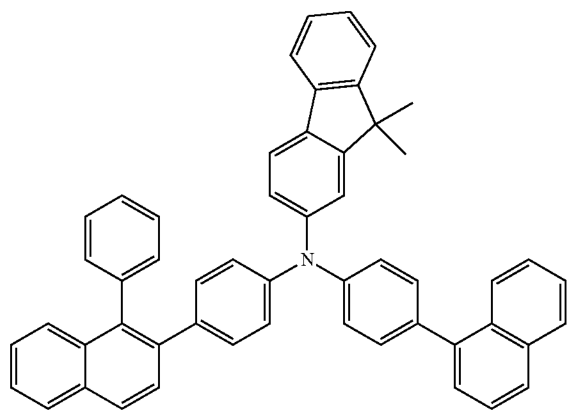

-continued
31
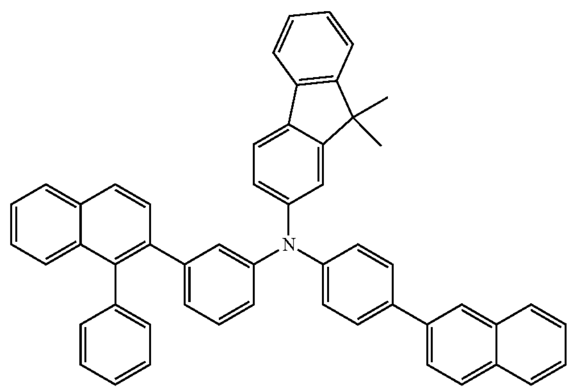
32
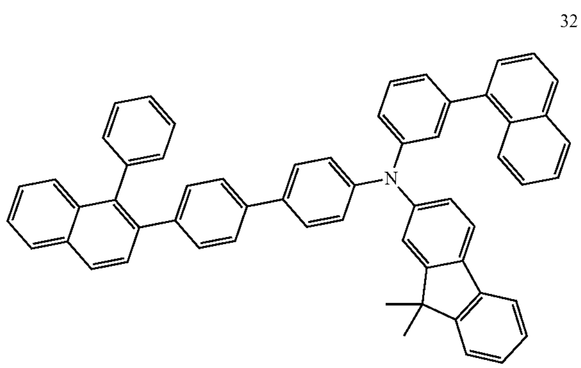
33
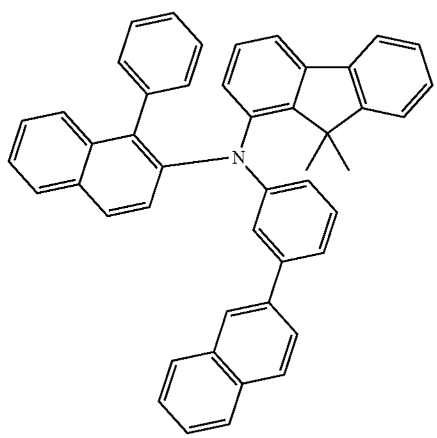
34
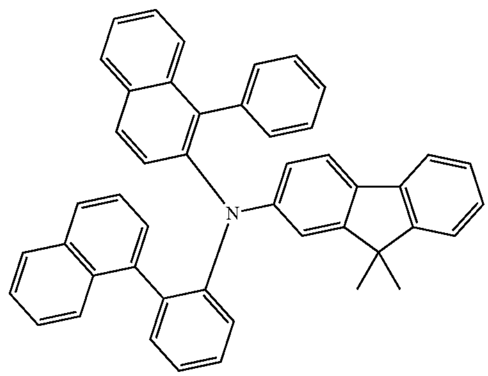
-continued
35
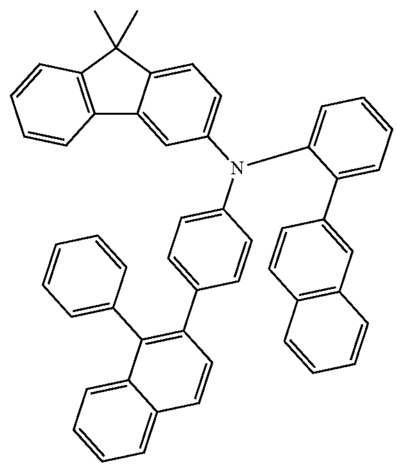
36
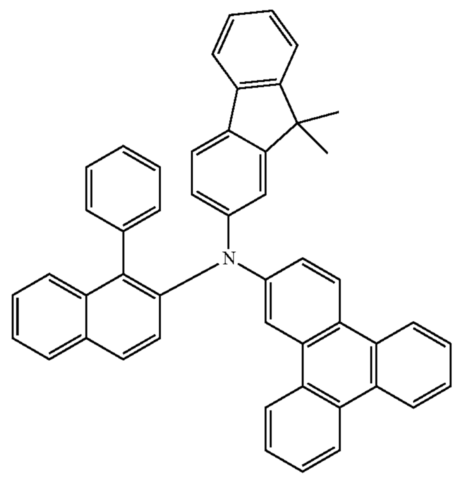
37
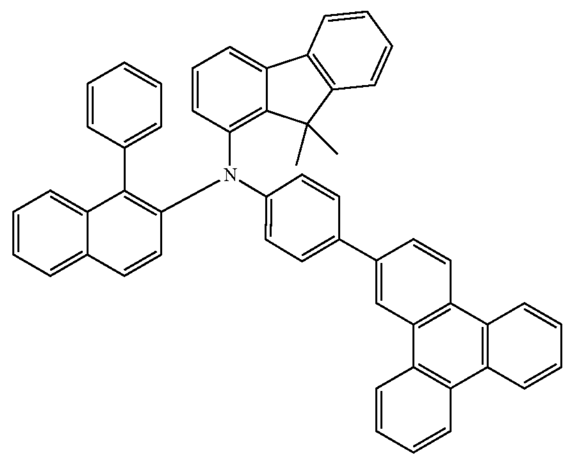

-continued
38
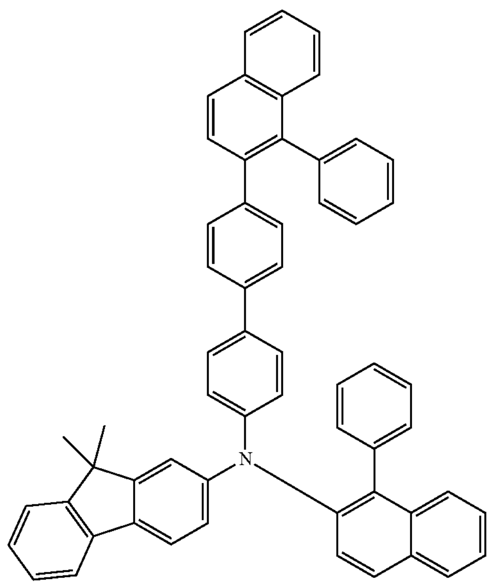
39
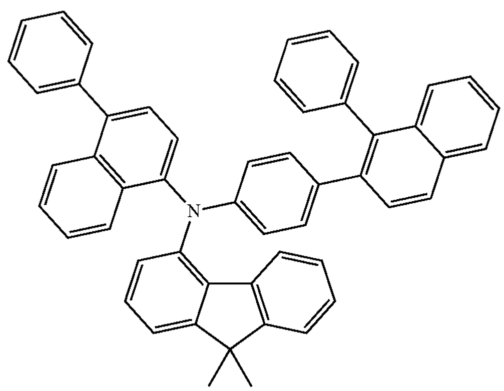
40
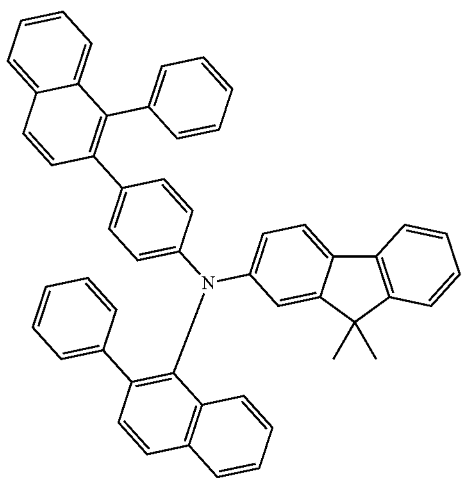
-continued
41
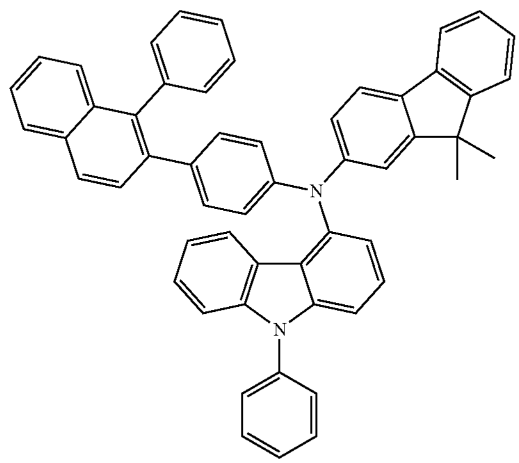
42
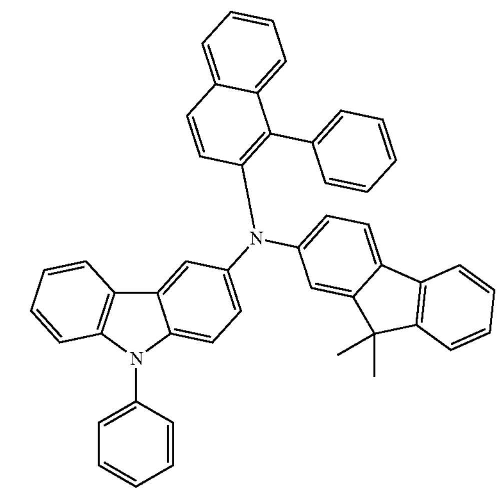
43
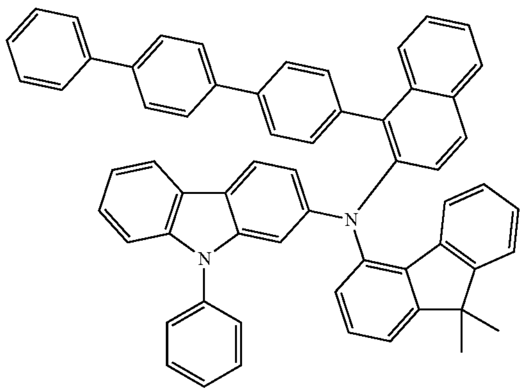

-continued
44
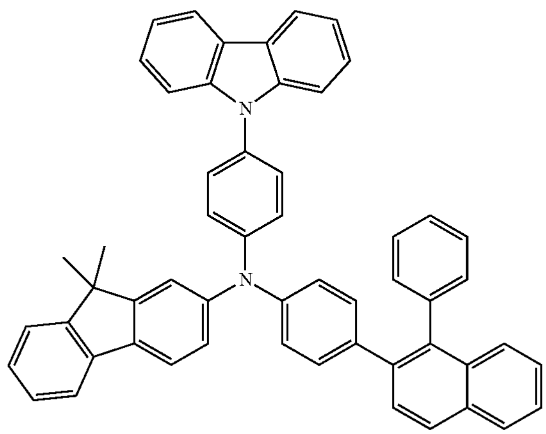
45
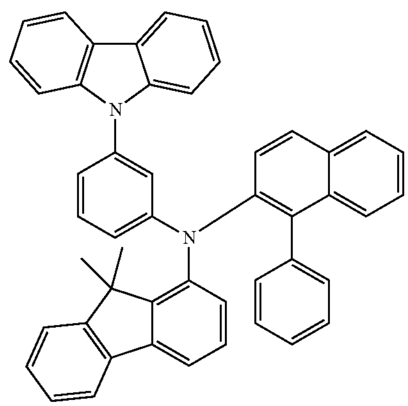
46
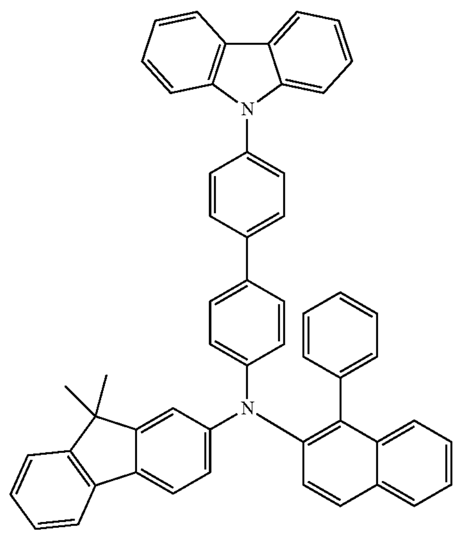
-continued
47
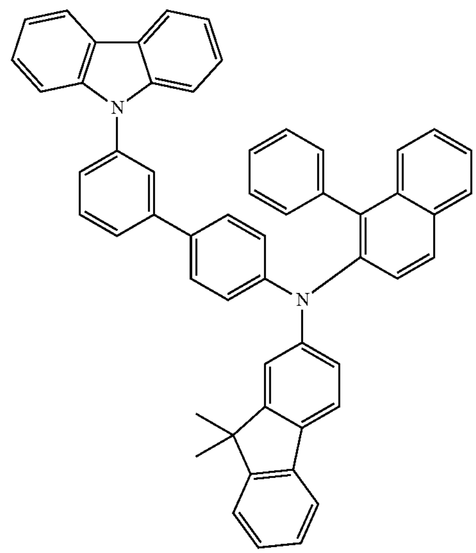
48
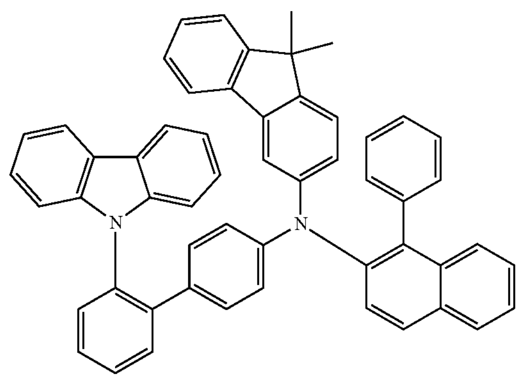
49
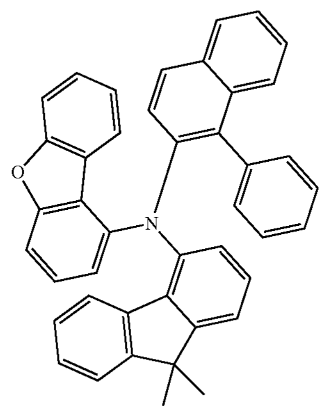

-continued
50
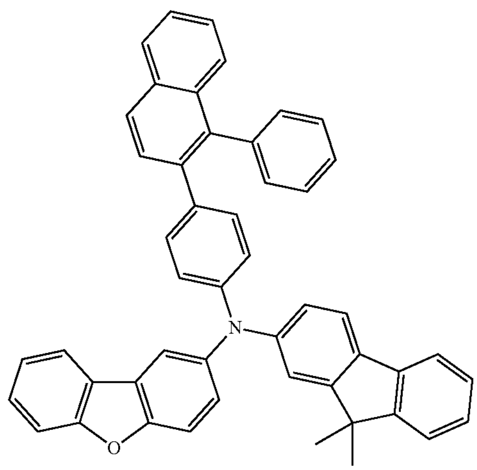
51
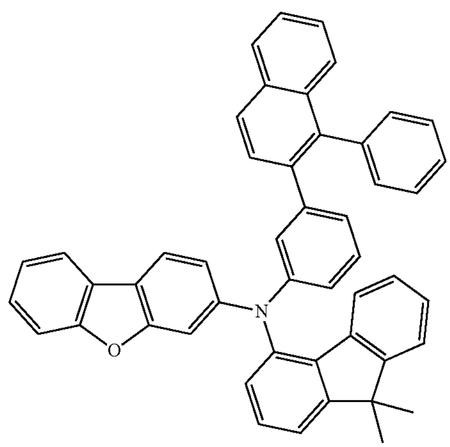
52
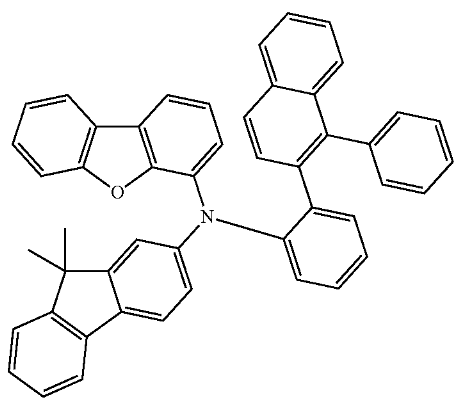
-continued
53
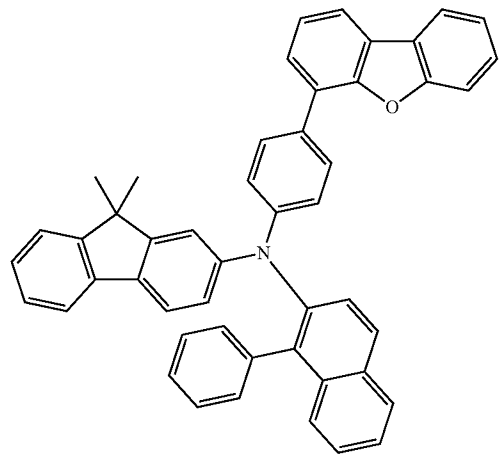
54
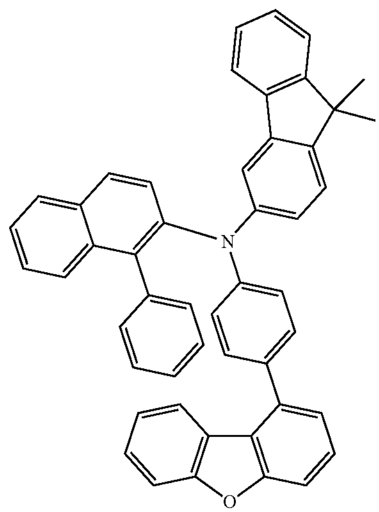
55
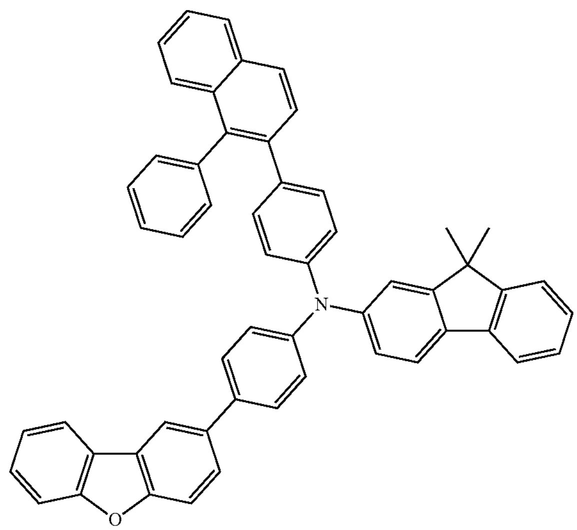

-continued
56
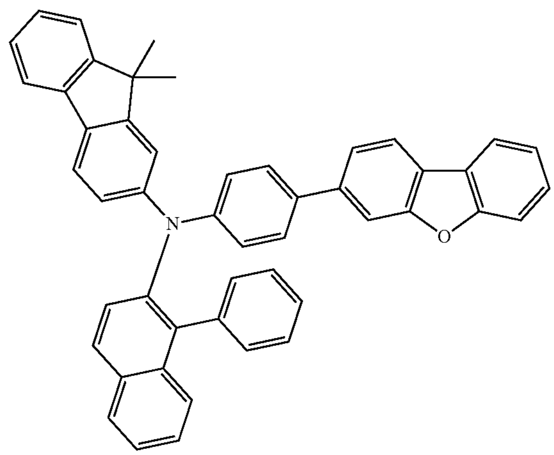
57
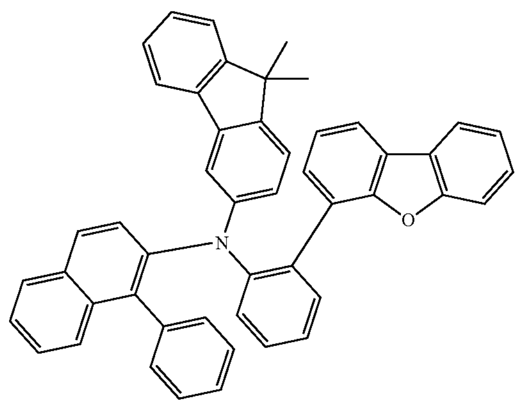
58
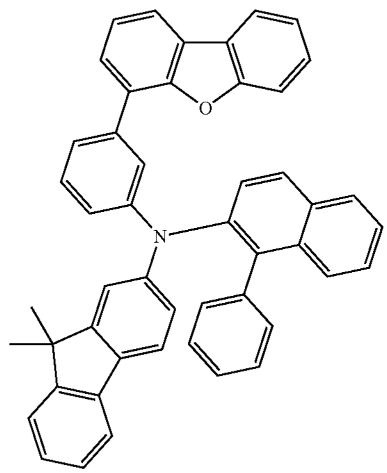
-continued
59
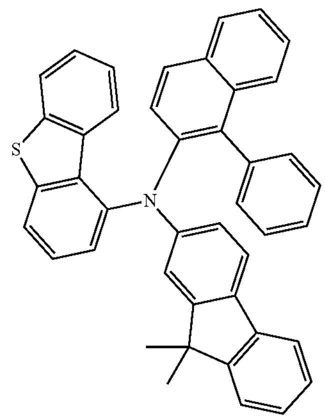
60
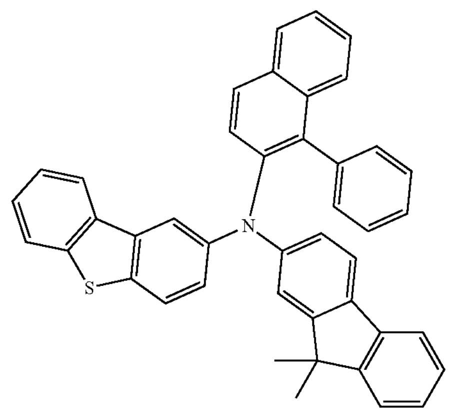
61
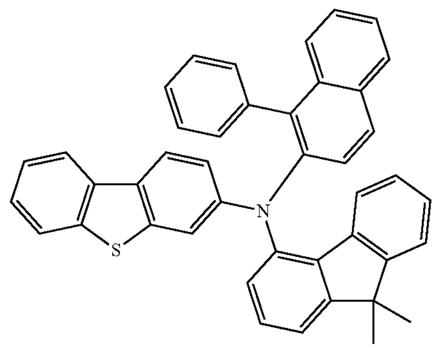
62
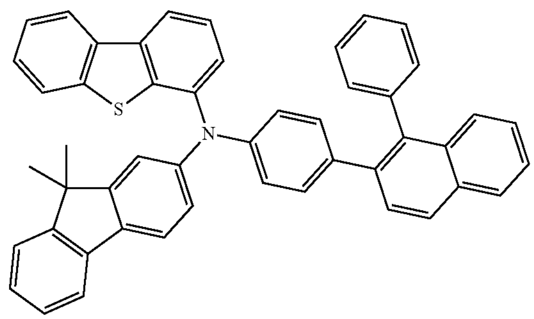

-continued
63
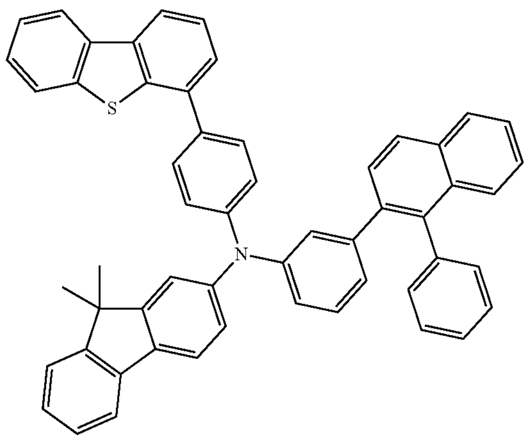
64
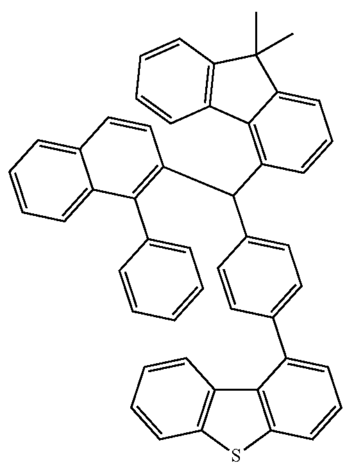
65
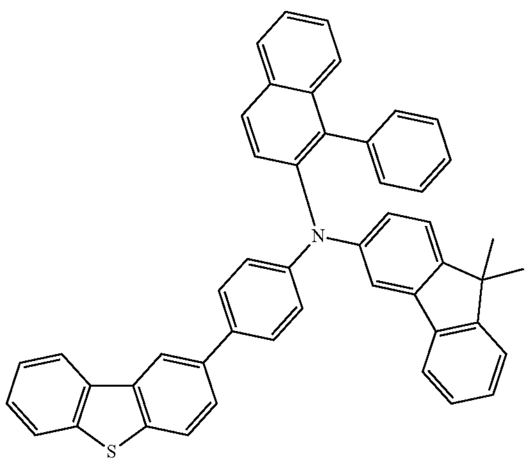
-continued
66
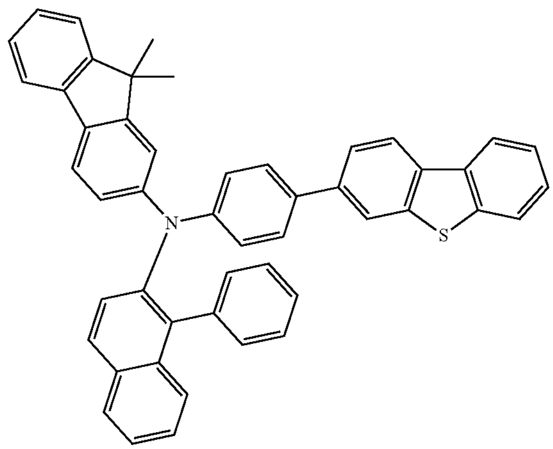
67
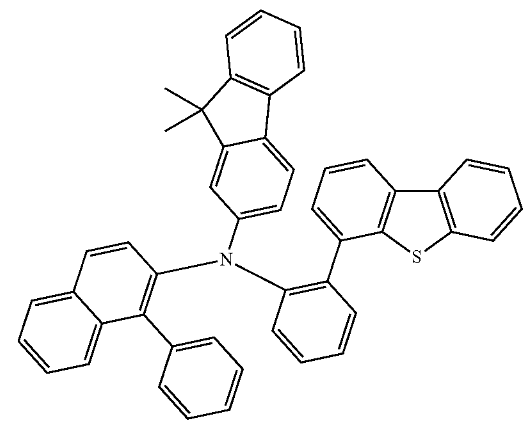
68
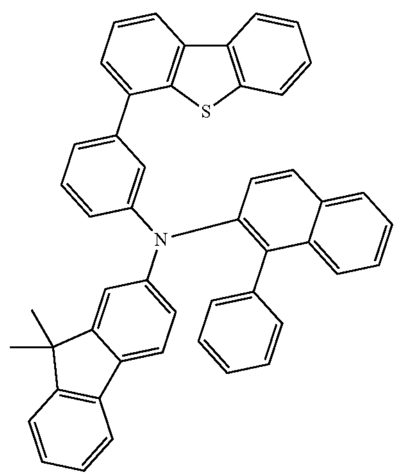

-continued
69
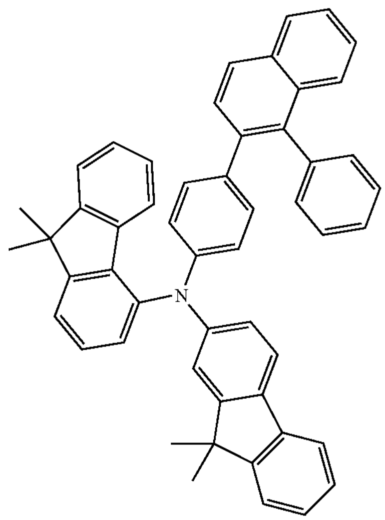
70
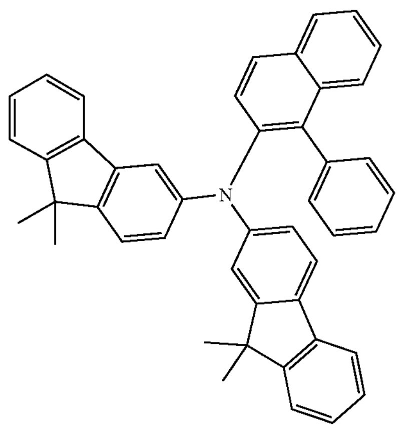
71
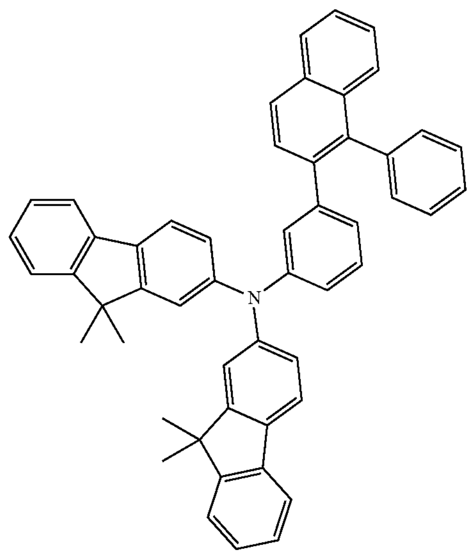
-continued
72
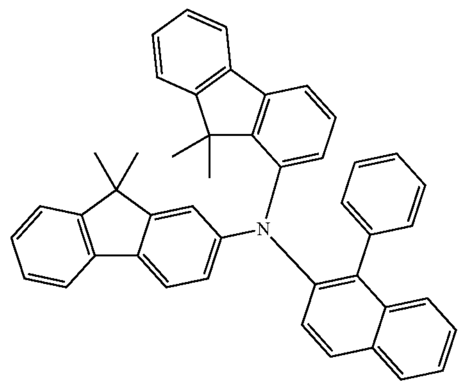
73
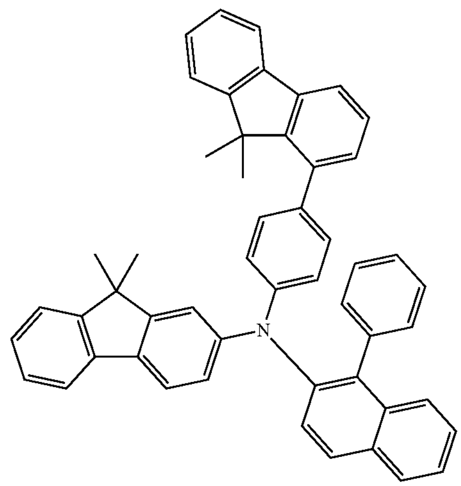
74
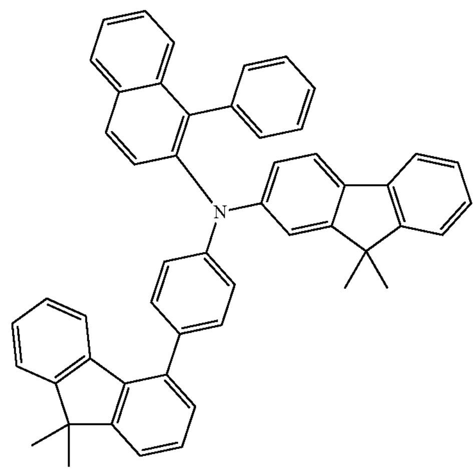

-continued
75
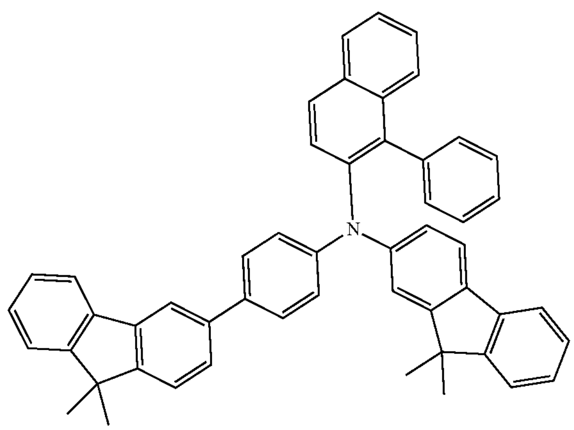
76
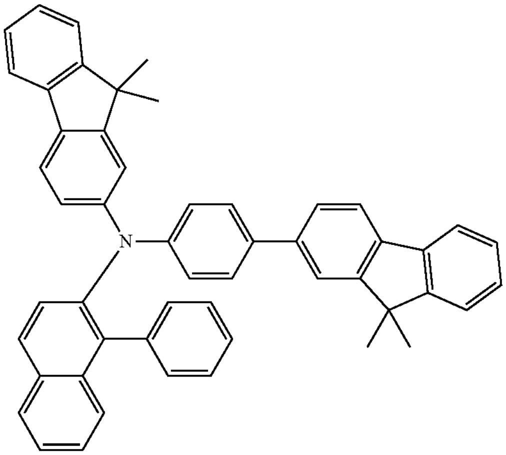
77
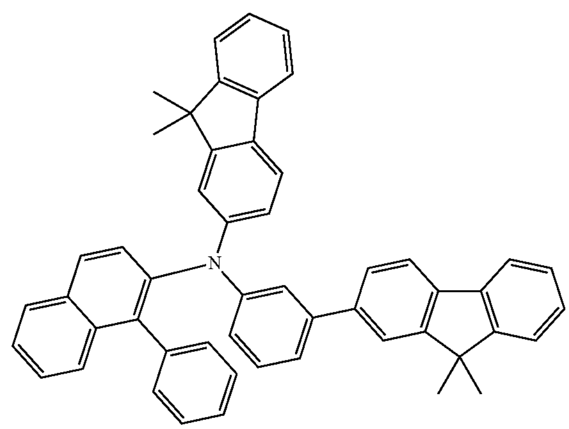
-continued
78
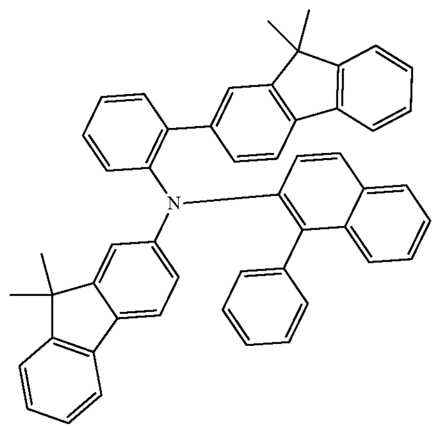
79
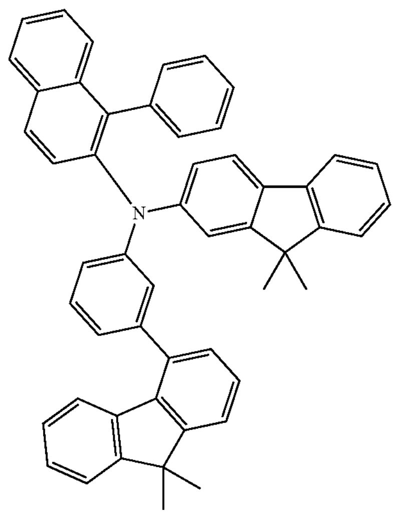
80
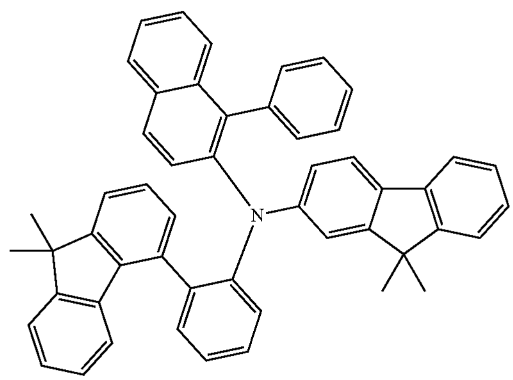

-continued
81
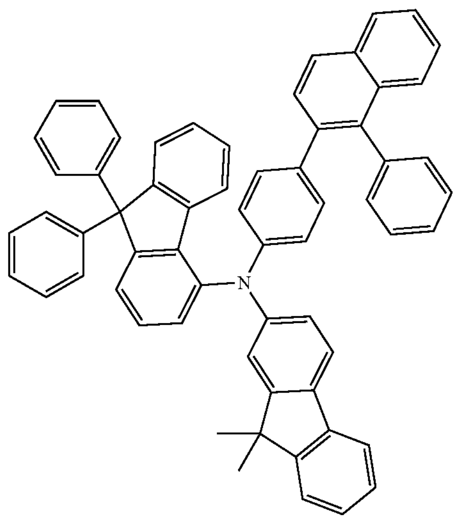
82
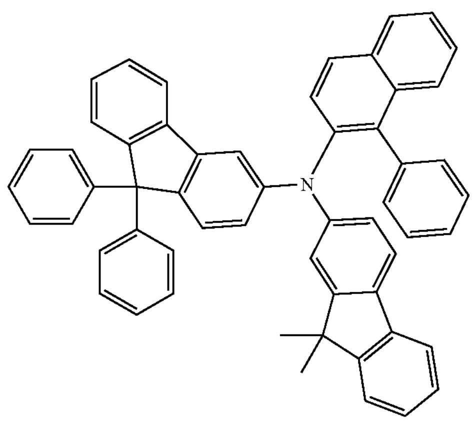
83
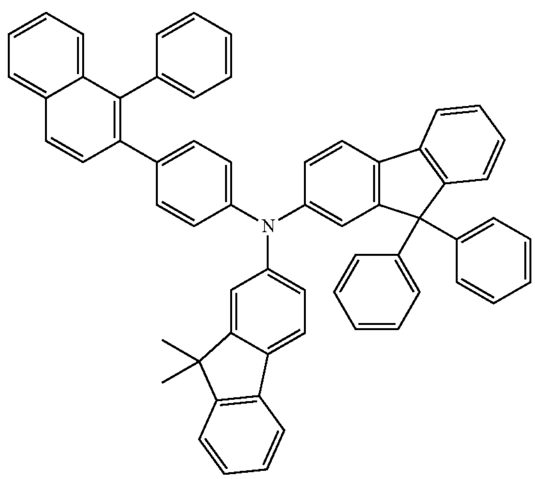
-continued
84
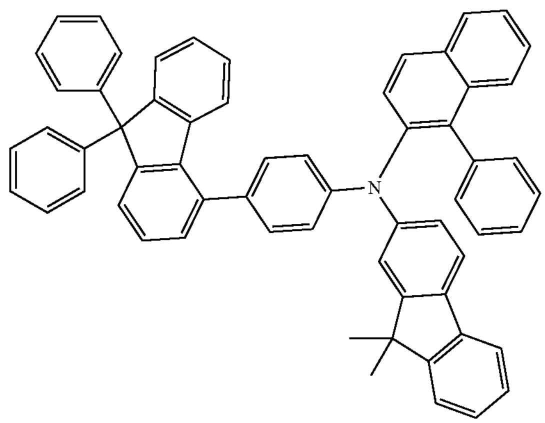
85
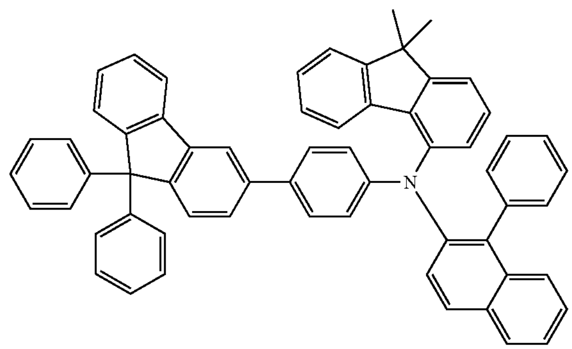
86
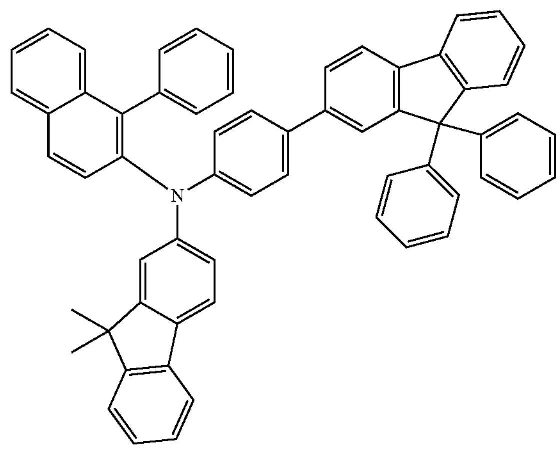

-continued
87
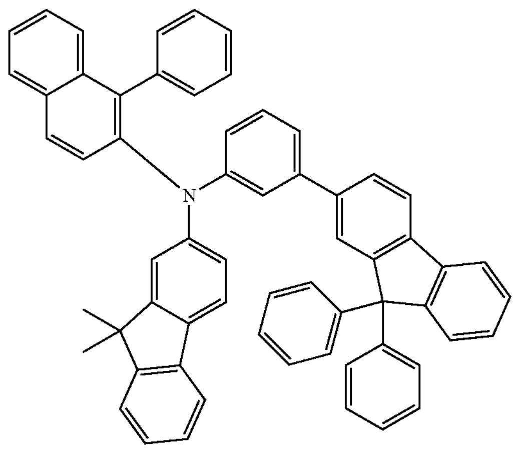
88
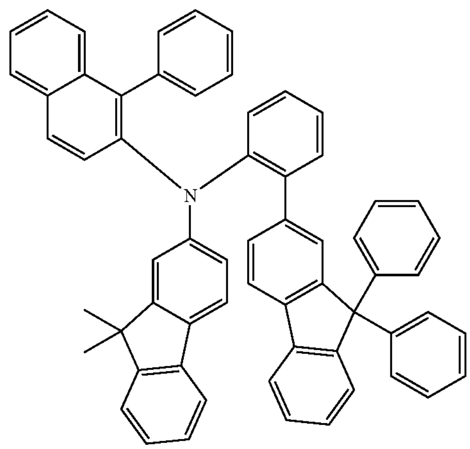
89
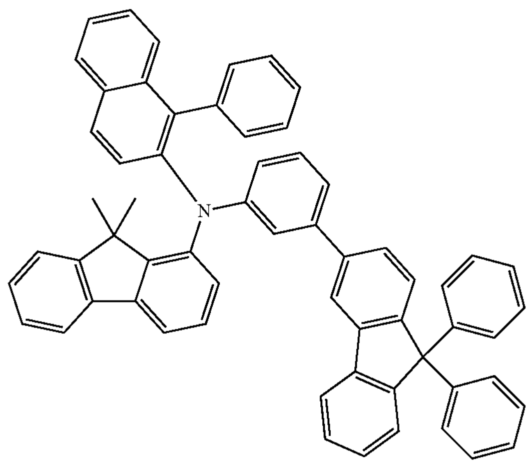
-continued
90
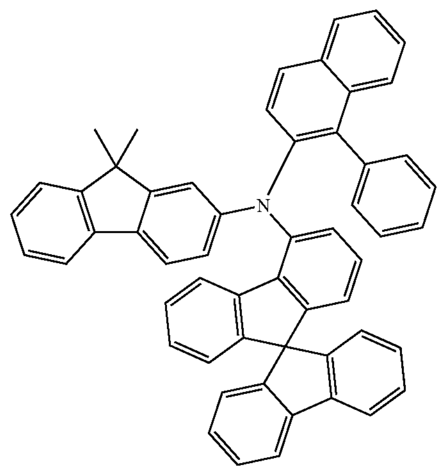
91
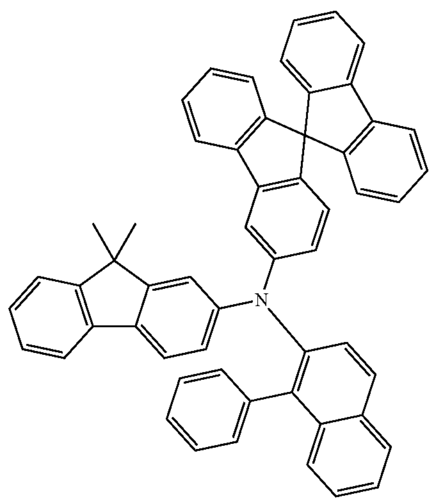
92
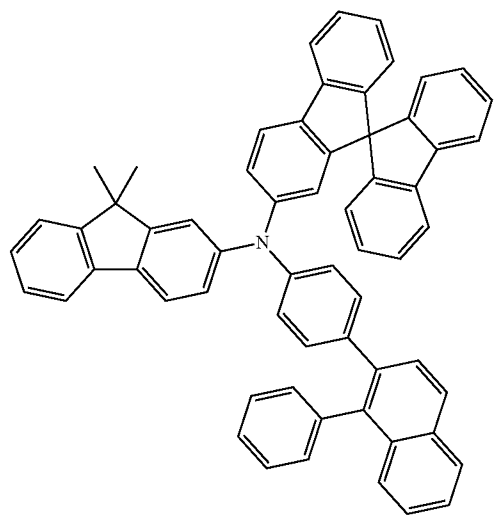

-continued
93
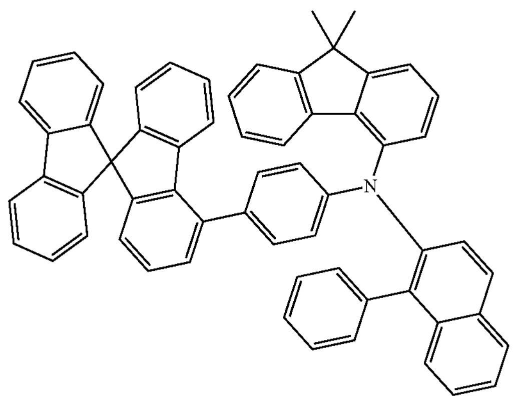
94
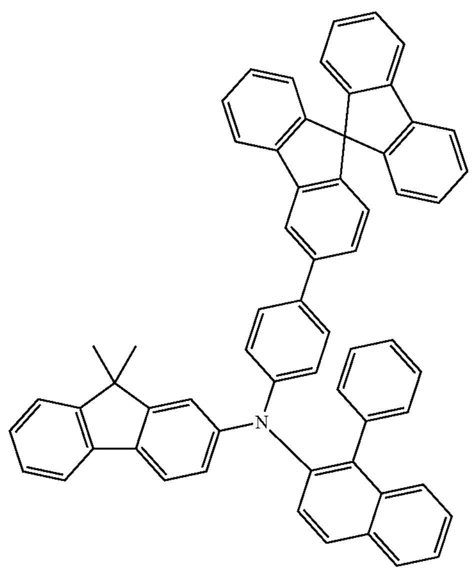
95
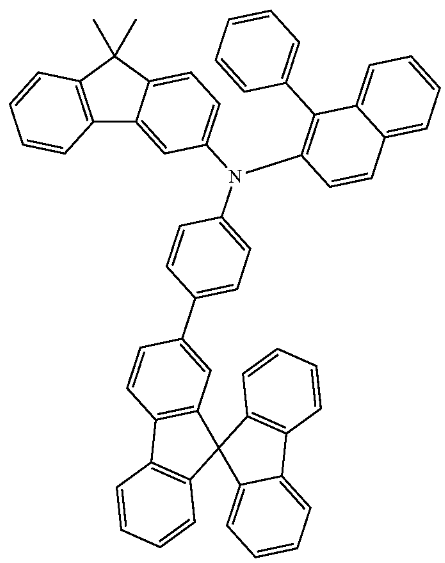
-continued
96
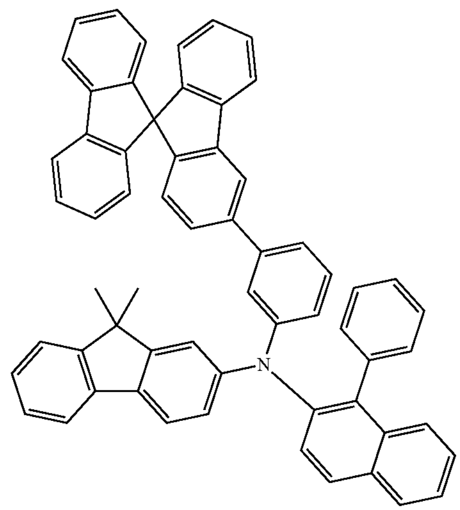
97
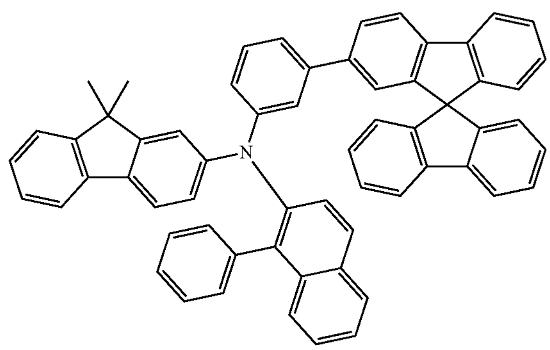
98
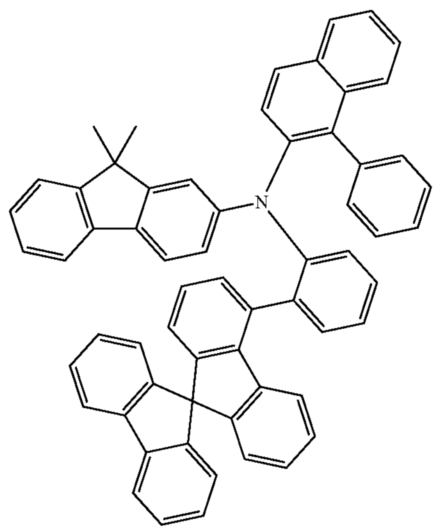

-continued
99
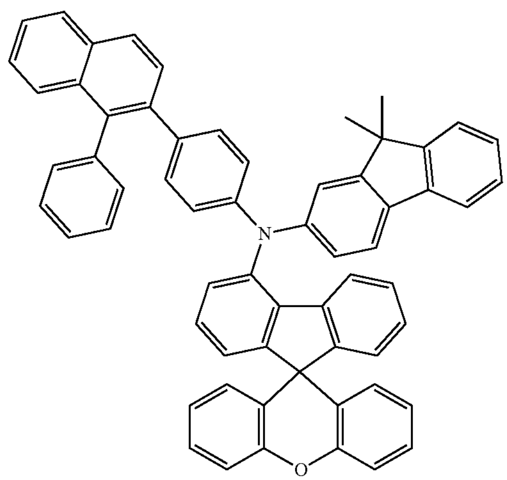
100
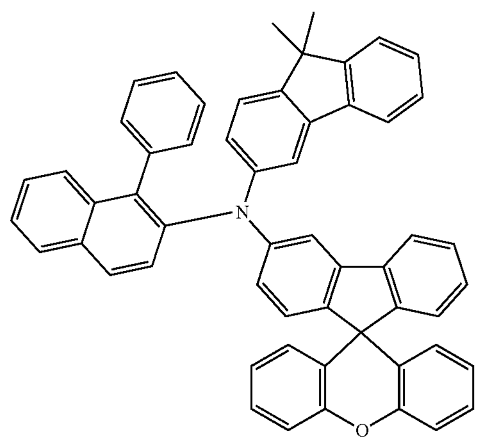
101
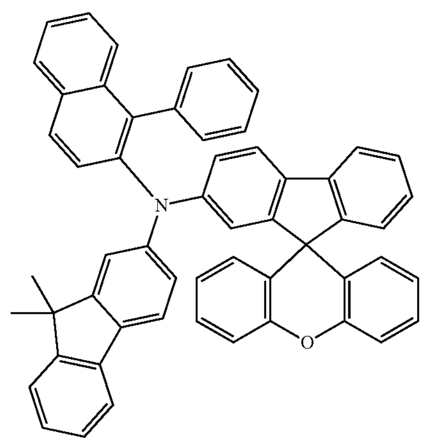
-continued
102
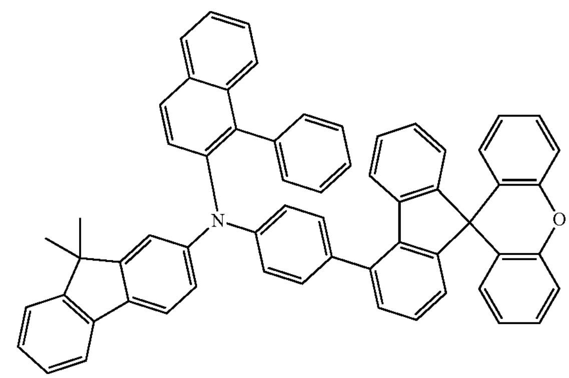
103
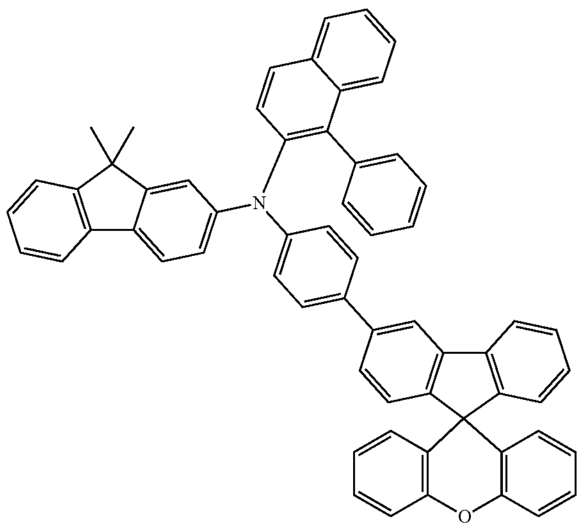
104
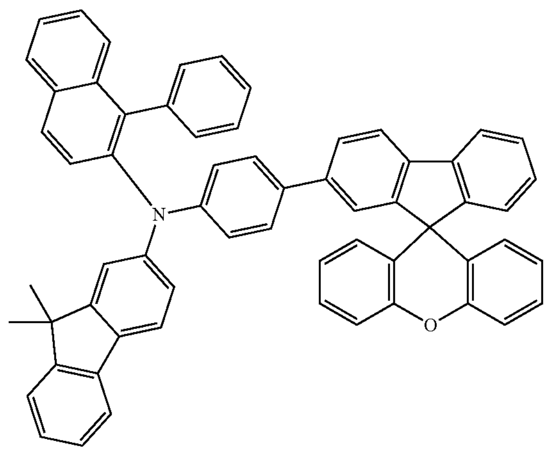

-continued
105
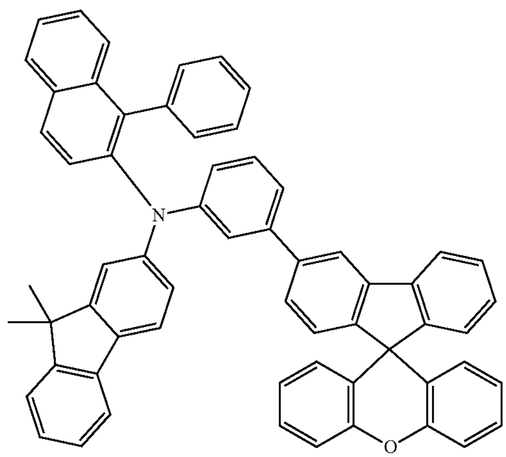
106
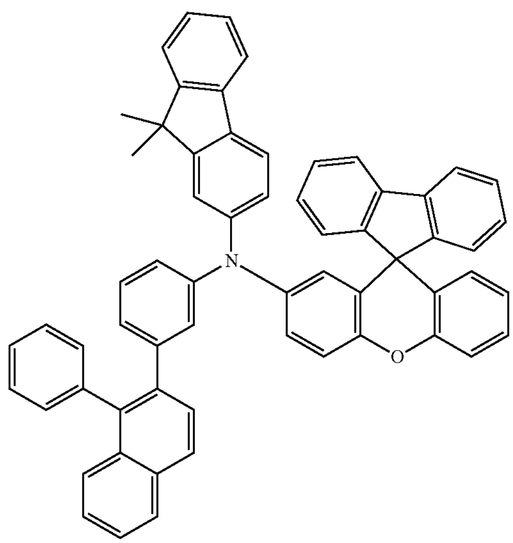
107
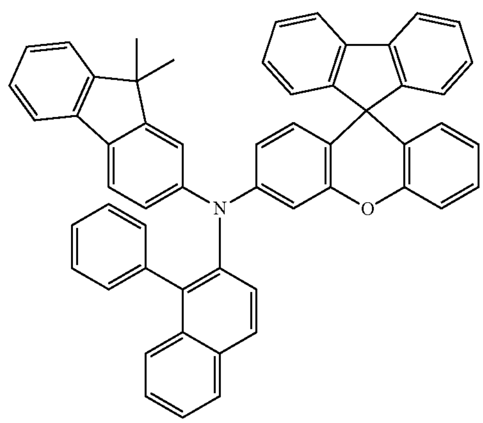
-continued
108
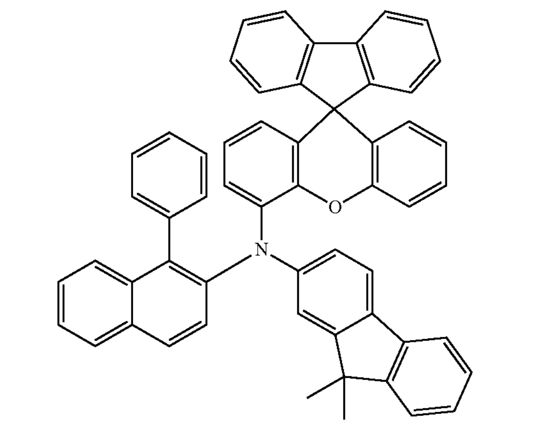
109
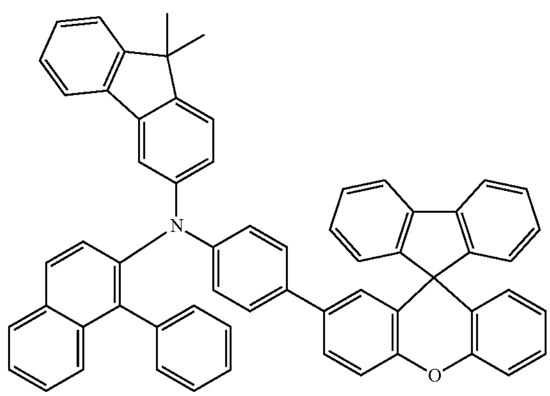
110
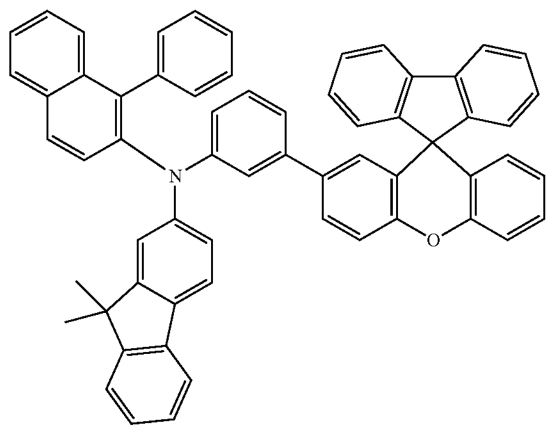
111
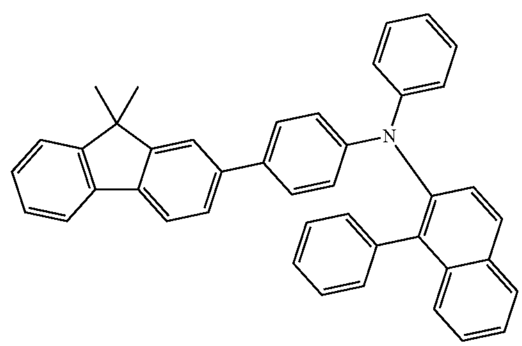

-continued
112
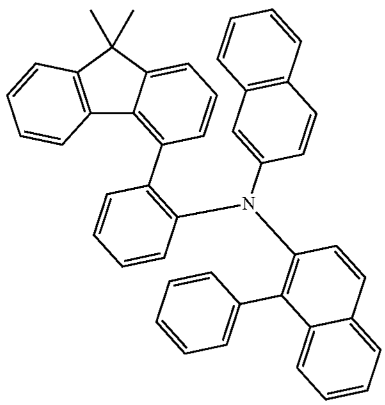
113
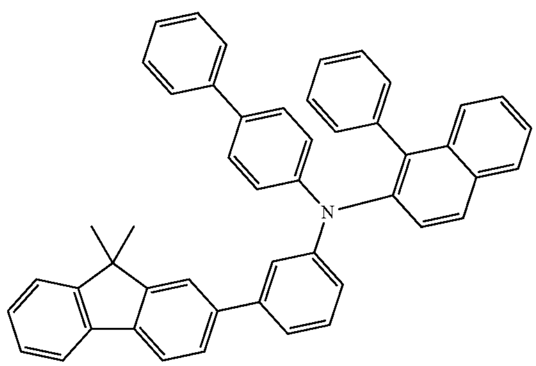
114
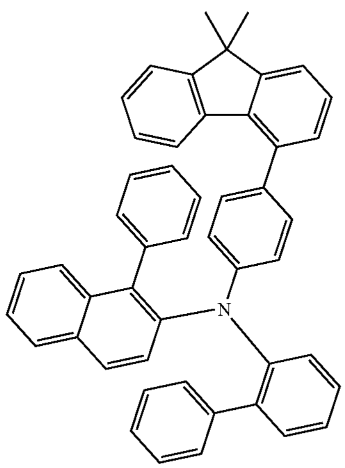
115
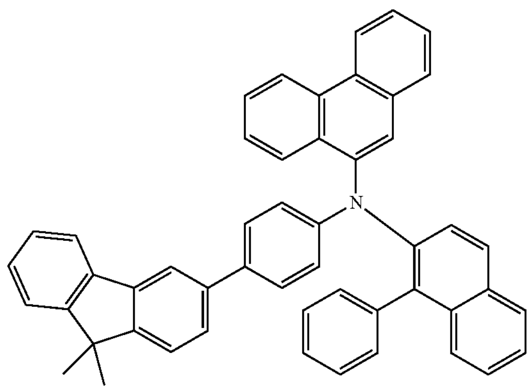
-continued
116
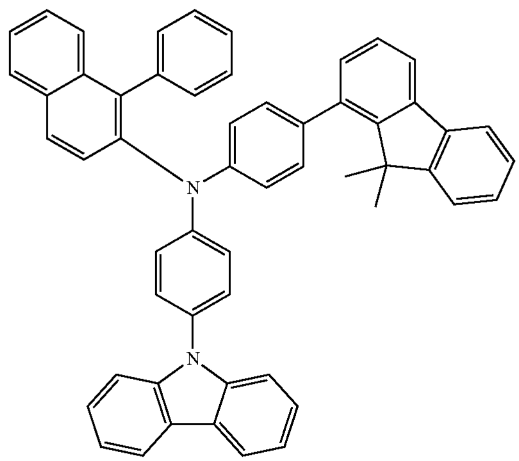
117
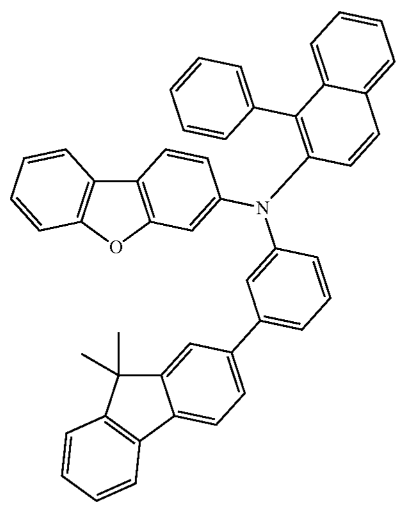
118
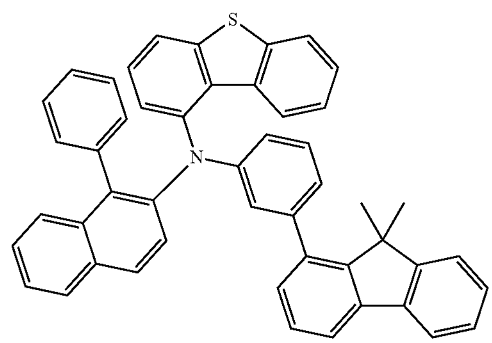

-continued
119
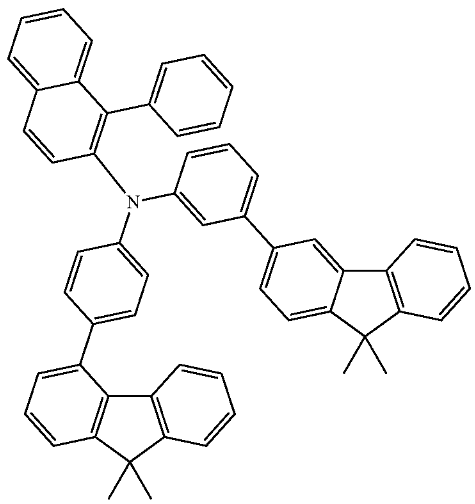
120
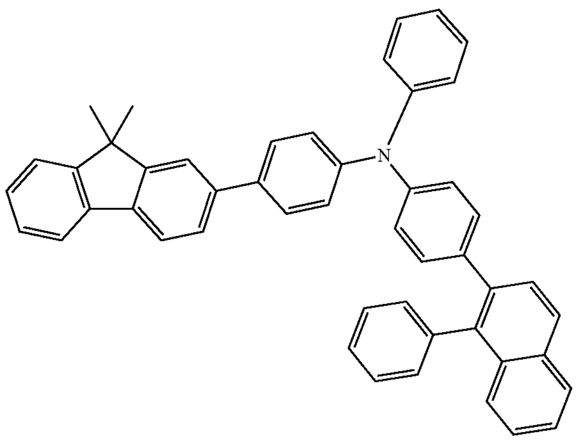
121
-continued
122
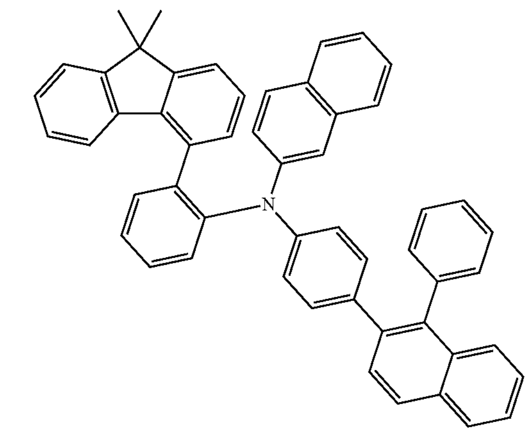
123
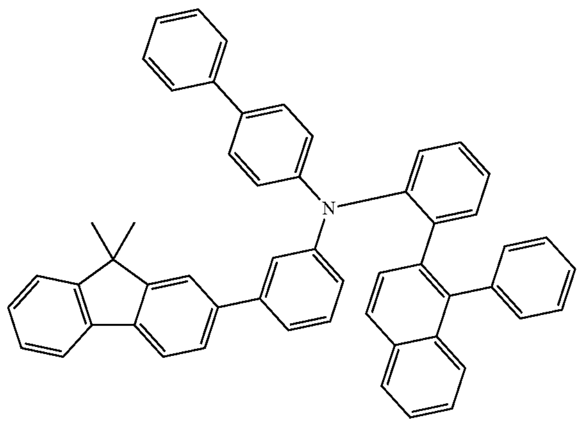
124
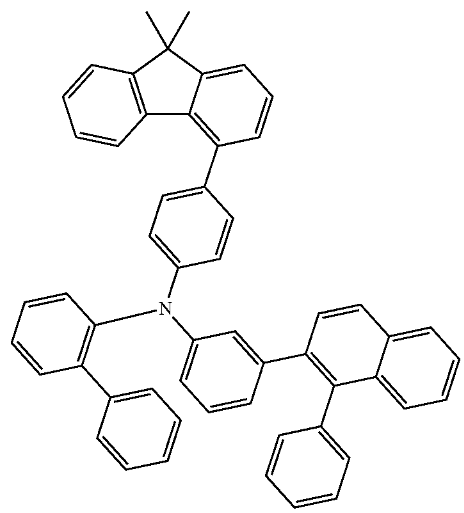

-continued
125
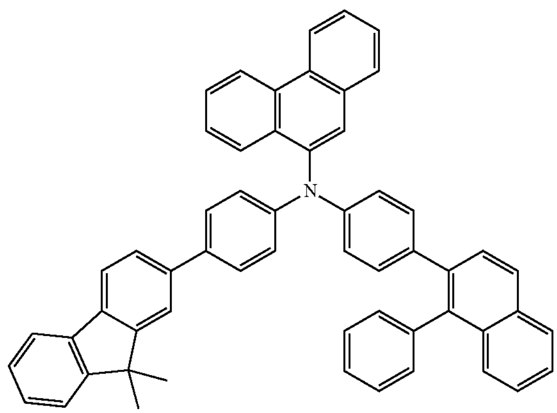
126
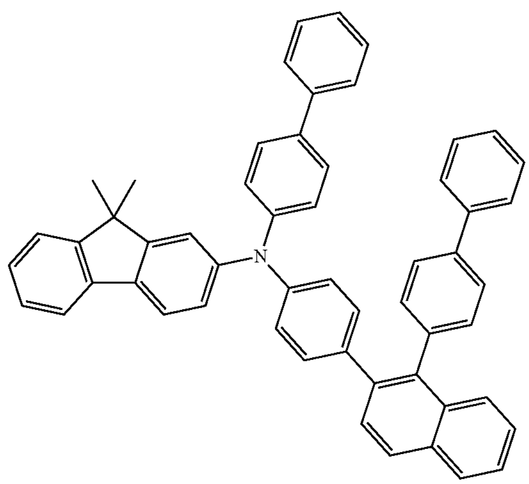
127
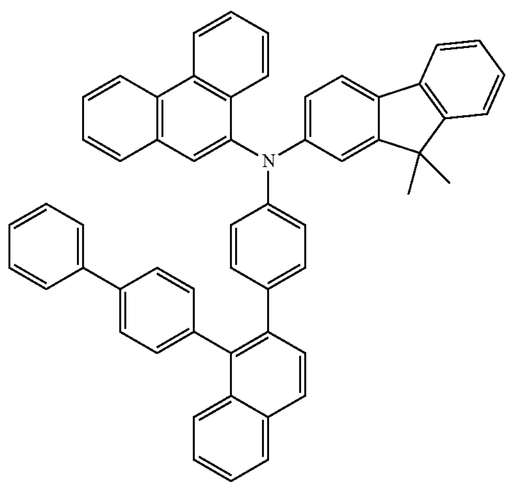
-continued
128
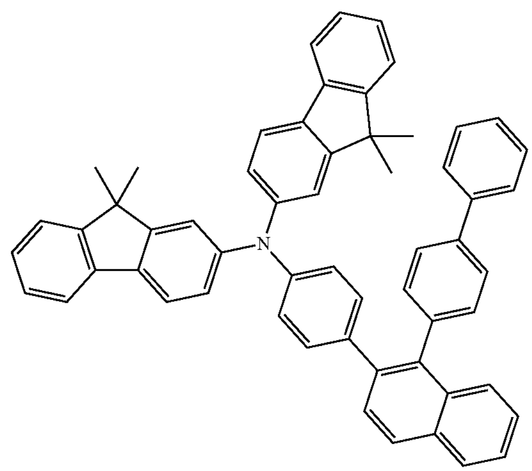
129
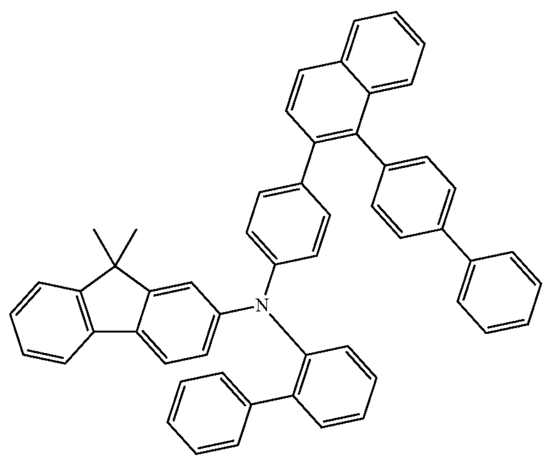
130
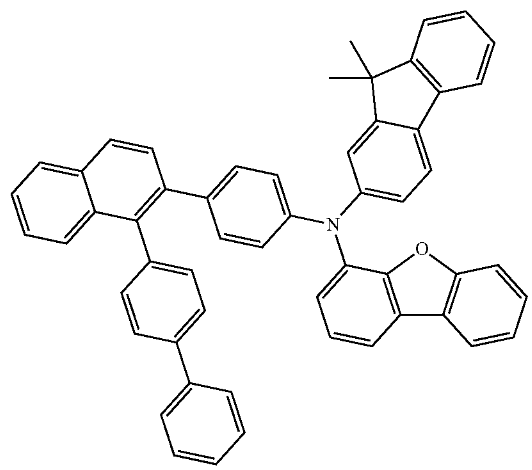

-continued
131
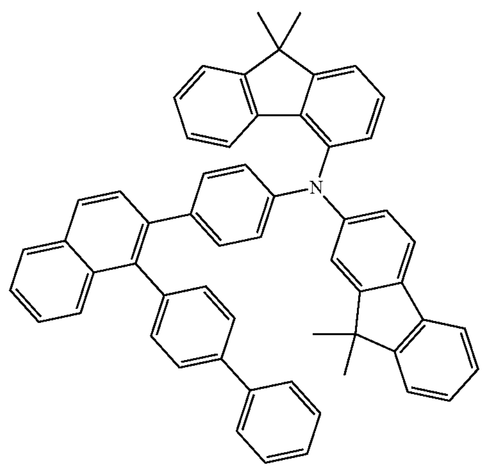
132
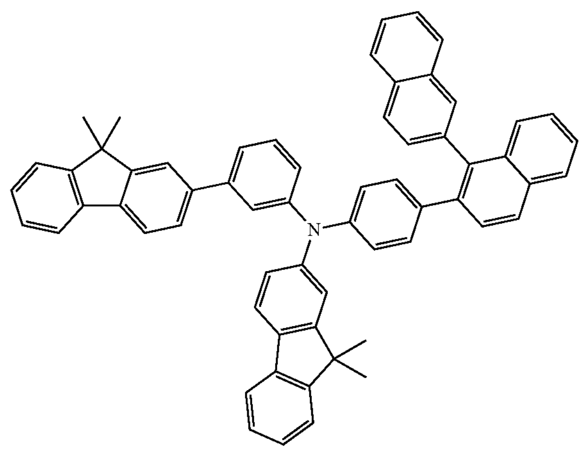
133
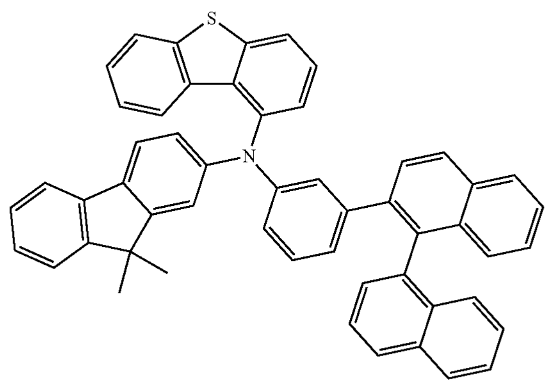
134
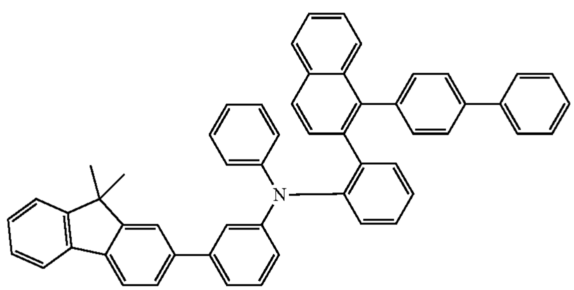
-continued
135
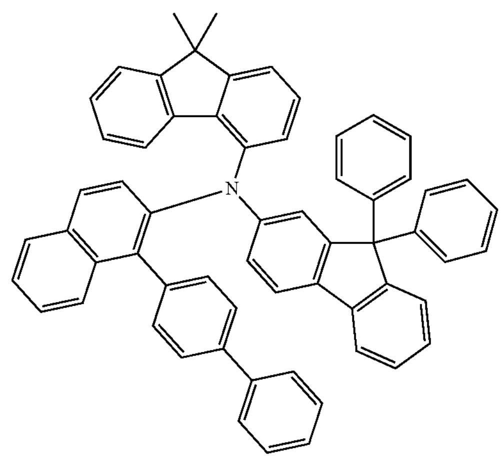
136
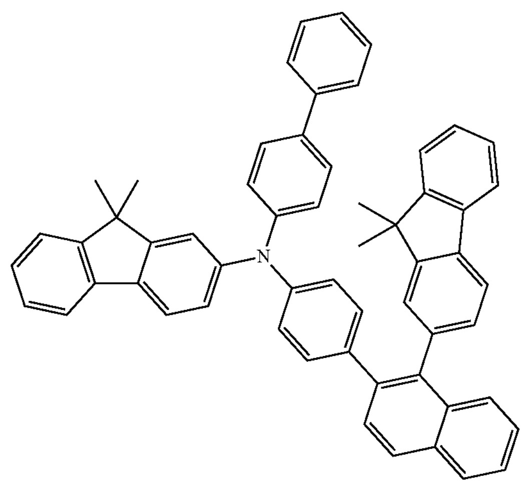
137
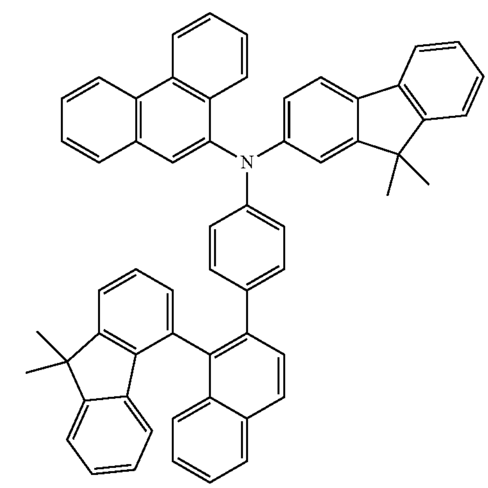

-continued
138
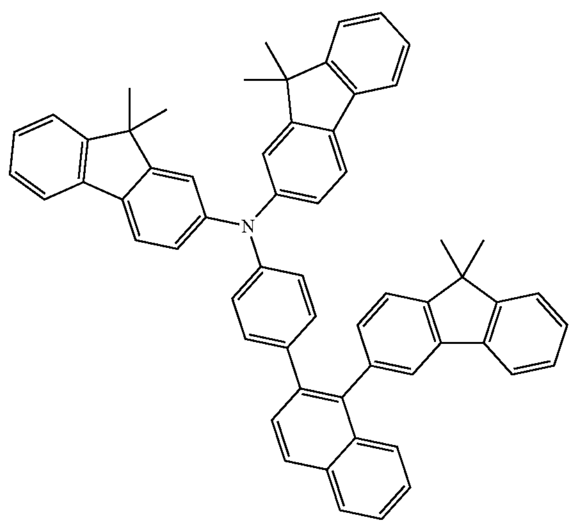
139
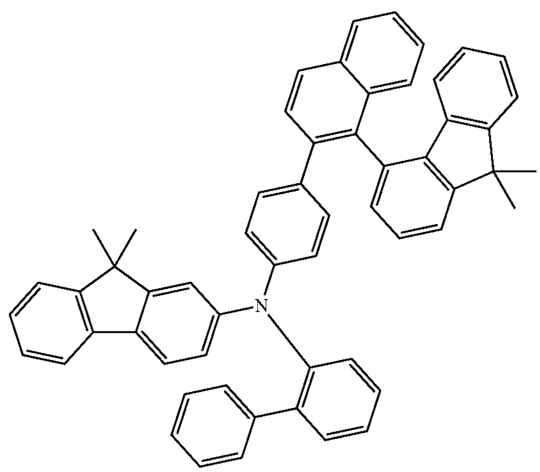
140
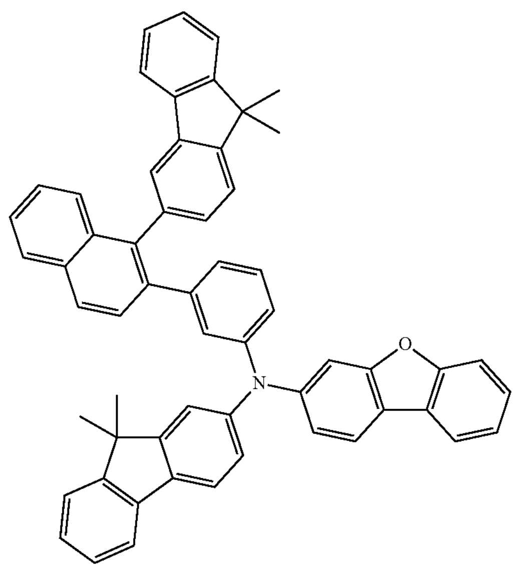
-continued
141
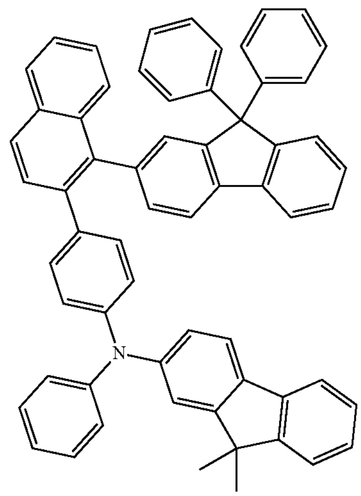
142
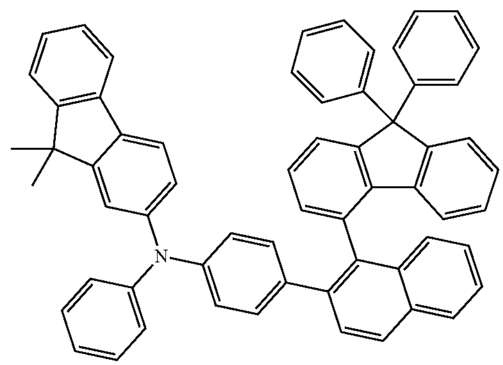
143
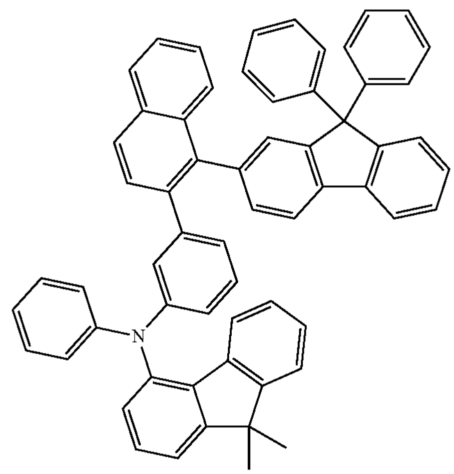

-continued
144
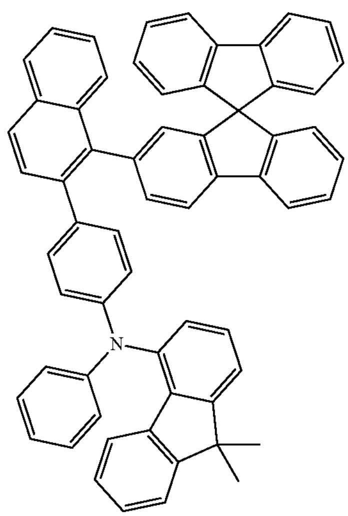
145
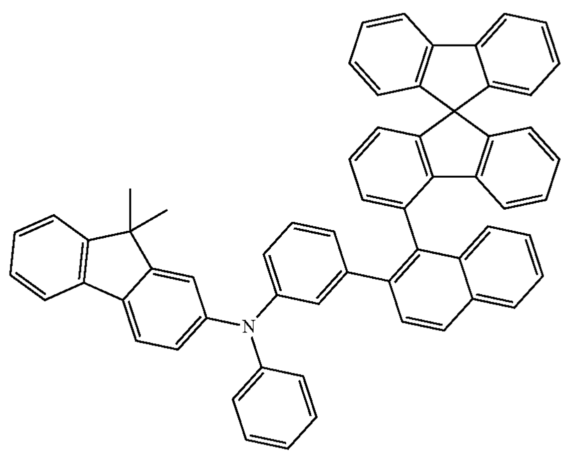
146
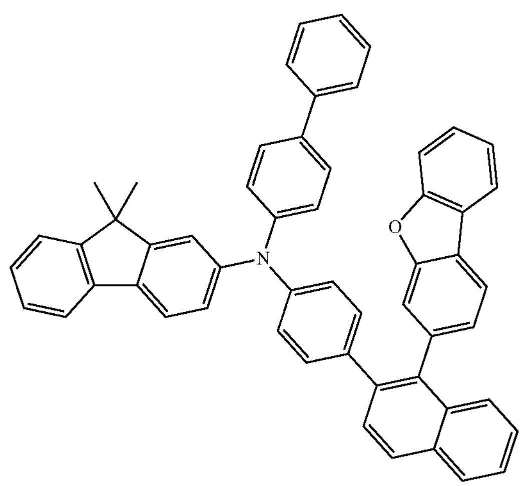
-continued
147
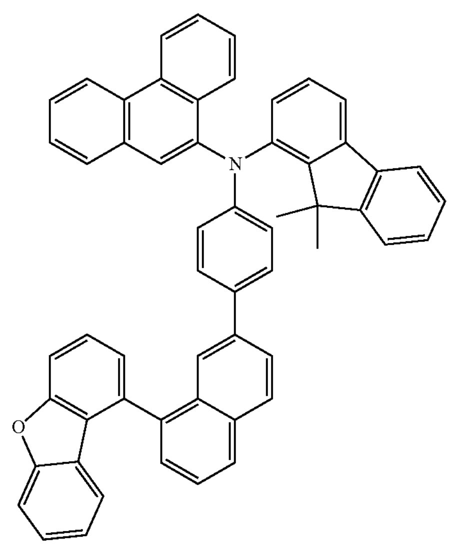
148
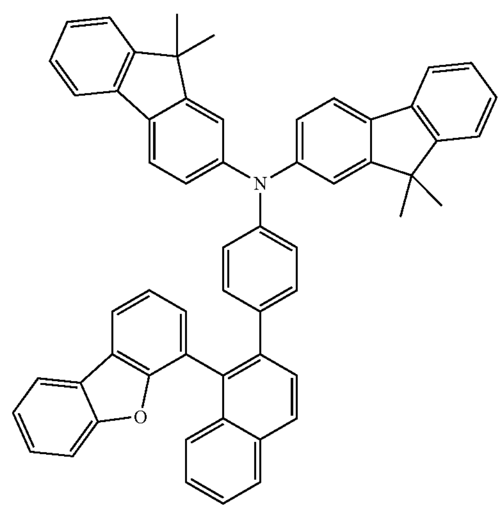
149
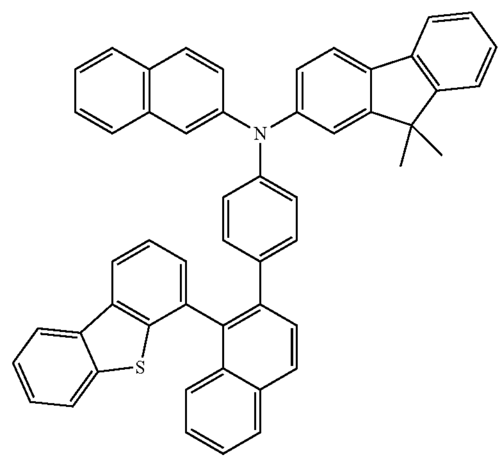

-continued
150
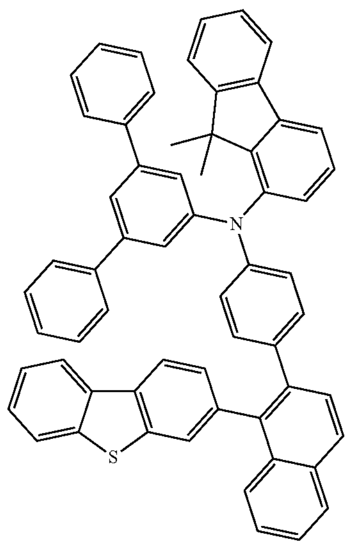
151
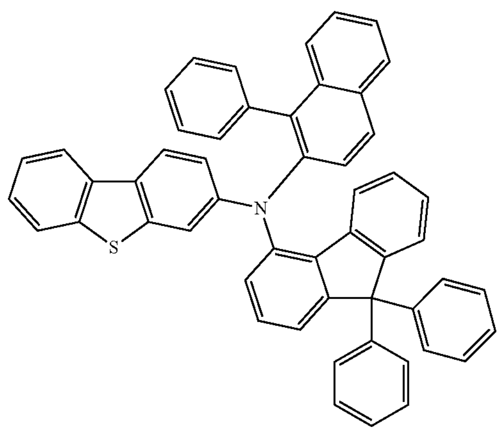
152
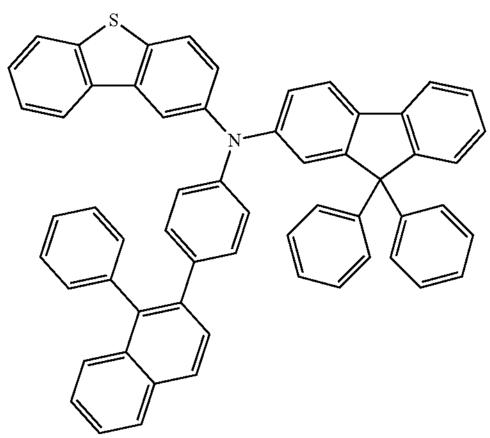
-continued
153
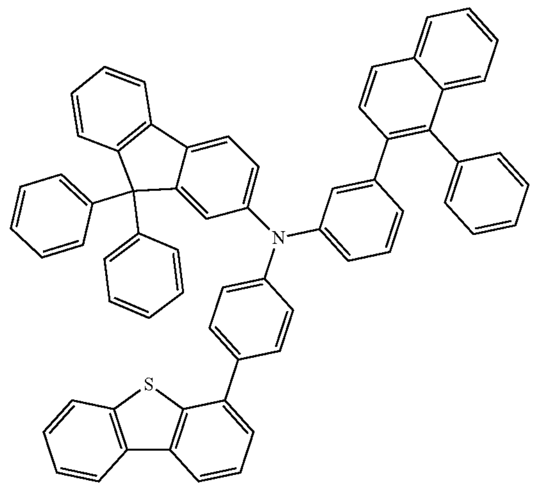
154
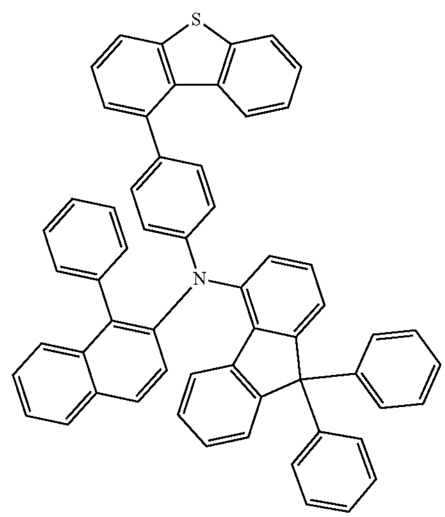
155
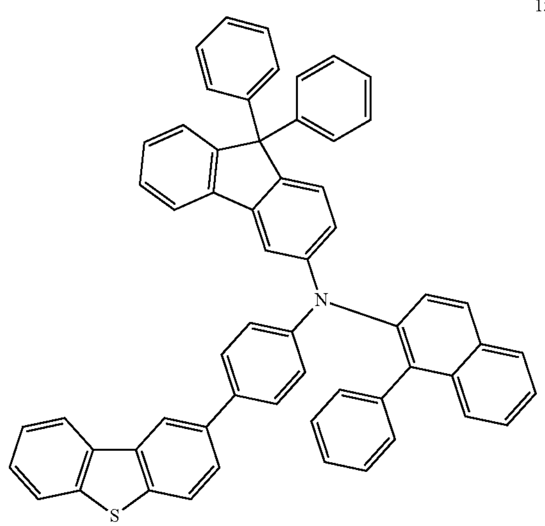

-continued
156
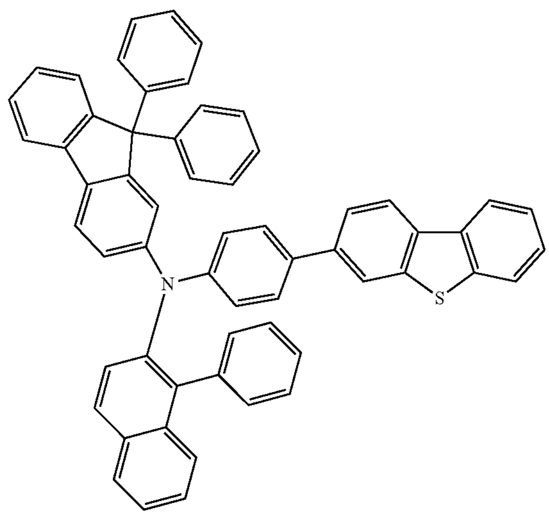
157
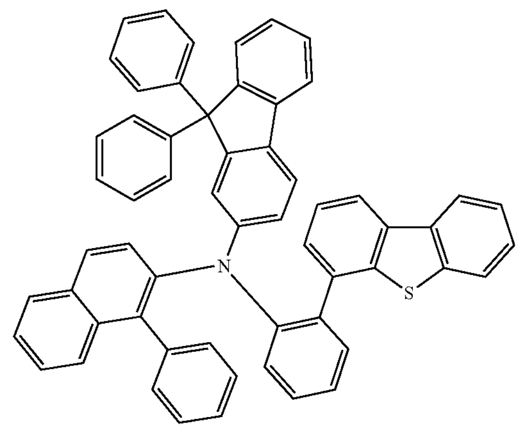
158
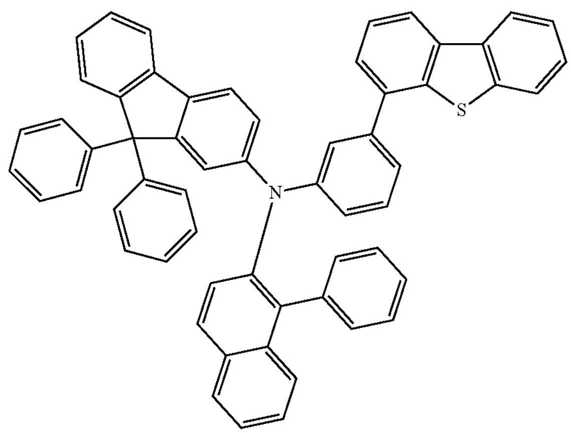
-continued
159
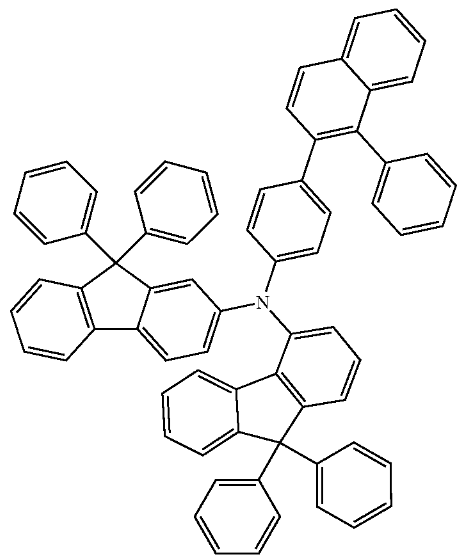
160
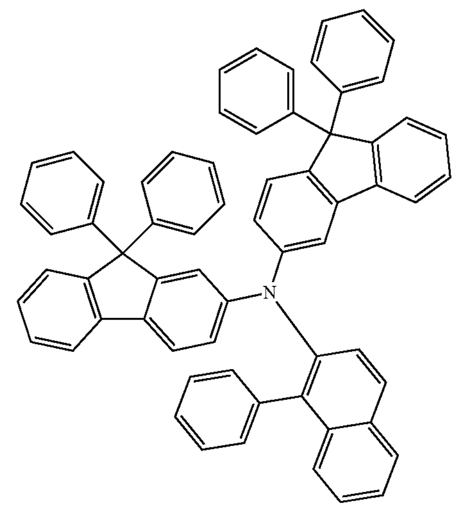
161
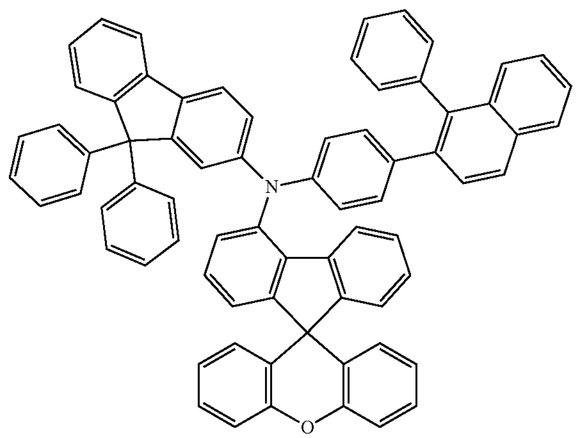

-continued
162
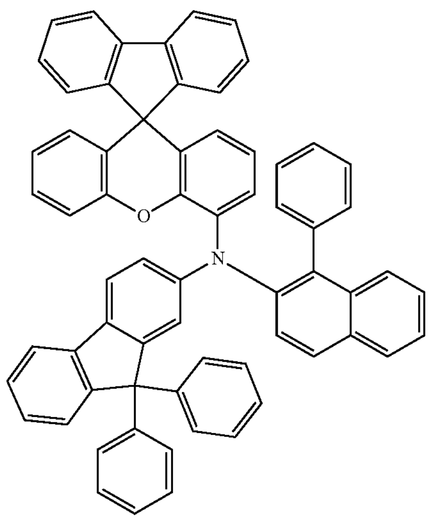
163
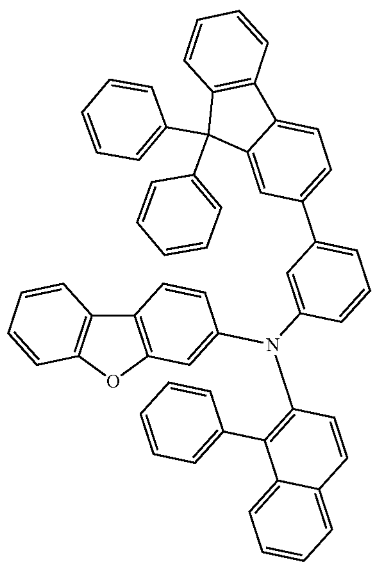
164
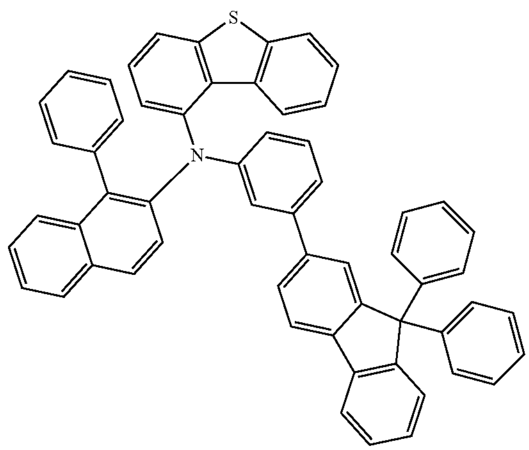
-continued
165
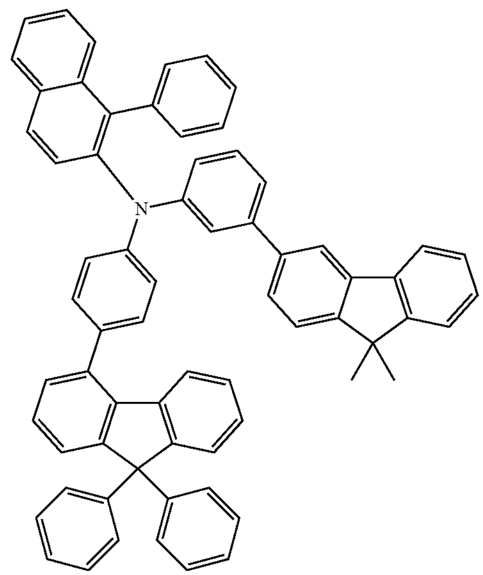
166
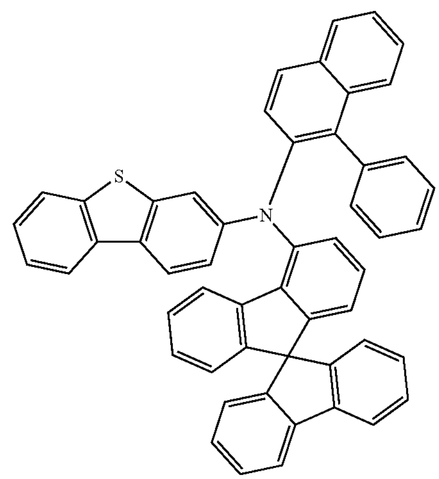
167
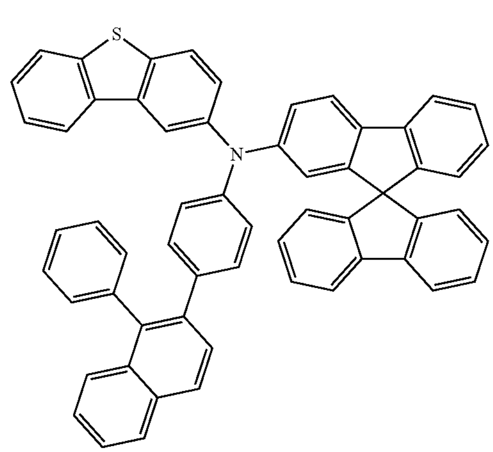

168
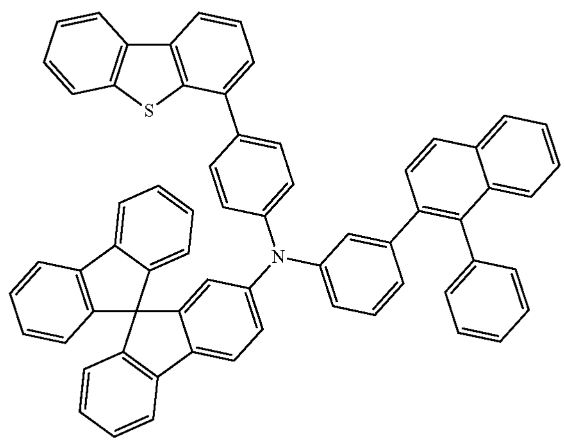
169
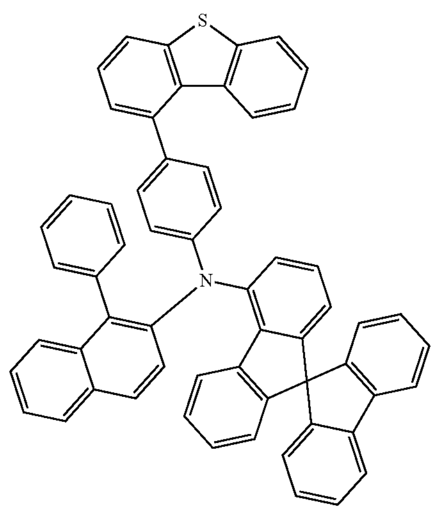
170
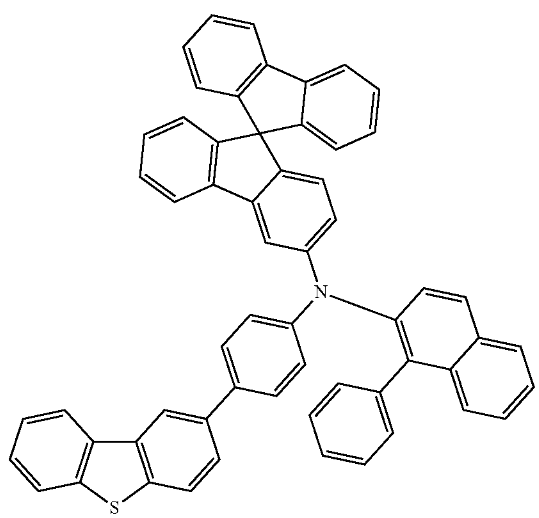
171
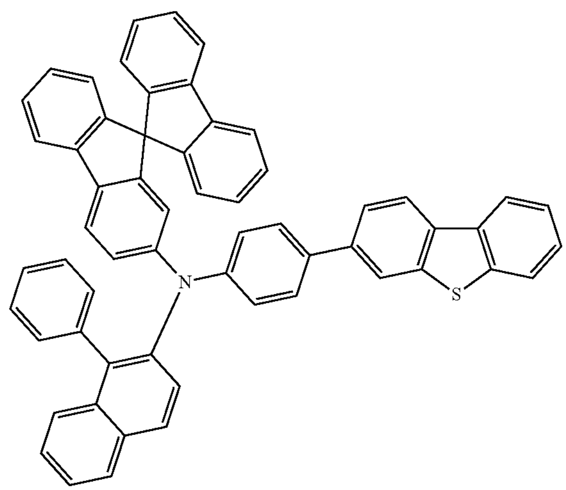
172
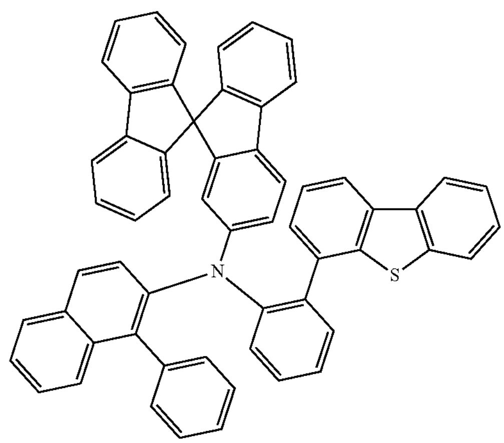
173
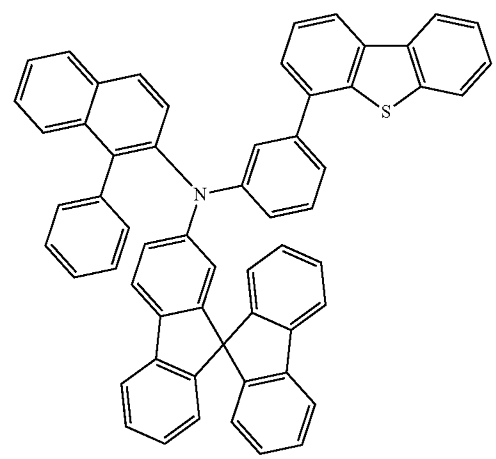

-continued
174
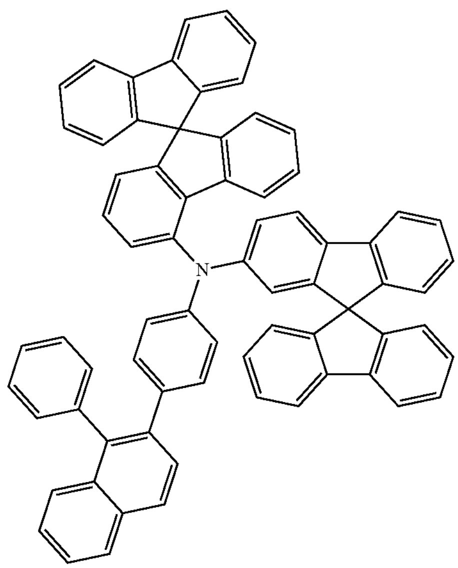
175
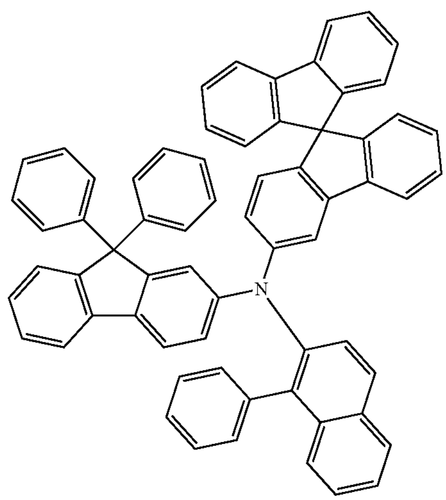
176
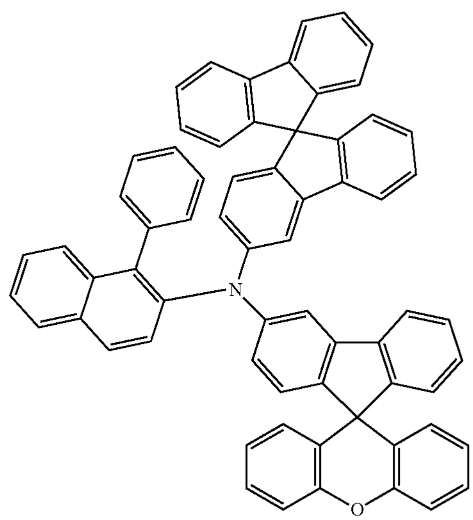
-continued
177
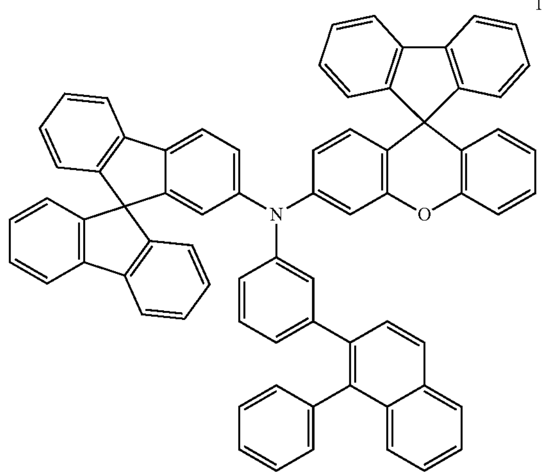
178
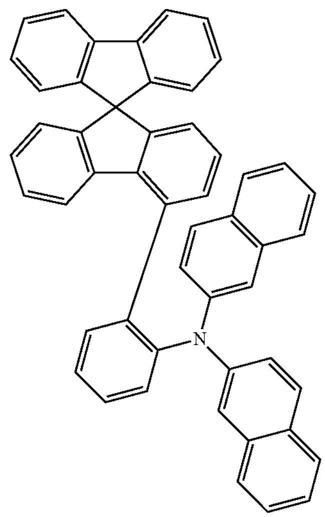
179
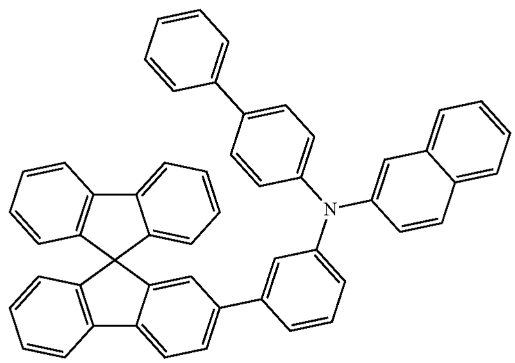

-continued
180
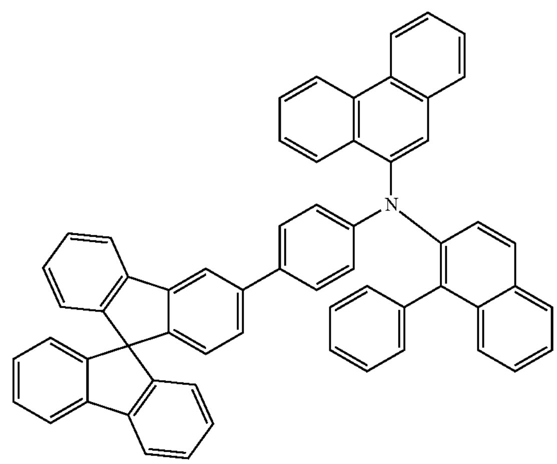
181
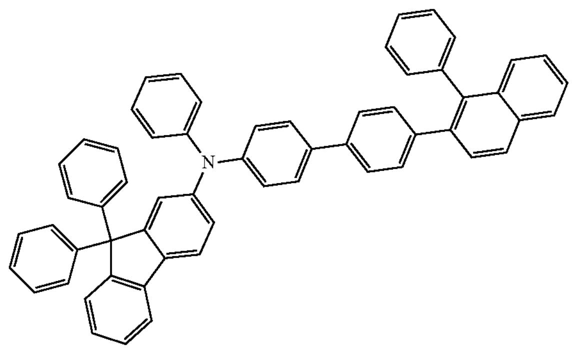
182
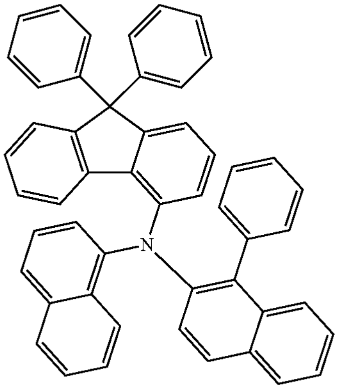
183
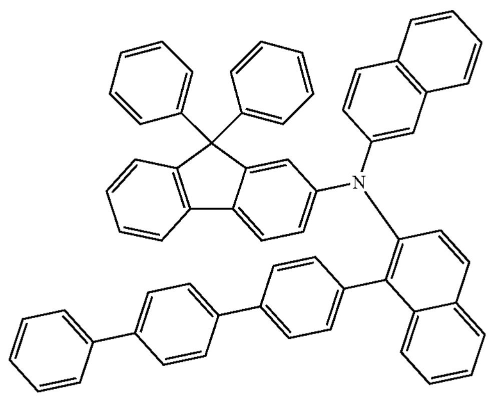
-continued
184
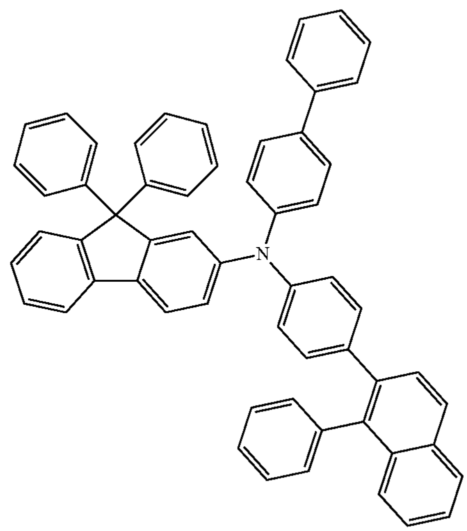
185
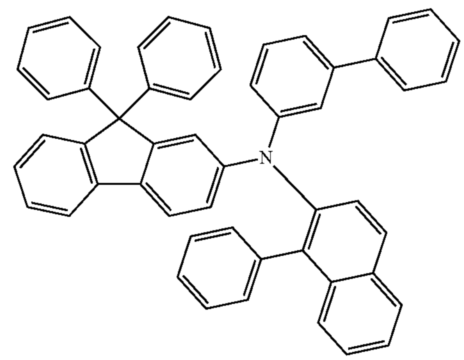
186
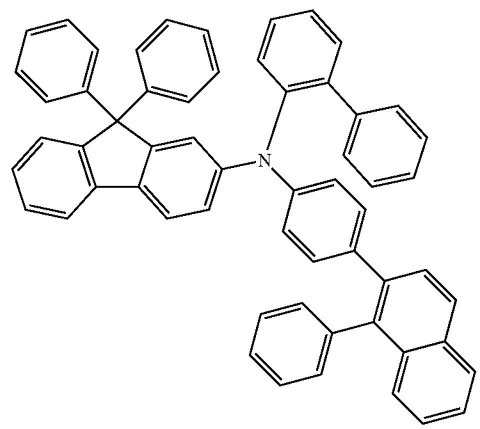

-continued
187
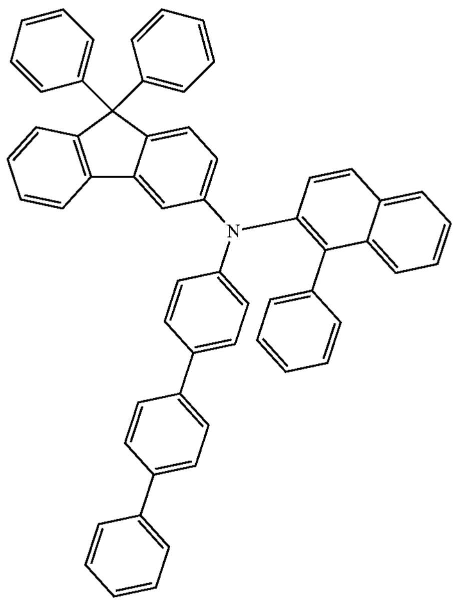
188
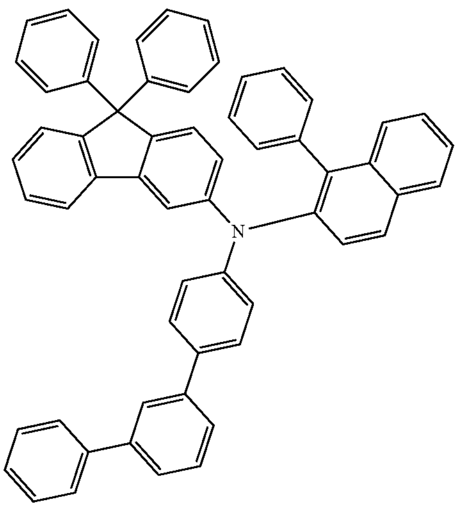
189
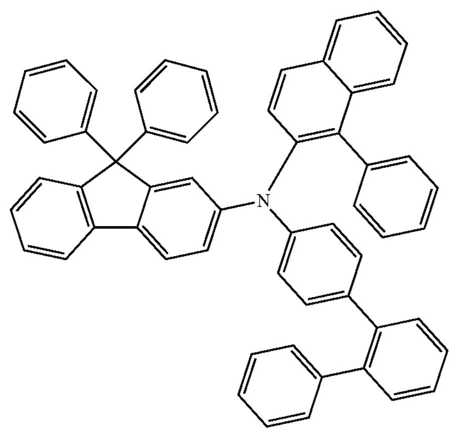
-continued
190
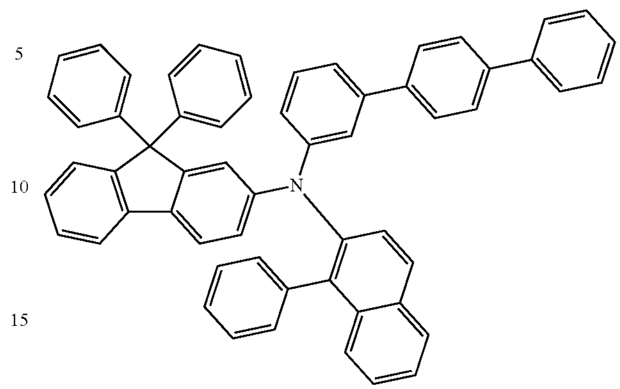
191
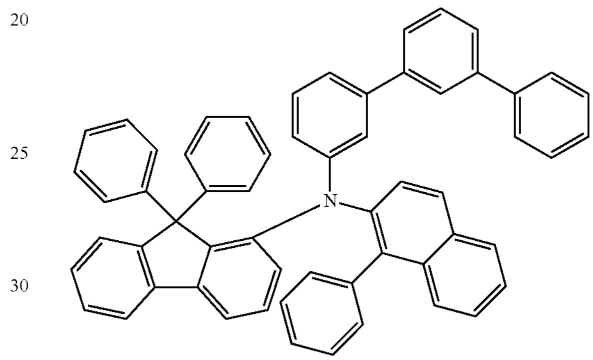
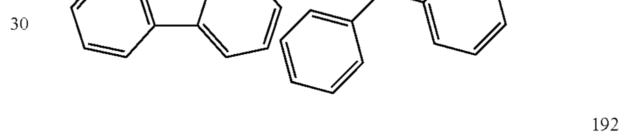
192
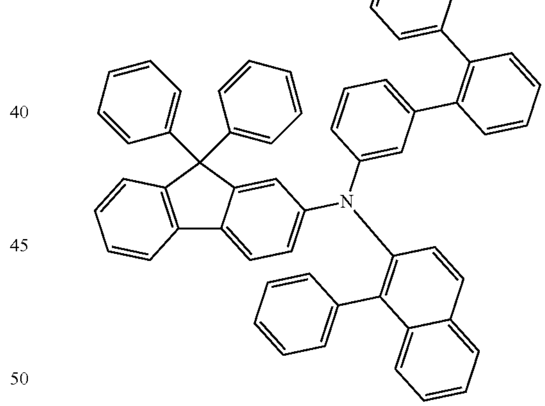
193
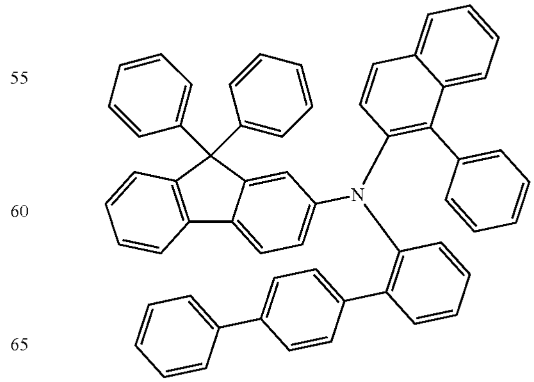

-continued
194
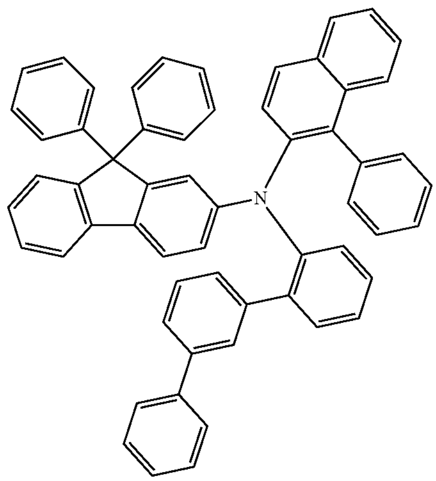
195
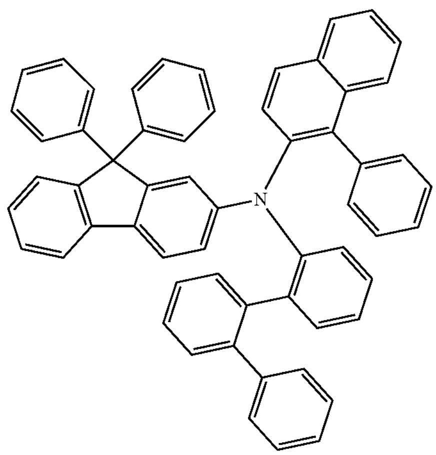
196
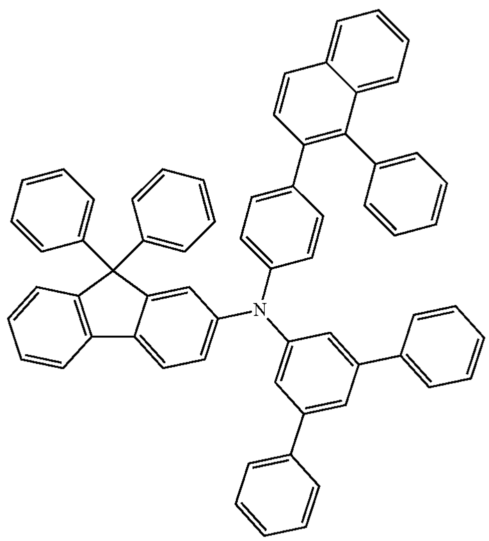
-continued
197
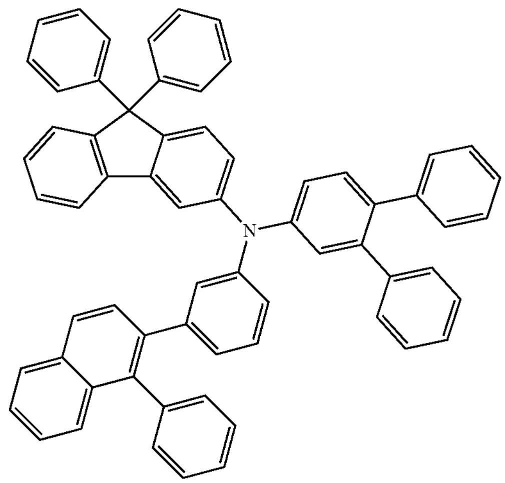
198
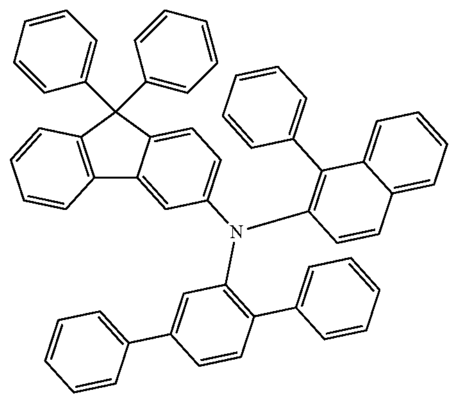
199
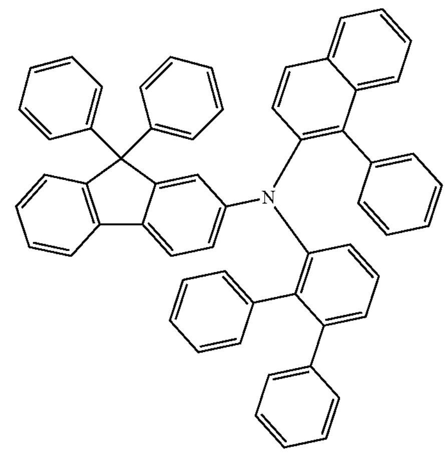

-continued
200
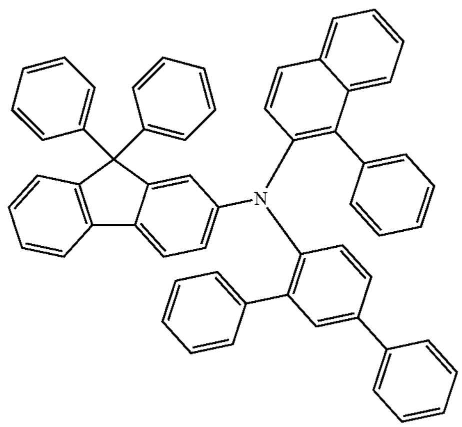
201
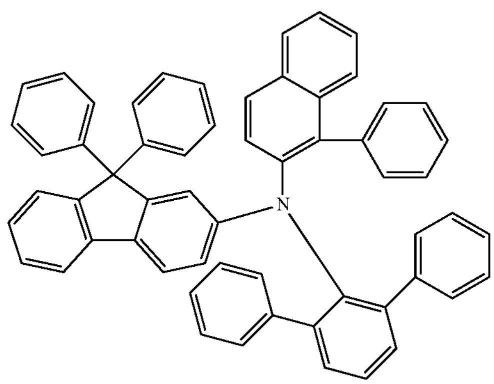
202
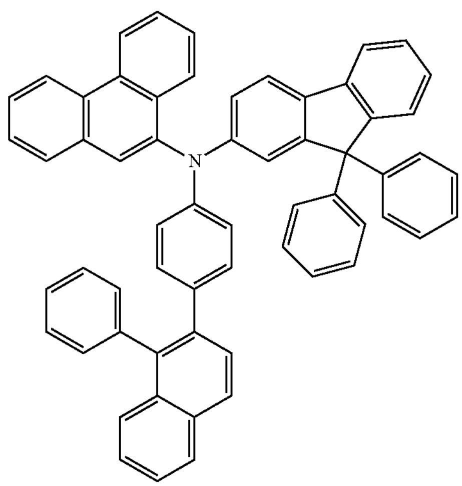
-continued
203
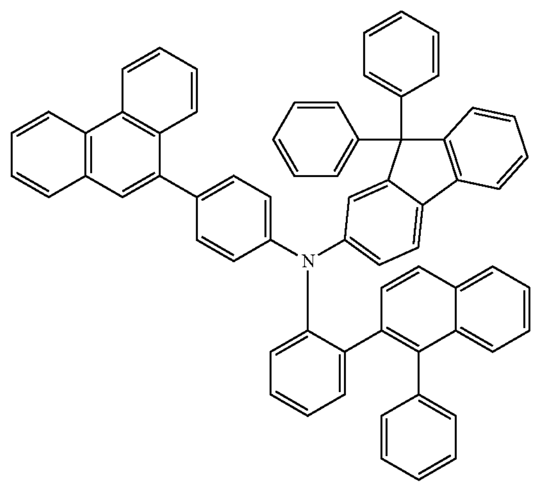
204
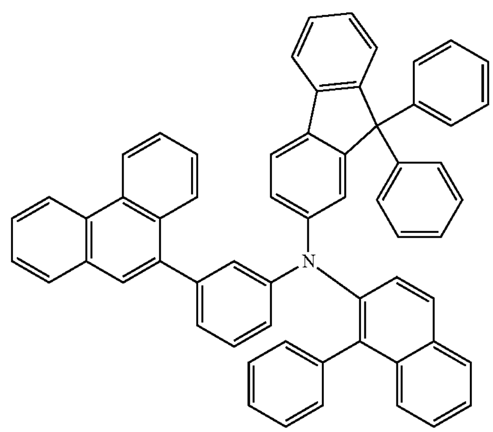
205
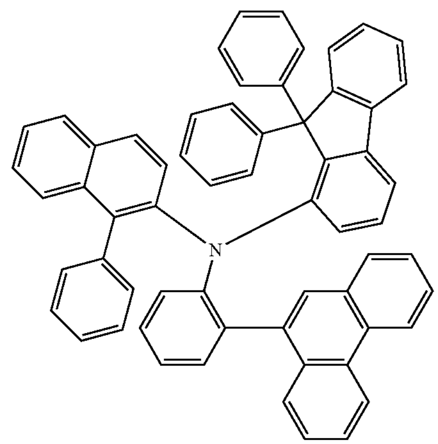

-continued
206
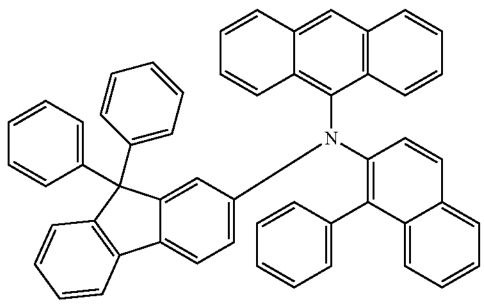
207
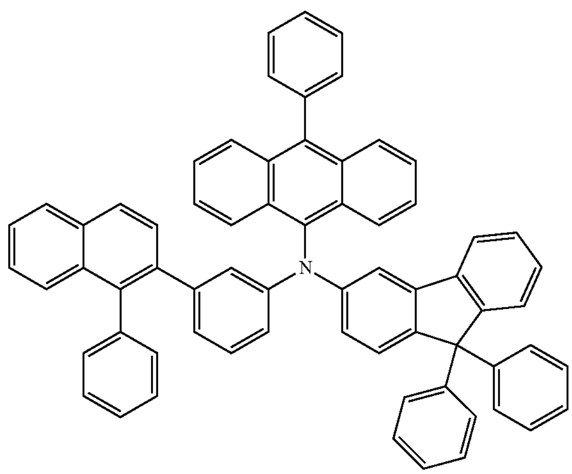
208
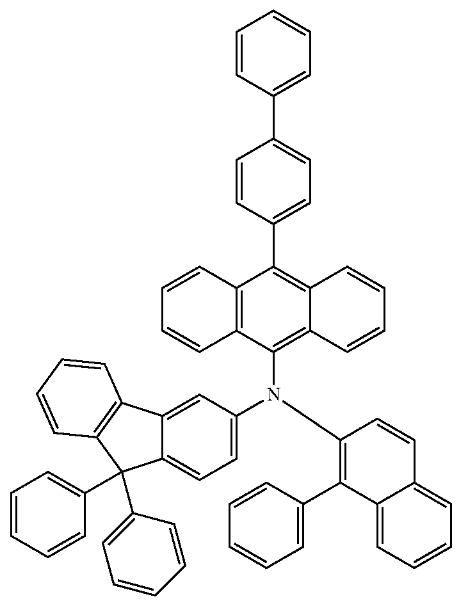
-continued
209
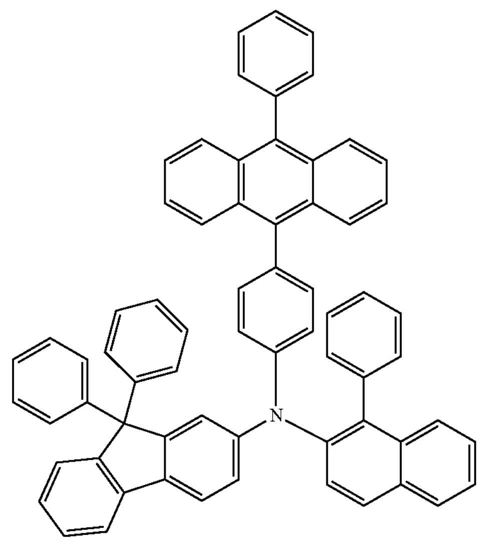
210
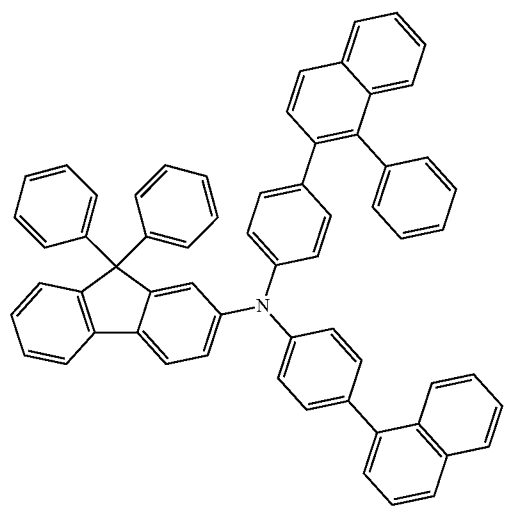
211
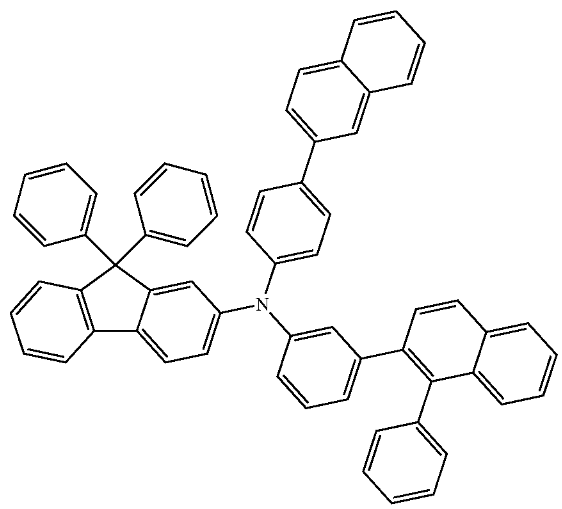

-continued
212
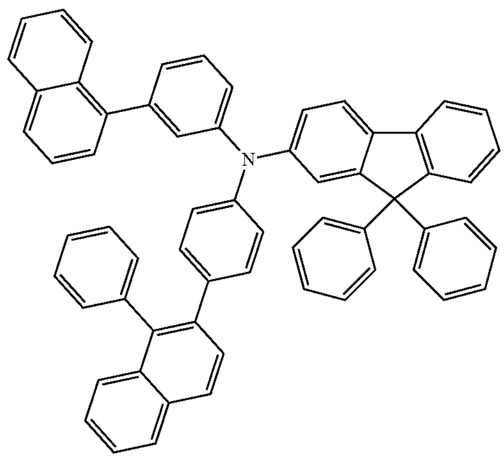
213
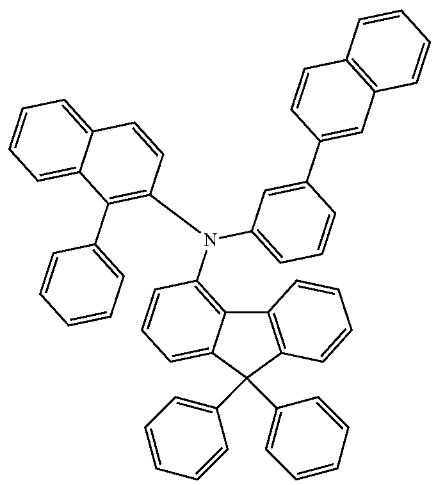
214
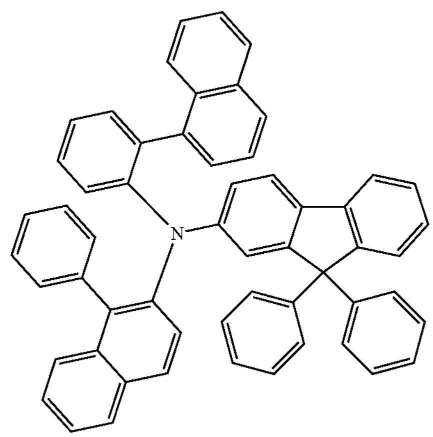
-continued
215
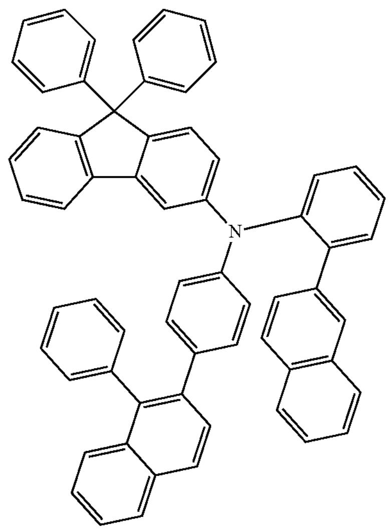
216
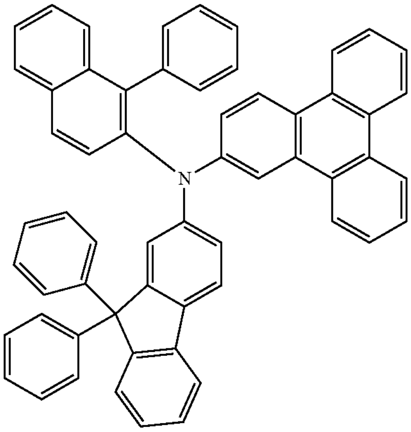
217
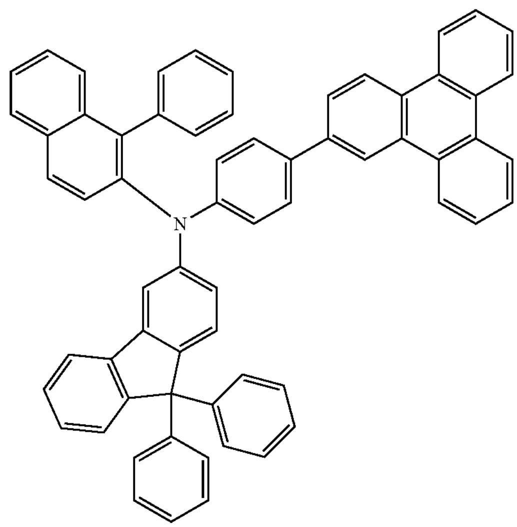

-continued
218
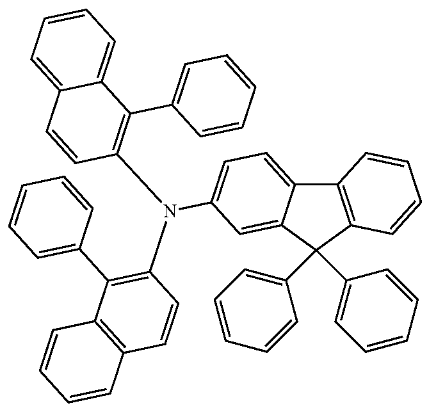
219
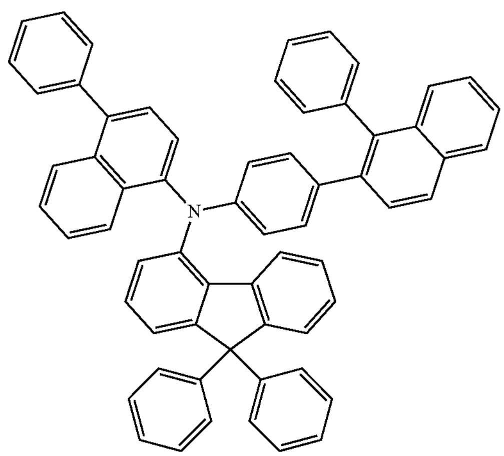
220
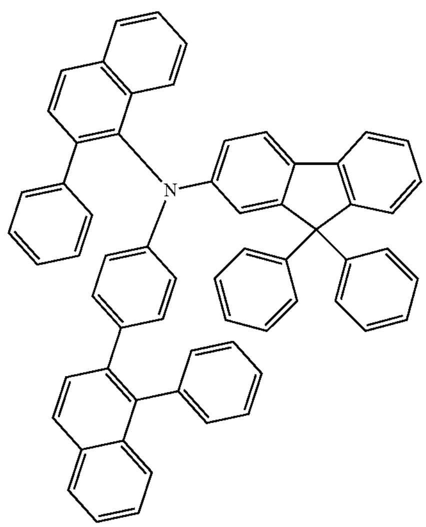
-continued
221
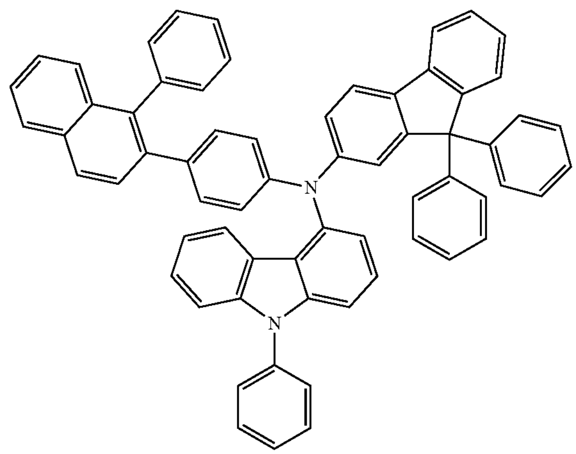
222
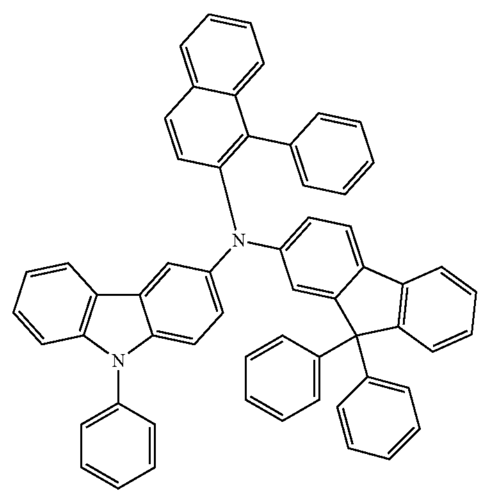
223
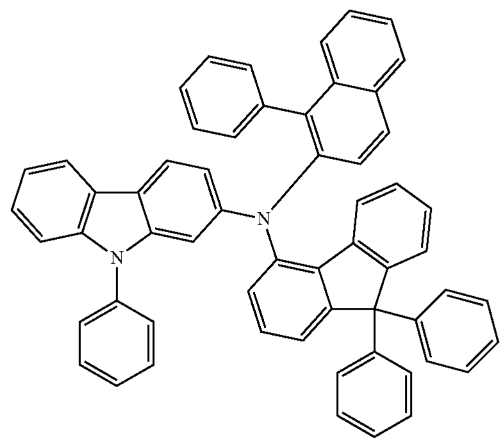

-continued
224
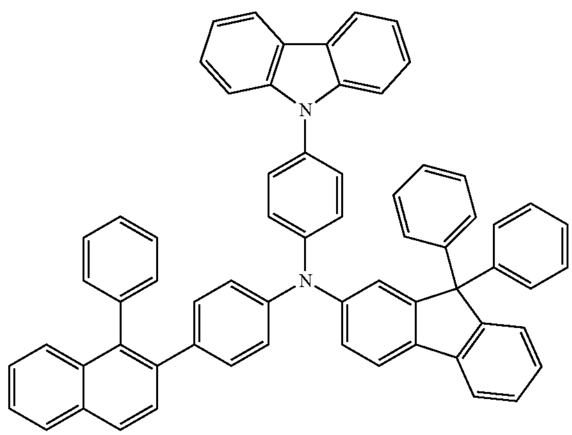
225
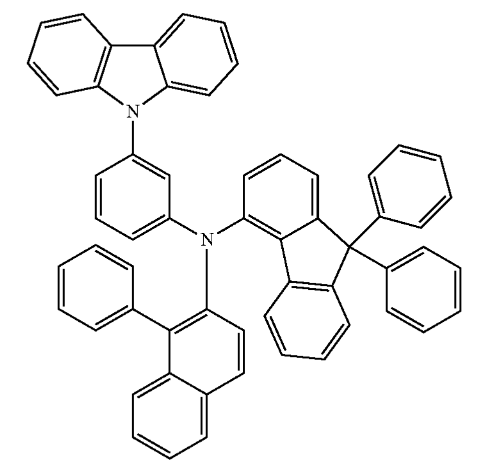
226
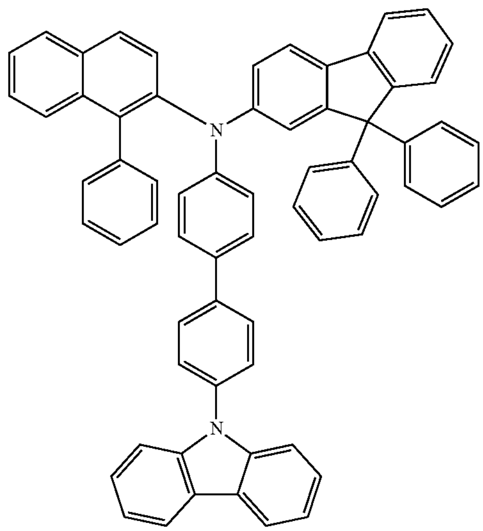
-continued
227
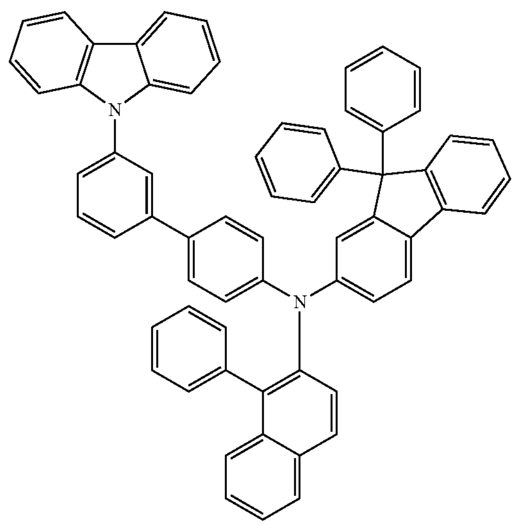
228
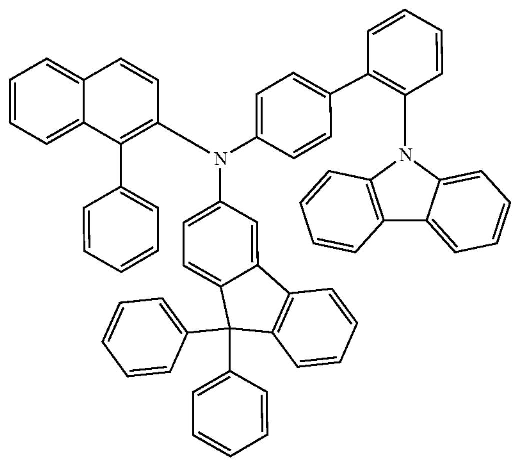
229
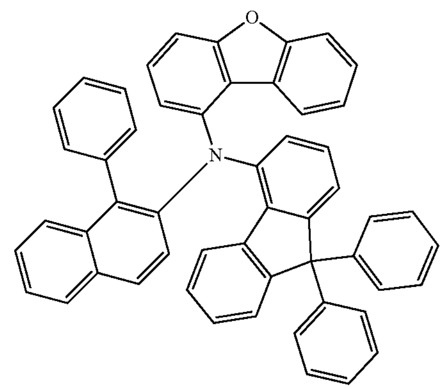

-continued
230
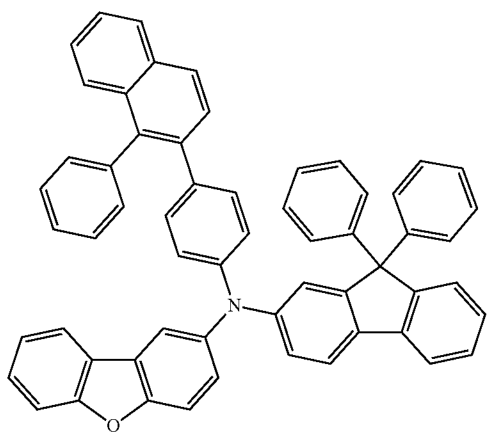
231
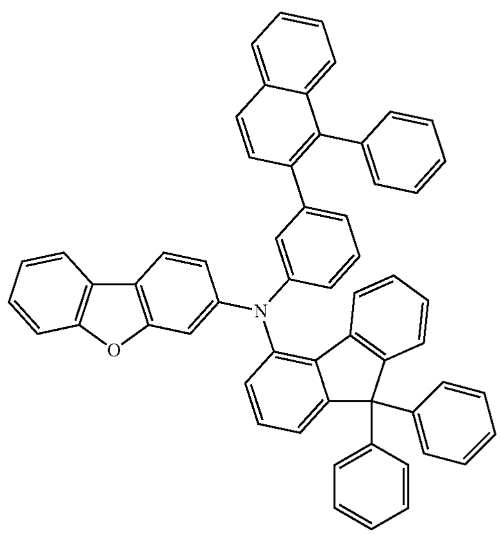
232
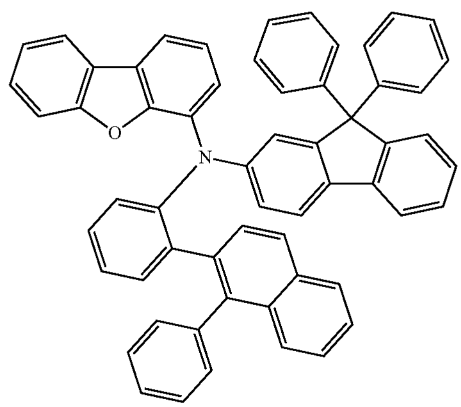
-continued
233
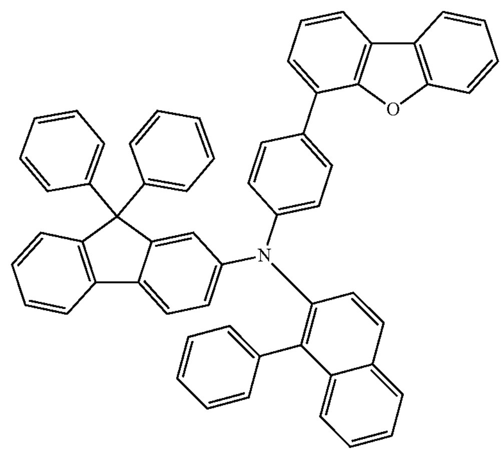
234
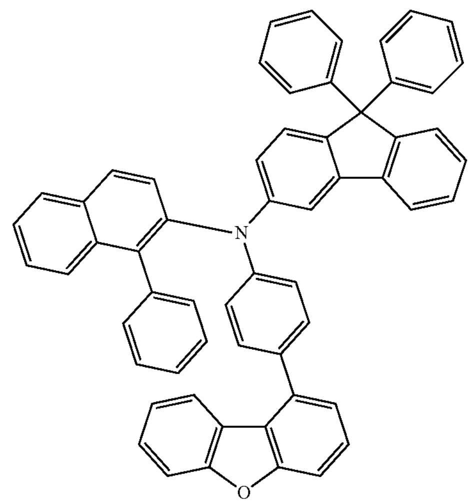
235
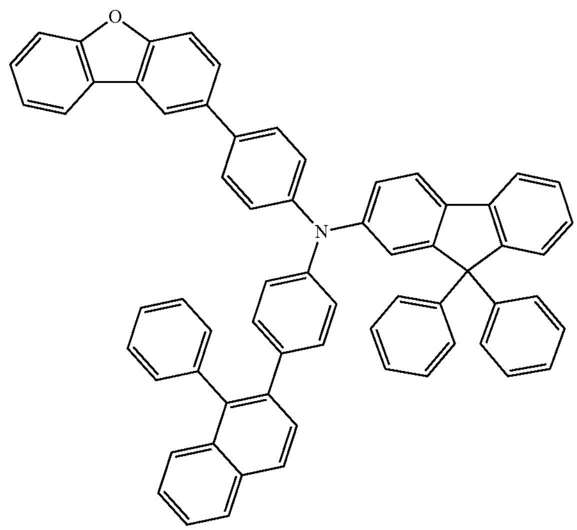

-continued
236
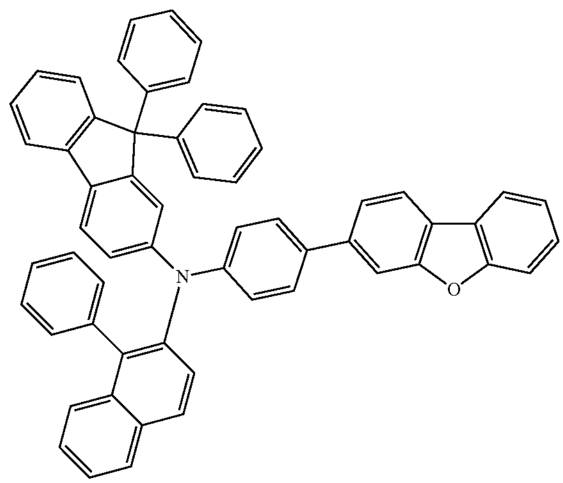
237
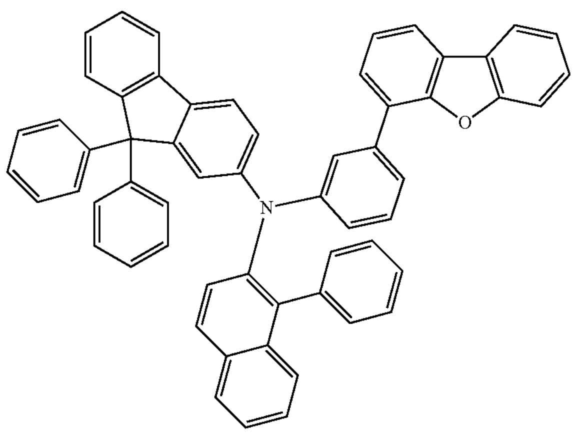
238
-continued
239
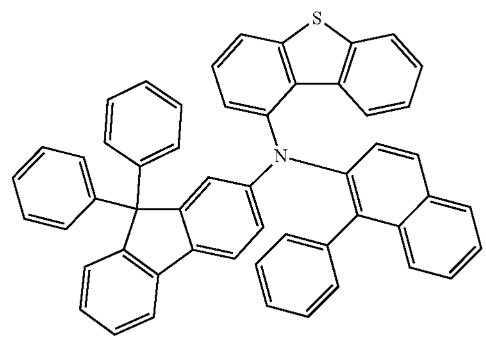
240
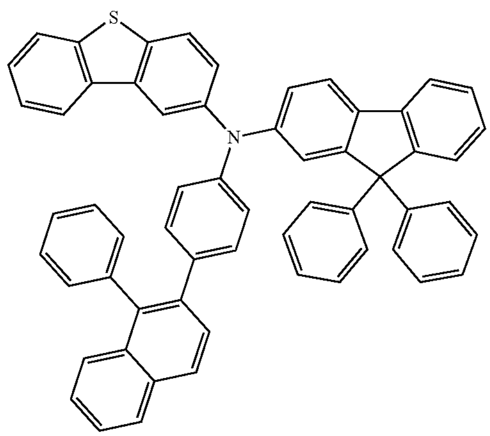
241
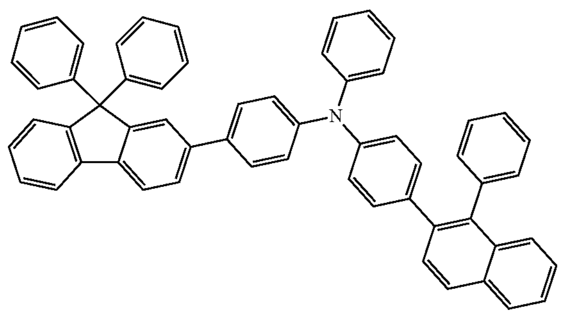
242
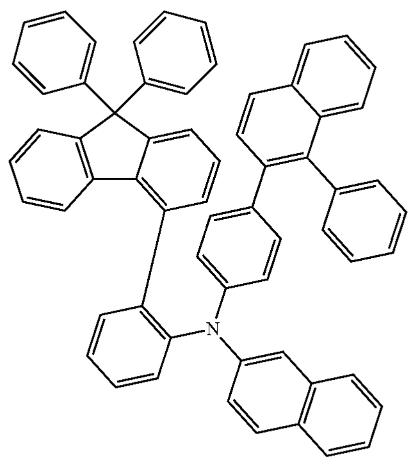

-continued
243
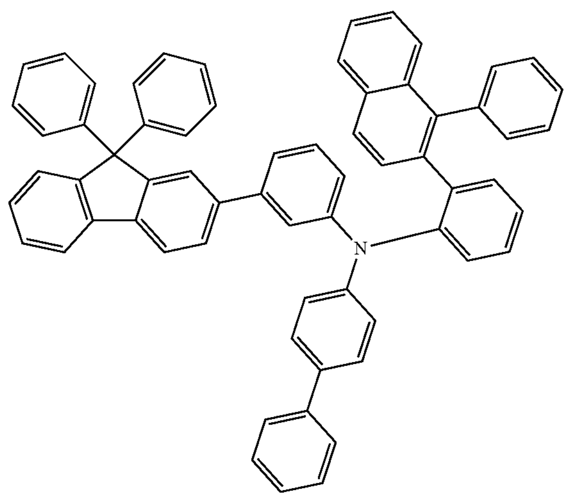
244
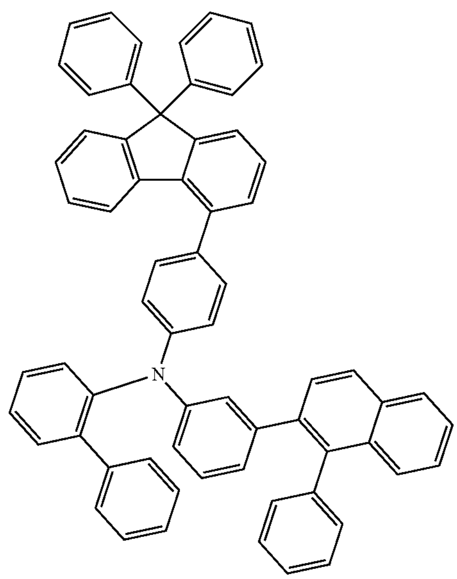
245
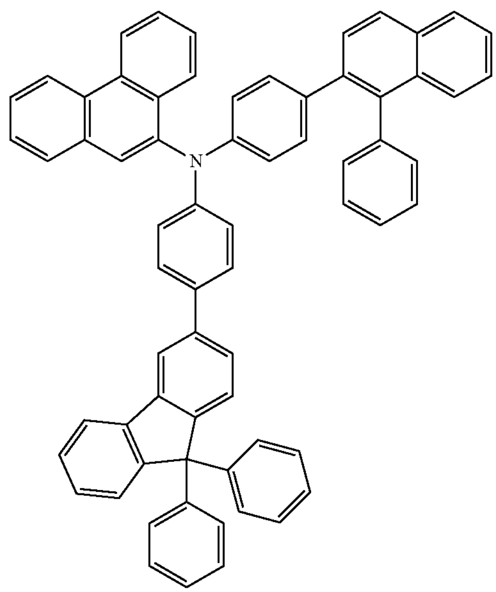
-continued
246
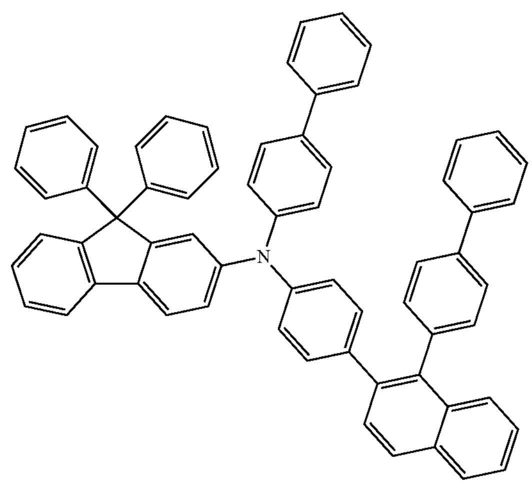
247
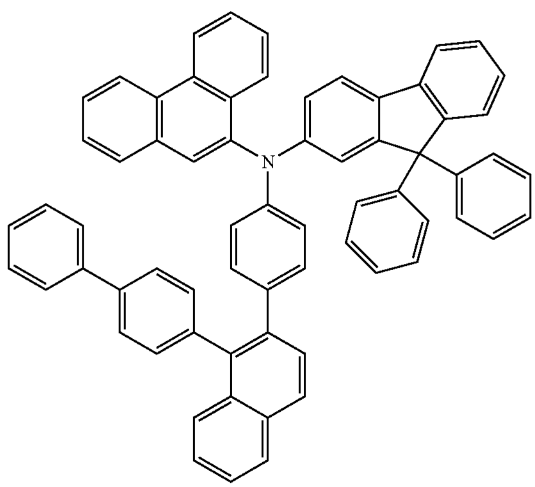
248
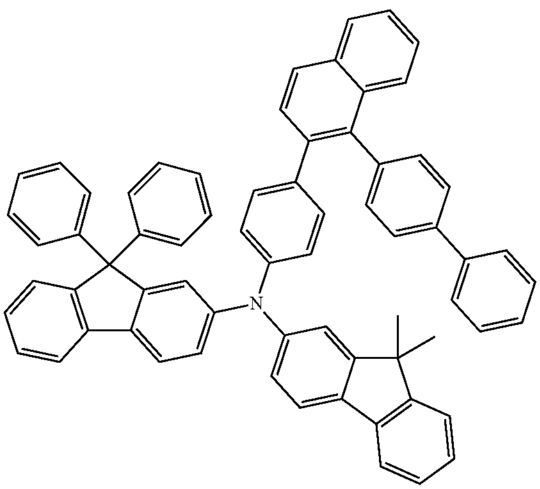

-continued
249
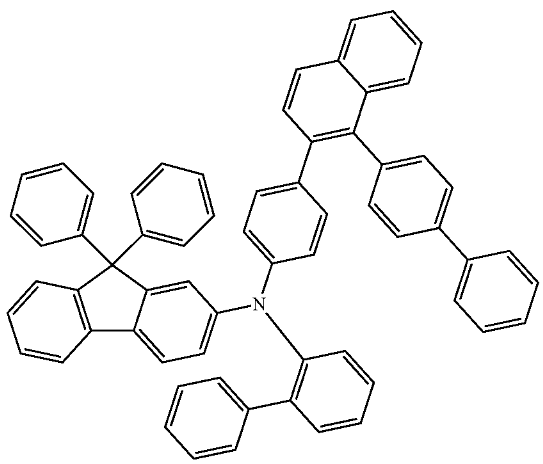
250
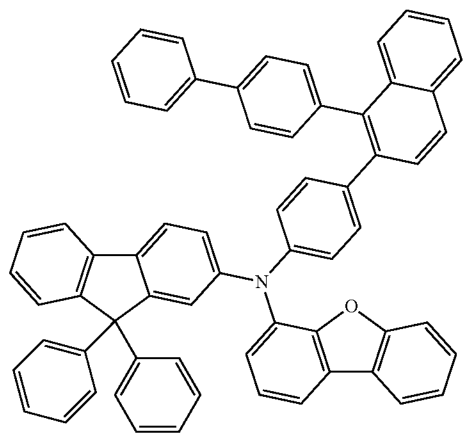
251
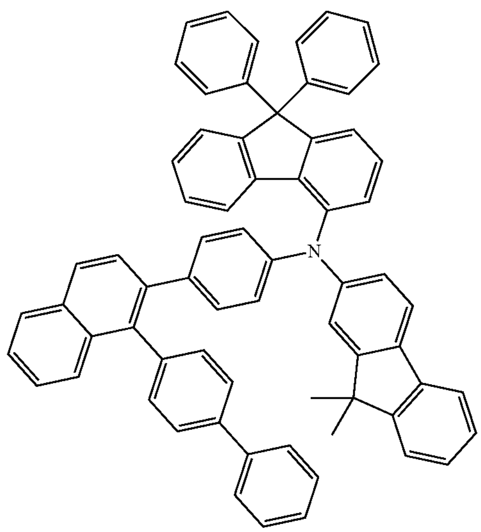
-continued
252
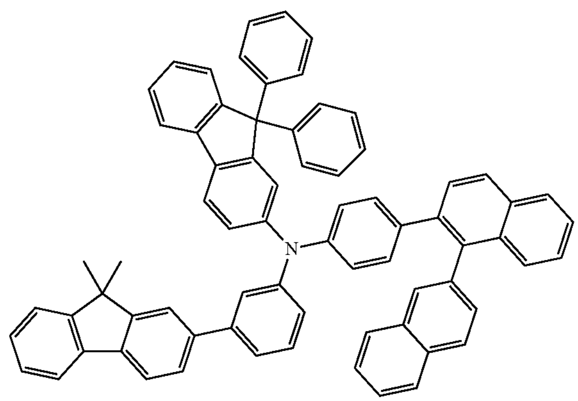
253
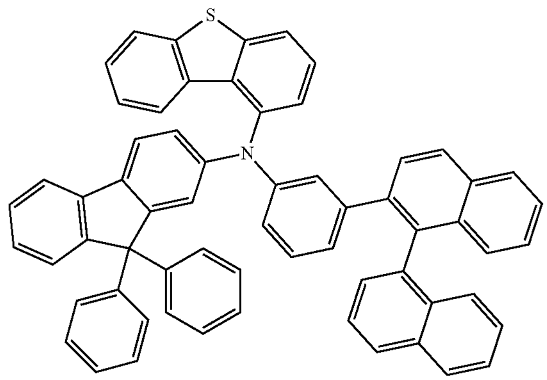
254
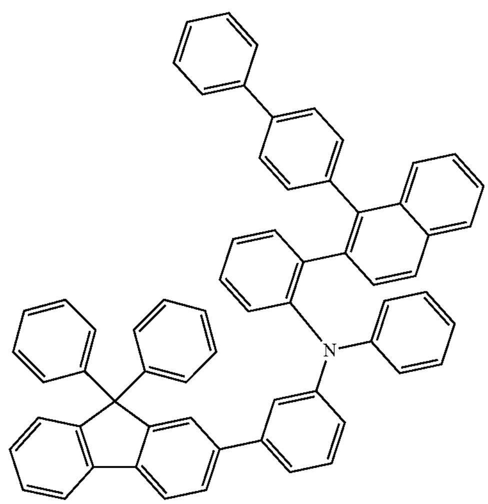

255
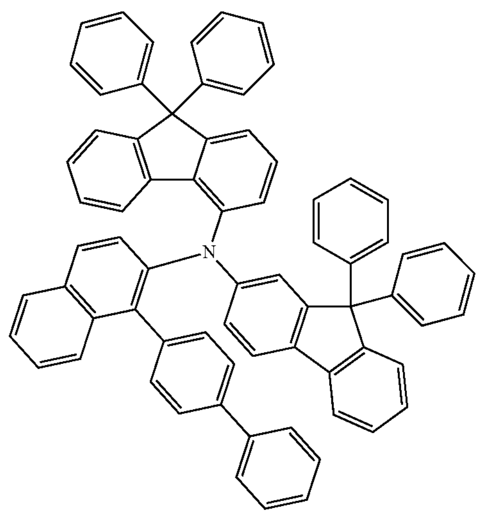
256
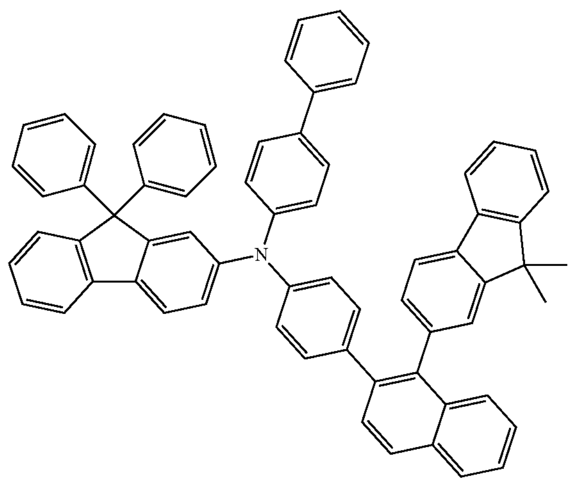
257
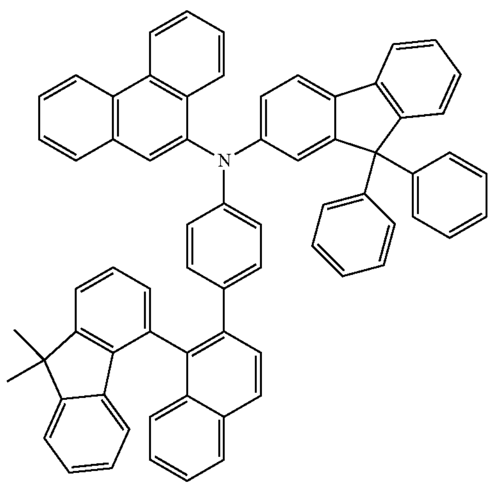
258
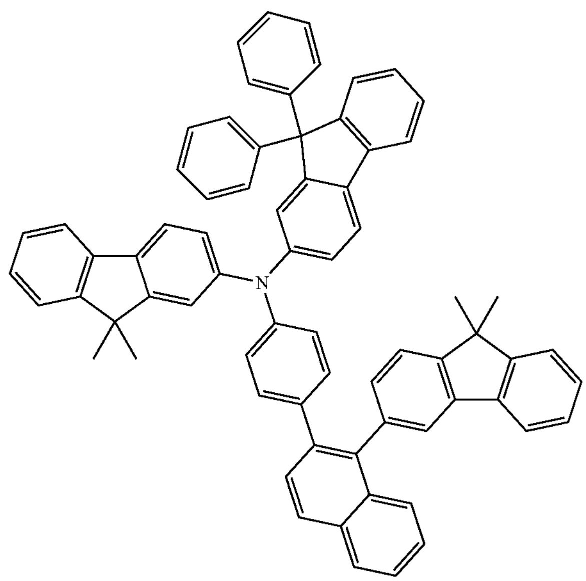
259
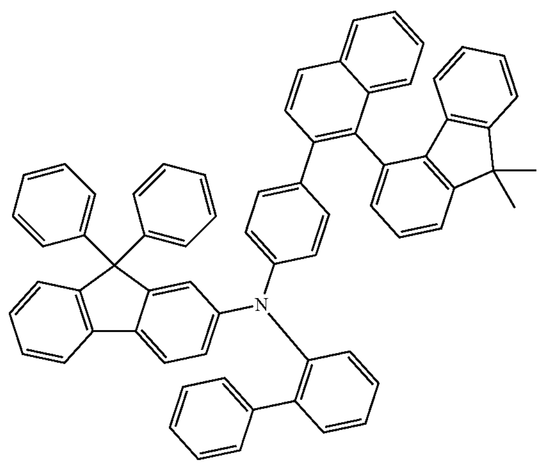
260
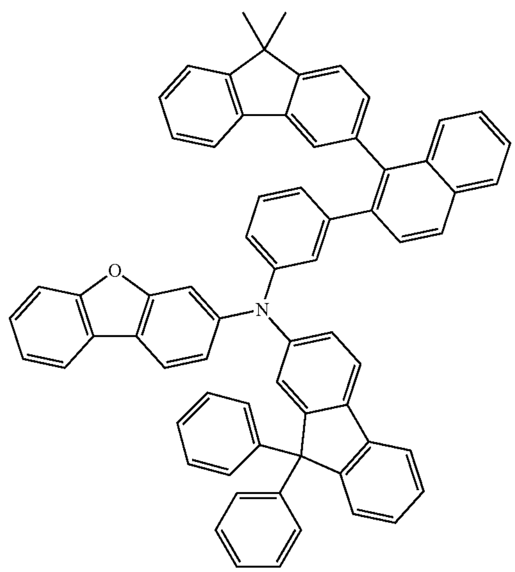

-continued
261
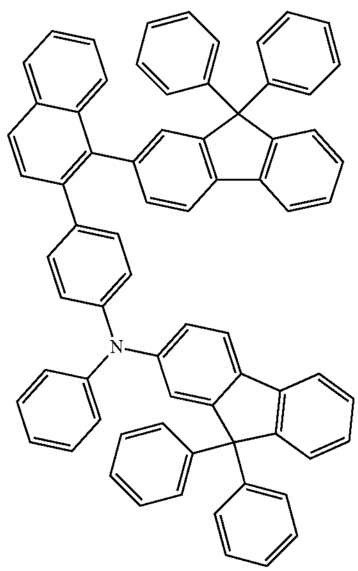
262
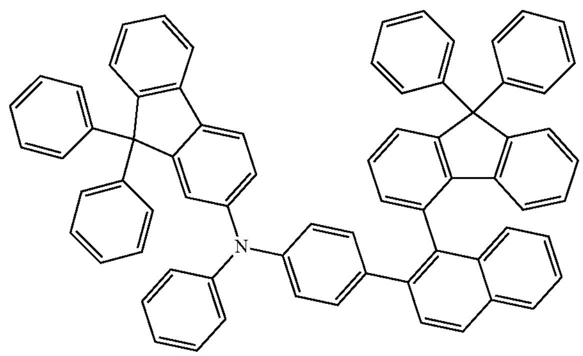
263
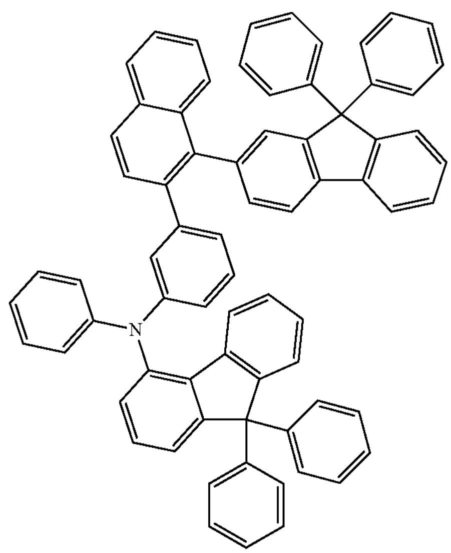
-continued
264
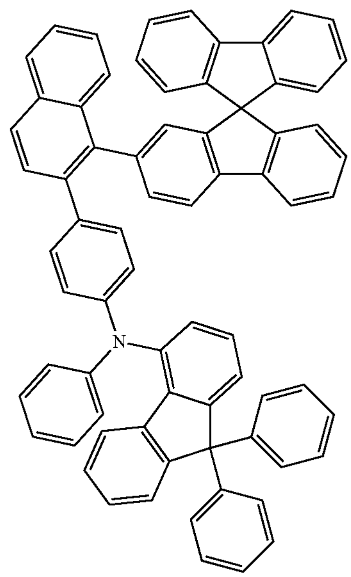
265
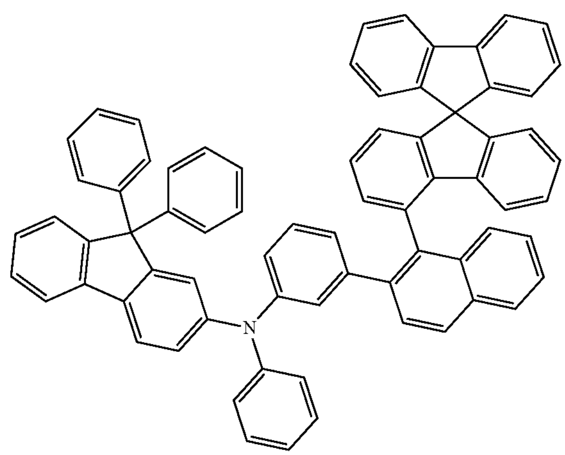
266
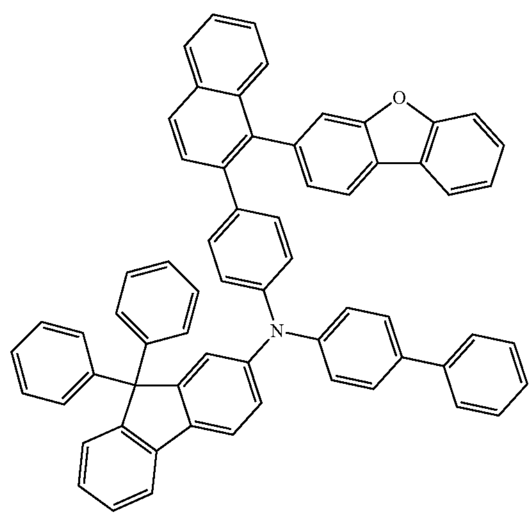

267
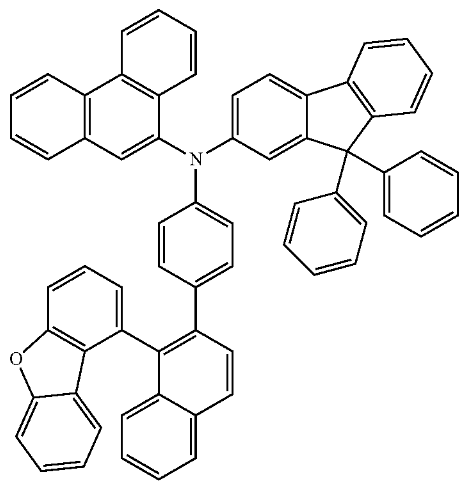
268
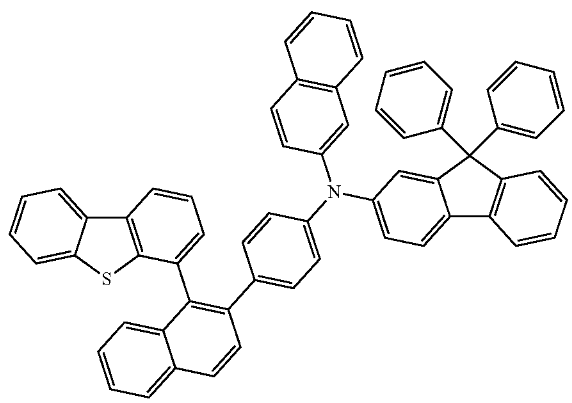
269
270
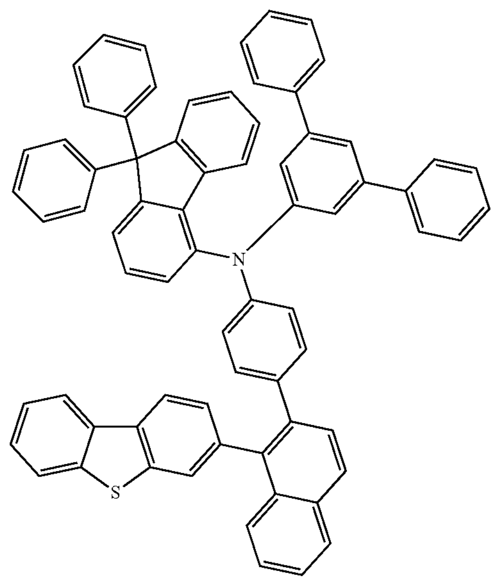
271
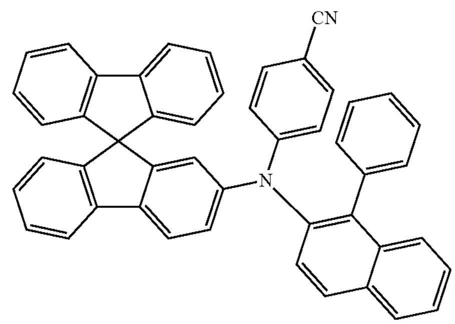
272
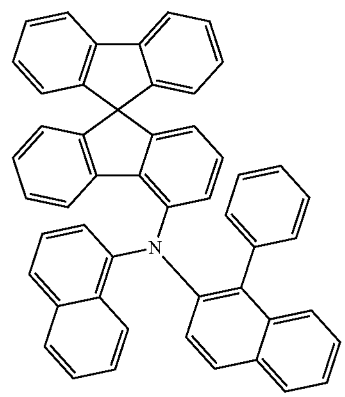

-continued
273
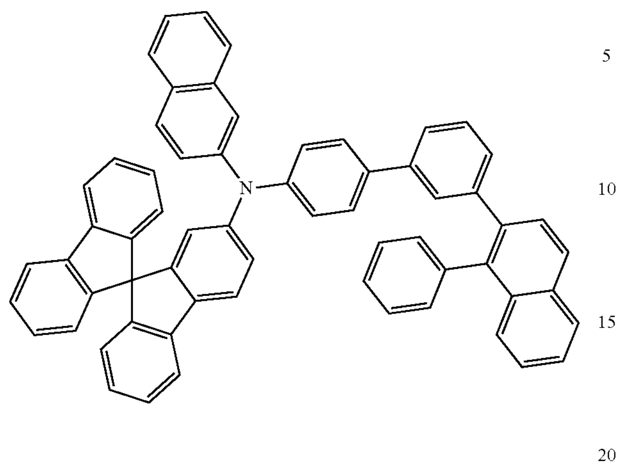
274
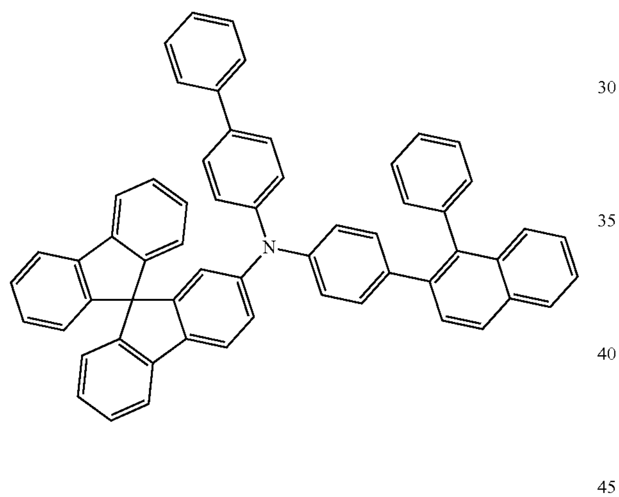
275
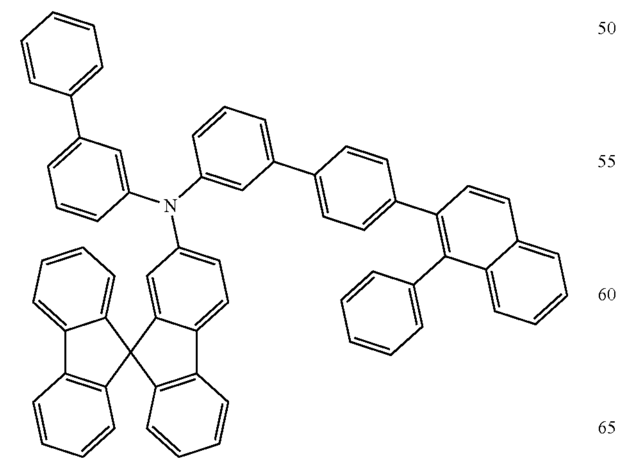
-continued
276
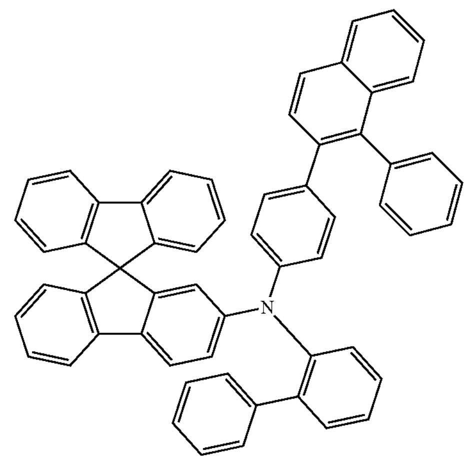
277
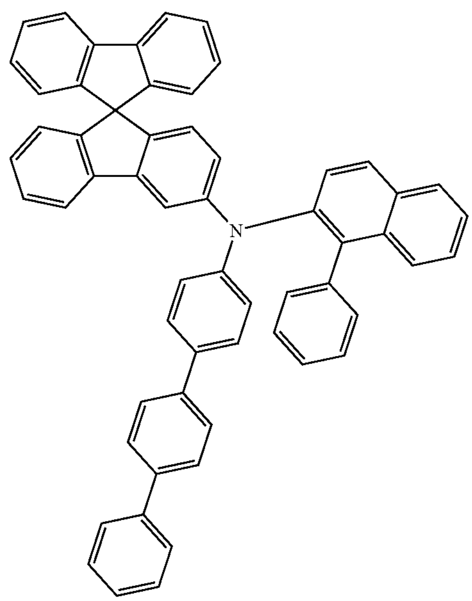
278
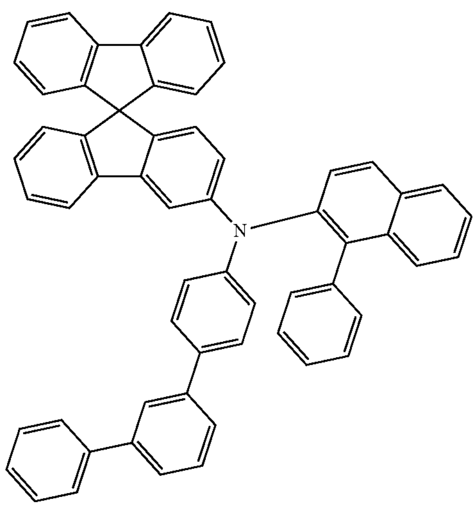

-continued
279
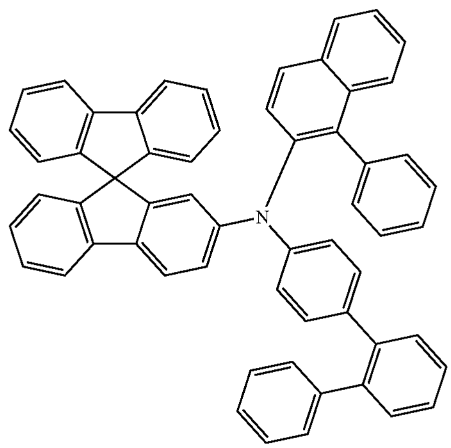
280
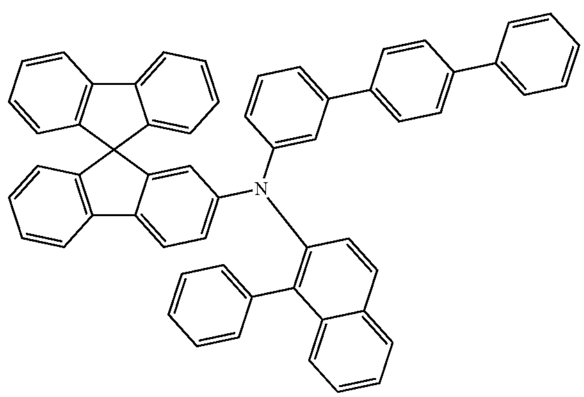
281
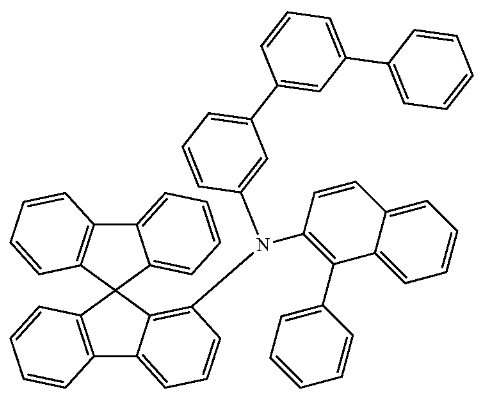
-continued
282
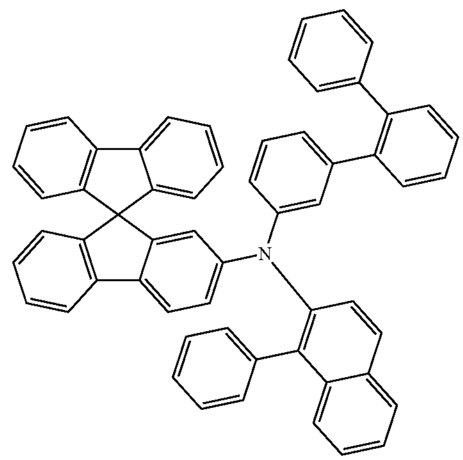
283
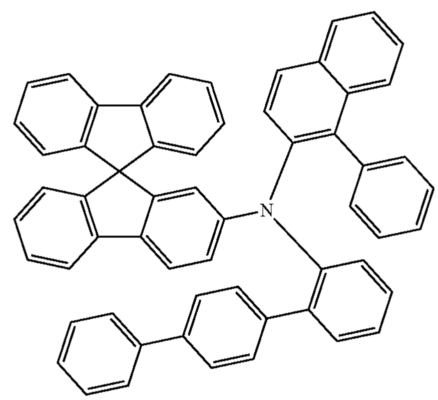
284
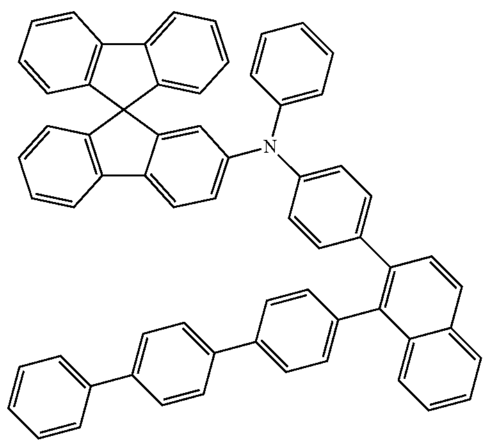

-continued
285
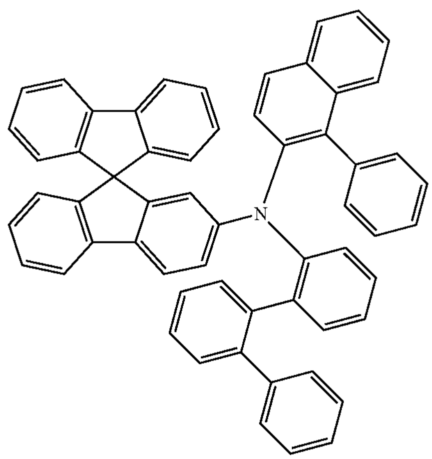
286
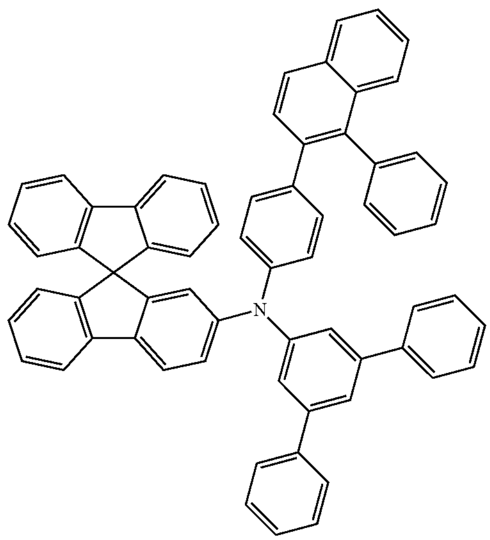
287
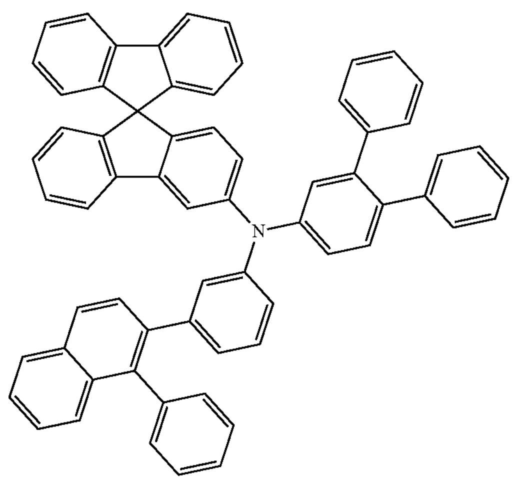
-continued
288
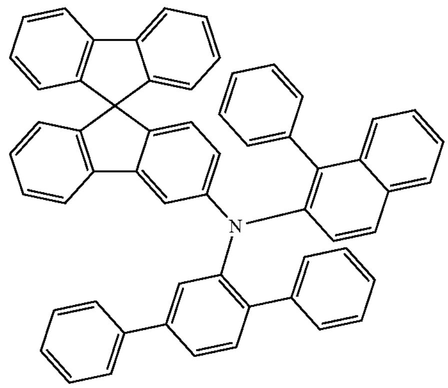
289
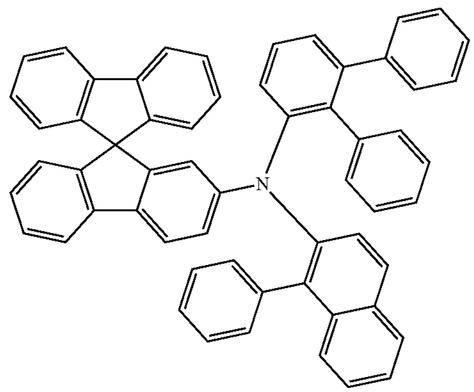
290
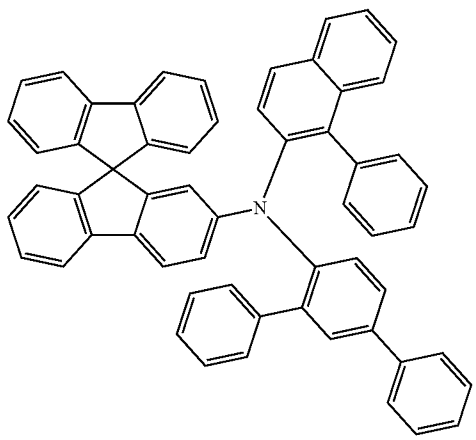
291
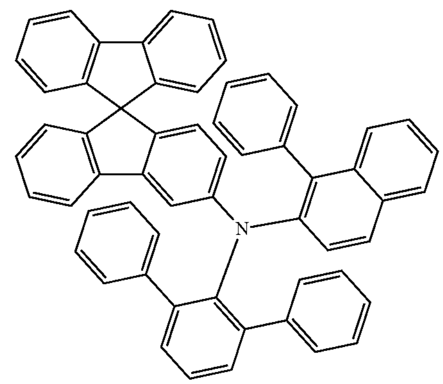

-continued
292
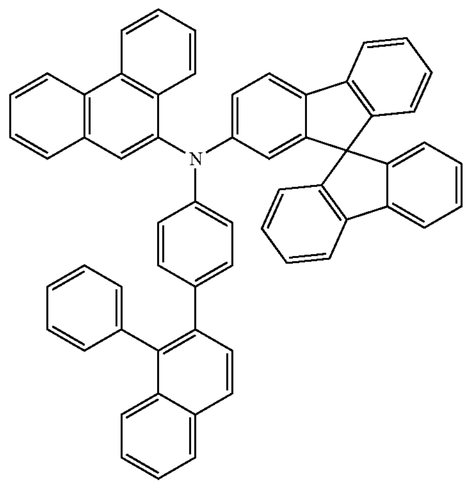
293
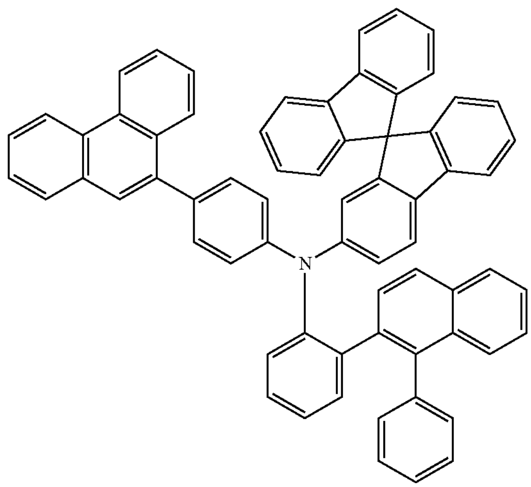
294
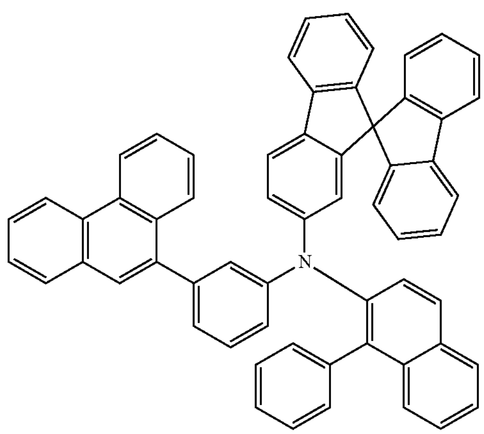
-continued
295
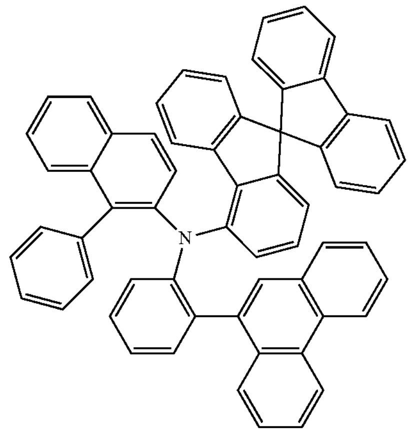
296
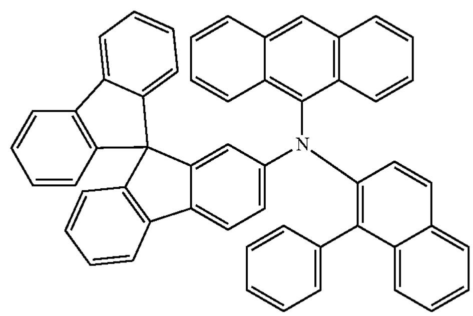
297
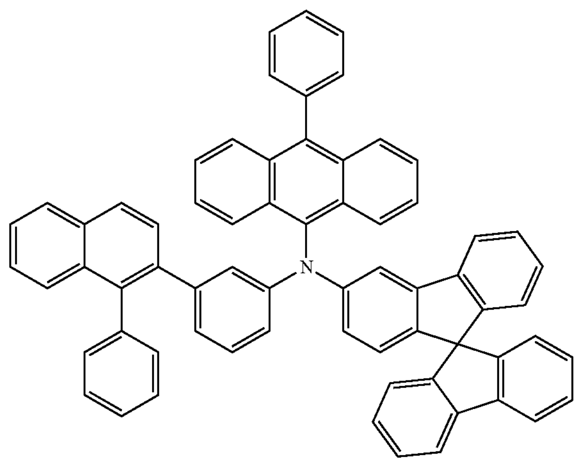

-continued
298
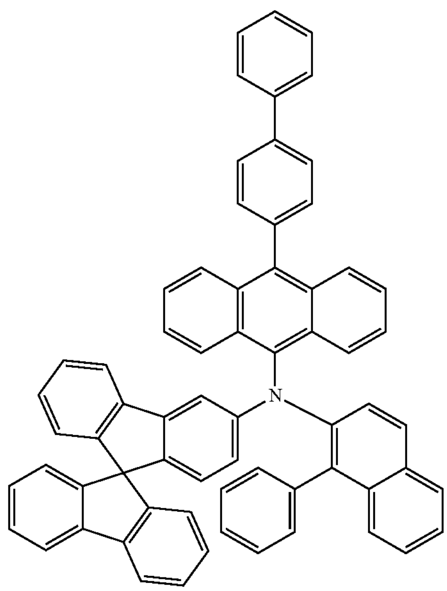
299
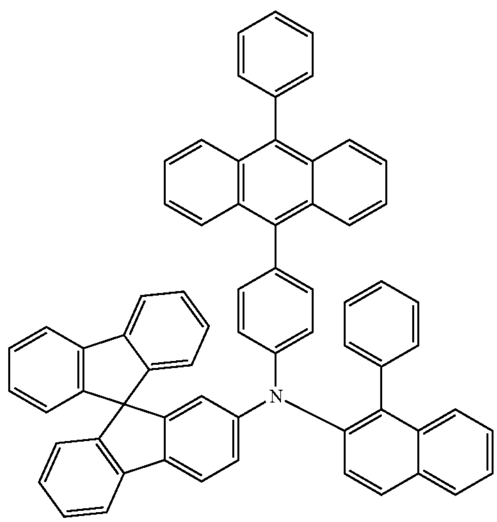
300
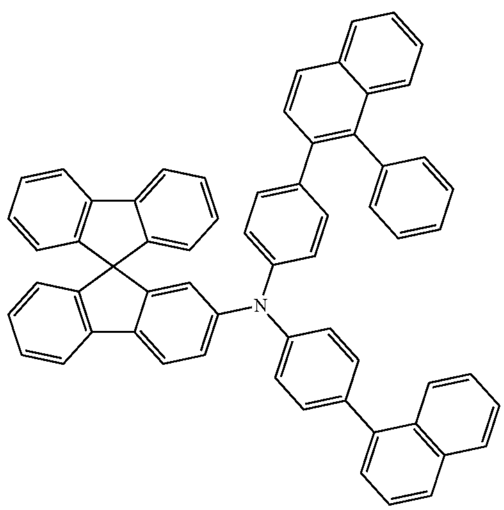
-continued
301
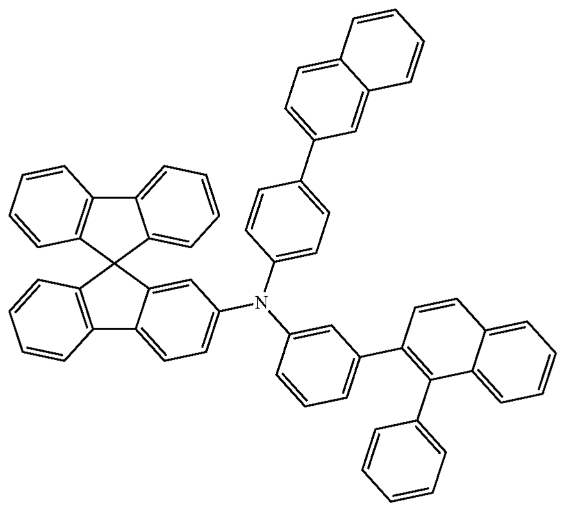
302
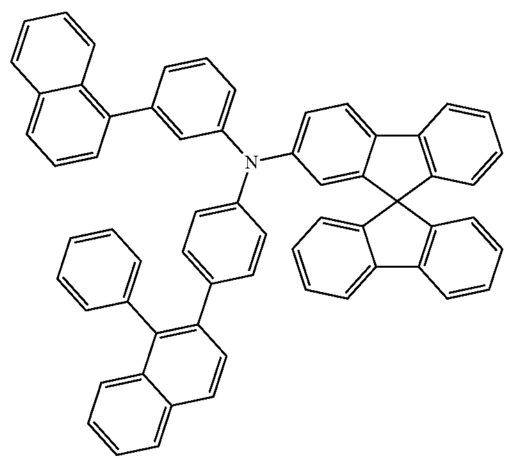
303
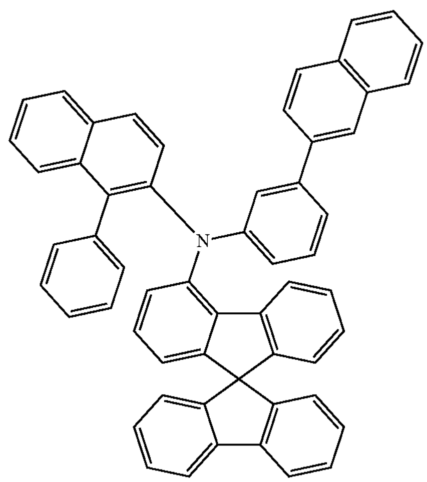

-continued
304
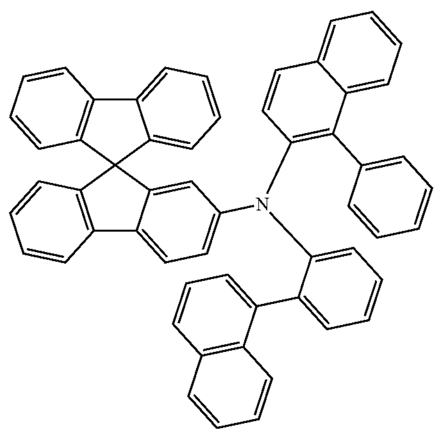
305
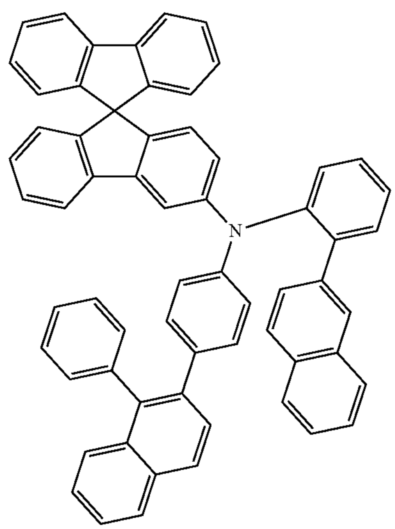
306
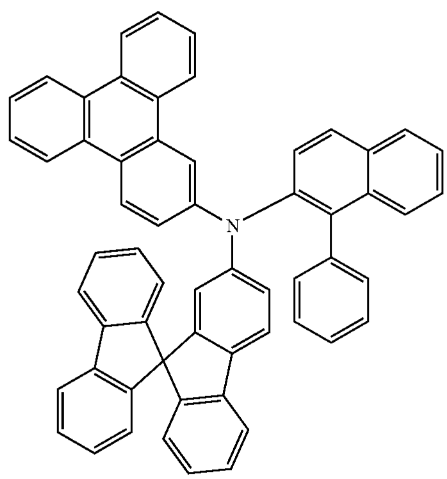
-continued
307
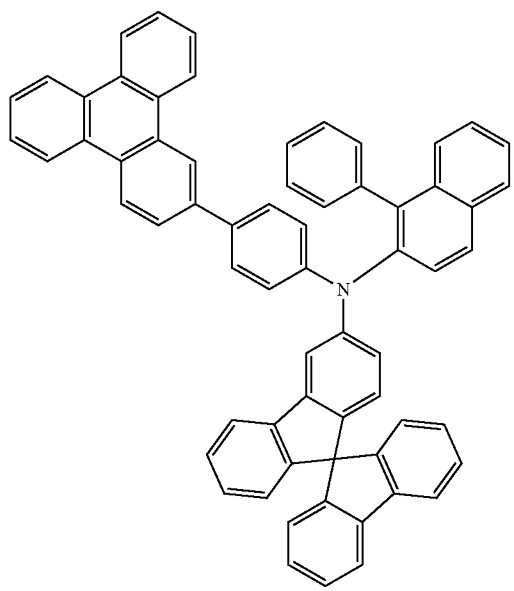
308
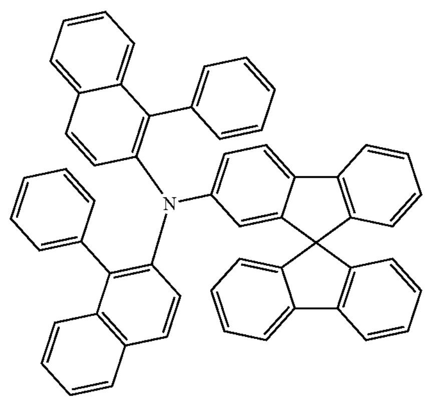
309
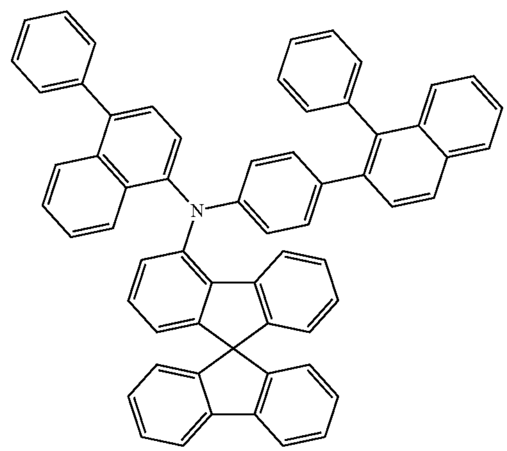

-continued
310
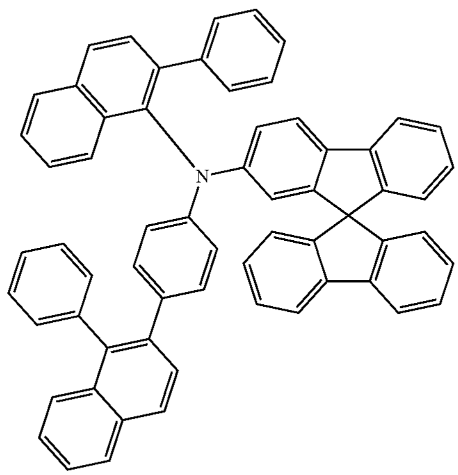
311
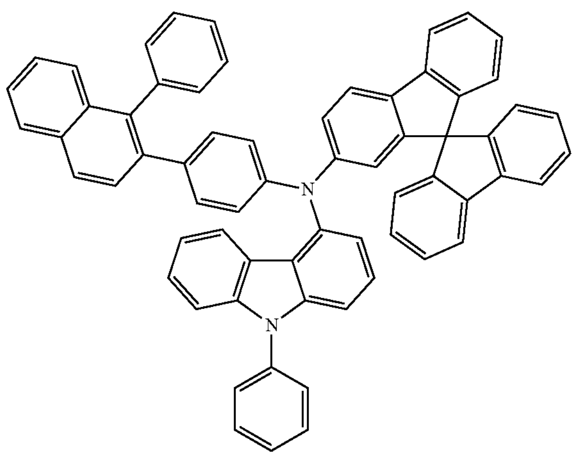
312
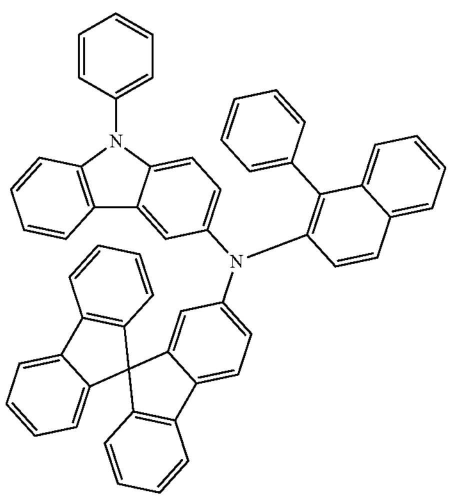
-continued
313
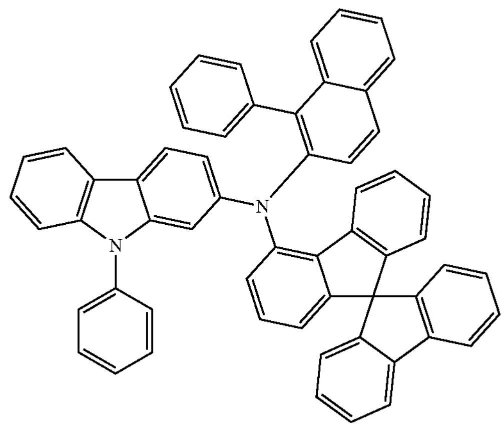
314
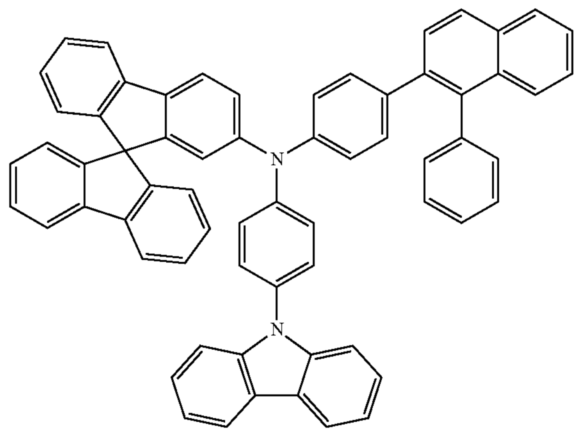
315
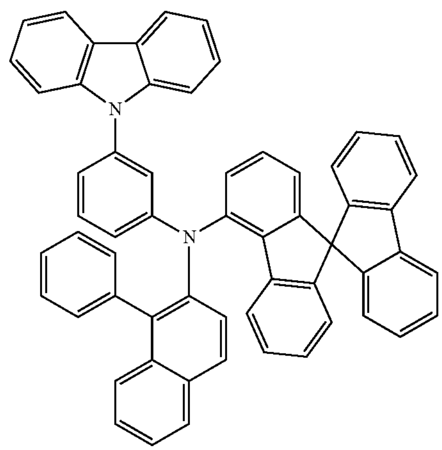

-continued
316
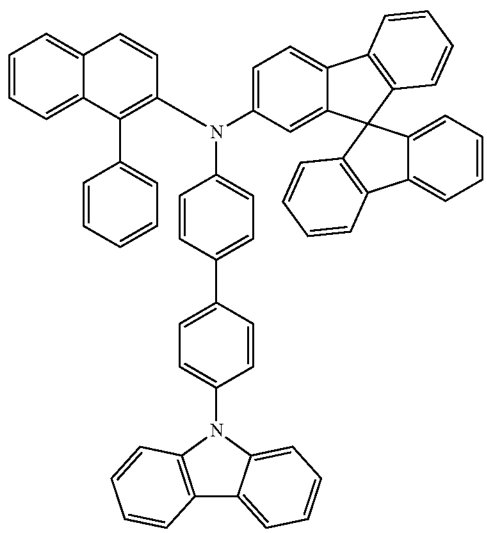
317
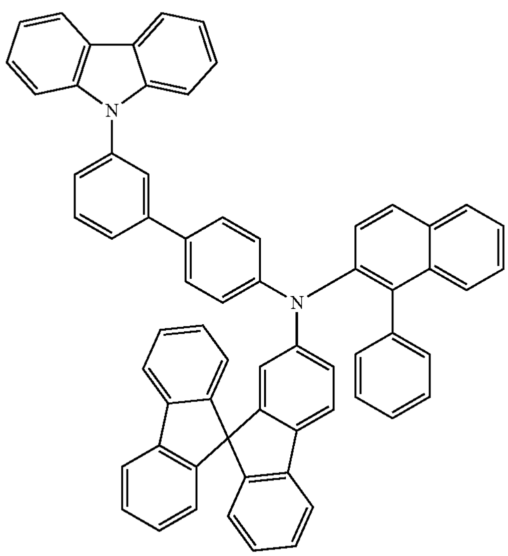
318
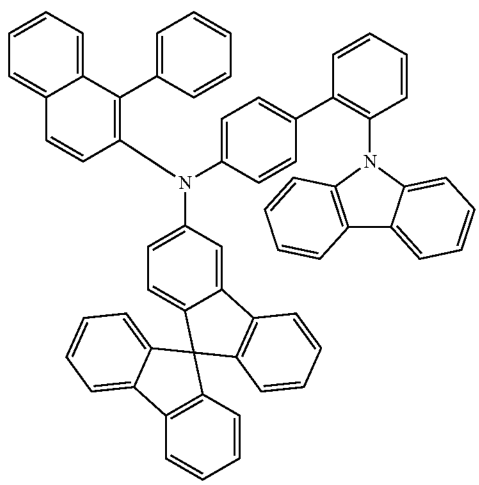
-continued
319
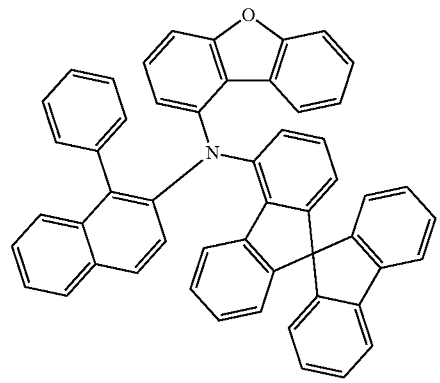
320
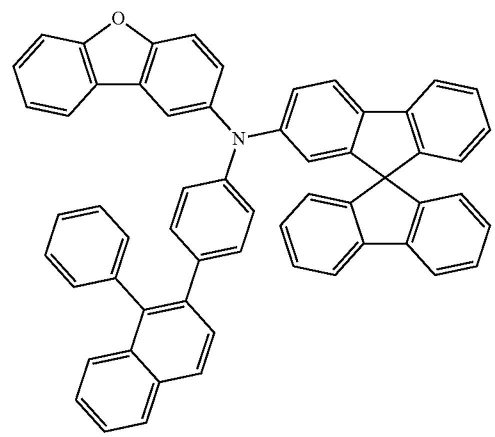
321
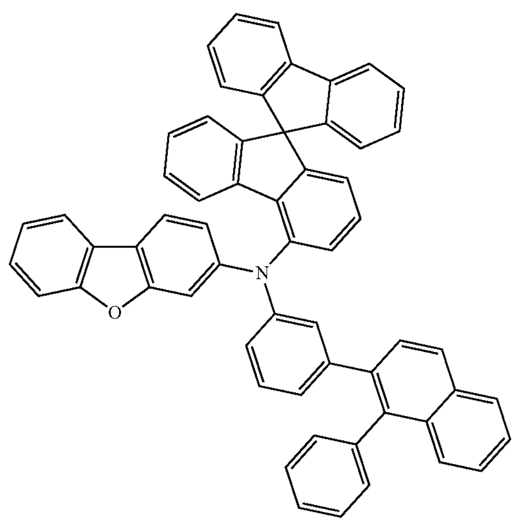

-continued
322
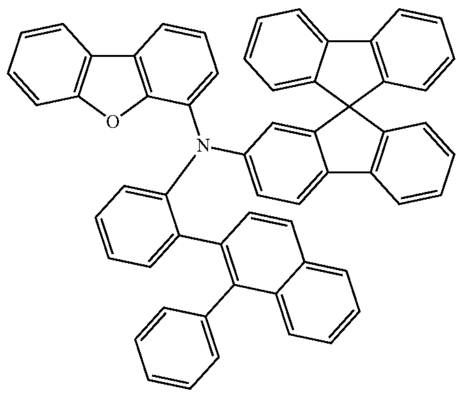
323
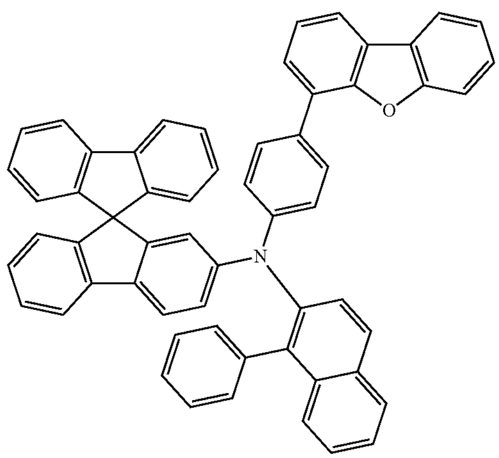
324
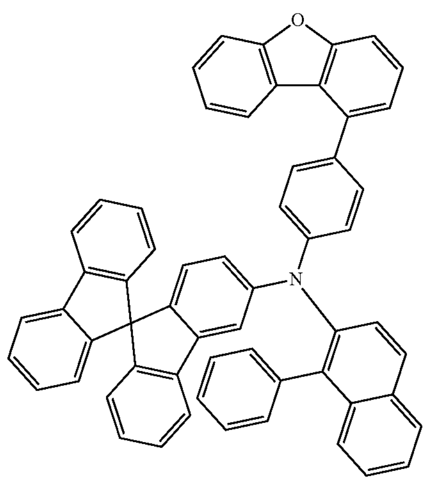
-continued
325
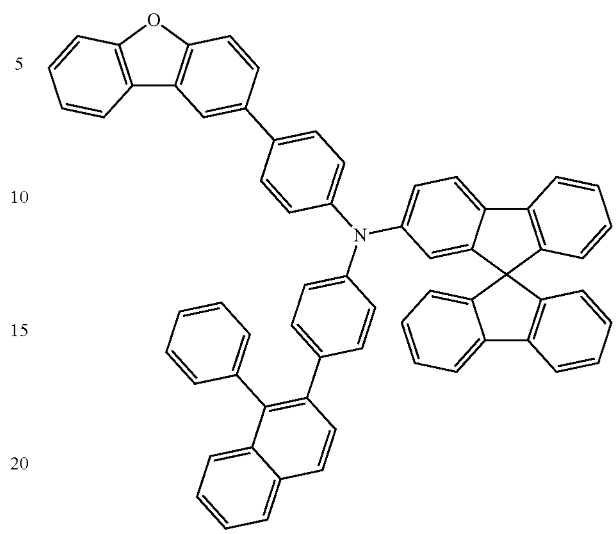
326
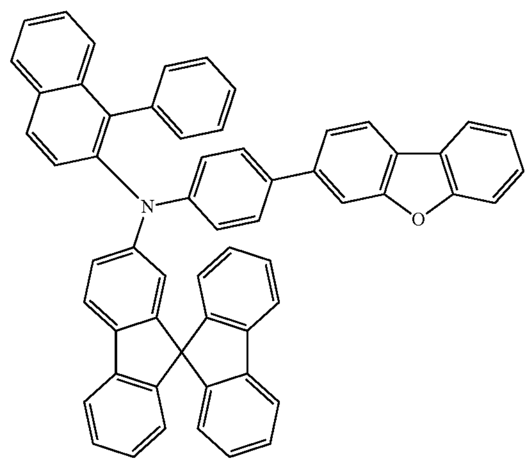
327
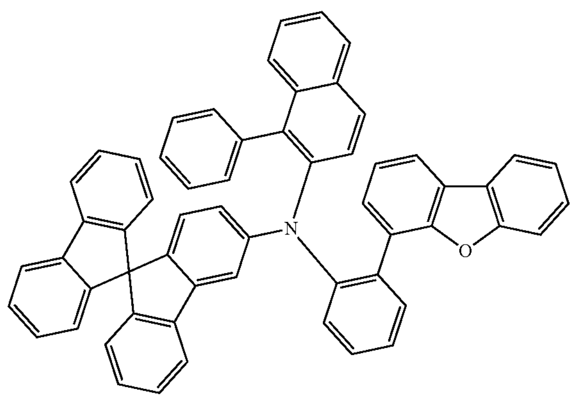

-continued
328
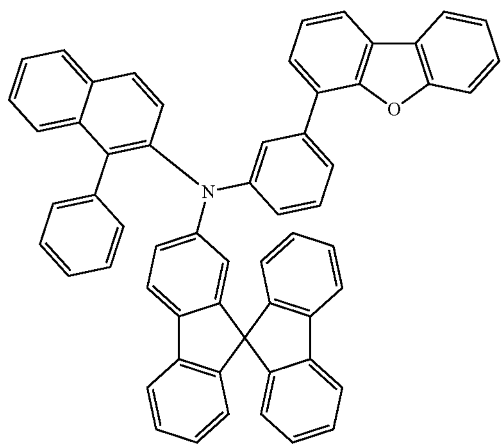
329
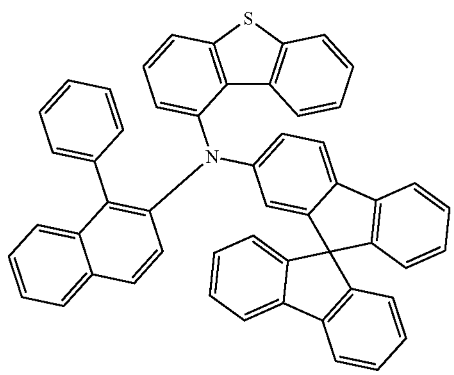
330
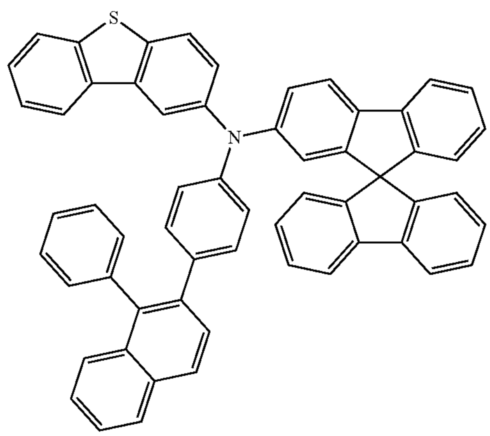
331
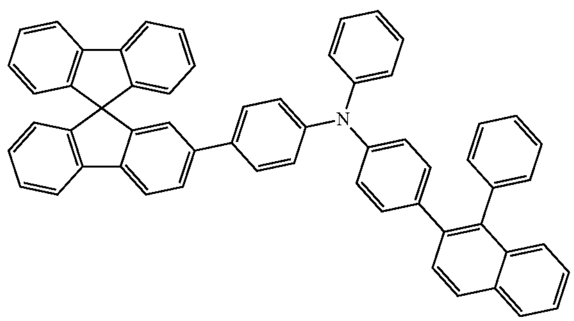
-continued
332
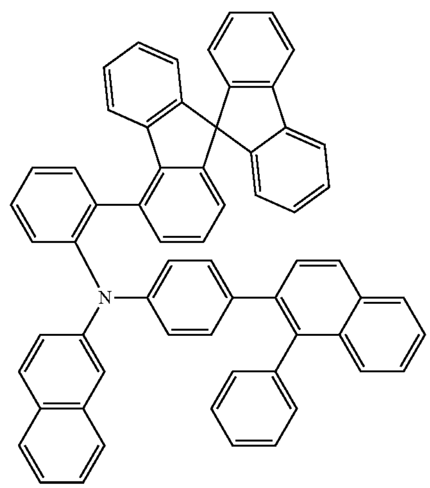
333
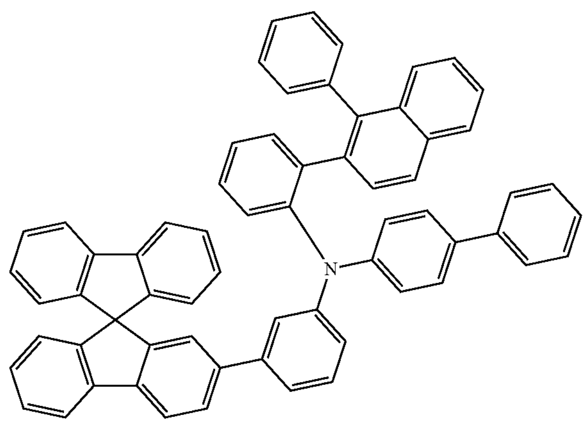
334
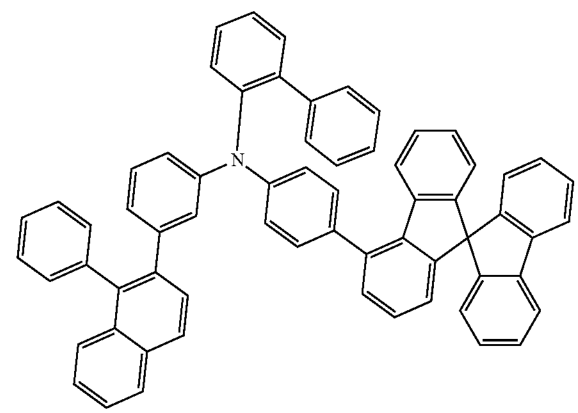

-continued
335
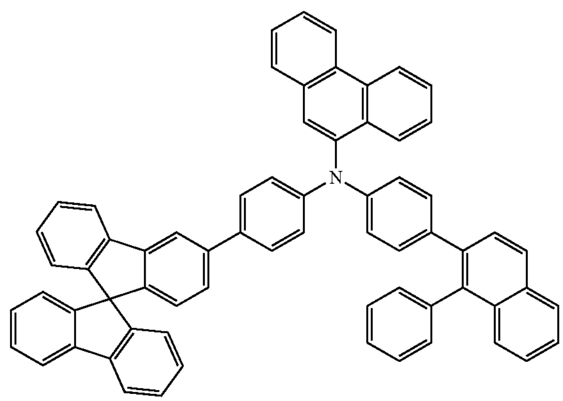
336
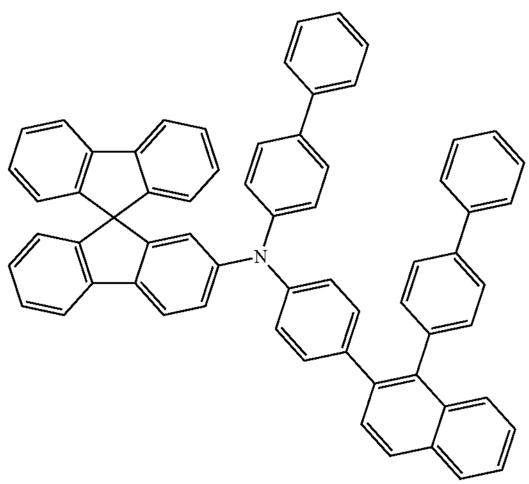
337
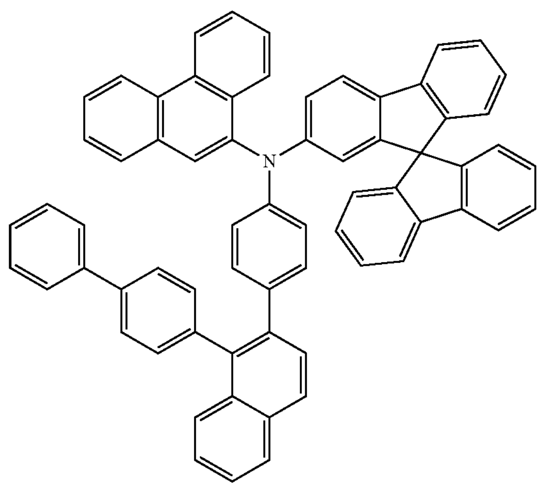
-continued
338
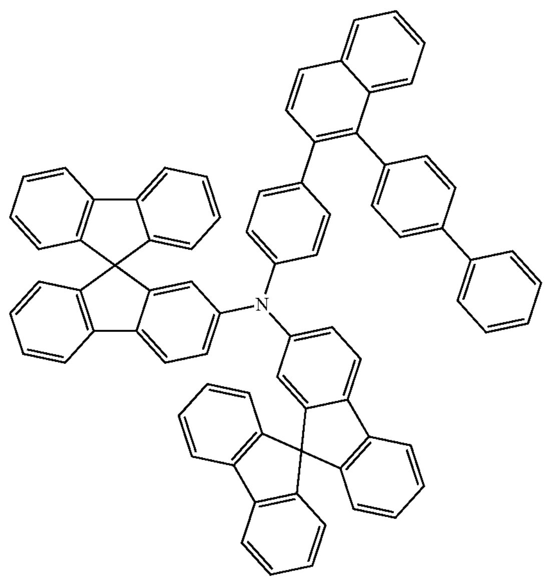
339
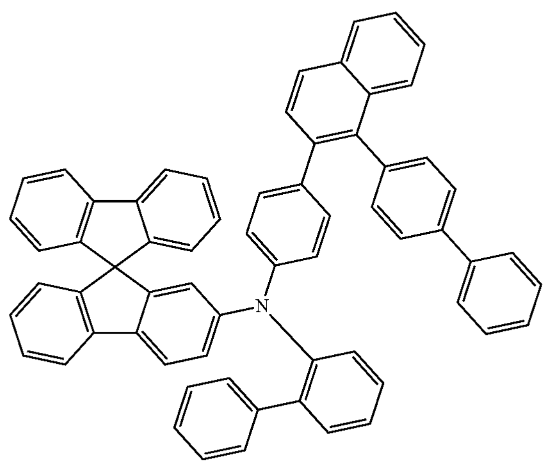
340
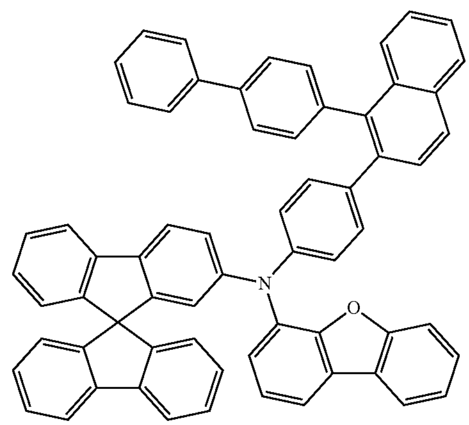

-continued
341
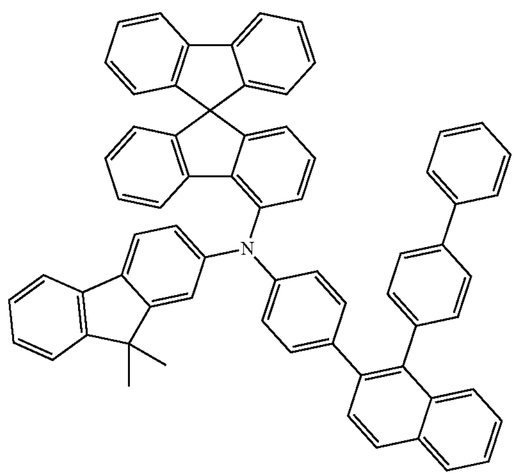
342
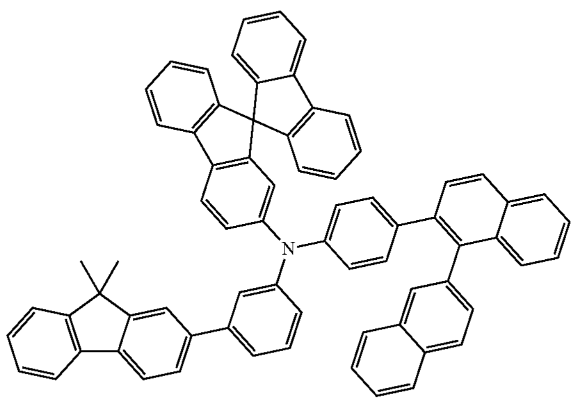
343
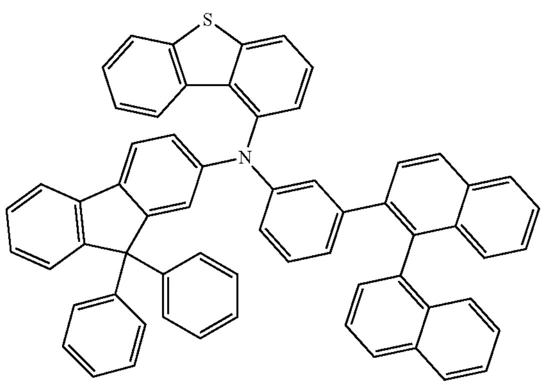
344
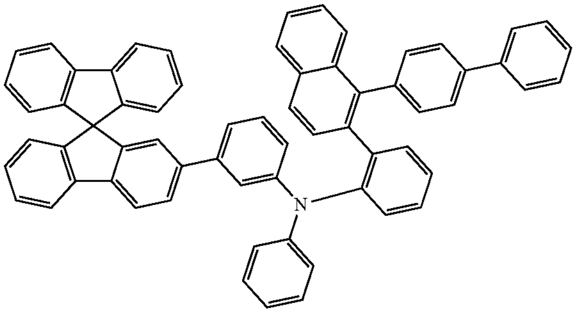
-continued
345
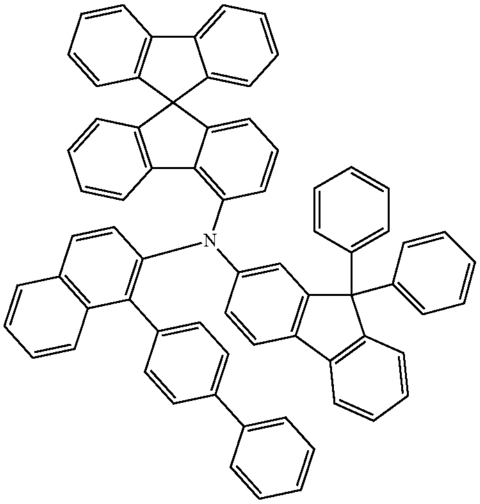
346
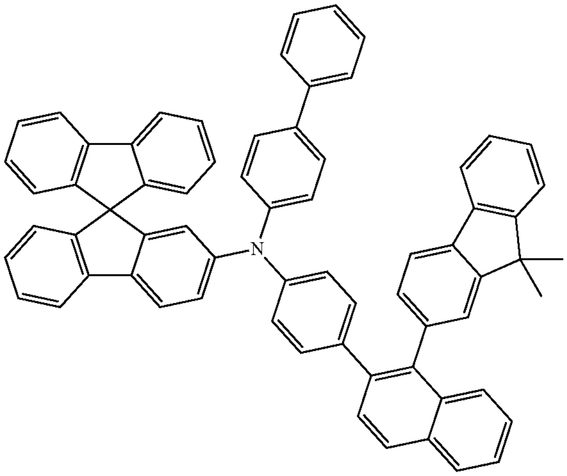
347
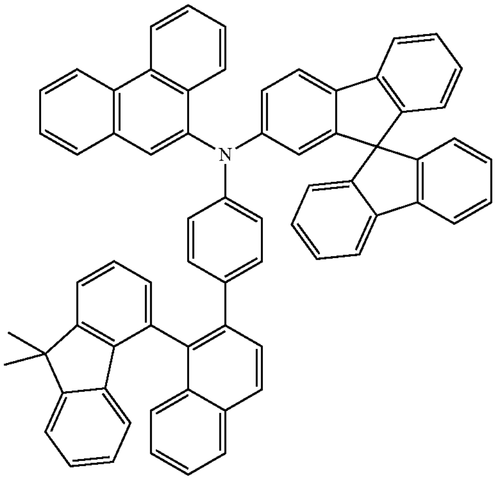

-continued
348
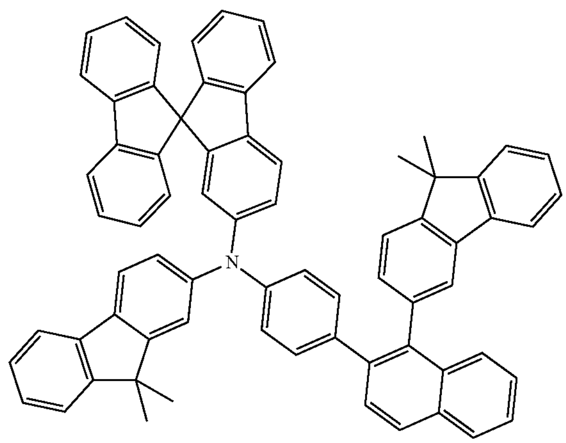
349
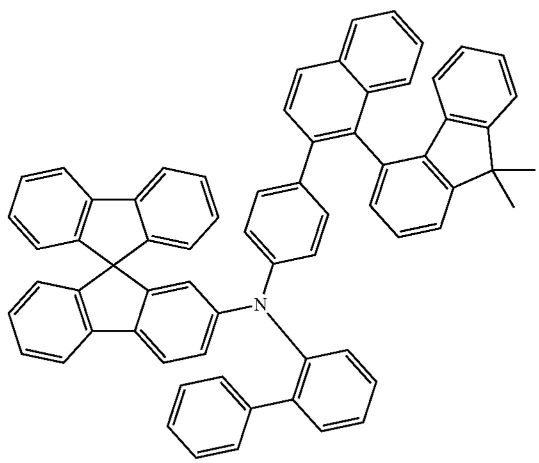
350
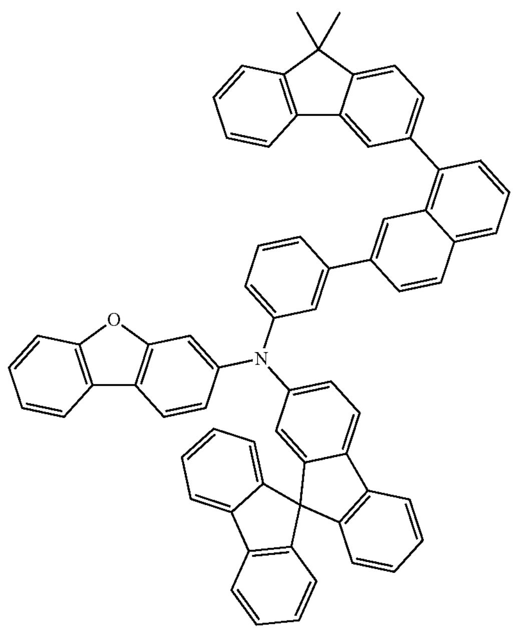
-continued
351
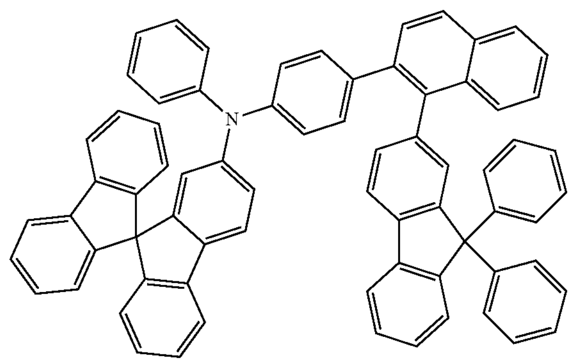
352
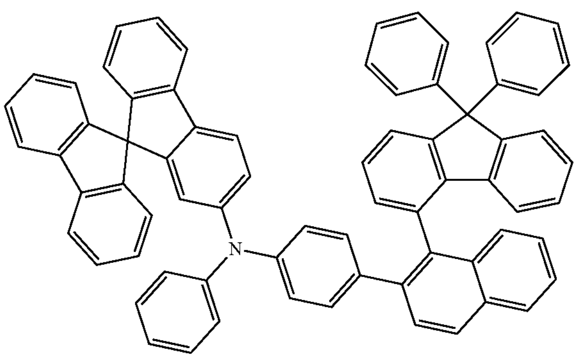
353
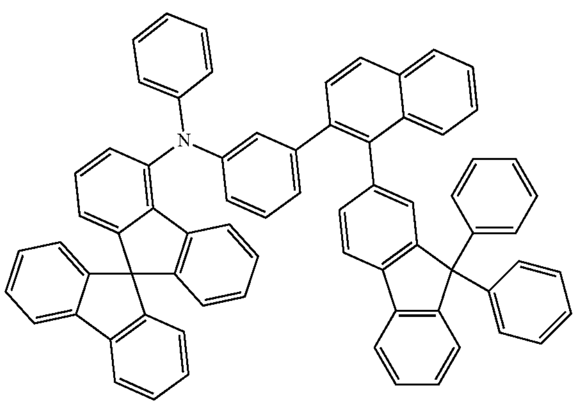
354
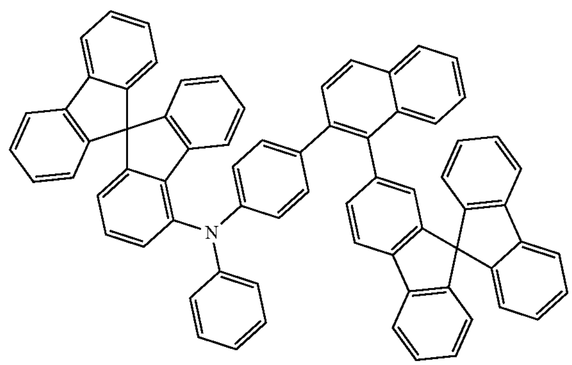

-continued

355

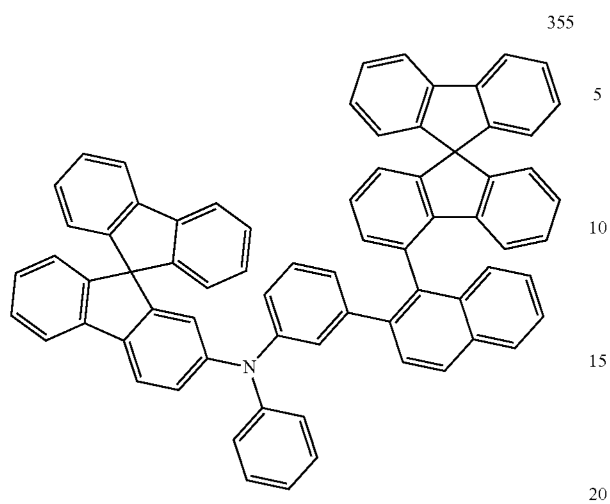

356

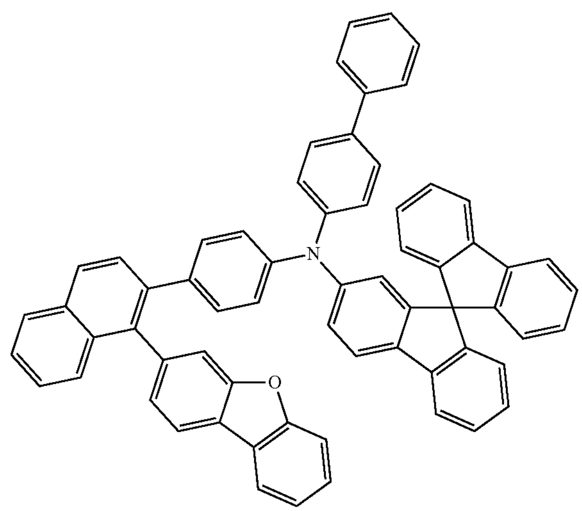

357

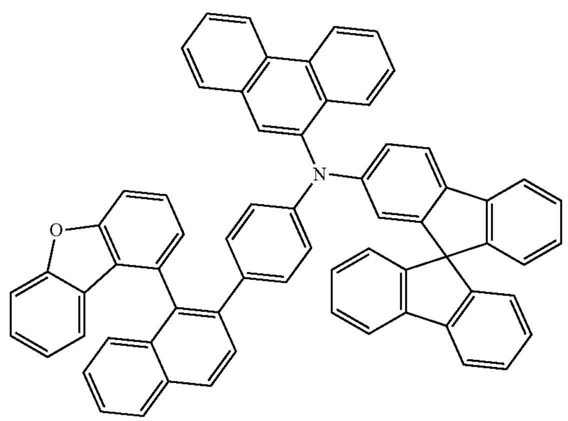

-continued

358

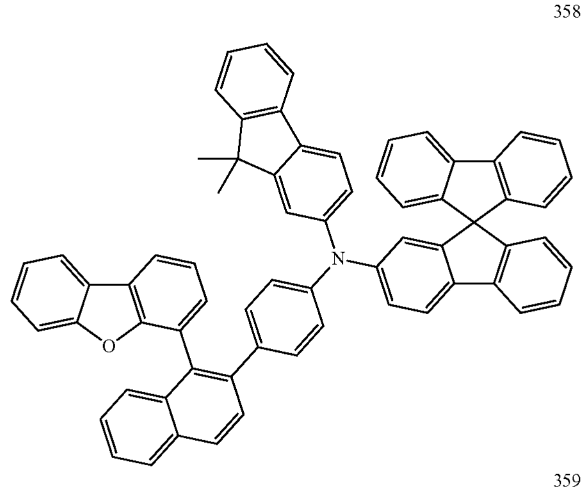

359

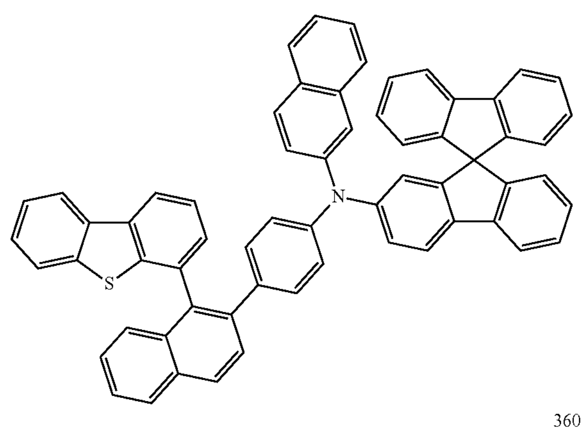

360

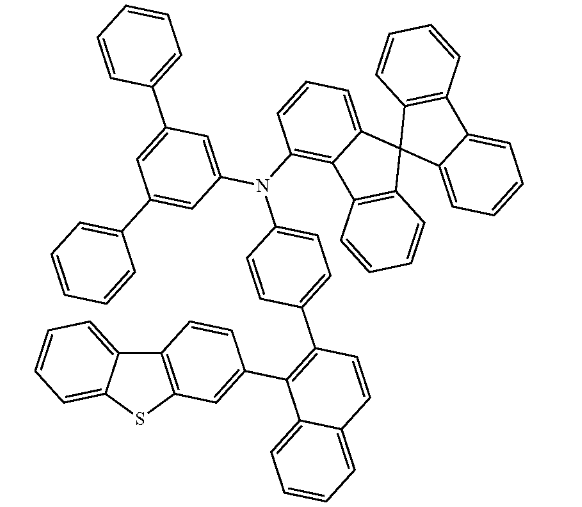

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the heterocyclic compound has a high glass transition temperature (Tg) and thereby has superior thermal stability. Such an increase in the thermal stability becomes an important factor in providing driving stability to a device.

The heterocyclic compound according to one embodiment of the present application may be prepared using a multi-step chemical reaction. Some intermediate compounds are prepared first, and from the intermediate compounds, the compound of Chemical Formula 1 may be prepared. More specifically, the heterocyclic compound according to one embodiment of the present application may be prepared based on preparation examples to describe later.

Another embodiment of the present application provides an organic light emitting device including the heterocyclic compound represented by Chemical Formula 1. The "organic light emitting device" may be expressed in terms such as an "organic light emitting diode", an "OLED", an "OLED device" and an "organic electroluminescent device".

One embodiment of the present application provides an organic light emitting device including a first electrode; a second electrode; and one or more organic material layers provided between the first electrode and the second electrode, wherein one or more layers of the organic material layers include the heterocyclic compound represented by Chemical Formula 1.

In one embodiment of the present application, the first electrode may be an anode, and the second electrode may be a cathode.

In another embodiment of the present application, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In another embodiment of the present application, the organic light emitting device may be a green organic light emitting device, and the heterocyclic compound according to Chemical Formula 1 may be used as a material of the green organic light emitting device.

In another embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present application may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present application may be formed in a single layer structure, but may be formed in a multilayer structure in which two or more organic material layers are laminated. For example, the organic light emitting device of the present disclosure may have a structure including a hole injection layer, a hole transfer layer, a hole auxiliary layer, a light emitting layer, an electron transfer layer, an electron injection layer and the like as the organic material layer. However, the structure of the organic light emitting device is not limited thereto, and may include a smaller number of organic material layers.

In the organic light emitting device of the present application, the organic material layer includes a hole transfer layer, and the hole transfer layer may include the heterocyclic compound. The hole transfer layer means a layer performing a role of receiving holes from a hole injection layer and transferring the holes to a light emitting layer. The heterocyclic compound is a material having proper hole mobility, and using the heterocyclic compound in the hole transfer layer may increase excitons formed in the light emitting layer. In other words, when using the heterocyclic compound in the hole transfer layer, the organic light emitting device may have superior driving, efficiency and lifetime.

In another organic light emitting device, the organic material layer includes a hole auxiliary layer, and the hole auxiliary layer may include the heterocyclic compound. The hole auxiliary layer means a layer performing a role of preventing electrons from passing over from a light emitting layer to a hole transfer layer by matching a proper energy level between the hole transfer layer and the light emitting layer. The heterocyclic compound is a material having proper hole mobility, and using the heterocyclic compound in the hole auxiliary layer may prevent a decrease in the excitons formed in the light emitting layer. In other words, when using the heterocyclic compound in the hole auxiliary layer, the organic light emitting device may have superior driving, efficiency and lifetime. The hole auxiliary layer may also perform a function of an electron blocking layer, and may be expressed as an electron blocking layer instead of the hole auxiliary layer.

The organic light emitting device of the present disclosure may further include one, two or more layers selected from the group consisting of a light emitting layer, a hole injection layer, a hole transfer layer, an electron injection layer, an electron transfer layer, a hole auxiliary layer and a hole blocking layer.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer including the compound represented by Chemical Formula 1 may further include other materials as necessary.

In addition, the organic light emitting device according to one embodiment of the present application includes an anode, a first stack provided on the anode and including a first light emitting layer, a charge generation layer provided on the first stack, a second stack provided on the charge generation layer and including a second light emitting layer, and a cathode provided on the second stack.

In addition, the first stack and the second stack may each independently further include one or more types of the hole injection layer, the hole transfer layer, the hole blocking layer, the electron transfer layer, the electron injection layer and the like described above.

The charge generation layer may be an N-type charge generation layer, and the charge generation layer may further include a dopant known in the art in addition to the heterocyclic compound represented by Chemical Formula 1.

As the organic light emitting device according to one embodiment of the present application, an organic light emitting device having a 2-stack tandem structure is illustrated in FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrenesulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

In the organic light emitting device of the present application, the organic material layer includes a light emitting layer, and the light emitting layer may include the heterocyclic compound as a host material of a light emitting material.

In the organic light emitting device of the present application, the light emitting layer may include two or more host materials, and at least one of the host materials may include the heterocyclic compound as a host material of a light emitting material.

In the organic light emitting device of the present application, the light emitting layer may include two or more host materials, at least one of the host materials is a p-type host material, and the p-type host material may include the heterocyclic compound as a host material of a light emitting material.

In the organic light emitting device of the present application, the light emitting layer may include two or more host materials, the two or more host materials each include one or more p-type host material and n-type host material, and the p-type host material may include the heterocyclic compound as a host material of a light emitting material.

When including the heterocyclic compound as a host material of a light emitting material, the organic light emitting device may have superior driving, efficiency and lifetime. In addition, when using the heterocyclic compound having a superior hole transfer ability as a p-type host material, the organic light emitting device may have more superior driving, efficiency and lifetime.

The organic light emitting device according to one embodiment of the present application may be a top-emission type, a bottom-emission type or a dual-emission type depending on the materials used.

The heterocyclic compound according to one embodiment of the present application may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

Preparation Example

[Preparation Example 1] Preparation of Compound 1

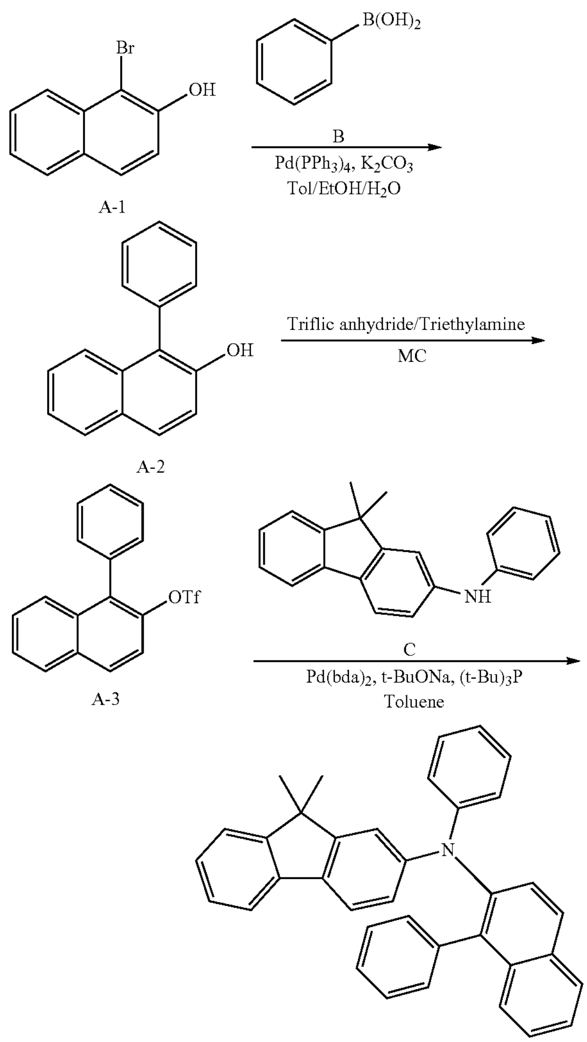

A-1

A-2

A-3

1

1) Preparation of Compound A-2

After dissolving 1-bromonaphthalen-2-ol (50 g, 224.14 mmol) and phenylboronic acid (28.7 g, 235.35 mmol) in toluene (500 ml), ethanol (100 ml) and $H_2O$ (100 ml), $Pd(PPh_3)_4$ (12.95 g, 11.21 mmol) and $K_2CO_3$ (92.93 g, 672.42 mmol) were introduced thereto, and the result was stirred for 5 hours under reflux. After the reaction was completed, methylene chloride (hereinafter, MC) was introduced to the reaction solution for dissolution, and the result was extracted with distilled water. After drying the organic layer with anhydrous $MgSO_4$, the solvent was removed using a rotary evaporator, and then the result was purified by column chromatography using dichloromethane and hexane as a developing solvent to obtain Compound A-2 (40 g, 82%).

2) Preparation of Compound A-3

Compound A-2 (40 g, 181.60 mmol) and trimethylamine (20.21 g, 199.76 mmol) were dissolved in MC (400 ml), and, while stirring the mixture in an ice bath, triflic anhydride (41.96 g, 199.76 mmol) was slowly added dropwise thereto. After that, the result was stirred for 3 hours at room temperature. After the reaction was completed, MC was introduced to the reaction solution for dissolution, and the result was extracted with distilled water. After drying the organic layer with anhydrous $MgSO_4$, the solvent was removed using a rotary evaporator, and then the result was purified by column chromatography using dichloromethane and hexane as a developing solvent to obtain Compound A-3 (58.2 g, 91%).

3) Preparation of Compound 1

After dissolving Compound A-3 (7 g, 19.87 mmol) and 9,9-dimethyl-N-phenyl-9H-fluoren-2-amine (5.67 g, 19.87 mmol) in toluene (140 ml), $Pd(dba)_2$ (1.14 g, 1.99 mmol), $P(t\text{-}Bu)_3$ (1.65 ml, 3.97 mmol) and t-BuONa (3.82 g, 39.74 mmol) were introduced thereto, and the result was stirred for 8 hours under reflux. After the reaction was completed, MC was introduced to the reaction solution for dissolution, and the result was extracted with distilled water. After drying the organic layer with anhydrous $MgSO_4$, the solvent was removed using a rotary evaporator, and then the result was purified by column chromatography using dichloromethane and hexane as a developing solvent to obtain Compound 1 (6.98 g, 72%).

As in the following Table 1, target compounds were synthesized in the same manner as in Preparation Example 1 except that Compound A was used instead of phenylboronic acid and Compound B was used instead of 9,9-dimethyl-N-phenyl-9H-fluoren-2-amine.

TABLE 1
| Compound No. | Compound A | Compound B |
|---|---|---|
| 5 | 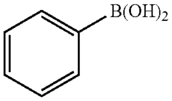 | 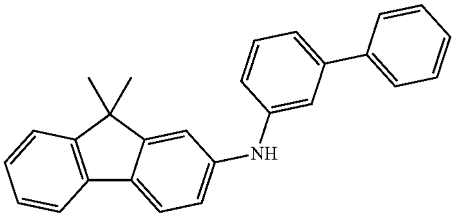 |
| 13 | 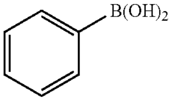 | 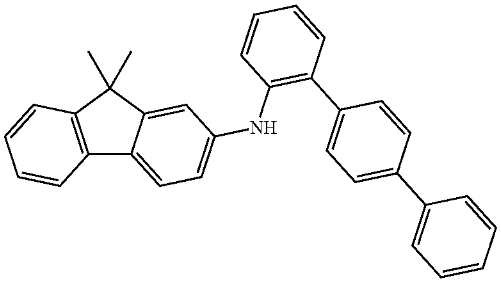 [SMILES: CC1(C)c2ccccc2-c2ccc(Nc3ccccc3-c3ccc(-c4ccccc4)cc3)cc21] |
| 24 | 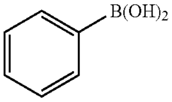 | 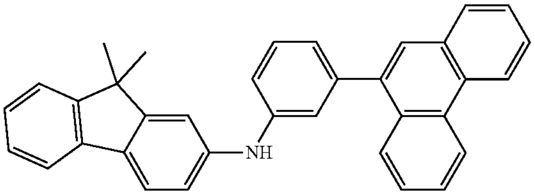 [SMILES: CC1(C)c2ccccc2-c2ccc(Nc3cccc(-c4cc5ccccc5c5ccccc45)c3)cc21] |
| 43 | 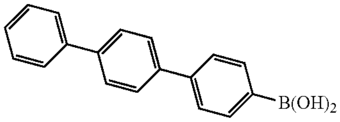 [SMILES: OB(O)c1ccc(-c2ccc(-c3ccccc3)cc2)cc1] | 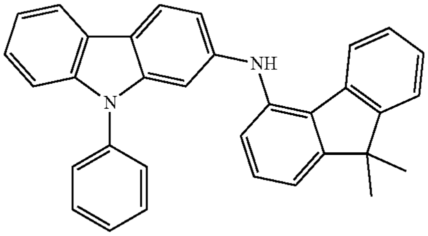 [SMILES: CC1(C)c2ccccc2-c2c(Nc3ccc4c5ccccc5n(-c5ccccc5)c4c3)cccc21] |
| 49 | 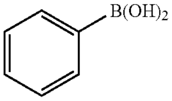 | 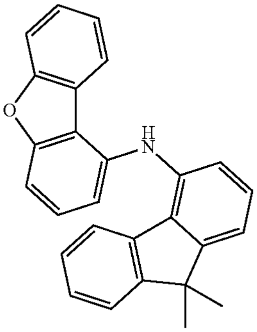 [SMILES: CC1(C)c2ccccc2-c2c(Nc3cccc4oc5ccccc5c34)cccc21] |

TABLE 1-continued
| | | |
|---|---|---|
| 60 | 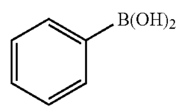 | 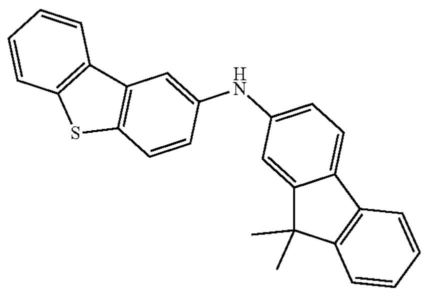 [SMILES: CC1(C)c2ccccc2-c2ccc(Nc3ccc4sc5ccccc5c4c3)cc21] |
| 70 | 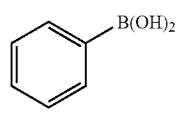 | 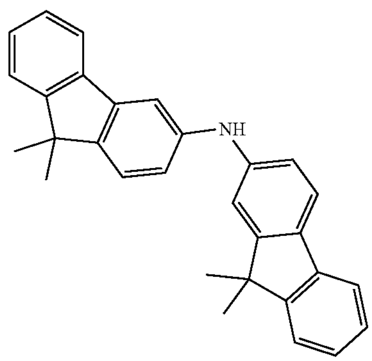 [SMILES: CC1(C)c2ccccc2-c2cc(Nc3ccc4c(c3)C(C)(C)c3ccccc3-4)ccc21] |
| 86 | 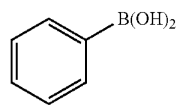 | 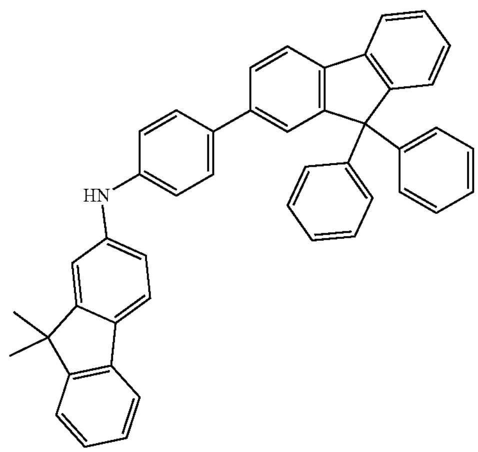 [SMILES: CC1(C)c2ccccc2-c2ccc(Nc3ccc(-c4ccc5c(c4)C(c4ccccc4)(c4ccccc4)c4ccccc4-5)cc3)cc21] |
| 91 | 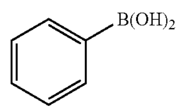 | 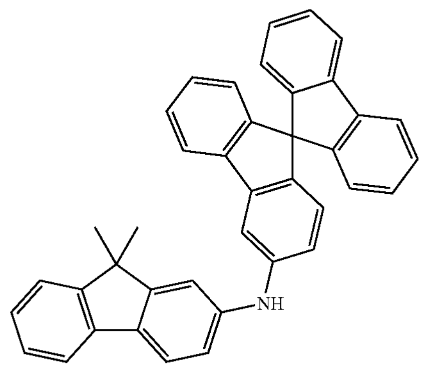 [SMILES: CC1(C)c2ccccc2-c2ccc(Nc3ccc4c(c3)-c3ccccc3C43c4ccccc4-c4ccccc43)cc21] |

TABLE 1-continued
| | | |
|---|---|---|
| 100 | 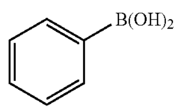 | 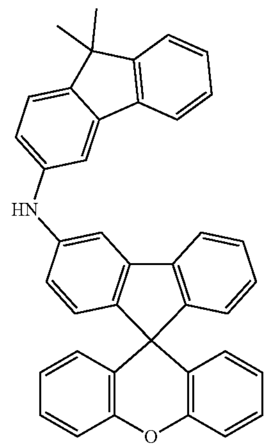 [SMILES: CC1(C)c2ccccc2-c2cc(Nc3ccc4c(c3)-c3ccccc3C43c4ccccc4Oc4ccccc43)ccc21] |
| 166 | 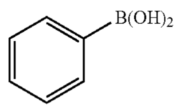 | 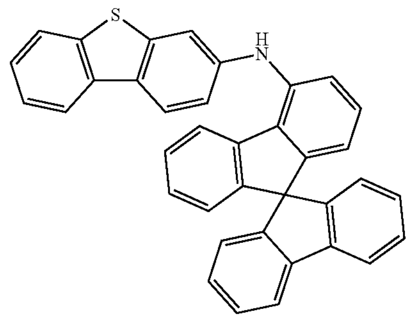 [SMILES: c1ccc2c(c1)-c1ccccc1C21c2ccccc2-c2c(Nc3ccc4c(c3)sc3ccccc34)cccc21] |
| 183 | 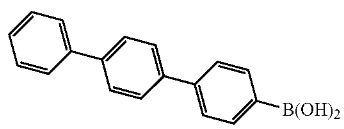 [SMILES: OB(O)c1ccc(-c2ccc(-c3ccccc3)cc2)cc1] | 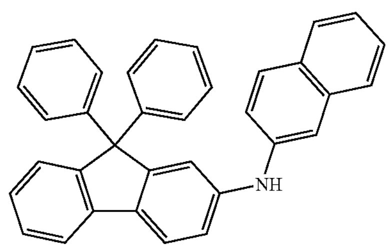 [SMILES: c1ccc(C2(c3ccccc3)c3ccccc3-c3ccc(Nc4ccc5ccccc5c4)cc32)cc1] |
| 223 | 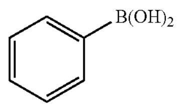 | 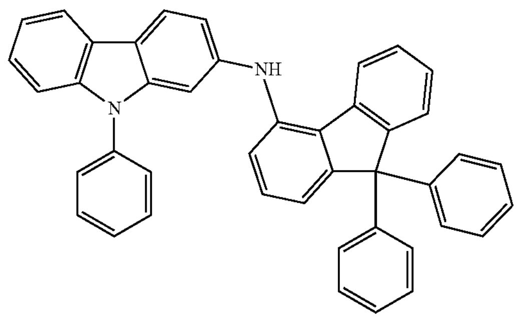 [SMILES: c1ccc(-n2c3ccccc3c3ccc(Nc4cccc5c4-c4ccccc4C5(c4ccccc4)c4ccccc4)cc32)cc1] |
| 271 | 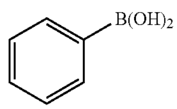 | 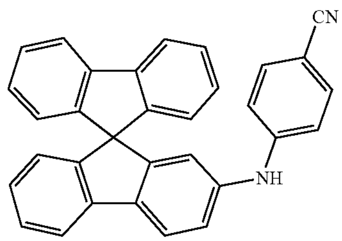 [SMILES: N#Cc1ccc(Nc2ccc3c(c2)C2(c4ccccc4-c4ccccc42)c2ccccc2-3)cc1] |

TABLE 1-continued
| | | |
|---|---|---|
| 308 | 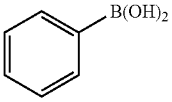 | 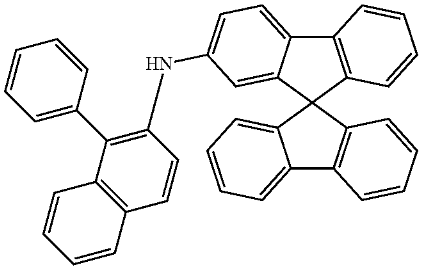 [SMILES: c1ccc(-c2c(Nc3ccc4c(c3)C3(c5ccccc5-c5ccccc53)c3ccccc3-4)ccc3ccccc23)cc1] |
| 324 | 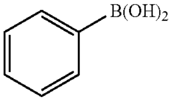 | 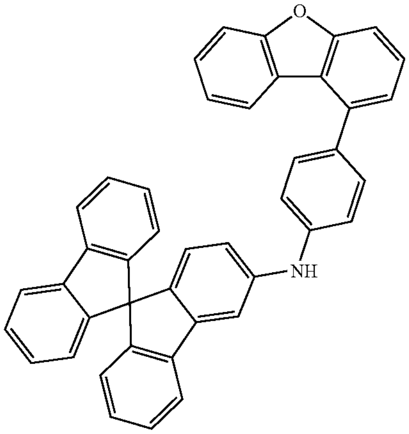 [SMILES: c1ccc2c(c1)-c1ccccc1C21c2ccccc2-c2cc(Nc3ccc(-c4cccc5oc6ccccc6c45)cc3)ccc21] |
| Compound No. | Target compound | Yield |
|---|---|---|
| 5 | 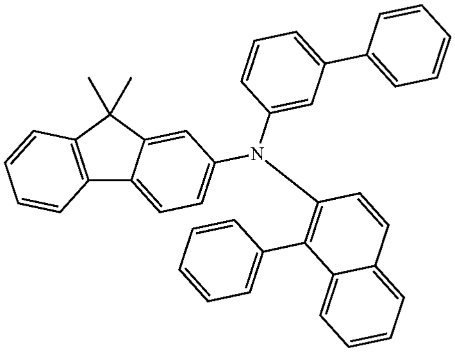 [SMILES: CC1(C)c2ccccc2-c2ccc(N(c3cccc(-c4ccccc4)c3)c3ccc4ccccc4c3-c3ccccc3)cc21] | 62% |
| 13 | 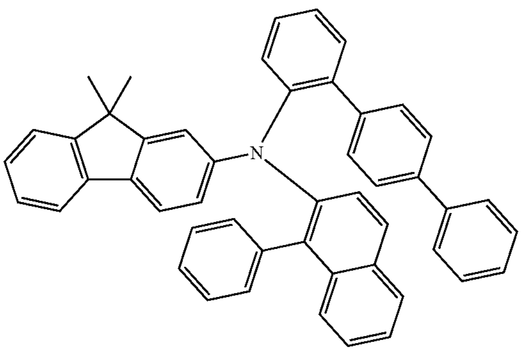 [SMILES: CC1(C)c2ccccc2-c2ccc(N(c3ccccc3-c3ccc(-c4ccccc4)cc3)c3ccc4ccccc4c3-c3ccccc3)cc21] | 71% |

TABLE 1-continued
| | | |
|---|---|---|
| 24 | 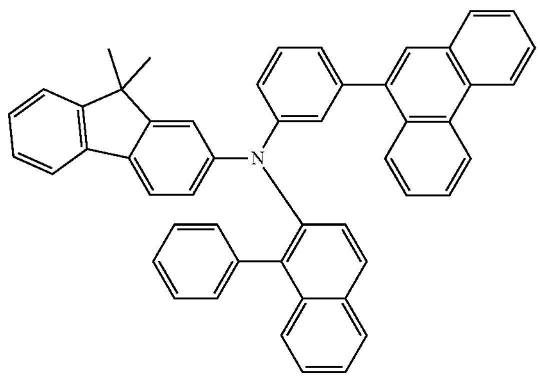 [SMILES: CC1(C)c2ccccc2-c2ccc(N(c3cccc(-c4cc5ccccc5c5ccccc45)c3)c3ccc4ccccc4c3-c3ccccc3)cc21] | 68% |
| 43 | 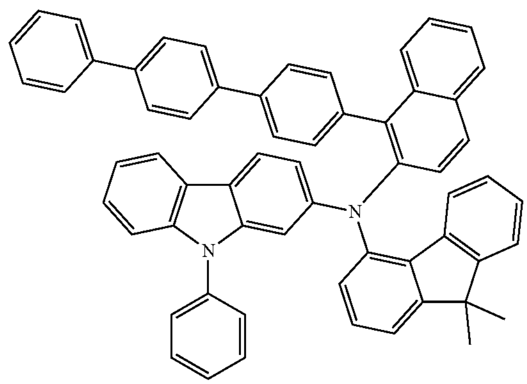 [SMILES: CC1(C)c2ccccc2-c2c(N(c3ccc4c5ccccc5n(-c5ccccc5)c4c3)c3ccc4ccccc4c3-c3ccc(-c4ccc(-c5ccccc5)cc4)cc3)cccc21] | 80% |
| 49 | 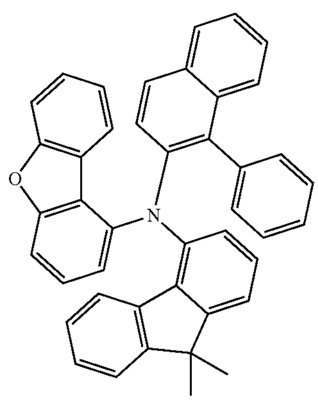 [SMILES: CC1(C)c2ccccc2-c2c(N(c3ccc4ccccc4c3-c3ccccc3)c3cccc4oc5ccccc5c34)cccc21] | 80% |
| 60 | 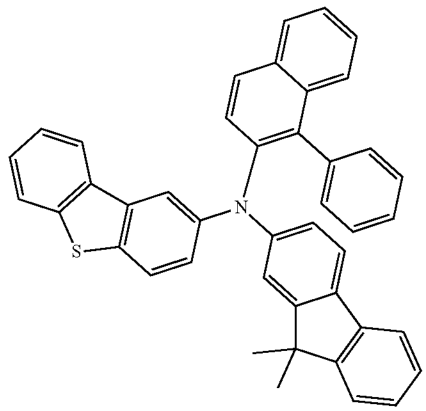 [SMILES: CC1(C)c2ccccc2-c2ccc(N(c3ccc4sc5ccccc5c4c3)c3ccc4ccccc4c3-c3ccccc3)cc21] | 75% |

TABLE 1-continued
| | | |
|---|---|---|
| 70 | 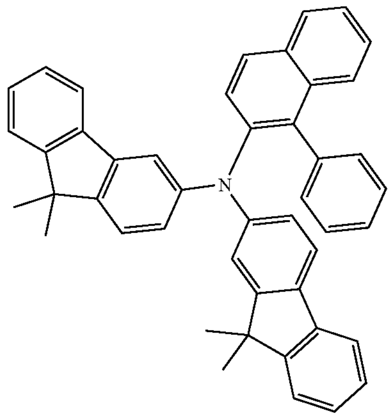 [SMILES: CC1(C)c2ccccc2-c2cc(N(c3ccc4c(c3)C(C)(C)c3ccccc3-4)c3ccc4ccccc4c3-c3ccccc3)ccc21] | 71% |
| 86 | 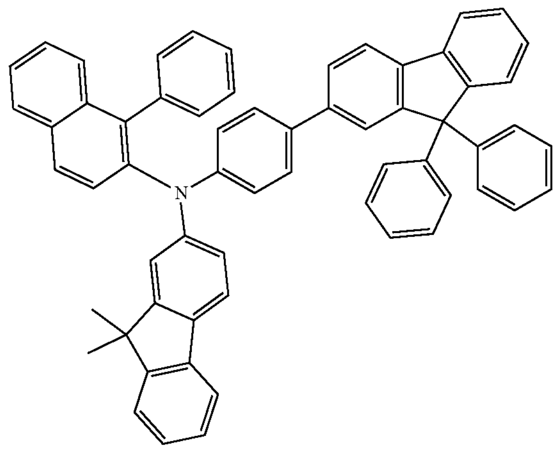 [SMILES: CC1(C)c2ccccc2-c2ccc(N(c3ccc(-c4ccc5c(c4)C(c4ccccc4)(c4ccccc4)c4ccccc4-5)cc3)c3ccc4ccccc4c3-c3ccccc3)cc21] | 63% |
| 91 | 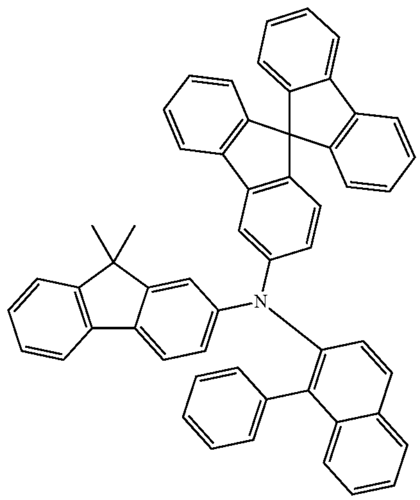 [SMILES: CC1(C)c2ccccc2-c2ccc(N(c3ccc4c(c3)-c3ccccc3C43c4ccccc4-c4ccccc43)c3ccc4ccccc4c3-c3ccccc3)cc21] | 82% |

TABLE 1-continued
| | | |
|---|---|---|
| 100 | 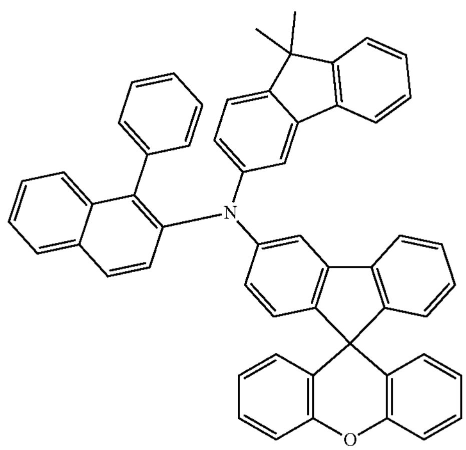 [SMILES: CC1(C)c2ccccc2-c2cc(N(c3ccc4c(c3)-c3ccccc3C43c4ccccc4Oc4ccccc43)c3ccc4ccccc4c3-c3ccccc3)ccc21] | 67% |
| 166 | 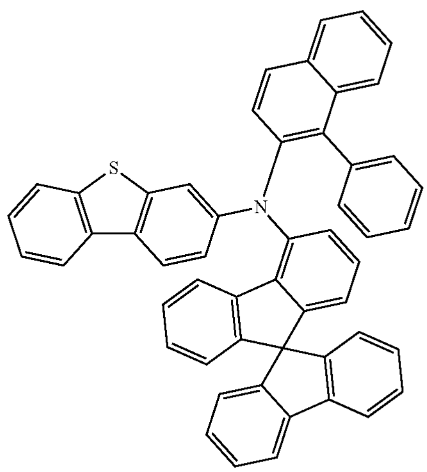 [SMILES: c1ccc(-c2c(N(c3ccc4c(c3)sc3ccccc34)c3cccc4c3-c3ccccc3C43c4ccccc4-c4ccccc43)ccc3ccccc23)cc1] | 81% |
| 183 | 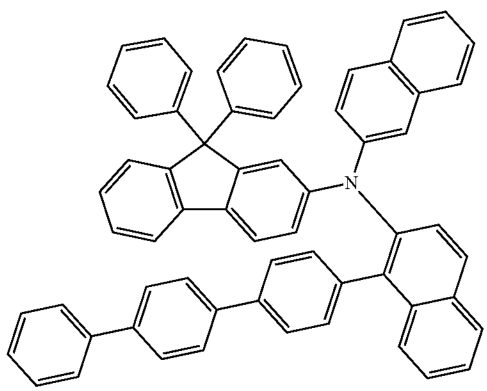 [SMILES: c1ccc(-c2ccc(-c3ccc(-c4c(N(c5ccc6c(c5)C(c5ccccc5)(c5ccccc5)c5ccccc5-6)c5ccc6ccccc6c5)ccc5ccccc45)cc3)cc2)cc1] | 71% |

TABLE 1-continued
| | | |
|---|---|---|
| 223 | 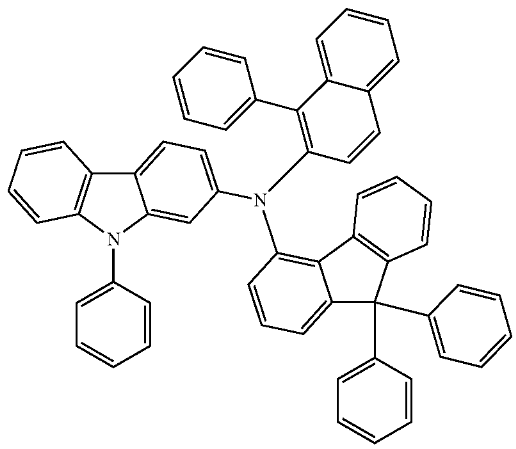 [SMILES: c1ccc(-c2c(N(c3ccc4c5ccccc5n(-c5ccccc5)c4c3)c3cccc4c3-c3ccccc3C4(c3ccccc3)c3ccccc3)ccc3ccccc23)cc1] | 63% |
| 271 | 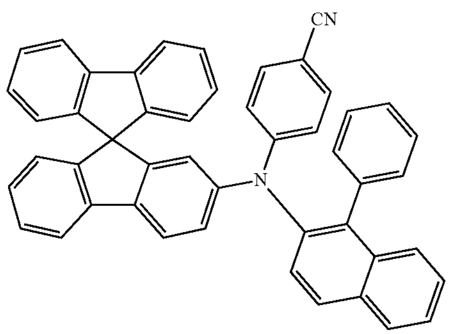 [SMILES: N#Cc1ccc(N(c2ccc3c(c2)C2(c4ccccc4-c4ccccc42)c2ccccc2-3)c2ccc3ccccc3c2-c2ccccc2)cc1] | 83% |
| 308 | 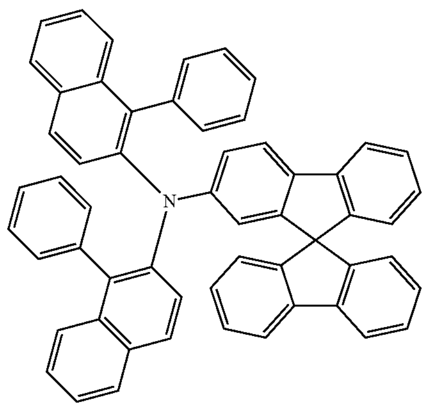 [SMILES: c1ccc(-c2c(N(c3ccc4c(c3)C3(c5ccccc5-c5ccccc53)c3ccccc3-4)c3ccc4ccccc4c3-c3ccccc3)ccc3ccccc23)cc1] | 51% |

TABLE 1-continued
| | | |
|---|---|---|
| 324 | 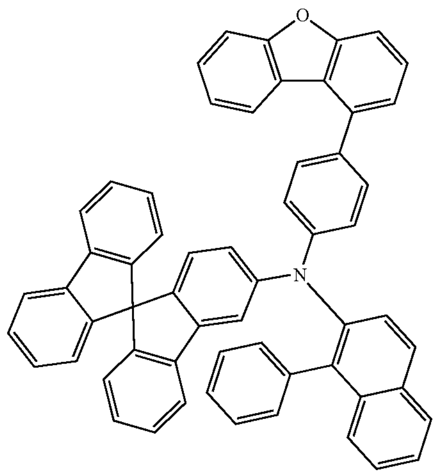 [SMILES: c1ccc(-c2c(N(c3ccc(-c4cccc5oc6ccccc6c45)cc3)c3ccc4c(c3)-c3ccccc3C43c4ccccc4-c4ccccc43)ccc3ccccc23)cc1] | 66% |
[Preparation Example 2] Preparation of Compound 125
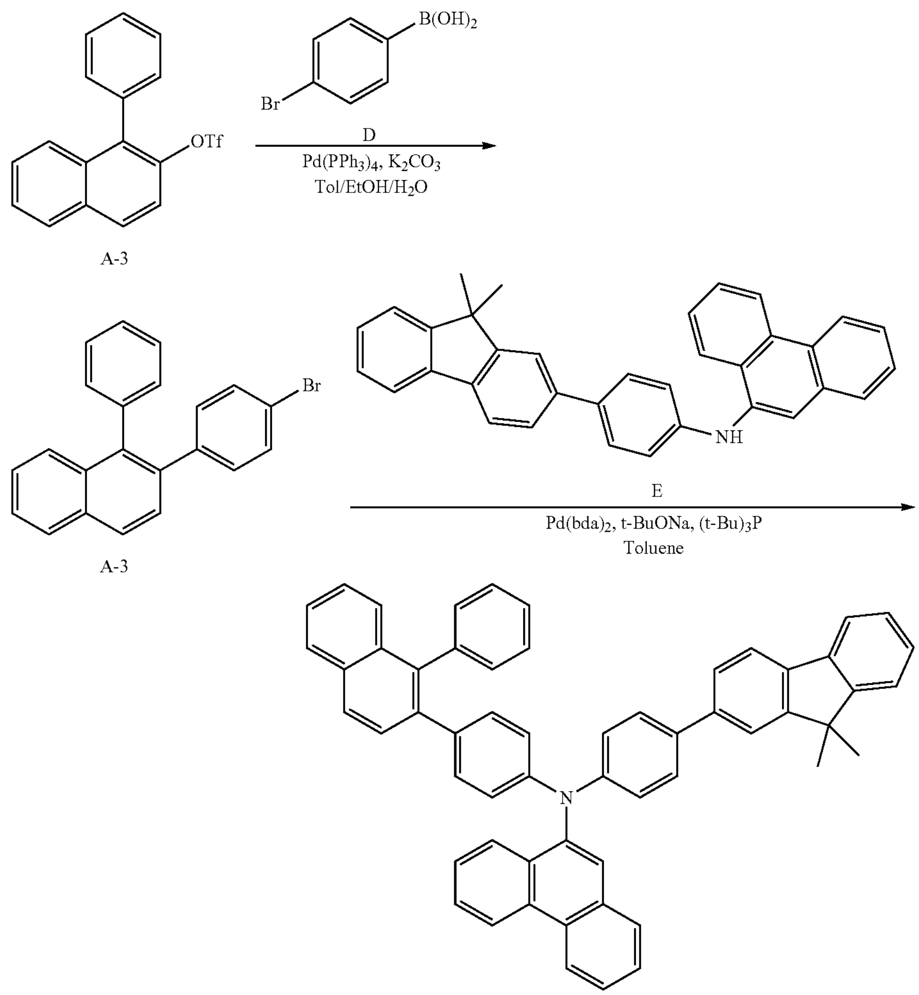
125

1) Preparation of Compound A-4

After dissolving Compound A-3 (21.7 g, 61.52 mmol) and (4-bromophenyl)boronic acid (12.97 g, 64.60 mmol) in toluene (300 ml), ethanol (60 ml) and $H_2O$ (60 ml), $Pd(PPh_3)_4$ (3.56 g, 3.08 mmol) and $K_2CO_3$ (25.51 g, 184.56 mmol) were introduced thereto, and the result was stirred for 2 hours under reflux. After the reaction was completed, MC was introduced to the reaction solution for dissolution, and the result was extracted with distilled water. After drying the organic layer with anhydrous $MgSO_4$, the solvent was removed using a rotary evaporator, and then the result was purified by column chromatography using dichloromethane and hexane as a developing solvent to obtain Compound A-4 (16.35 g, 74%).

2) Preparation of Compound 125

After dissolving Compound A-4 (7.14 g, 19.87 mmol) and N-(4-(9,9-dimethyl-9H-fluoren-2-yl)phenyl)phenanthren-9-amine (9.17 g, 19.87 mmol) in toluene (140 ml), $Pd(dba)_2$ (1.14 g, 1.99 mmol), $P(t\text{-}Bu)_3$ (1.65 ml, 3.97 mmol) and t-BuONa (3.82 g, 39.74 mmol) were introduced thereto, and the result was stirred for 12 hours under reflux. After the reaction was completed, MC was introduced to the reaction solution for dissolution, and the result was extracted with distilled water. After drying the organic layer with anhydrous $MgSO_4$, the solvent was removed using a rotary evaporator, and then the result was purified by column chromatography using dichloromethane and hexane as a developing solvent to obtain Compound 125 (12.79 g, 87%).

As in the following Table 2, target compounds were synthesized in the same manner as in Preparation Example 2 except that Compound C was used instead of A-3, Compound D was used instead of (4-bromophenyl)boronic acid, and Compound E was used instead of N-(4-(9,9-dimethyl-9H-fluoren-2-yl)phenyl) phenanthren-9-amine.

TABLE 2

| Compound No. | Compound C | Compound D | Compound E |
|---|---|---|---|
| 3 | 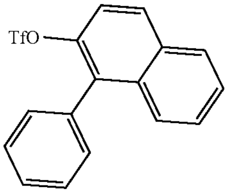 [SMILES: O=S(=O)(Oc1ccc2ccccc2c1-c1ccccc1)C(F)(F)F] | 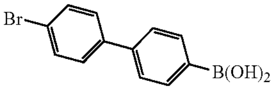 [SMILES: OB(O)c1ccc(-c2ccc(Br)cc2)cc1] | 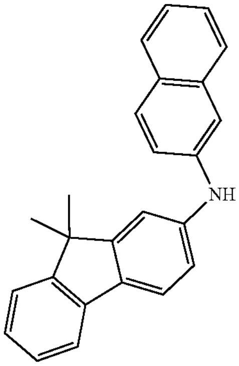 [SMILES: CC1(C)c2ccccc2-c2ccc(Nc3ccc4ccccc4c3)cc21] |
| 16 | 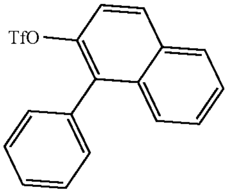 [SMILES: O=S(=O)(Oc1ccc2ccccc2c1-c1ccccc1)C(F)(F)F] | 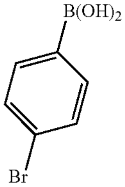 | 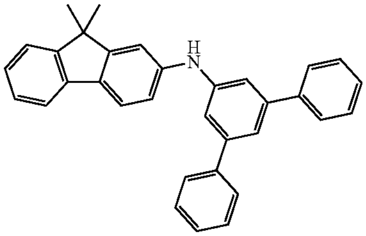 [SMILES: CC1(C)c2ccccc2-c2ccc(Nc3cc(-c4ccccc4)cc(-c4ccccc4)c3)cc21] |
| 21 | 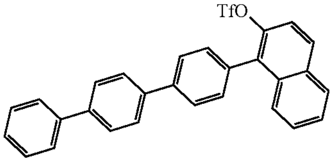 [SMILES: O=S(=O)(Oc1ccc2ccccc2c1-c1ccc(-c2ccc(-c3ccccc3)cc2)cc1)C(F)(F)F] | 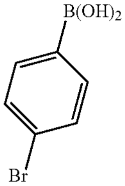 | 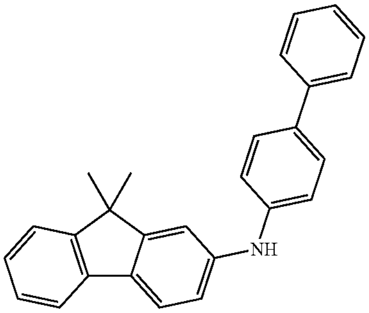 [SMILES: CC1(C)c2ccccc2-c2ccc(Nc3ccc(-c4ccccc4)cc3)cc21] |

TABLE 2-continued
| | | | |
|---|---|---|---|
| 22 | 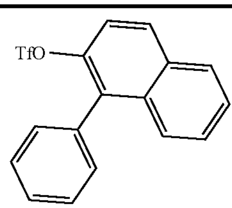 | 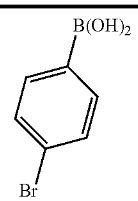 | 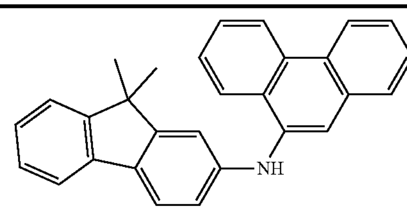 |
| 30 | 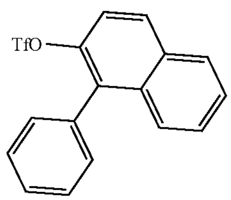 [SMILES: O=S(=O)(Oc1ccc2ccccc2c1-c1ccccc1)C(F)(F)F] | 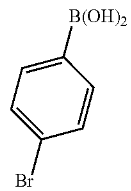 | 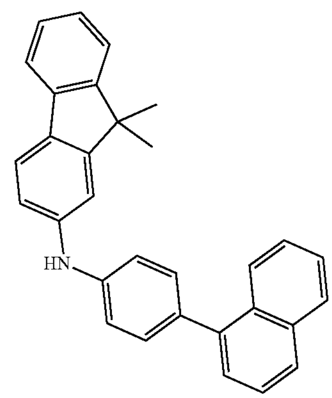 [SMILES: CC1(C)c2ccccc2-c2ccc(Nc3ccc(-c4cccc5ccccc45)cc3)cc21] |
| 32 | 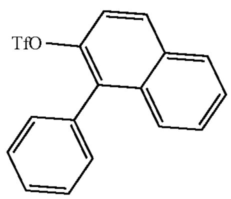 [SMILES: O=S(=O)(Oc1ccc2ccccc2c1-c1ccccc1)C(F)(F)F] | 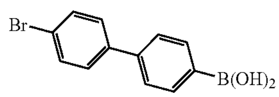 [SMILES: OB(O)c1ccc(-c2ccc(Br)cc2)cc1] | 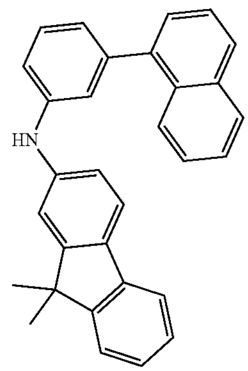 [SMILES: CC1(C)c2ccccc2-c2ccc(Nc3cccc(-c4cccc5ccccc45)c3)cc21] |
| 38 | 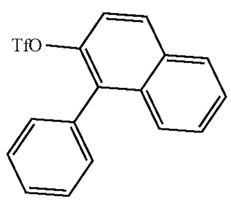 [SMILES: O=S(=O)(Oc1ccc2ccccc2c1-c1ccccc1)C(F)(F)F] | 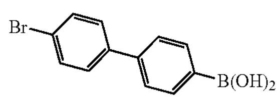 [SMILES: OB(O)c1ccc(-c2ccc(Br)cc2)cc1] | 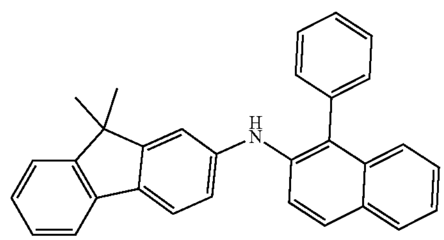 [SMILES: CC1(C)c2ccccc2-c2ccc(Nc3ccc4ccccc4c3-c3ccccc3)cc21] |
| 69 | 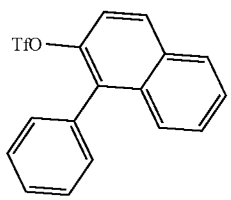 [SMILES: O=S(=O)(Oc1ccc2ccccc2c1-c1ccccc1)C(F)(F)F] | 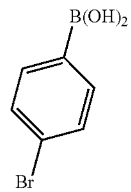 | 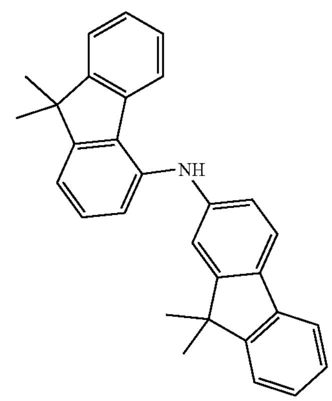 [SMILES: CC1(C)c2ccccc2-c2ccc(Nc3cccc4c3-c3ccccc3C4(C)C)cc21] |

TABLE 2-continued
| | | | |
|---|---|---|---|
| 81 | 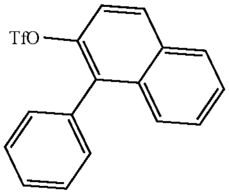 [SMILES: O=S(=O)(Oc1ccc2ccccc2c1-c1ccccc1)C(F)(F)F] | 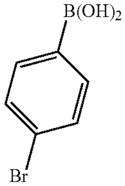 | 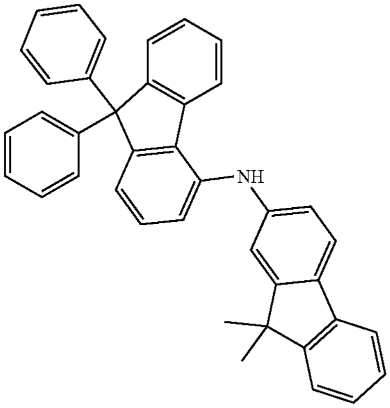 [SMILES: CC1(C)c2ccccc2-c2ccc(Nc3cccc4c3-c3ccccc3C4(c3ccccc3)c3ccccc3)cc21] |
| 83 | 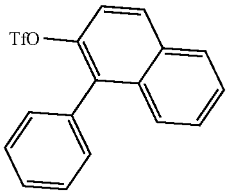 [SMILES: O=S(=O)(Oc1ccc2ccccc2c1-c1ccccc1)C(F)(F)F] | 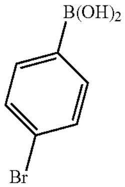 | 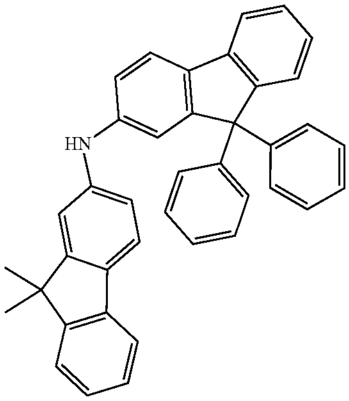 [SMILES: CC1(C)c2ccccc2-c2ccc(Nc3ccc4c(c3)C(c3ccccc3)(c3ccccc3)c3ccccc3-4)cc21] |
| 92 | 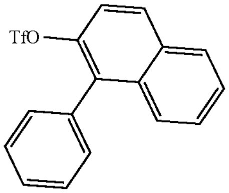 [SMILES: O=S(=O)(Oc1ccc2ccccc2c1-c1ccccc1)C(F)(F)F] | 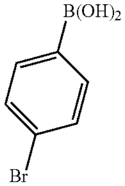 | 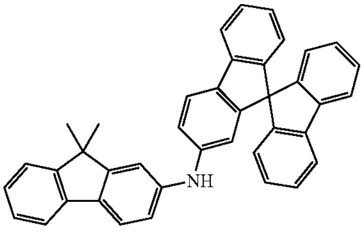 [SMILES: CC1(C)c2ccccc2-c2ccc(Nc3ccc4c(c3)C3(c5ccccc5-c5ccccc53)c3ccccc3-4)cc21] |
| 126 | 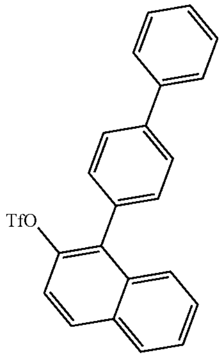 [SMILES: O=S(=O)(Oc1ccc2ccccc2c1-c1ccc(-c2ccccc2)cc1)C(F)(F)F] | 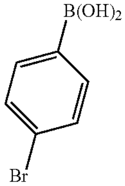 | 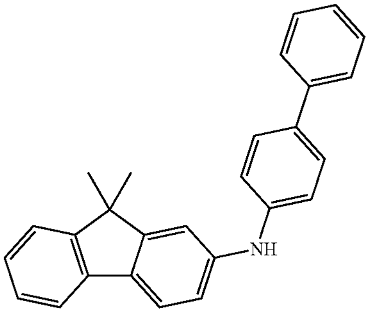 [SMILES: CC1(C)c2ccccc2-c2ccc(Nc3ccc(-c4ccccc4)cc3)cc21] |

TABLE 2-continued
| | | | |
|---|---|---|---|
| 136 | 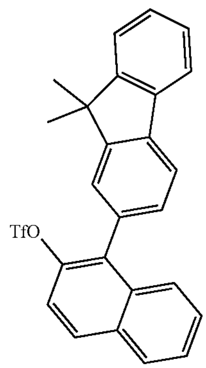 [SMILES: CC1(C)c2ccccc2-c2ccc(-c3c(OS(=O)(=O)C(F)(F)F)ccc4ccccc34)cc21] | 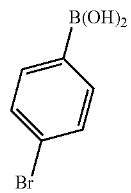 | 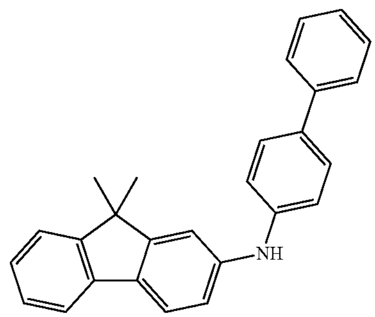 [SMILES: CC1(C)c2ccccc2-c2ccc(Nc3ccc(-c4ccccc4)cc3)cc21] |
| 152 | 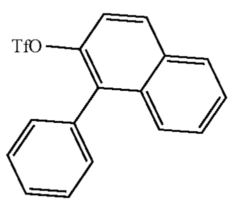 [SMILES: O=S(=O)(Oc1ccc2ccccc2c1-c1ccccc1)C(F)(F)F] | 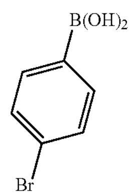 | 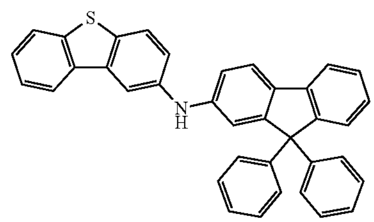 [SMILES: c1ccc(C2(c3ccccc3)c3ccccc3-c3ccc(Nc4ccc5sc6ccccc6c5c4)cc32)cc1] |
| 181 | 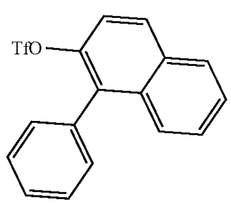 | 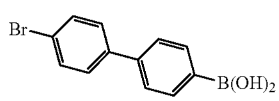 [SMILES: OB(O)c1ccc(-c2ccc(Br)cc2)cc1] | 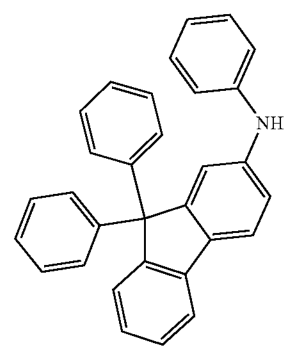 [SMILES: c1ccc(Nc2ccc3c(c2)C(c2ccccc2)(c2ccccc2)c2ccccc2-3)cc1] |
| 184 | 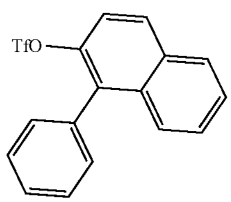 [SMILES: O=S(=O)(Oc1ccc2ccccc2c1-c1ccccc1)C(F)(F)F] | 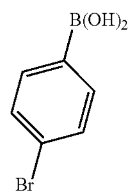 | 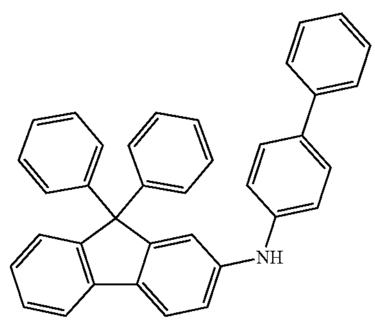 [SMILES: c1ccc(-c2ccc(Nc3ccc4c(c3)C(c3ccccc3)(c3ccccc3)c3ccccc3-4)cc2)cc1] |
| 224 | 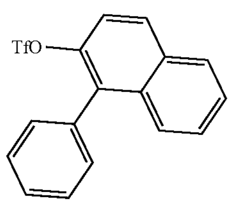 [SMILES: O=S(=O)(Oc1ccc2ccccc2c1-c1ccccc1)C(F)(F)F] | 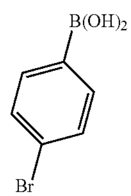 | 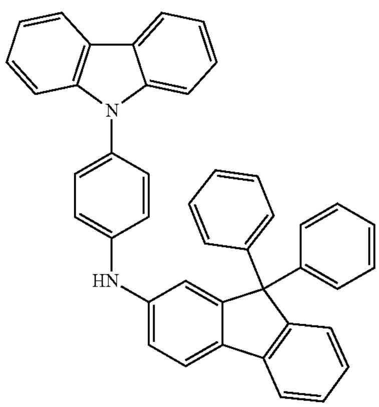 [SMILES: c1ccc(C2(c3ccccc3)c3ccccc3-c3ccc(Nc4ccc(-n5c6ccccc6c6ccccc65)cc4)cc32)cc1] |

TABLE 2-continued
| | | | |
|---|---|---|---|
| 240 | 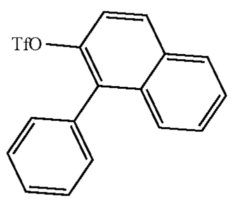 [SMILES: O=S(=O)(Oc1ccc2ccccc2c1-c1ccccc1)C(F)(F)F] | 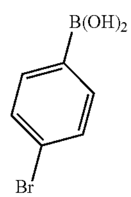 | 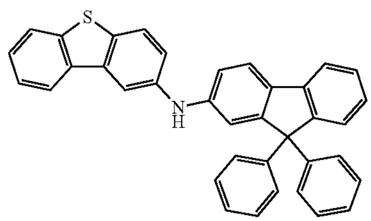 [SMILES: c1ccc(C2(c3ccccc3)c3ccccc3-c3ccc(Nc4ccc5sc6ccccc6c5c4)cc32)cc1] |
| 241 | 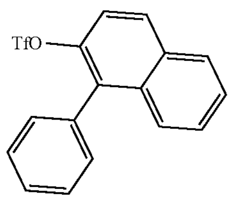 [SMILES: O=S(=O)(Oc1ccc2ccccc2c1-c1ccccc1)C(F)(F)F] | 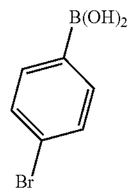 | 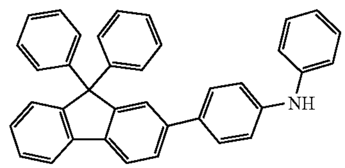 [SMILES: c1ccc(Nc2ccc(-c3ccc4c(c3)C(c3ccccc3)(c3ccccc3)c3ccccc3-4)cc2)cc1] |
| 252 | 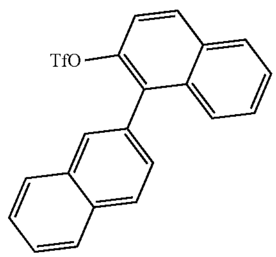 [SMILES: O=S(=O)(Oc1ccc2ccccc2c1-c1ccc2ccccc2c1)C(F)(F)F] | 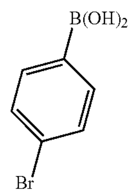 | 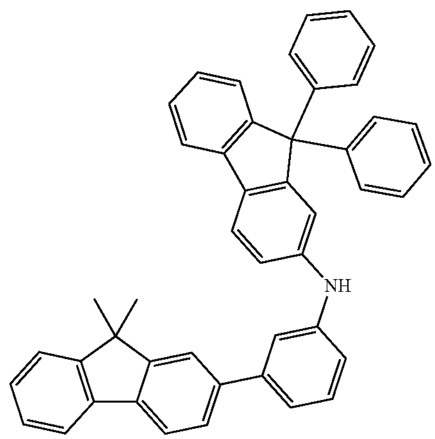 [SMILES: CC1(C)c2ccccc2-c2ccc(-c3cccc(Nc4ccc5c(c4)C(c4ccccc4)(c4ccccc4)c4ccccc4-5)c3)cc21] |
| 262 | 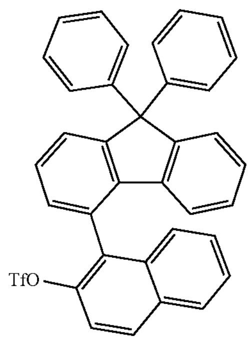 [SMILES: O=S(=O)(Oc1ccc2ccccc2c1-c1cccc2c1-c1ccccc1C2(c1ccccc1)c1ccccc1)C(F)(F)F] | 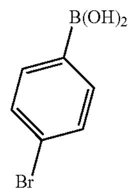 | 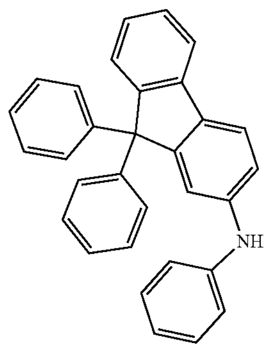 [SMILES: c1ccc(Nc2ccc3c(c2)C(c2ccccc2)(c2ccccc2)c2ccccc2-3)cc1] |
| 264 | 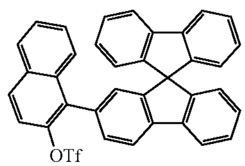 [SMILES: O=S(=O)(Oc1ccc2ccccc2c1-c1ccc2c(c1)C1(c3ccccc3-c3ccccc31)c1ccccc1-2)C(F)(F)F] | 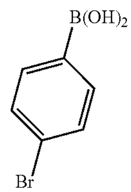 | 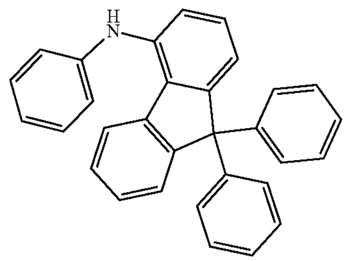 [SMILES: c1ccc(Nc2cccc3c2-c2ccccc2C3(c2ccccc2)c2ccccc2)cc1] |

TABLE 2-continued
| | | | |
|---|---|---|---|
| 273 | 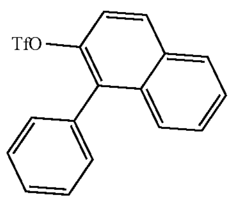 [SMILES: O=S(=O)(Oc1ccc2ccccc2c1-c1ccccc1)C(F)(F)F] | 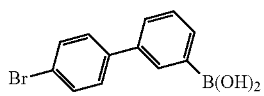 | 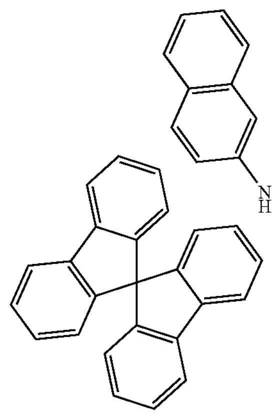 |
| 275 | 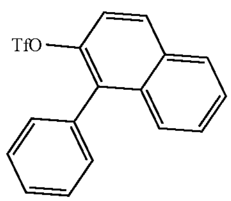 [SMILES: O=S(=O)(Oc1ccc2ccccc2c1-c1ccccc1)C(F)(F)F] | 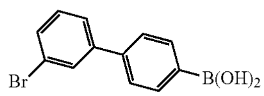 [SMILES: OB(O)c1ccc(-c2cccc(Br)c2)cc1] | 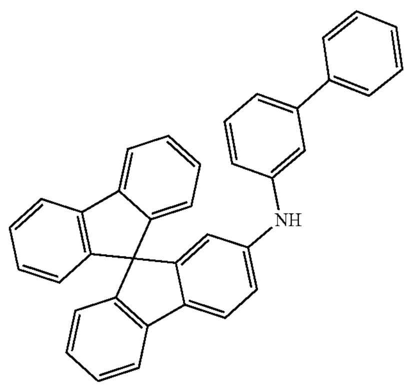 [SMILES: c1ccc(-c2cccc(Nc3ccc4c(c3)C3(c5ccccc5-c5ccccc53)c3ccccc3-4)c2)cc1] |
| 284 | 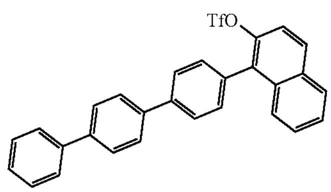 [SMILES: O=S(=O)(Oc1ccc2ccccc2c1-c1ccc(-c2ccc(-c3ccccc3)cc2)cc1)C(F)(F)F] | 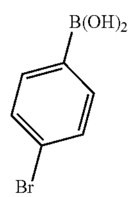 | 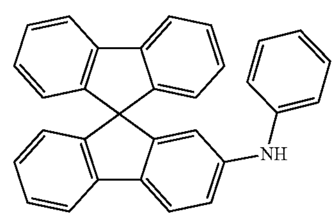 [SMILES: c1ccc(Nc2ccc3c(c2)C2(c4ccccc4-c4ccccc42)c2ccccc2-3)cc1] |
| 337 | 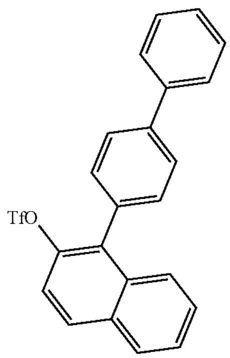 [SMILES: O=S(=O)(Oc1ccc2ccccc2c1-c1ccc(-c2ccccc2)cc1)C(F)(F)F] | 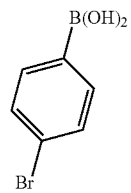 | 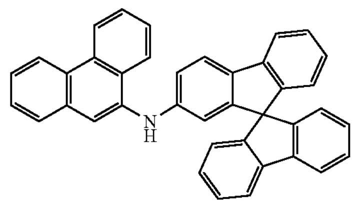 [SMILES: c1ccc2c(c1)-c1ccccc1C21c2ccccc2-c2ccc(Nc3cc4ccccc4c4ccccc34)cc21] |

TABLE 2-continued
| | | | |
|---|---|---|---|
| 356 | 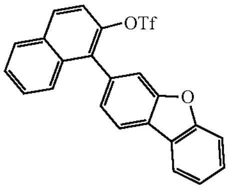 [SMILES: O=S(=O)(Oc1ccc2ccccc2c1-c1ccc2c(c1)oc1ccccc12)C(F)(F)F] | 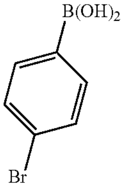 | 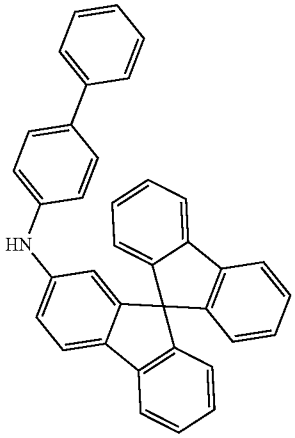 [SMILES: c1ccc(-c2ccc(Nc3ccc4c(c3)C3(c5ccccc5-c5ccccc53)c3ccccc3-4)cc2)cc1] |
| 359 | 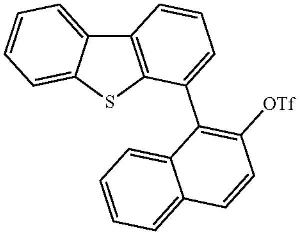 [SMILES: O=S(=O)(Oc1ccc2ccccc2c1-c1cccc2c1sc1ccccc12)C(F)(F)F] | 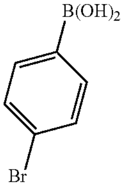 | 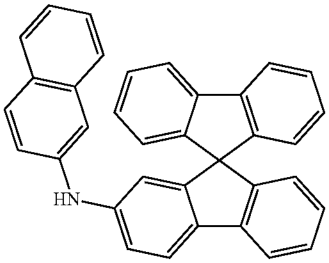 [SMILES: c1ccc2c(c1)-c1ccccc1C21c2ccccc2-c2ccc(Nc3ccc4ccccc4c3)cc21] |
| Compound No. | Target compound | Yield |
|---|---|---|
| 3 | 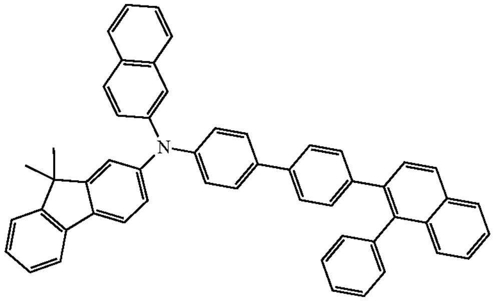 [SMILES: CC1(C)c2ccccc2-c2ccc(N(c3ccc(-c4ccc(-c5ccc6ccccc6c5-c5ccccc5)cc4)cc3)c3ccc4ccccc4c3)cc21] | 81% |
| 16 | 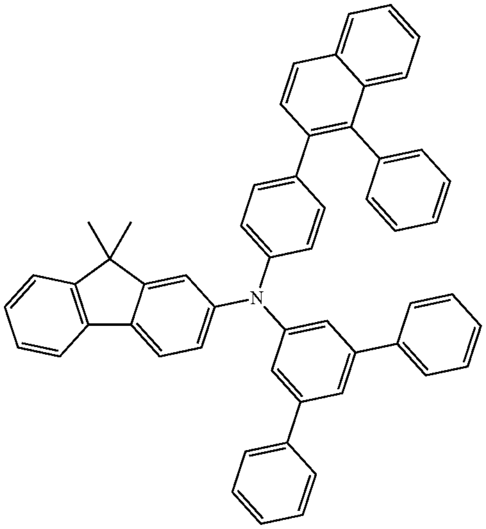 [SMILES: CC1(C)c2ccccc2-c2ccc(N(c3ccc(-c4ccc5ccccc5c4-c4ccccc4)cc3)c3cc(-c4ccccc4)cc(-c4ccccc4)c3)cc21] | 62% |

TABLE 2-continued
| | | |
|---|---|---|
| 21 | 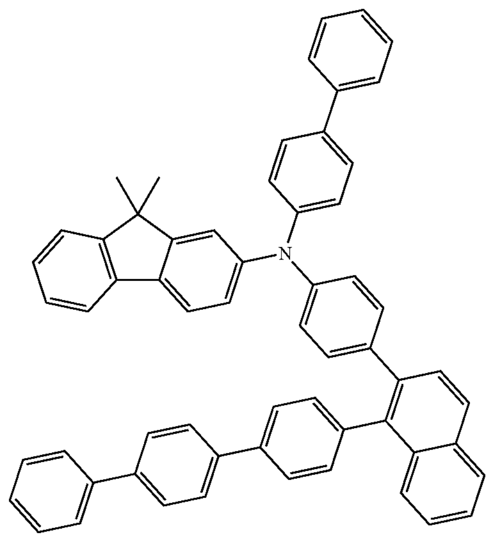 [SMILES: CC1(C)c2ccccc2-c2ccc(N(c3ccc(-c4ccccc4)cc3)c3ccc(-c4ccc5ccccc5c4-c4ccc(-c5ccc(-c6ccccc6)cc5)cc4)cc3)cc21] | 76% |
| 22 | 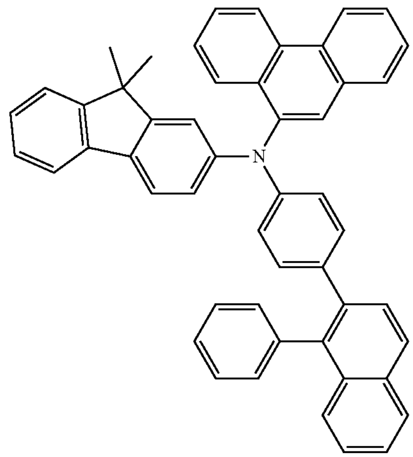 [SMILES: CC1(C)c2ccccc2-c2ccc(N(c3ccc(-c4ccc5ccccc5c4-c4ccccc4)cc3)c3cc4ccccc4c4ccccc34)cc21] | 78% |
| 30 | 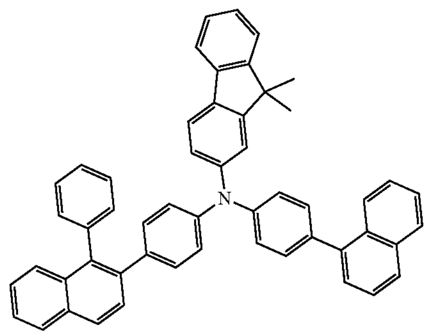 [SMILES: CC1(C)c2ccccc2-c2ccc(N(c3ccc(-c4ccc5ccccc5c4-c4ccccc4)cc3)c3ccc(-c4cccc5ccccc45)cc3)cc21] | 86% |
| 32 | 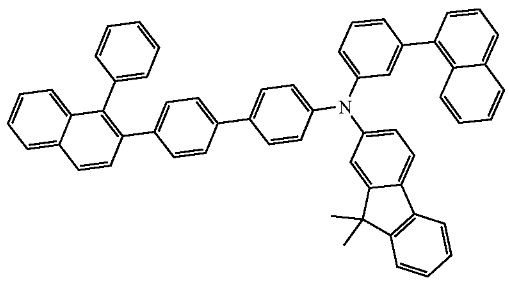 [SMILES: CC1(C)c2ccccc2-c2ccc(N(c3ccc(-c4ccc(-c5ccc6ccccc6c5-c5ccccc5)cc4)cc3)c3cccc(-c4cccc5ccccc45)c3)cc21] | 91% |

TABLE 2-continued
| | | |
|---|---|---|
| 38 | 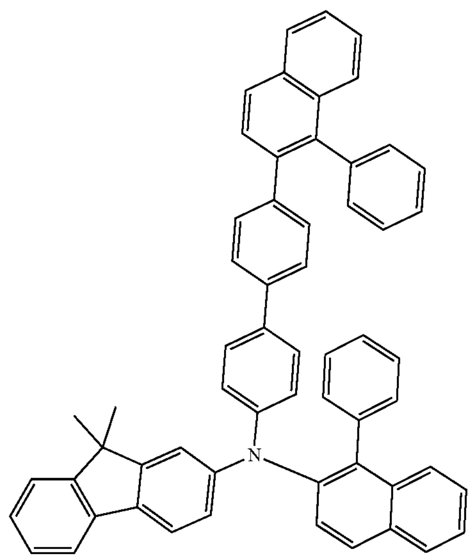 [SMILES: CC1(C)c2ccccc2-c2ccc(N(c3ccc(-c4ccc(-c5ccc6ccccc6c5-c5ccccc5)cc4)cc3)c3ccc4ccccc4c3-c3ccccc3)cc21] | 62% |
| 69 | 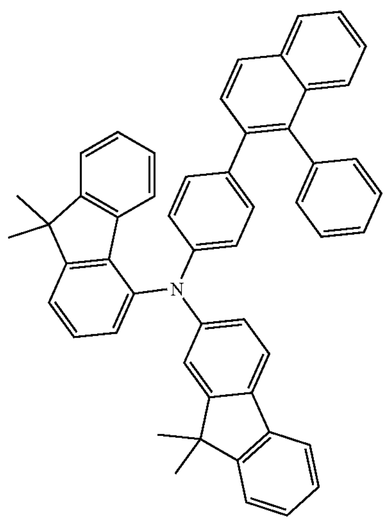 [SMILES: CC1(C)c2ccccc2-c2ccc(N(c3ccc(-c4ccc5ccccc5c4-c4ccccc4)cc3)c3cccc4c3-c3ccccc3C4(C)C)cc21] | 78% |
| 81 | 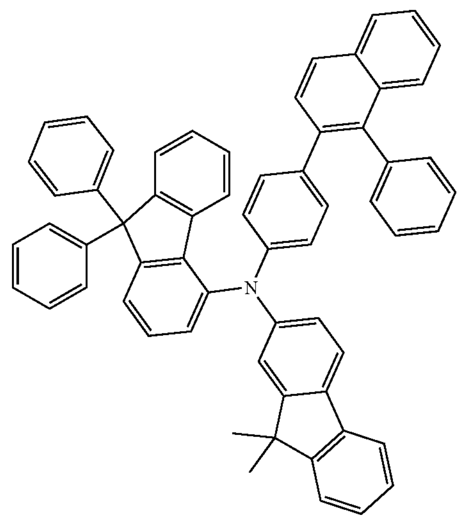 [SMILES: CC1(C)c2ccccc2-c2ccc(N(c3ccc(-c4ccc5ccccc5c4-c4ccccc4)cc3)c3cccc4c3-c3ccccc3C4(c3ccccc3)c3ccccc3)cc21] | 77% |

TABLE 2-continued
| | | |
|---|---|---|
| 83 | 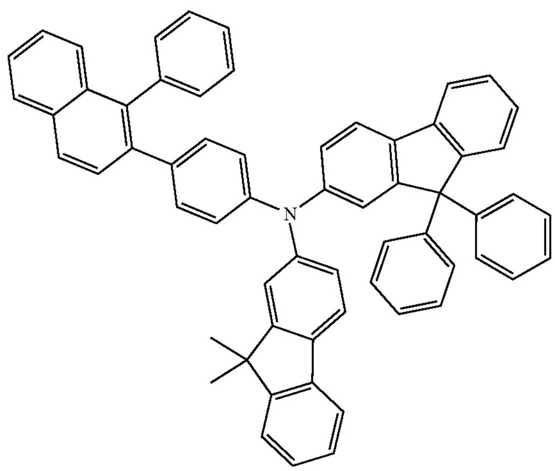 [SMILES: CC1(C)c2ccccc2-c2ccc(N(c3ccc(-c4ccc5ccccc5c4-c4ccccc4)cc3)c3ccc4c(c3)C(c3ccccc3)(c3ccccc3)c3ccccc3-4)cc21] | 69% |
| 92 | 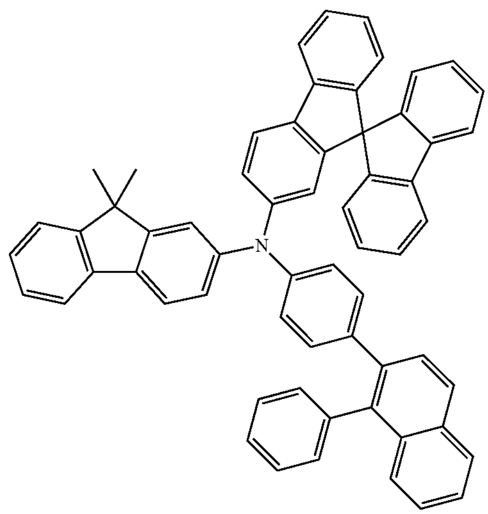 [SMILES: CC1(C)c2ccccc2-c2ccc(N(c3ccc(-c4ccc5ccccc5c4-c4ccccc4)cc3)c3ccc4c(c3)C3(c5ccccc5-c5ccccc53)c3ccccc3-4)cc21] | 83% |
| 126 | 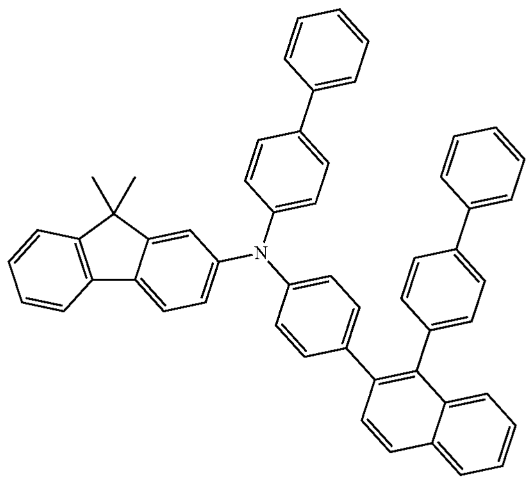 [SMILES: CC1(C)c2ccccc2-c2ccc(N(c3ccc(-c4ccccc4)cc3)c3ccc(-c4ccc5ccccc5c4-c4ccc(-c5ccccc5)cc4)cc3)cc21] | 89% |

TABLE 2-continued
| | | |
|---|---|---|
| 136 | 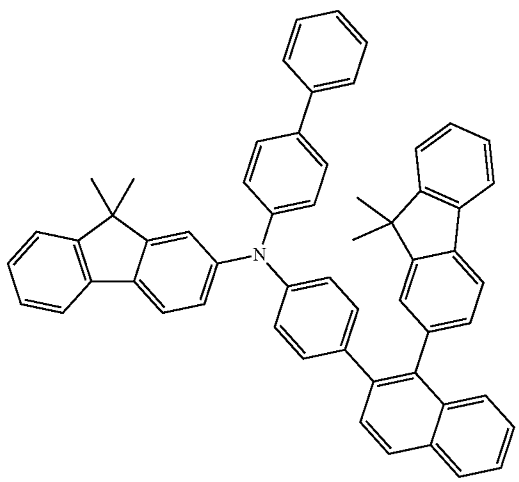 [SMILES: CC1(C)c2ccccc2-c2ccc(-c3c(-c4ccc(N(c5ccc(-c6ccccc6)cc5)c5ccc6c(c5)C(C)(C)c5ccccc5-6)cc4)ccc4ccccc34)cc21] | 88% |
| 152 | 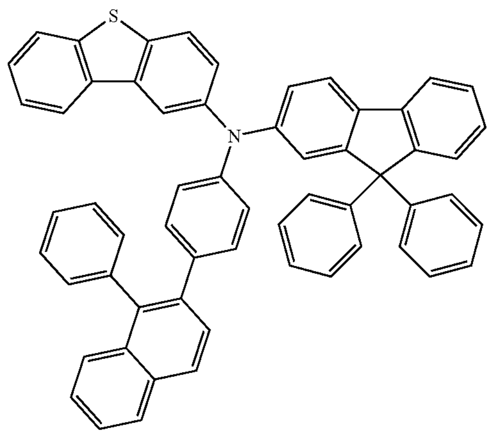 [SMILES: c1ccc(-c2c(-c3ccc(N(c4ccc5c(c4)C(c4ccccc4)(c4ccccc4)c4ccccc4-5)c4ccc5sc6ccccc6c5c4)cc3)ccc3ccccc23)cc1] | 67% |
| 181 | 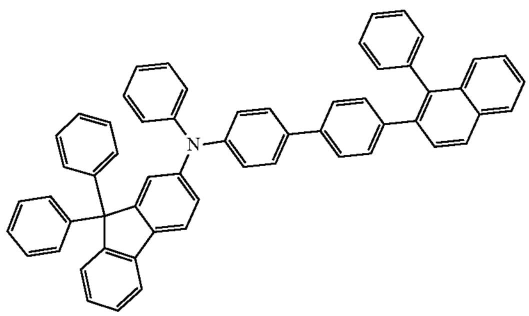 [SMILES: c1ccc(-c2c(-c3ccc(-c4ccc(N(c5ccccc5)c5ccc6c(c5)C(c5ccccc5)(c5ccccc5)c5ccccc5-6)cc4)cc3)ccc3ccccc23)cc1] | 73% |

TABLE 2-continued
| | | |
|---|---|---|
| 184 | 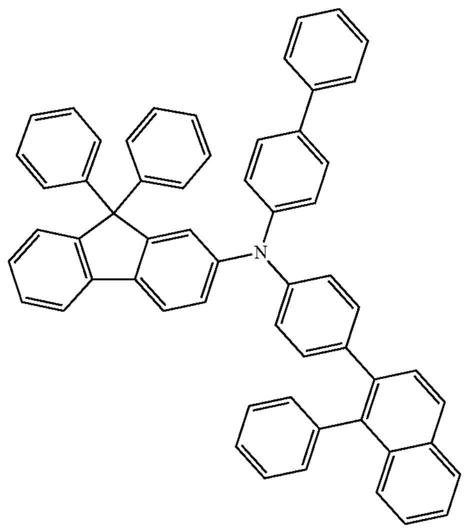 [SMILES: c1ccc(-c2ccc(N(c3ccc(-c4ccc5ccccc5c4-c4ccccc4)cc3)c3ccc4c(c3)C(c3ccccc3)(c3ccccc3)c3ccccc3-4)cc2)cc1] | 85% |
| 224 | 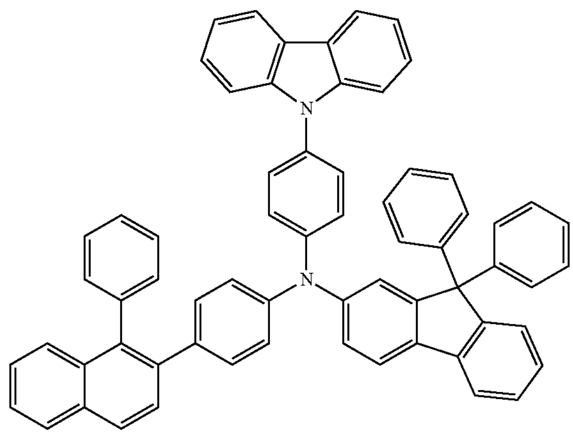 [SMILES: c1ccc(-c2c(-c3ccc(N(c4ccc(-n5c6ccccc6c6ccccc65)cc4)c4ccc5c(c4)C(c4ccccc4)(c4ccccc4)c4ccccc4-5)cc3)ccc3ccccc23)cc1] | 72% |
| 240 | 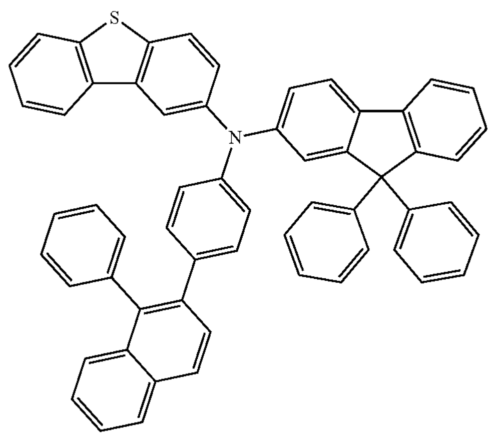 [SMILES: c1ccc(-c2c(-c3ccc(N(c4ccc5c(c4)C(c4ccccc4)(c4ccccc4)c4ccccc4-5)c4ccc5sc6ccccc6c5c4)cc3)ccc3ccccc23)cc1] | 74% |

TABLE 2-continued
| | | |
|---|---|---|
| 241 | 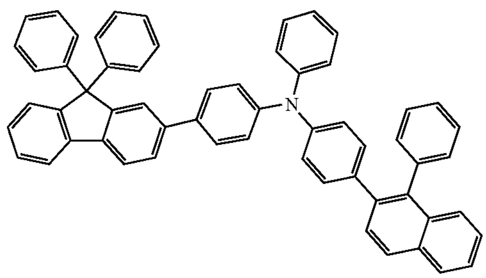 [SMILES: c1ccc(-c2c(-c3ccc(N(c4ccccc4)c4ccc(-c5ccc6c(c5)C(c5ccccc5)(c5ccccc5)c5ccccc5-6)cc4)cc3)ccc3ccccc23)cc1] | 69% |
| 252 | 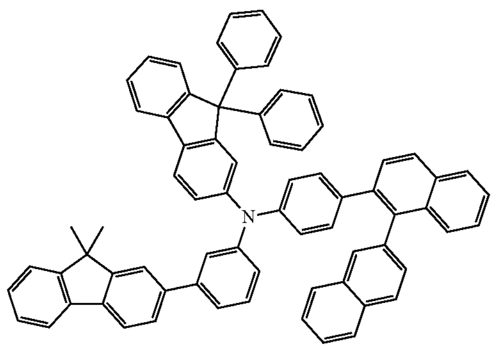 [SMILES: CC1(C)c2ccccc2-c2ccc(-c3cccc(N(c4ccc(-c5ccc6ccccc6c5-c5ccc6ccccc6c5)cc4)c4ccc5c(c4)C(c4ccccc4)(c4ccccc4)c4ccccc4-5)c3)cc21] | 76% |
| 262 | 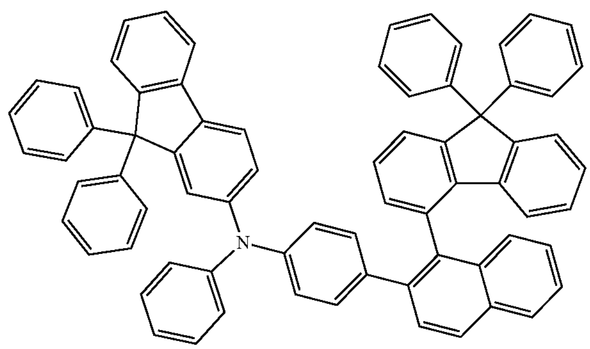 [SMILES: c1ccc(N(c2ccc(-c3ccc4ccccc4c3-c3cccc4c3-c3ccccc3C4(c3ccccc3)c3ccccc3)cc2)c2ccc3c(c2)C(c2ccccc2)(c2ccccc2)c2ccccc2-3)cc1] | 71% |
| 264 | 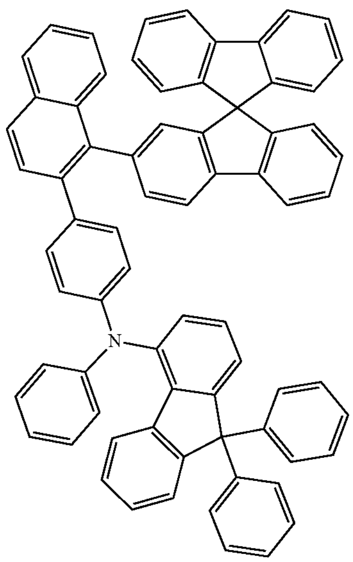 [SMILES: c1ccc(N(c2ccc(-c3ccc4ccccc4c3-c3ccc4c(c3)C3(c5ccccc5-c5ccccc53)c3ccccc3-4)cc2)c2cccc3c2-c2ccccc2C3(c2ccccc2)c2ccccc2)cc1] | 66% |

TABLE 2-continued
| | | |
|---|---|---|
| 273 | 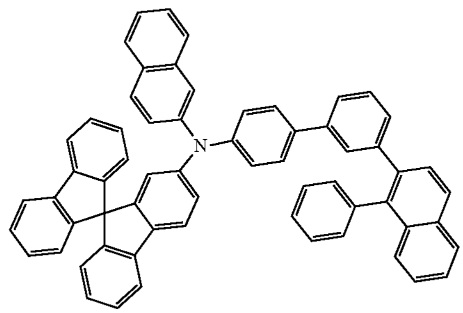 [SMILES: c1ccc(-c2c(-c3cccc(-c4ccc(N(c5ccc6c(c5)C5(c7ccccc7-c7ccccc75)c5ccccc5-6)c5ccc6ccccc6c5)cc4)c3)ccc3ccccc23)cc1] | 77% |
| 275 | 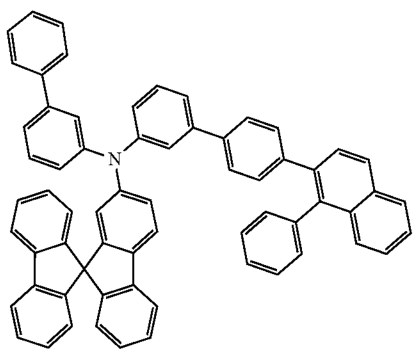 [SMILES: c1ccc(-c2cccc(N(c3cccc(-c4ccc(-c5ccc6ccccc6c5-c5ccccc5)cc4)c3)c3ccc4c(c3)C3(c5ccccc5-c5ccccc53)c3ccccc3-4)c2)cc1] | 64% |
| 284 | 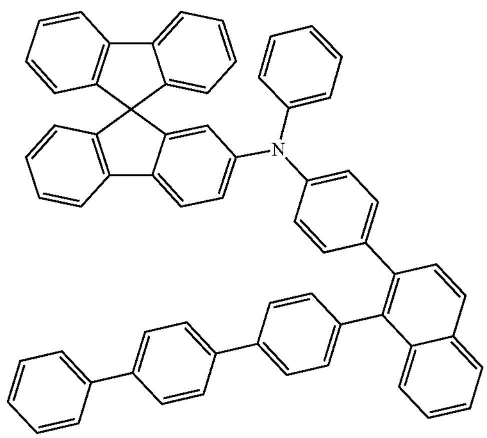 [SMILES: c1ccc(-c2ccc(-c3ccc(-c4c(-c5ccc(N(c6ccccc6)c6ccc7c(c6)C6(c8ccccc8-c8ccccc86)c6ccccc6-7)cc5)ccc5ccccc45)cc3)cc2)cc1] | 83% |

TABLE 2-continued
| | | |
|---|---|---|
| 337 | 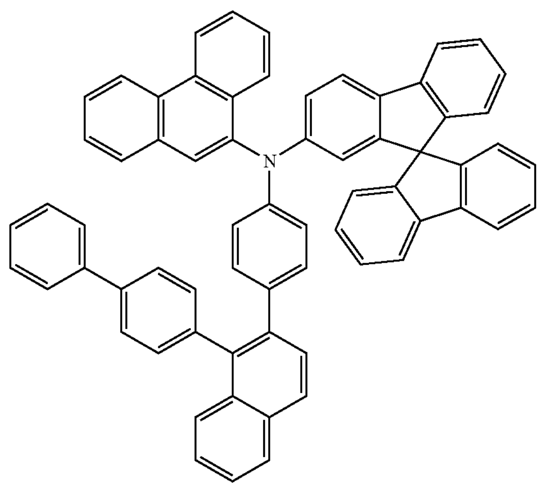 [SMILES: c1ccc(-c2ccc(-c3c(-c4ccc(N(c5ccc6c(c5)C5(c7ccccc7-c7ccccc75)c5ccccc5-6)c5cc6ccccc6c6ccccc56)cc4)ccc4ccccc34)cc2)cc1] | 70% |
| 356 | 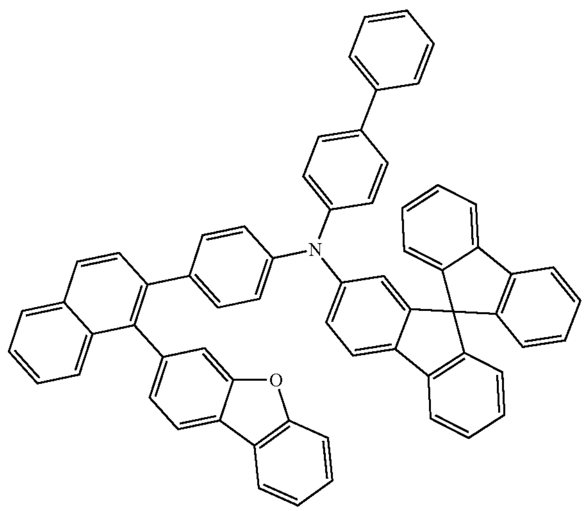 [SMILES: c1ccc(-c2ccc(N(c3ccc(-c4ccc5ccccc5c4-c4ccc5c(c4)oc4ccccc45)cc3)c3ccc4c(c3)C3(c5ccccc5-c5ccccc53)c3ccccc3-4)cc2)cc1] | 80% |
| 359 | 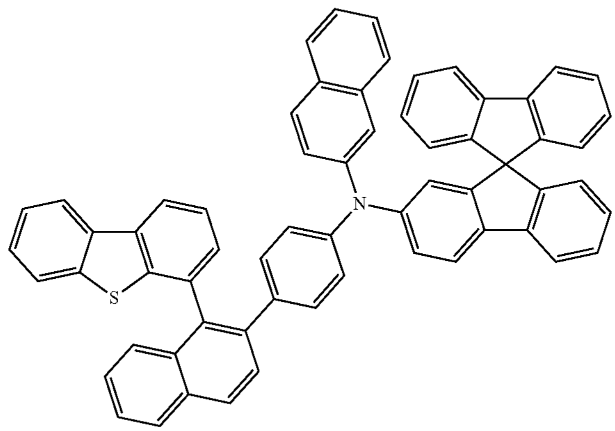 [SMILES: c1ccc2c(c1)-c1ccccc1C21c2ccccc2-c2ccc(N(c3ccc(-c4ccc5ccccc5c4-c4cccc5c4sc4ccccc45)cc3)c3ccc4ccccc4c3)cc21] | 75% |

Compounds described in the present specification were prepared in the same manner as in the preparation examples, and synthesis identification results of the prepared compounds are shown in the following Table 3 and Table 4. The following Table 3 shows measurement values of $^1$H NMR (DMSO, 300 MHz), and the following Table 4 shows measurement values of FD-mass

TABLE 3

| Compound | $^1$H NMR (DMSO, 300 MHz) |
|---|---|
| 1 | δ = 8.80(1H, d), 7.97-7.86(4H, m), 7.76(1H, d), 7.51-7.20(14H, m), 7.08(2H, d), 7.00(1H, t), 1.69(6H, s) |
| 3 | δ = 8.93(1H, d), 8.31(1H, d), 8.26(1H, d), 7.90-7.86(2H, m), 7.78-7.65(5H, m), 7.55-7.28(21H, m), 7.16(1H, d), 7.11(1H, s), 1.69(6H, s) |
| 5 | δ = 8.80(1H, d), 7.97-7.86(4H, m), 7.76(3H, d), 7.55-7.17(19H, m), 1.69(6H, m) |
| 13 | δ = 8.80(1H, d), 8.10(1H, d), 7.97-7.86(4H, m), 7.76(3H, d), 7.55-7.16(22H, m), 1.69(6H, s) |
| 16 | δ = 8.93(1H, d), 8.31(1H, d), 8.26(1H, d), 7.90(1H, d), 7.86(1H, d), 7.75-7.28(29H, m), 7.16(1H, d), 1.69(6H, s) |
| 21 | δ = 8.93(1H, d), 8.31(1H, d), 8.26(1H, d), 7.90(1H, d), 7.86(1H, d), 7.75-7.72(5H, m), 7.55-7.25(28H, m), 7.16(1H, d), 1.69(6H, s) |
| 22 | δ = 8.98(1H, d), 8.93(1H, d), 8.84(1H, d), 8.31(1H, d), 8.26(1H, d), 8.11(1H, d), 7.90(2H, d), 7.86(1H, d), 7.72-7.49(14H, m), 7.41-7.28(7H, m), 7.16(1H, d), 1.69(6H, s) |
| 24 | δ = 9.08(1H, d), 8.84(1H, d), 8.80(1H, d), 8.27(1H, d), 8.05(1H, s), 7.97-7.86(5H, m), 7.70-7.17(21H, m), 1.69(6H, s) |
| 30 | δ = 8.95(1H, d), 8.93(1H, d), 8.50(1H, d), 8.31-8.20(3H, m), 8.09(1H, d), 7.90(1H, d), 7.86(1H, d), 7.77-7.65(4H, m), 7.55-7.52(9H, m), 7.41-7.28(10H, m), 7.16(1H, d), 1.69(6H, s) |
| 32 | δ = 8.95(1H, d), 8.93(1H, d), 8.50(1H, d), 8.31-8.20(3H, m), 8.09(1H, d), 7.90-7.86(2H, m), 7.77-7.54(12H, m), 7.41-7.16(16H, m), 1.69(6H, s) |
| 38 | δ = 8.93(1H, d), 8.80(1H, d), 8.31(1H, d), 8.26(1H, d), 7.97-7.86(4H, m), 7.76-7.65(4H, m), 7.55-7.16(25H, m), 1.69(6H, s) |
| 43 | δ = 8.80(1H, d), 8.39(1H, d), 8.19(1H, d), 7.97-7.89(3H, m), 7.75(2H, d), 7.62-7.38(12H, m), 7.28-7.16(15H, m), 6.40(1H, d), 1.69(6H, s) |
| 49 | δ = 8.80(1H, d), 7.98-7.89(4H, m), 7.76(1H, d), 7.55-7.16(18H, m), 6.91(1H, d), 1.69(6H, s) |
| 60 | δ = 8.80(1H, d), 8.46(1H, d), 7.97-7.85(7H, m), 7.76(1H, d), 7.56-7.16(15H, m), 1.69(6H, s) |
| 69 | δ = 8.93(1H, d), 8.31(1H, d), 8.26(1H, d), 7.90-7.86(3H, m), 7.72(1H, d), 7.65(2H, d), 7.55(7H, d), 7.41-7.16(13H, m), 1.69(12H, s) |
| 70 | δ = 8.80(1H, d), 7.97-7.86(5H, m), 7.76(1H, d), 7.62(1H, s), 7.55-7.16(16H, m), 7.06(1H, d), 1.69(12H, s) |
| 81 | δ = 8.93(1H, d), 8.31(1H, d), 8.26(1H, d), 7.90-7.86(3H, m), 7.72(1H, d), 7.65(2H, d), 7.55(7H, d), 7.41-7.10(23H, m), 1.69(6H, s) |
| 83 | δ = 8.93(1H, d), 8.31-8.26(2H, m), 7.90(2H, d), 7.86(2H, d), 7.72(1H, d), 7.65(2H, d), 7.55(7H, d), 7.41-7.16(22H, m), 1.69(6H, s) |
| 86 | δ = 8.80(1H, d), 8.09(1H, d), 7.97-7.86(6H, m), 7.78-7.76(2H, m), 7.55-7.10(29H, m), 1.69(6H, s) |
| 91 | δ = 8.80(1H, d), 7.97-7.86(7H, m), 7.76(1H, d), 7.61-7.16(23H, m), 7.05(1H, d), 1.69(6H, s) |
| 92 | δ = 8.93(1H, d), 8.31(1H, d), 8.26(1H, d), 7.90-7.85(4H, m), 7.72(1H, d),7.65(2H, d),7.55-7.23(23H, m),7.16(1H, d), 7.06(1H, d), 1.69(6H, s) |
| 100 | δ = 8.80(1H, d), 7.97-7.89(4H, m), 7.76(1H, d), 7.62-7.01(27H, m), 1.69(6H, s) |
| 125 | δ = 8.98(1H, d), 8.93(1H, d), 8.84(1H, d), 8.31(1H, d), 8.26(1H, d), 8.11(1H, d), 8.09(1H, d), 7.90(2H, d), 7.89(1H, d), 7.78-7.49(17H, m), 7.41-7.28(8H, m), 1.69(6H, s) |
| 126 | δ = 8.93(1H, d), 8.31(1H, d), 8.26(1H, d), 7.90(1H, d), 7.86(1H, d), 7.75(4H, d), 7.72(1H, d), 7.55-7.25(24H, m), 7.16(1H, d), 1.69(6H, s) |
| 136 | δ = 8.93(1H, d), 8.31(1H, d), 8.26(1H, d), 8.09(1H, d), 7.90-7.86(4H, m), 7.78-7.72(4H, m), 7.55-7.28(20H, m), 7.16(1H, d), 1.69(12H, s) |
| 152 | δ = 8.93(1H, d), 8.45(1H, d), 8.31(1H, d), 8.26(1H, d), 7.95-7.85(5H, m), 7.72-7.10(30H, m) |
| 166 | δ = 8.80(1H, d), 8.45(1H, d), 8.01-7.89(7H, m), 7.76(1H, d), 7.64(1H, s), 7.56-7.20(22H, m) |
| 181 | δ = 8.93(1H, d), 8.31(1H, d), 8.26(1H, d), 7.90-7.86(2H, m), 7.72(1H, d), 7.65(2H, d), 7.55(6H, d), 7.41-7.00(27H, m) |
| 183 | δ = 8.80(1H, d), 7.97-.7.86(4H, m), 7.78-7.71(5H, m), 7.55-7.10(33H, m) |
| 184 | δ = 8.93(1H, d), 8.31-8.26(2H, m), 7.90-7.86(2H, m), 7.75-7.65(5H, m), 7.55-7.10(31H, m) |
| 223 | δ = 8.80(1H, d), 7.46(1H, d), 8.19(1H, d), 7.97-7.89(3H, m), 7.76(1H, d), 7.62-7.38(14H, m), 7.28-7.10(18H, m), 6.40(1H, d) |

TABLE 3-continued

| Compound | $^1$H NMR (DMSO, 300 MHz) |
|---|---|
| 224 | δ = 8.93(1H, d), 8.55(1H, d), 8.31-8.19(3H, m), 7.94(1H, d), 7.86(1H, d), 7.72-7.16(36H, m) |
| 240 | δ = 8.93(1H, d), 8.45(1H, d), 8.31(1H, d), 8.26(1H, d), 7.95-7.85(5H, m), 7.72-7.10(30H, m) |
| 241 | δ = 8.93(1H, d), 8.31(1H, d), 8.26(1H, d), 8.09(1H, d), 7.90(1H, d), 7.89(1H, s), 7.78-7.65(4H, m), 7.55(8H, d), 7.41-7.00(23H, m) |
| 252 | δ = 8.93(1H, d), 8.31(1H, d), 8.26(1H, d), 8.09-7.99(4H, m), 7.90-7.86(4H, m), 7.78(1H, d), 7.72(1H, d), 7.63-7.54(8H, m), 7.40-7.10(22H, m), 1.69(6H, s) |
| 262 | δ = 8.93(1H, d), 8.31(1H, d), 8.26(1H, d), 7.90-7.86(3H, m), 7.72-7.65(3H, m), 7.54-7.10(40H, m) |
| 264 | δ = 8.93(1H, d), 8.31(1H, d), 8.26(1H, d), 8.08(1H, d), 7.90-7.89(4H, d), 7.72(1H, d), 7.68(1H, d), 7.55(6H, d), 7.45-7.00(30H, m) |
| 271 | δ = 8.80(1H, d), 7.97-7.86(6H, m), 7.76(1H, d), 7.55-7.16(22H, m) |
| 273 | δ = 8.93(1H, d), 8.31(1H, d), 8.26(1H, d), 7.94-7.86(5H, m), 7.78-7.28(31H, m), 7.16(1H, d), 7.11(1H, s) |
| 275 | δ = 8.93(1H, d), 8.31(1H, d), 8.26(1H, d), 7.90-7.86(4H, m), 7.75-7.65(5H, m), 7.55-7.16(31H, m) |
| 284 | δ = 8.93(1H, d), 8.31(1H, d), 8.26(1H, d), 7.90-7.86(4H, m), 7.75-.7.72(3H, m), 7.54-7.24(30H, m), 7.08-7.00(3H, m) |
| 308 | δ = 8.80(2H, d), 7.97-7.86(8H, m), 7.76(2H, d), 7.51-7.16(25H, m) |
| 324 | δ = 8.80(1H, d), 7.98-7.69(9H, m), 7.57-7.20(26H, m), 7.06(1H, d) |
| 337 | δ = 8.98(1H, d), 8.93(1H, d), 8.84(1H, d), 8.31(1H, d), 8.26(1H, d), 8.11(1H, d), 7.90-7.86(5H, m), 7.68-7.25(31H, m), 7.16(1H, d) |
| 356 | δ = 8.93(1H, d), 8.31(1H, d), 8.26(1H, d), 8.03(1H, d), 7.98(1H, d), 7.90-7.72(9H, m), 7.55-7.27(26H, m), 7.16(1H, d) |
| 359 | δ = 8.93(1H, d), 8.55(1H, d), 8.45(1H, d), 8.32-8.26(3H, m), 7.93-7.86(5H, m),7.78-7.70(4H, m),7.56-7.27(22H, m),7.16(1H, d), 7.11(1H, s) |

TABLE 4

| Compound | FD-MS | Compound | FD-MS |
|---|---|---|---|
| 1 | m/z = 487.65 (C37H29N = 487.23) | 3 | m/z = 689.90 (C53H39N = 689.31) |
| 5 | m/z = 563.74 (C43H33N = 563.26) | 13 | m/z = 639.84 (C49H37N = 639.29) |
| 16 | m/z = 715.94 (C55H41N = 715.32) | 21 | m/z = 792.04 (C61H45N = 791.36) |
| 22 | m/z = 663.86 (C51H37N = 663.29) | 24 | m/z = 663.86 (C51H37N = 663.29) |
| 30 | m/z = 689.90 (C53H39N = 689.31) | 32 | m/z = 766.00 (C59H43N = 765.34) |
| 38 | m/z = 766.00 (C59H43N = 765.34) | 43 | m/z = 805.04 (C61H44N2 = 804.35) |
| 49 | m/z = 577.73 (C43H31NO = 577.24) | 60 | m/z = 593.79 (C43H31NS = 593.22) |
| 69 | m/z = 679.91 (C52H41N = 679.32) | 70 | m/z = 603.81 (C46H37N = 603.29) |
| 81 | m/z = 804.05 (C62H45N = 803.36) | 83 | m/z = 804.05 (C62H45N = 803.36) |
| 86 | m/z = 804.05 (C62H45N = 803.36) | 91 | m/z = 725.93 (C56H39N = 725.31) |
| 92 | m/z = 802.03 (C62H43N = 801.34) | 100 | m/z = 741.93 (C56H39NO = 741.30) |
| 125 | m/z = 739.96 (C57H41N = 739.32) | 126 | m/z = 715.94 (C55H41N = 715.32) |
| 136 | m/z = 756.00 (C58H45N = 756.36) | 152 | m/z = 794.03 (C59H39NS = 793.28) |
| 166 | m/z = 715.91 (C53H33NS = 715.23) | 181 | m/z = 763.98 (C59H41N = 763.32) |
| 183 | m/z = 814.04 (C63H43N = 813.34) | 184 | m/z = 763.98 (C59H41N = 763.32) |
| 223 | m/z = 776.98 (C59H40N2 = 776.32) | 224 | m/z = 853.08 (C65H44N2 = 852.35) |
| 240 | m/z = 794.03 (C59H39NS = 793.28) | 241 | m/z = 763.98 (C59H41N = 763.32) |
| 252 | m/z = 930.21 (C72H51N = 929.40) | 262 | m/z = 928.19 (C72H49N = 927.39) |
| 264 | m/z = 926.17 (C72H47N = 925.37) | 271 | m/z = 634.78 (C48H30N2 = 634.24) |
| 273 | m/z = 812.03 (C63H41N = 811.32) | 275 | m/z = 838.07 (C65H43N = 837.34) |
| 284 | m/z = 838.07 (C65H43N = 837.34) | 308 | m/z = 735.93 (C57H37N = 735.29) |
| 324 | m/z = 775.95 (C59H37NO = 775.29) | 337 | m/z = 862.09 (C67H43N = 861.34) |
| 356 | m/z = 852.05 (C65H41NO = 851.32) | 359 | m/z = 842.07 (C63H39NS = 841.23) |

Experimental Example

Experimental Example 1

(1) Manufacture of Organic Light Emitting Device

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

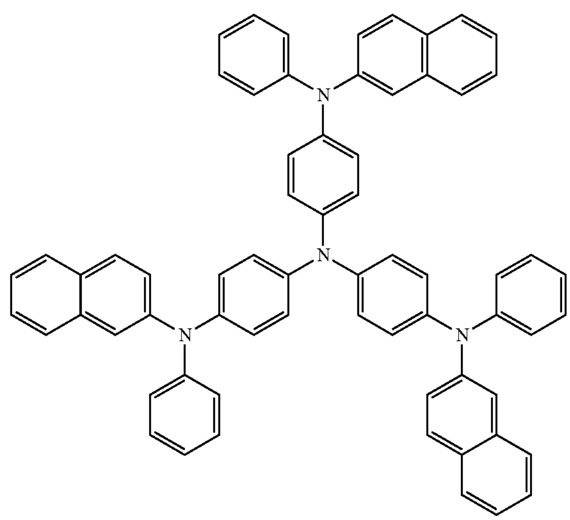

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)—N,N'-diphenyl-4,4'-diamine (NPB) was introduced, and evaporated by applying a current to the cell to deposit a hole transfer layer having a thickness of 300 Å on the hole injection layer.

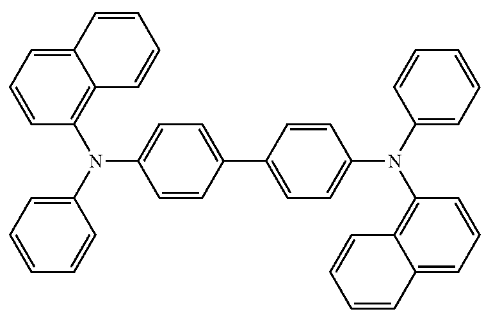

NPB

A light emitting layer was thermal vacuum deposited thereon as follows. As the light emitting layer, a compound of 9-[4-(4,6-diphenyl-1,3,5-triazin-2-yl)phenyl]-9'-phenyl-3,3'-bi-9H-carbazole was deposited to a thickness of 400 Å as a host, and as a green phosphorescent dopant, $Ir(ppy)_3$ was doped by 7% with respect to the host material weight and deposited. After that, BCP was deposited to a thickness of 60 Å as a hole blocking layer, and $Alq_3$ was deposited to a thickness of 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the organic light emitting device were vacuum sublimation purified under $10^{-6}$ torr to $10^{-8}$ torr for each material to be used in the organic light emitting device manufacture.

Organic light emitting devices were manufactured in the same manner except that compounds shown in the following Table 5 were used instead of the compound NPB used when forming the hole transfer layer in the manufacturing process of the organic light emitting device of Experimental Example 1.

Specifically, compounds used in the hole transfer layer in Examples 1 to 46 and Comparative Examples 1 to 4 are as shown in the following Table 5.

Herein, in the following Table 5, hole transfer compounds M1 to M3 of Comparative Examples 2 to 4 other than the NPB of Comparative Example 1 are as follows.

M1

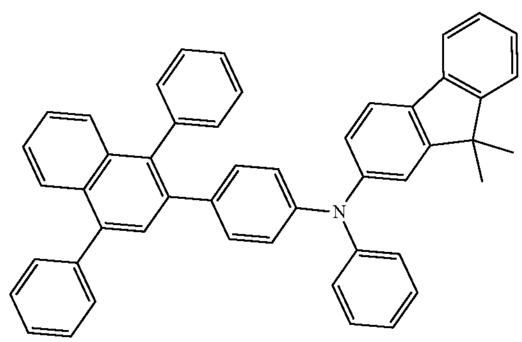

M2

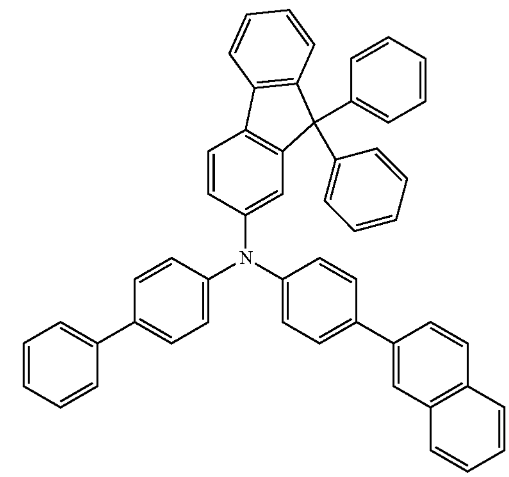

M3

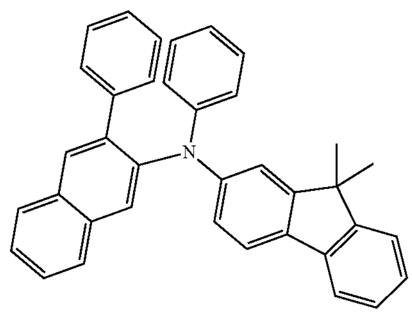

(2) Driving Voltage and Light Emission Efficiency of Organic Light Emitting Device For each of the organic light emitting devices manufactured as above, electroluminescent (EL) properties were measured using M7000 manufactured by McScience Inc., and with the measurement results, $T_{90}$ was measured when standard luminance was 6,000 cd/m$^2$ through a lifetime measurement system (M6000) manufactured by McScience Inc. Herein, $T_{90}$ means a lifetime (unit: h, time), a time taken to be 90% with respect to initial luminance.

Measured properties of the organic light emitting device of the present disclosure are as shown in the following Table 5.

TABLE 5

| | Compound | Driving Voltage (V) | Light Emission Efficiency (cd/A) | Lifetime ($T_{90}$) |
|---|---|---|---|---|
| Example 1 | 1 | 3.78 | 119.59 | 167 |
| Example 2 | 3 | 3.52 | 127.88 | 251 |
| Example 3 | 5 | 3.55 | 121.32 | 270 |
| Example 4 | 13 | 3.51 | 130.54 | 254 |
| Example 5 | 16 | 4.24 | 124.32 | 244 |
| Example 6 | 21 | 4.12 | 120.33 | 200 |
| Example 7 | 22 | 4.36 | 118.99 | 253 |
| Example 8 | 24 | 3.53 | 126.71 | 266 |
| Example 9 | 30 | 4.48 | 123.68 | 238 |
| Example 10 | 32 | 3.99 | 124.23 | 246 |
| Example 11 | 38 | 4.27 | 130.12 | 249 |
| Example 12 | 43 | 3.61 | 128.76 | 250 |
| Example 13 | 49 | 3.88 | 129.52 | 251 |
| Example 14 | 60 | 3.51 | 129.11 | 244 |
| Example 15 | 69 | 4.42 | 128.17 | 231 |
| Example 16 | 70 | 4.48 | 132.81 | 222 |
| Example 17 | 81 | 3.49 | 138.67 | 221 |
| Example 18 | 83 | 3.87 | 128.76 | 200 |
| Example 19 | 86 | 3.92 | 128.11 | 203 |
| Example 20 | 91 | 4.12 | 126.08 | 198 |
| Example 21 | 92 | 3.73 | 126.79 | 209 |
| Example 22 | 100 | 4.69 | 123.97 | 211 |
| Example 23 | 125 | 3.51 | 140.11 | 218 |
| Example 24 | 126 | 3.91 | 138.62 | 231 |
| Example 25 | 136 | 3.62 | 137.55 | 238 |
| Example 26 | 152 | 3.88 | 130.79 | 251 |
| Example 27 | 166 | 3.91 | 129.34 | 263 |
| Example 28 | 181 | 4.32 | 128.59 | 241 |
| Example 29 | 183 | 4.11 | 129.19 | 253 |
| Example 30 | 184 | 4.20 | 123.55 | 231 |
| Example 31 | 223 | 3.77 | 137.26 | 264 |
| Example 32 | 224 | 3.59 | 129.87 | 274 |
| Example 33 | 240 | 3.97 | 129.58 | 197 |
| Example 34 | 241 | 3.92 | 132.99 | 253 |
| Example 35 | 252 | 3.91 | 134.59 | 167 |
| Example 36 | 262 | 3.89 | 127.85 | 192 |
| Example 37 | 264 | 3.55 | 132.16 | 261 |
| Example 38 | 271 | 3.97 | 126.85 | 221 |
| Example 39 | 273 | 4.12 | 126.29 | 213 |
| Example 40 | 275 | 4.10 | 127.62 | 190 |
| Example 41 | 284 | 4.27 | 130.16 | 173 |
| Example 42 | 308 | 4.01 | 121.76 | 200 |
| Example 43 | 324 | 3.99 | 126.99 | 237 |
| Example 44 | 337 | 3.88 | 130.86 | 212 |
| Example 45 | 356 | 3.98 | 127.88 | 233 |
| Example 46 | 359 | 3.62 | 126.17 | 261 |
| Comparative Example 1 | NPB | 4.51 | 110.59 | 150 |
| Comparative Example 2 | M1 | 4.38 | 117.11 | 187 |
| Comparative Example 3 | M2 | 4.19 | 116.58 | 190 |
| Comparative Example 4 | M3 | 4.03 | 120.02 | 133 |

From Experimental Example 1, it was identified that the organic light emitting devices of Examples 1 to 46 using the compounds according to the present application when forming the hole transfer layer had superior light emission efficiency and lifetime compared to the organic light emitting devices of Comparative Examples 1 to 4 not using the compounds according to the present application when forming the hole transfer layer.

This relates to hole mobility, and hole mobility is affected by orientation and space size formed by interactions between materials during deposition. M1 of Comparative Example 2 has a tri-substituted structure, and uniform orientation is difficult to form therein and deposition occurs in an irregular form resulting in a decrease in the hole mobility and thereby affecting driving and efficiency. M2 of Comparative Example 3 has a mono-substituted structure and has excellent hole mobility by forming uniform orientation compared to a tri-substituted structure, however, it is difficult to form space due to the linear structure during deposition making it difficult to readily form holes, and driving and efficiency are somewhat inferior by having less favorable hole mobility compared to a bi-substituted structure.

In addition, M3 of Comparative Example 3 has a bi-substituted structure and has similar orientation and space size formed during deposition, which may result in similar hole mobility compared to when using the compound according to the present application, however, when examining the structure three-dimensionally, it was identified that the structure substituted at the second and the third positions of the naphthyl group had steric hindrance occurring between the substituents compared to the structure substituted at the first and the second positions making the molecule unstable resulting in unfavorable lifetime properties of the device.

Experimental Example 2

(1) Manufacture of Organic Light Emitting Device

A transparent ITO electrode thin film obtained from glass for an organic light emitting device (manufactured by Samsung-Corning Co., Ltd.) was ultrasonic cleaned using trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

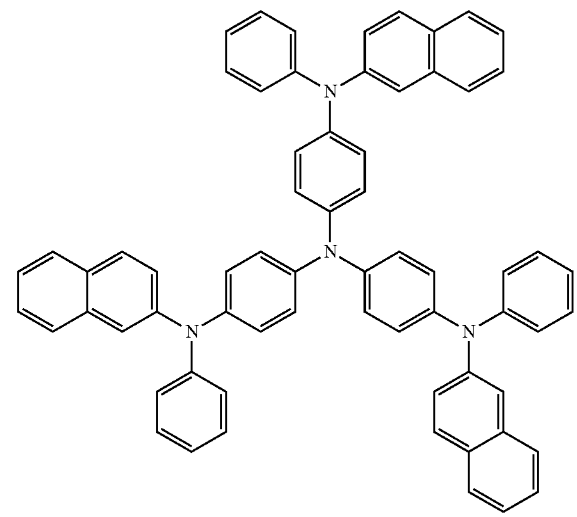

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)—N,N'-diphenyl-4, 4'-diamine (NPB) was introduced, and evaporated by applying a current to the cell to deposit a hole transfer layer having a thickness of 300 Å on the hole injection layer.

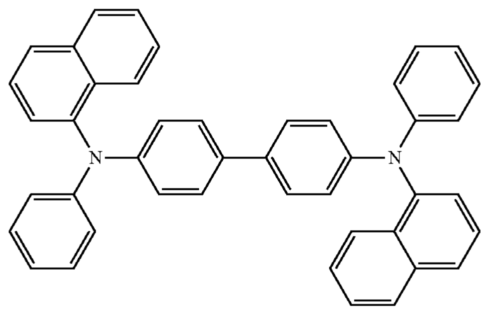

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material weight.

H1

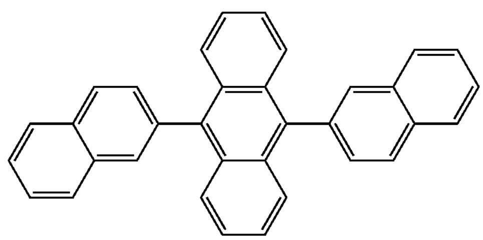

D1

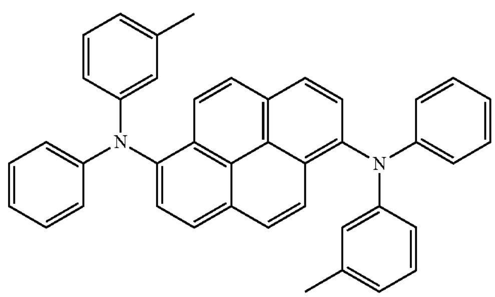

Subsequently, as an electron transfer layer, a compound of the following structural formula E1 was deposited to a thickness of 300 Å.

E1

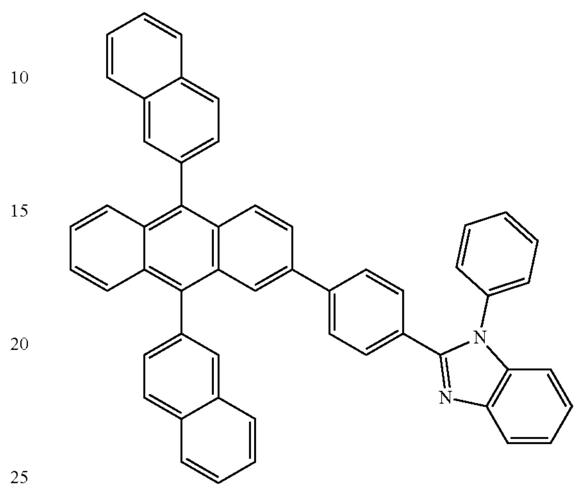

As an electron injection layer, lithium fluoride (LiF) was deposited to a thickness of 10 Å, and an Al cathode was employed to a thickness of 1,000 Å, and as a result, an organic light emitting device was manufactured. Meanwhile, all the organic compounds required to manufacture the organic light emitting device were vacuum sublimation purified under $10^{-6}$ torr to $10^{-8}$ torr for each material to be used in the organic light emitting device manufacture.

Organic light emitting devices were manufactured in the same manner as in Experimental Example 2 except that a hole transfer layer having a thickness of 150 Å was formed using NPB and then a hole auxiliary layer having a thickness of 50 Å was formed on the hole transfer layer using compounds shown in the following Table 6.

Specifically, compounds used in the hole auxiliary layer in Examples 47 to 92 and Comparative Examples 5 to 7 are as shown in the following Table 6.

Herein, in the following Table 6, Compounds M1 to M3 of the hole auxiliary layer of Comparative Examples 5 to 7 are as follows.

M1

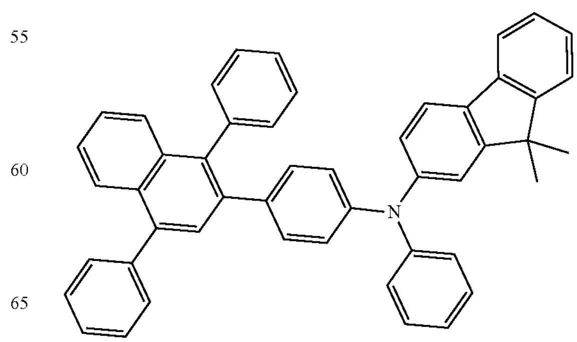

-continued

M2

M3

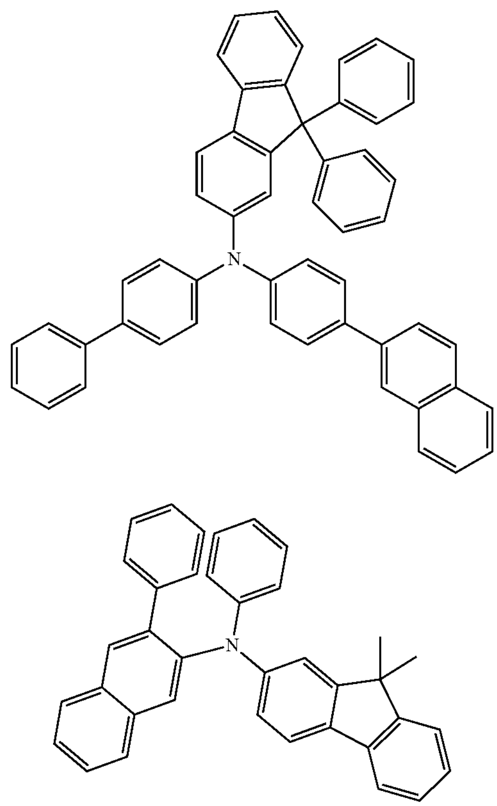

(2) Driving Voltage and Light Emission Efficiency of Organic Light Emitting Device For each of the organic light emitting devices manufactured as above, electroluminescent (EL) properties were measured using M7000 manufactured by McScience Inc., and with the measurement results, $T_{95}$ was measured when standard luminance was 6,000 cd/$m^2$ through a lifetime measurement system (M6000) manufactured by McScience Inc. Herein, $T_{95}$ means a lifetime (unit: h, time), a time taken to be 95% with respect to initial luminance.

Measured properties of the organic light emitting device of the present disclosure are as shown in the following Table 6.

TABLE 6

| | Compound | Driving Voltage (V) | Light Emission Efficiency (cd/A) | Lifetime ($T_{95}$) |
|---|---|---|---|---|
| Example 47 | 1 | 5.71 | 7.12 | 53 |
| Example 48 | 3 | 5.88 | 7.09 | 43 |
| Example 49 | 5 | 5.74 | 6.99 | 49 |
| Example 50 | 13 | 5.68 | 7.03 | 59 |
| Example 51 | 16 | 5.16 | 7.55 | 65 |
| Example 52 | 21 | 5.22 | 7.41 | 56 |
| Example 53 | 22 | 5.31 | 7.27 | 57 |
| Example 54 | 24 | 5.33 | 7.58 | 58 |
| Example 55 | 30 | 5.82 | 7.18 | 51 |
| Example 56 | 32 | 5.37 | 7.92 | 45 |
| Example 57 | 38 | 5.55 | 7.31 | 51 |
| Example 58 | 43 | 5.88 | 6.97 | 42 |
| Example 59 | 49 | 5.78 | 6.99 | 53 |
| Example 60 | 60 | 5.61 | 6.94 | 58 |
| Example 61 | 69 | 5.79 | 7.11 | 40 |
| Example 62 | 70 | 5.23 | 7.29 | 56 |
| Example 63 | 81 | 5.85 | 6.97 | 48 |

TABLE 6-continued

| | Compound | Driving Voltage (V) | Light Emission Efficiency (cd/A) | Lifetime ($T_{95}$) |
|---|---|---|---|---|
| Example 64 | 83 | 5.31 | 7.27 | 51 |
| Example 65 | 86 | 6.01 | 6.90 | 40 |
| Example 66 | 91 | 5.28 | 6.99 | 57 |
| Example 67 | 92 | 4.94 | 7.00 | 51 |
| Example 68 | 100 | 6.09 | 6.97 | 53 |
| Example 69 | 125 | 5.83 | 6.91 | 44 |
| Example 70 | 126 | 5.77 | 6.97 | 52 |
| Example 71 | 136 | 5.79 | 6.90 | 49 |
| Example 72 | 152 | 5.99 | 6.91 | 50 |
| Example 73 | 166 | 5.41 | 7.00 | 59 |
| Example 74 | 181 | 5.48 | 6.95 | 49 |
| Example 75 | 183 | 5.72 | 6.93 | 46 |
| Example 76 | 184 | 5.97 | 6.98 | 47 |
| Example 77 | 223 | 6.01 | 6.91 | 41 |
| Example 78 | 224 | 5.93 | 7.07 | 45 |
| Example 79 | 240 | 5.57 | 7.21 | 50 |
| Example 80 | 241 | 5.88 | 6.92 | 55 |
| Example 81 | 252 | 5.65 | 6.96 | 53 |
| Example 82 | 262 | 5.79 | 6.97 | 49 |
| Example 83 | 264 | 6.02 | 7.09 | 43 |
| Example 84 | 271 | 5.41 | 7.35 | 44 |
| Example 85 | 273 | 5.99 | 7.10 | 41 |
| Example 86 | 275 | 5.66 | 6.99 | 52 |
| Example 87 | 284 | 5.59 | 7.12 | 54 |
| Example 88 | 308 | 5.61 | 7.08 | 49 |
| Example 89 | 324 | 5.70 | 7.17 | 45 |
| Example 90 | 337 | 5.99 | 7.03 | 40 |
| Example 91 | 356 | 5.78 | 7.31 | 58 |
| Example 92 | 359 | 5.81 | 7.27 | 52 |
| Comparative Example 5 | M1 | 6.10 | 6.90 | 40 |
| Comparative Example 6 | M2 | 6.08 | 6.98 | 42 |
| Comparative Example 7 | M3 | 5.99 | 7.01 | 18 |

From Experimental Example 2, it was identified that the organic light emitting devices of Examples 47 to 92 using the compounds according to the present application when forming the hole auxiliary layer had superior light emission efficiency and lifetime compared to the organic light emitting devices of Comparative Examples 5 to 7 not using the compounds according to the present application when forming the hole auxiliary layer.

This means that, when using the compound according to the present application as a hole auxiliary layer, the hole auxiliary layer more effectively performs a role of preventing electrons in the light emitting layer from passing over to the hole transfer layer like an electron blocking layer compared when not using the compound according to the present application, and, in addition thereto, more effectively tunes energy level and light emission wavelength between the light emitting layer and the hole transfer layer, which has an effect of improving color purity.

This is due to the fact that the degree of electron blocking and the tuning of energy level and light emission wavelength between the light emitting layer and the hole transfer layer are also affected by orientation and space size formed by interactions between materials during deposition, and, as described above, it is considered to be an effect obtained from differences in the orientation properties and space sizes between the compound of the present application and M1 to M3.

Experimental Example 3

1) Manufacture of Organic Light Emitting Device

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. As a host of the light emitting layer, a compound described in the following Table 7 was used as a single host, or two host compounds were deposited in one source of supply using an n-host (n-type host) having a favorable electron transfer ability as a first host and a p-host (p-type host) having a favorable hole transfer ability as a second host, and to the host, $(piq)_2(Ir)$ (acac), a red phosphorescent dopant, was doped by 3% with respect to the host material weight or $Ir(ppy)_3$, a green phosphorescent dopant, was doped by 7% with respect to the host material weight, and the result was deposited to a thickness of 500 Å.

After that, BCP was deposited to a thickness of 60 Å as a hole blocking layer, and $Alq_3$ was deposited to a thickness of 200 Å thereon as an electron transfer layer.

Herein, when using the two hosts, the compound used as the n-host is as follows.

X

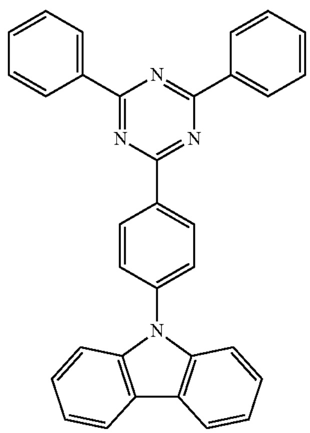

-continued

Y

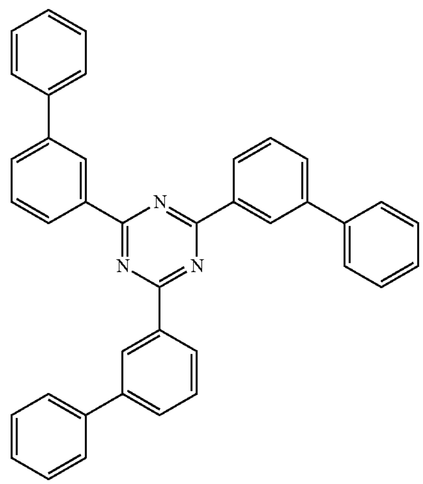

Z

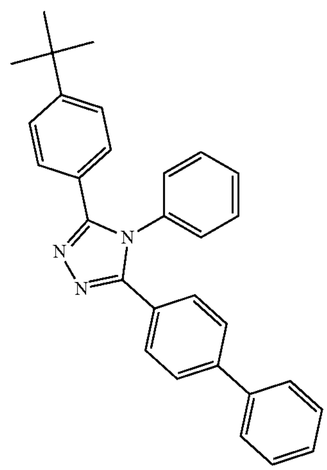

Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Specifically, compounds used as the host in Examples 93 to 117 and Comparative Examples 8 to 13 are as shown in the following Table 7.

Herein, in the following Table 7, Compounds M1 to M3 used as the host of Comparative Examples 8 to 13 are as follows.

M1

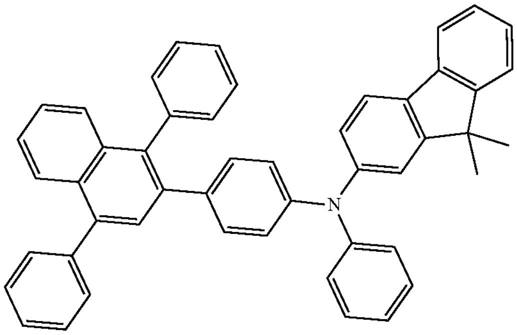

M2

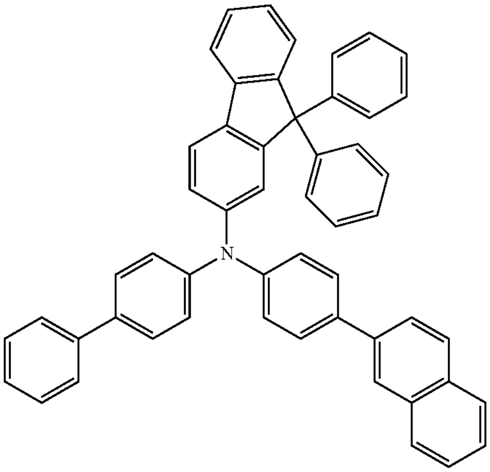

M3

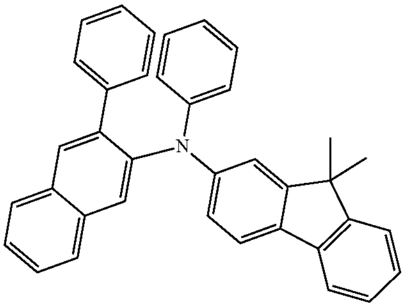

Meanwhile, all the organic compounds required to manufacture the organic light emitting device were vacuum sublimation purified under $10^{-6}$ torr to $10^{-8}$ torr for each material to be used in the organic light emitting device manufacture.

2) Driving Voltage and Light Emission Efficiency of Organic Light Emitting Device For each of the organic light emitting devices manufactured as above, electroluminescent (EL) properties were measured using M7000 manufactured by McScience Inc., and with the measurement results, $T_{95}$ was measured when standard luminance was 6,000 cd/m$^2$ through a lifetime measurement system (M6000) manufactured by McScience Inc. Results of measuring driving voltage, light emission efficiency, light emitting color and lifetime of the organic light emitting device manufactured according to the present disclosure are as shown in the following Table 7.

TABLE 7

| | First Holst | Second Host | Driving Voltage (V) | Light Emission Efficiency (cd/A) | Light Emitting Color | Lifetime ($T_{95}$) |
|---|---|---|---|---|---|---|
| Example 93 | 21 | | 3.71 | 18.5 | Red | 101 |
| Example 94 | | | 3.88 | 15.1 | Green | 108 |
| Example 95 | 126 | | 3.89 | 17.6 | Red | 98 |
| Example 96 | | | 4.02 | 14.3 | Green | 102 |
| Example 97 | 136 | | 3.77 | 19.7 | Red | 116 |
| Example 98 | | | 3.99 | 16.9 | Green | 118 |
| Example 99 | 284 | | 3.70 | 18.8 | Red | 94 |
| Example 100 | | | 3.80 | 17.1 | Green | 102 |
| Example 101 | 337 | | 3.81 | 19.1 | Red | 106 |
| Example 102 | | | 3.98 | 18.4 | Green | 108 |
| Example 103 | X | 21 | 3.69 | 24.6 | Red | 156 |
| Example 104 | | 126 | 3.61 | 23.6 | Red | 178 |
| Example 105 | | 136 | 3.57 | 23.2 | Red | 149 |
| Example 106 | | 284 | 3.59 | 23.8 | Red | 164 |
| Example 107 | | 337 | 3.70 | 21.9 | Red | 133 |
| Example 108 | Y | 21 | 3.79 | 22.9 | Green | 139 |
| Example 109 | | 126 | 3.71 | 23.7 | Green | 150 |
| Example 110 | | 136 | 3.63 | 23.8 | Green | 148 |
| Example 111 | | 284 | 3.66 | 21.0 | Green | 150 |
| Example 112 | | 337 | 3.62 | 22.3 | Green | 160 |
| Example 113 | Z | 21 | 3.66 | 24.0 | Red | 138 |
| Example 114 | | 126 | 3.62 | 25.1 | Red | 132 |
| Example 115 | | 136 | 3.59 | 23.9 | Red | 129 |
| Example 116 | | 284 | 3.58 | 24.7 | Red | 141 |
| Example 117 | | 337 | 3.59 | 23.1 | Red | 131 |
| Comparative Example 8 | M1 | | 4.45 | 7.2 | Red | 50 |
| Comparative Example 9 | X | M1 | 4.39 | 18.2 | Red | 111 |
| Comparative Example 10 | M2 | | 4.31 | 8.7 | Green | 64 |
| Comparative Example 11 | Y | M2 | 4.12 | 17.5 | Green | 138 |
| Comparative Example 12 | M3 | | 4.12 | 9.4 | Red | 21 |
| Comparative Example 13 | Z | M3 | 3.99 | 20.9 | Red | 102 |

From Experimental Example 3, it was identified that the organic light emitting devices of Examples 93 to 102 forming the light emitting layer using the compound according to the present application as a single host material had superior light emission efficiency and lifetime compared to the organic light emitting devices of Comparative Examples 8, 10 and 12 not using the compound according to the present application as a single host material when forming the light emitting layer using a single host material.

In addition, from Experimental Example 3, it was identified that the organic light emitting devices of Examples 103 to 117 forming the light emitting layer using a first host material corresponding to the n-host and the compound according to the present application as a second host material corresponding to the p-host at the same time had superior light emission efficiency and lifetime compared to the organic light emitting devices of Comparative Examples 9, 12 and 13 forming the light emitting layer using a first host material corresponding to the n-host and using a compound that is not the compound according to the present application as a second host material corresponding to the p-host at the same time.

In addition, it was also identified that the organic light emitting devices of Examples 93 to 102 forming the light emitting layer using the compound according to the present application as a single host material had similar or sometimes superior light emission efficiency and lifetime compared to the organic light emitting devices of Comparative Examples 9, 12 and 13 forming the light emitting layer using a first host material corresponding to the n-host and using a compound that is not the compound according to the present application as a second host material corresponding to the p-host at the same time.

Considering that an organic light emitting device using an n-host (n-type host) having a favorable electron transfer ability as a first host and a p-host (p-type host) having a favorable hole transfer ability as a second host generally has superior light emission efficiency and lifetime compared to an organic light emitting device using a single host material, this means that light emission efficiency and lifetime of an organic light emitting device may be significantly improved when using the compound according to the present application as a host material.

This is considered to be due to the fact that, when using the compound according to the present application as a host material, holes and electrons may be efficiently injected to a light emitting layer from each charge transfer layer. As described above, this is also considered to be due to an influence by orientation and space size formed by interactions between materials during deposition.

This is due to the fact that efficiently injecting holes and electrons to a light emitting layer is also affected by orientation and space size formed by interactions between materials during deposition, and, as described above, it is considered to be an effect obtained from differences in the orientation properties and space sizes between the compound of the present application and M1 to M3.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

The invention claimed is:

1. A heterocyclic compound represented by the following Chemical Formula 1:

[Chemical Formula 1]

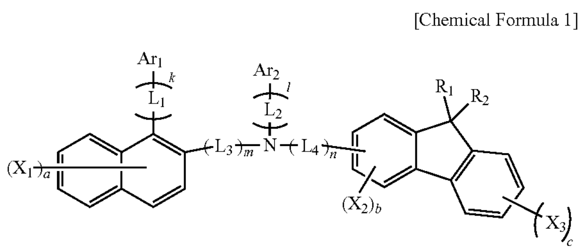

wherein, in Chemical Formula 1, $L_1$ to $L_4$ are the same as or different from each other, and each is independently a direct bond; or an unsubstituted phenylene group, $Ar_1$ of Chemical Formula 1 is represented by any one of the following chemical formulae,

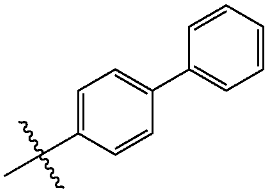
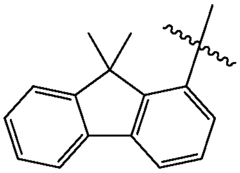
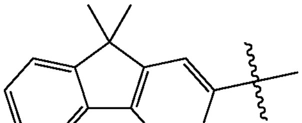
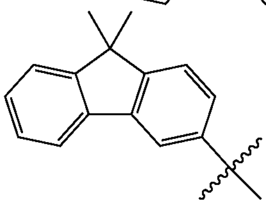
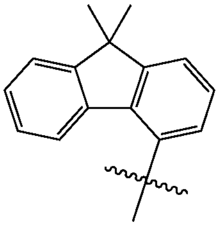
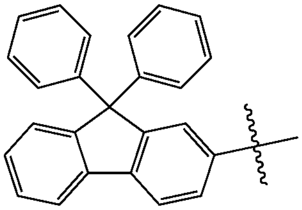
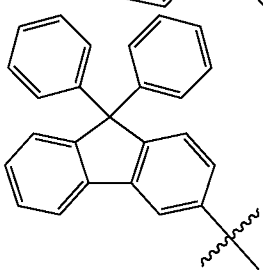
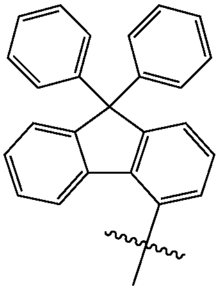
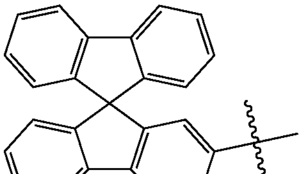
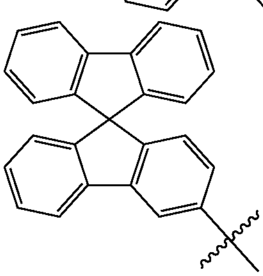
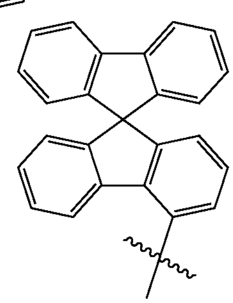
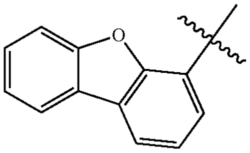
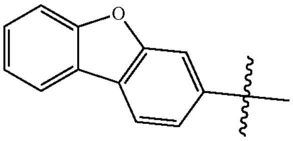

-continued

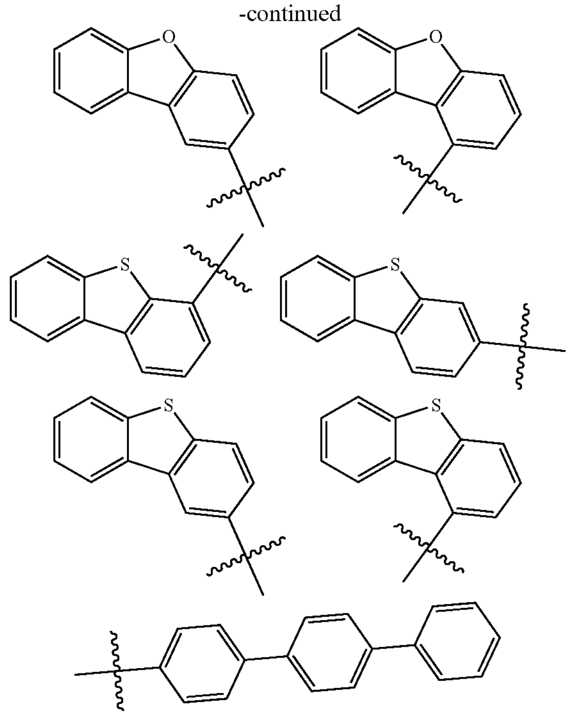

$Ar_2$ is an unsubstituted phenyl group, an unsubstituted biphenyl group; an unsubstituted terphenyl group, an unsubstituted naphthyl group, an unsubstituted phenanthrenyl group, an unsubstituted dimethylfluorenyl group, an unsubstituted diphenylfluorenyl group, an unsubstituted dibenzofuran group, an unsubstituted dibenzothiophene group, or an unsubstituted spirobifluorenyl group;

$R_1$ and $R_2$ are the same as or different from each other, and each is independently an unsubstituted methyl group; an unsubstituted phenyl group; or two or more groups adjacent to each other bonded to each other to form an unsubstituted spirobifluorenyl group, $X_1$ to $X_3$ are the same as or different from each other, and each is independently hydrogen; or deuterium;

k, l, m and n are each independently an integer of 1 to 3;

a is an integer of 1 to 6;

b is an integer of 1 to 3;

c is an integer of 1 to 4; and when k, l, m, n, a, b and c are 2 or greater, substituents in the parentheses are the same as or different from each other.

2. The heterocyclic compound of claim 1, wherein Chemical Formula 1 is represented by any one of the following Chemical Formulae 2 to 5:

[Chemical Formula 2]

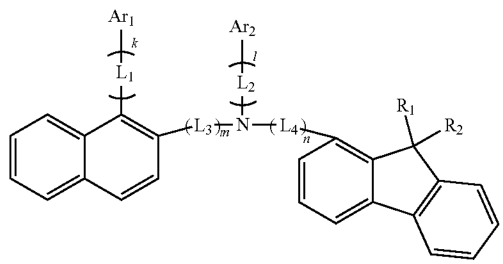

-continued

[Chemical Formula 3]

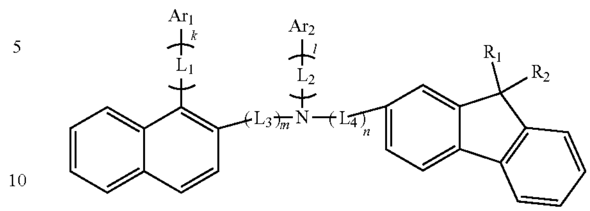

[Chemical Formula 4]

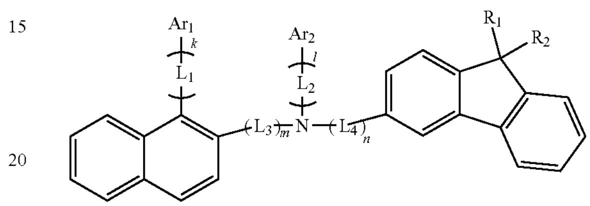

[Chemical Formula 5]

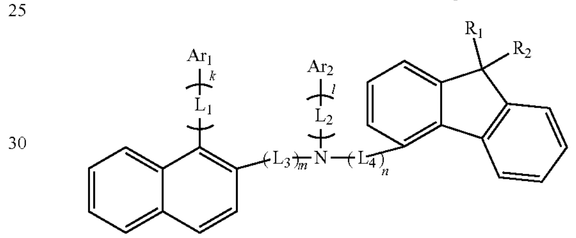

in Chemical Formulae 2 to 5, each substituent has the same definition as in Chemical Formula 1.

3. A heterocyclic compound selected from the following compounds:

21

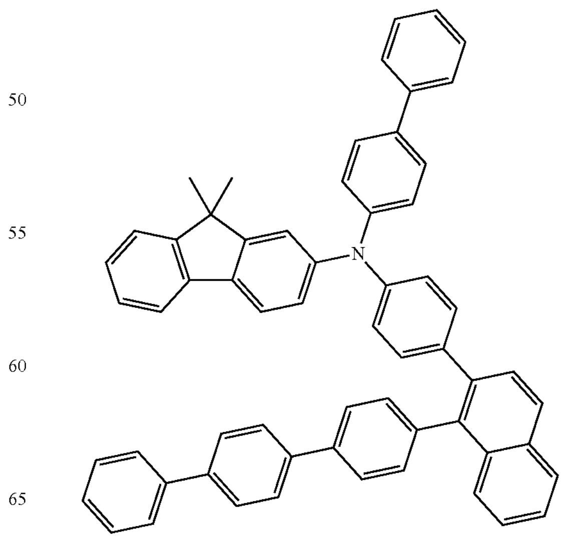

-continued
126
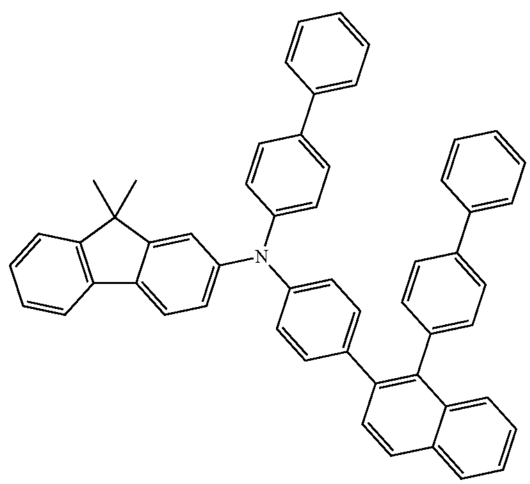
127
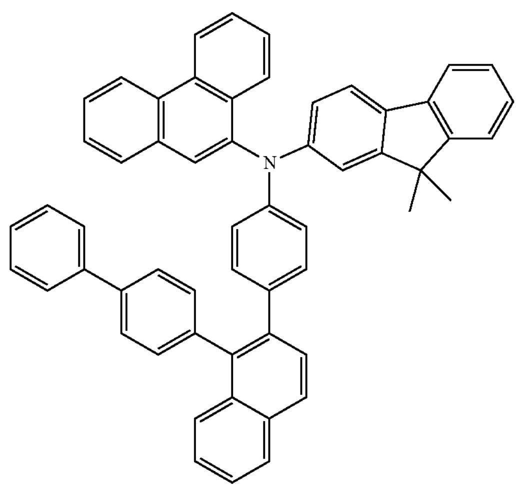
128
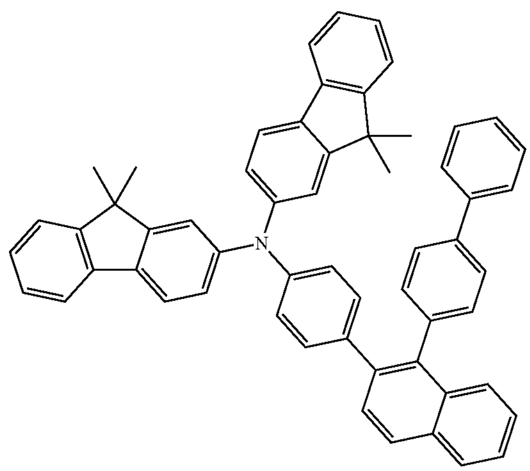
-continued
129
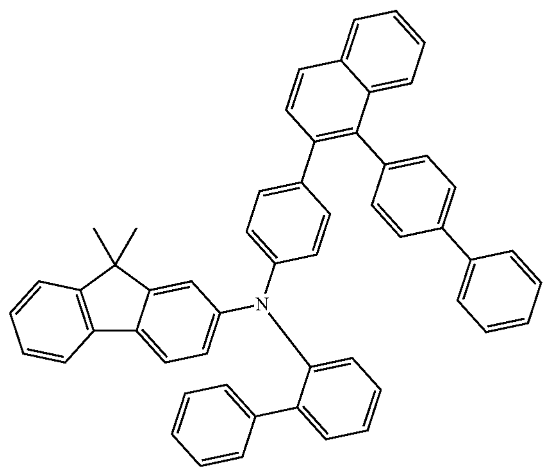
130
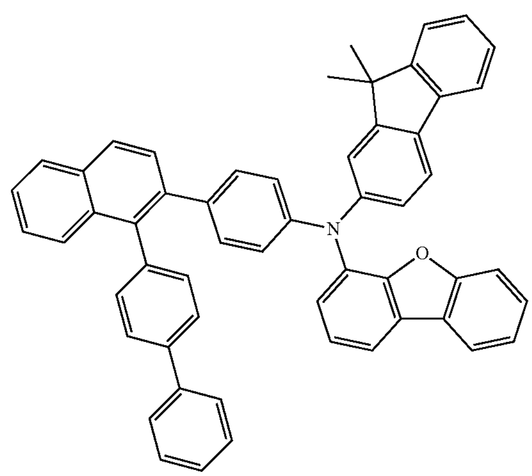
131
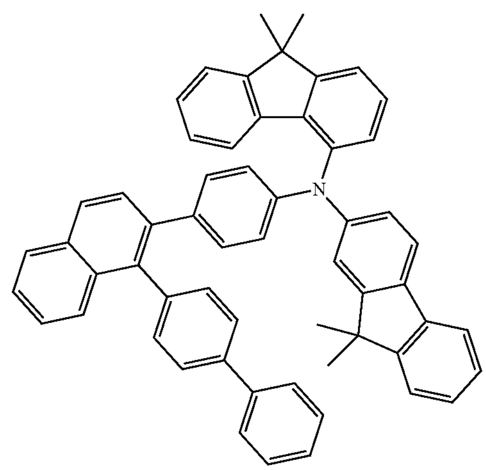

-continued
132
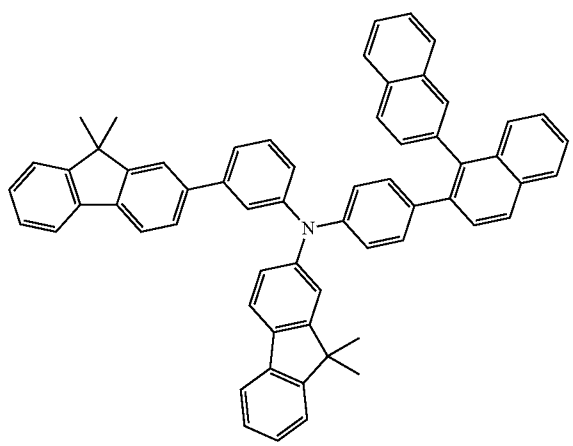
133
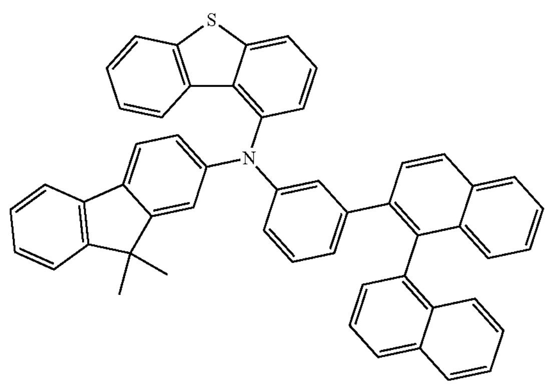
134
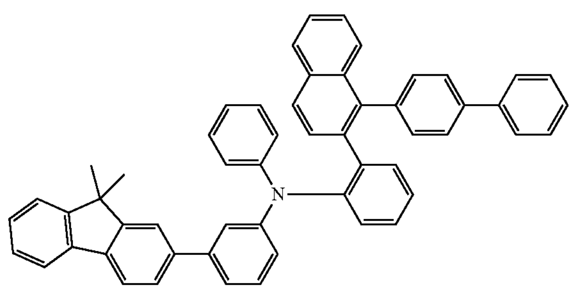
135
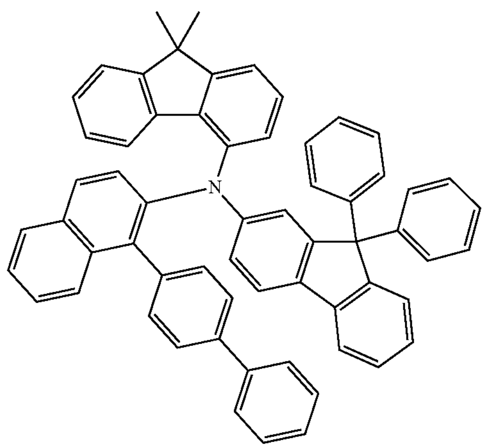
-continued
136
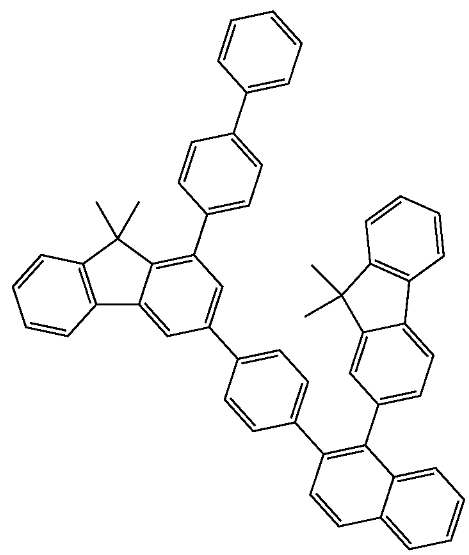
137
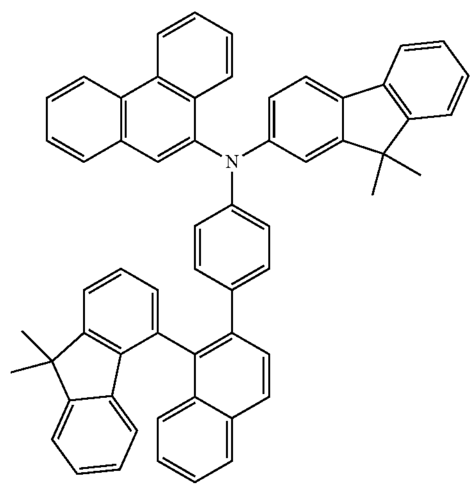
138
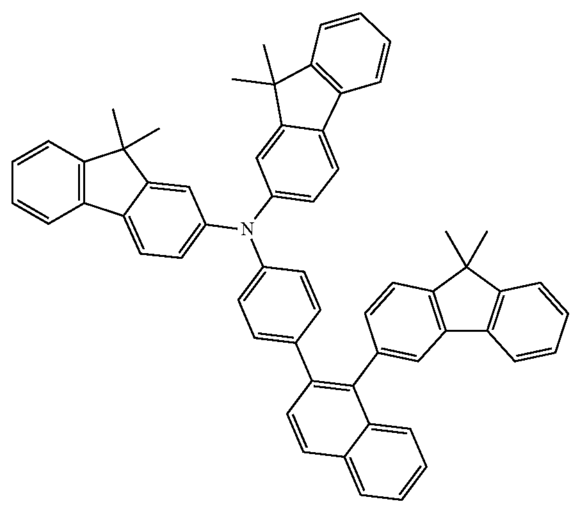

-continued
139
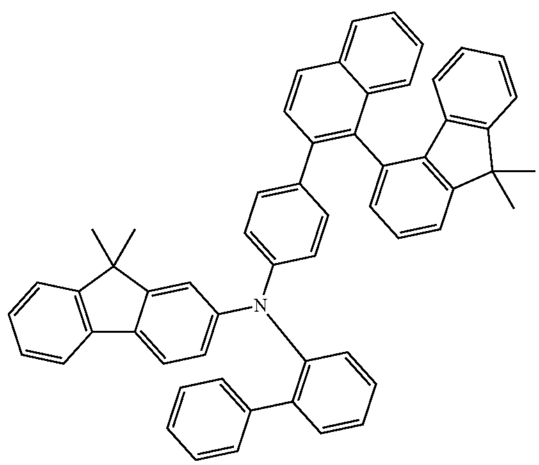
140
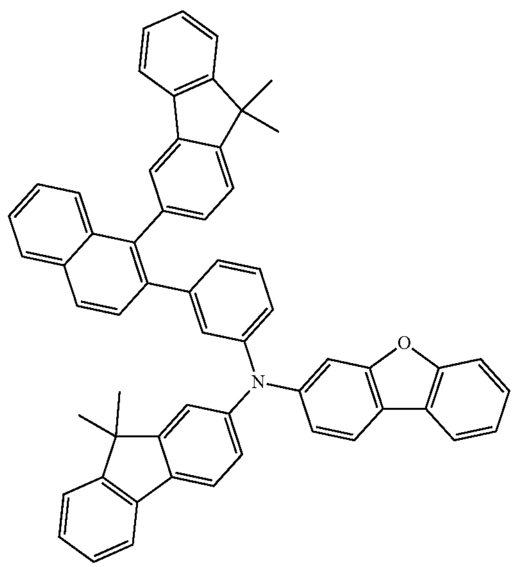
141
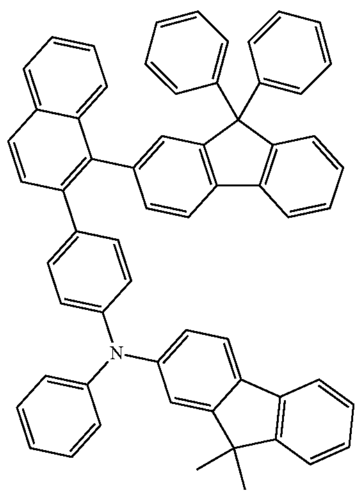
-continued
142
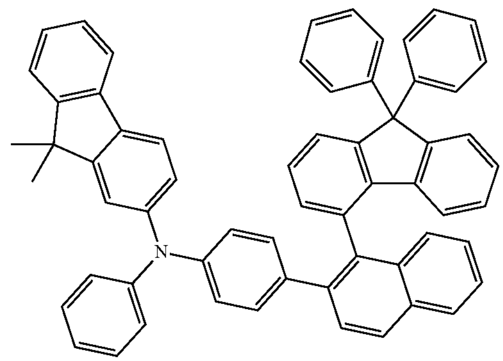
143
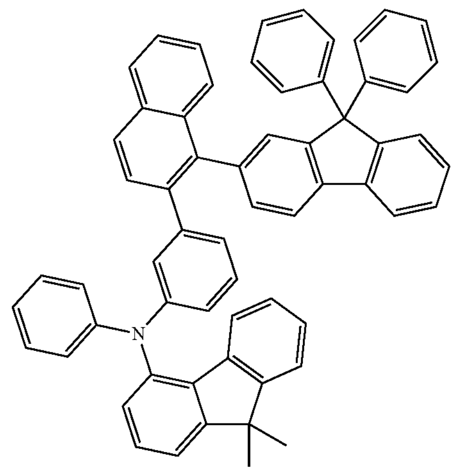
144
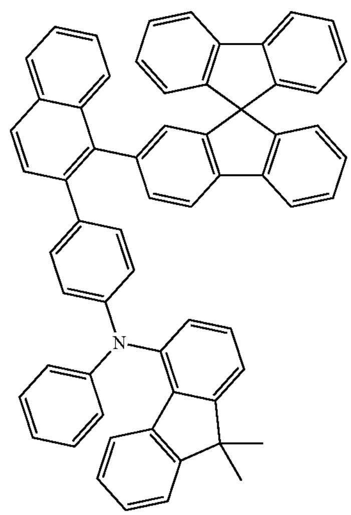

-continued
145
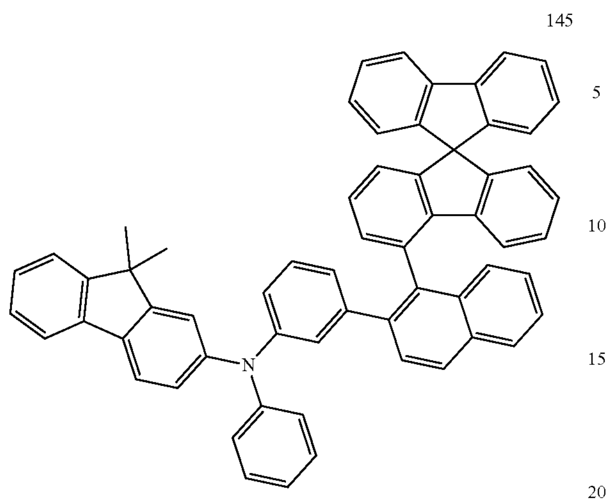
148
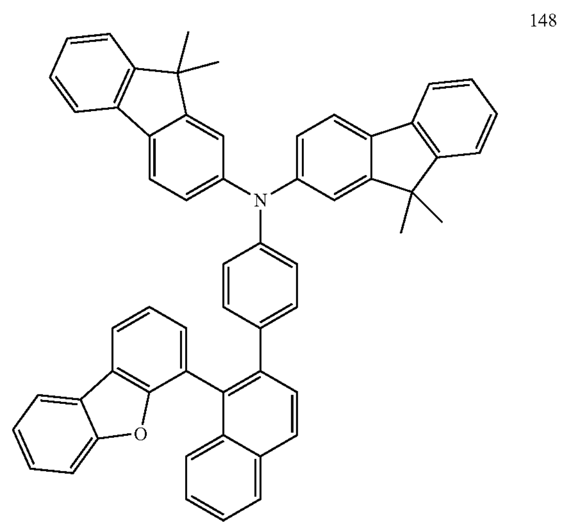
146
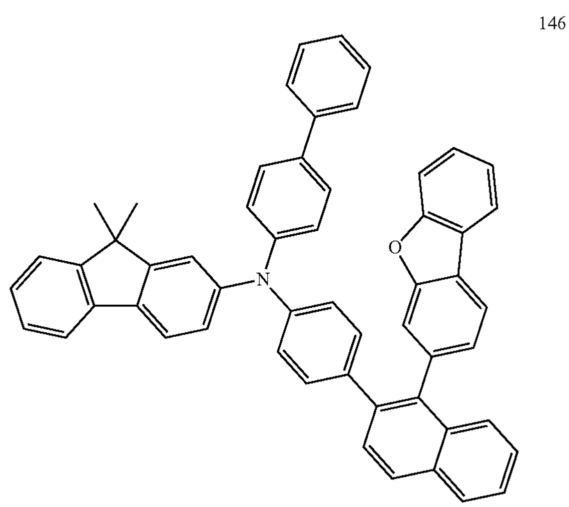
149
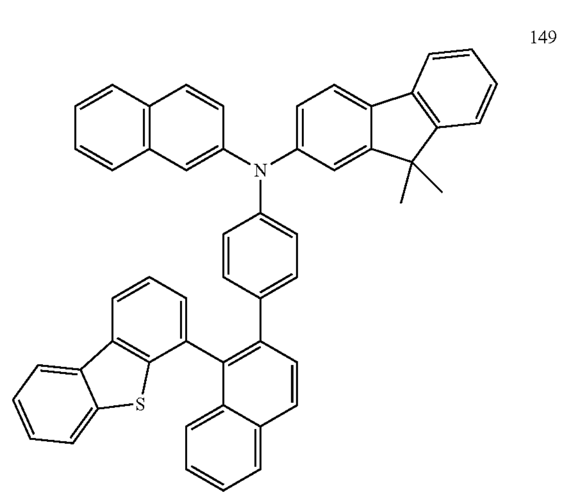
147
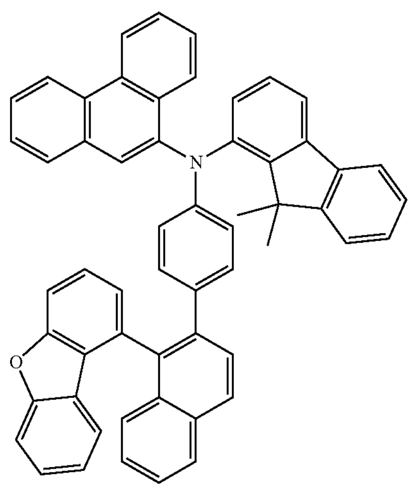
150
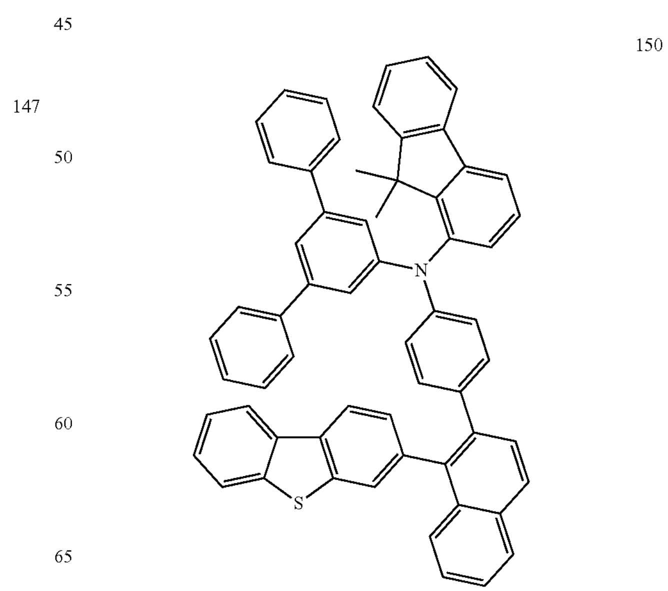
-continued -continued
183
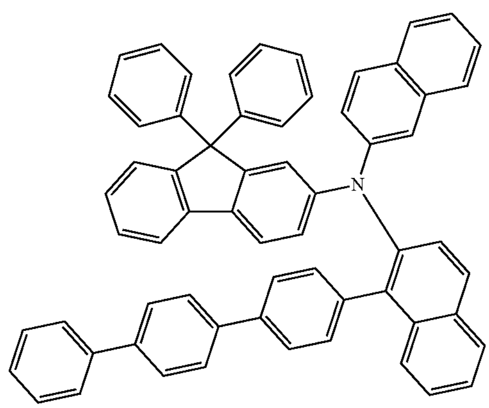
346
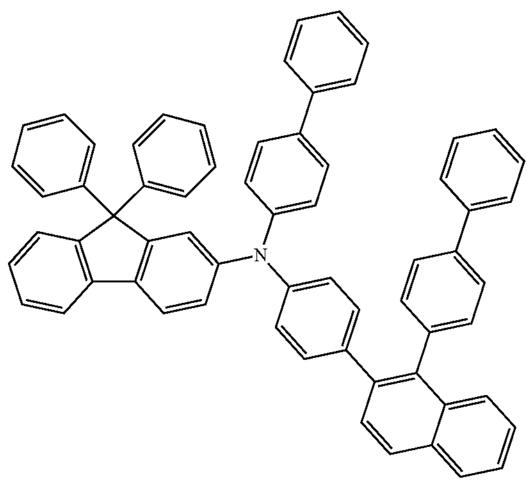
347
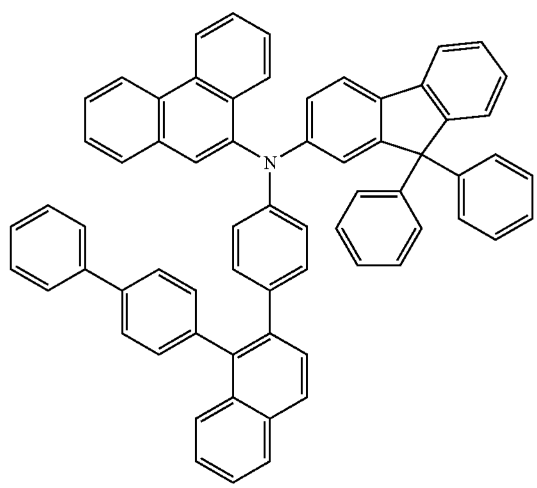
-continued
248
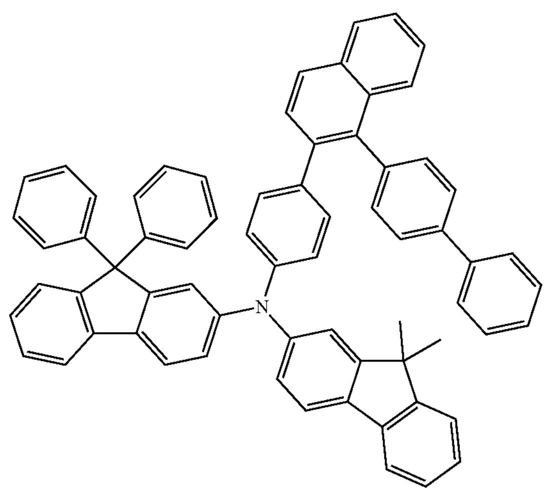
249
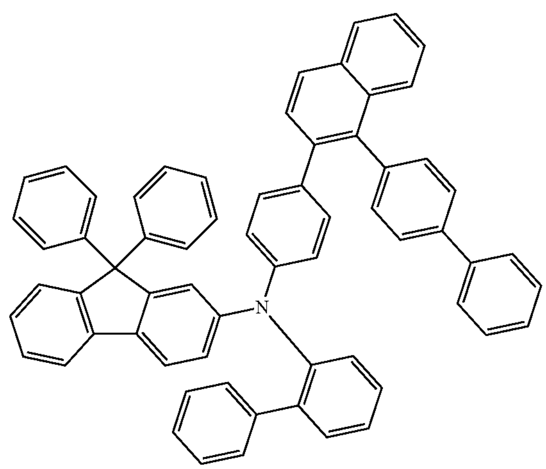
250
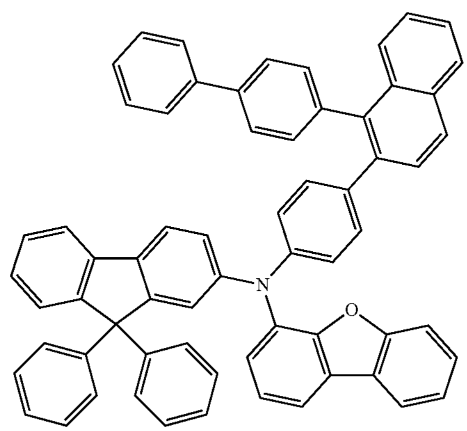

-continued
251
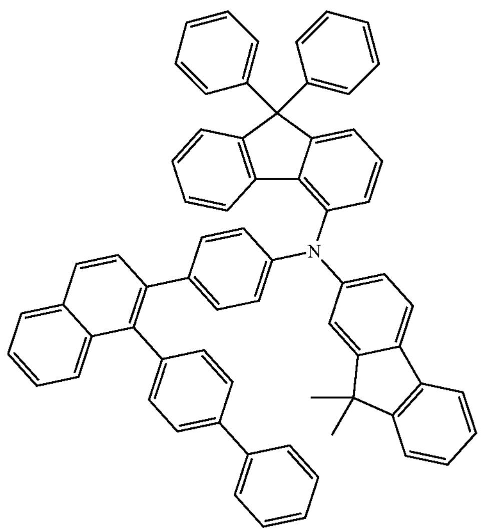
252
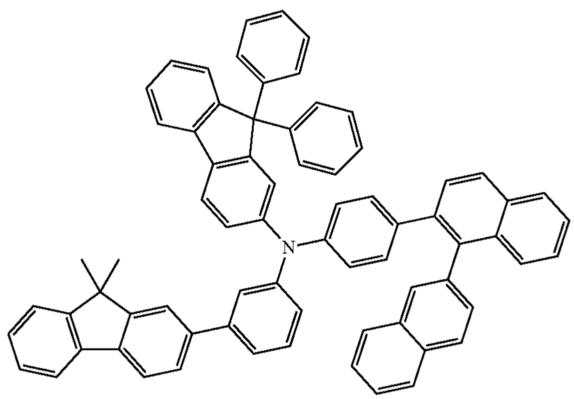
253
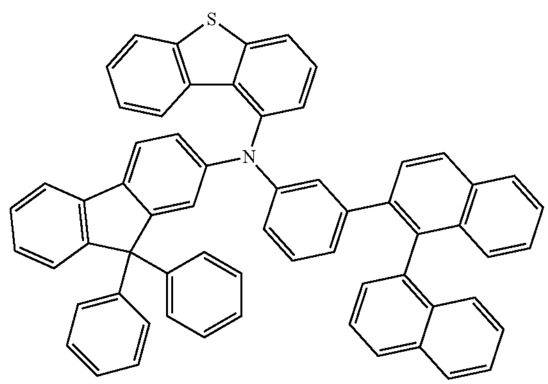
-continued
254
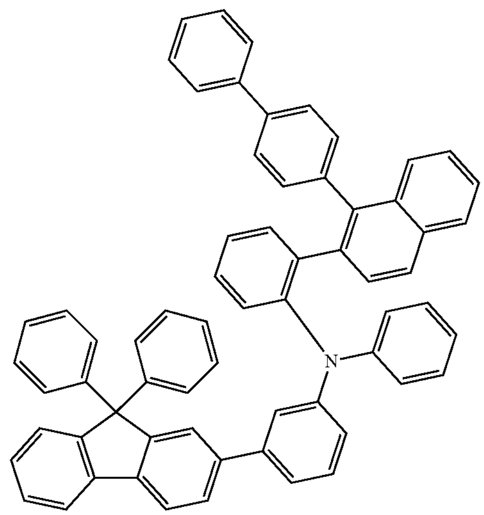
255
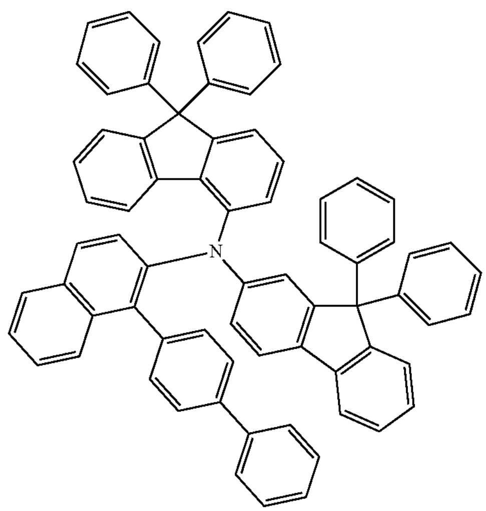
256
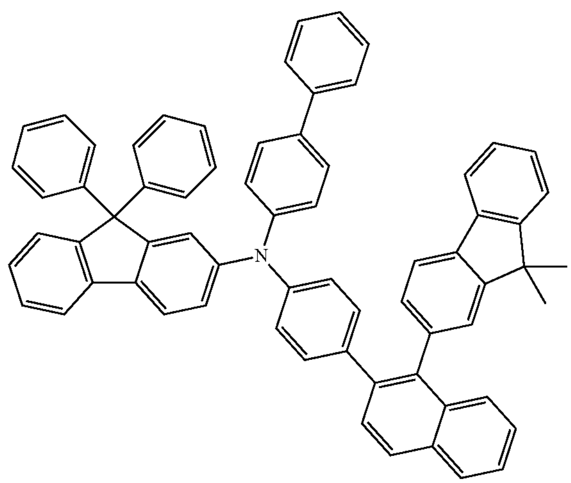

-continued
257
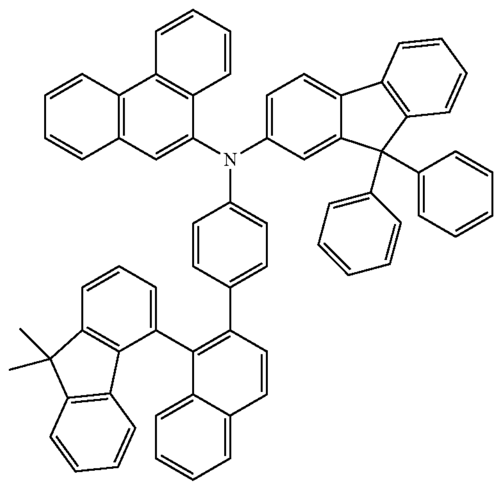
258
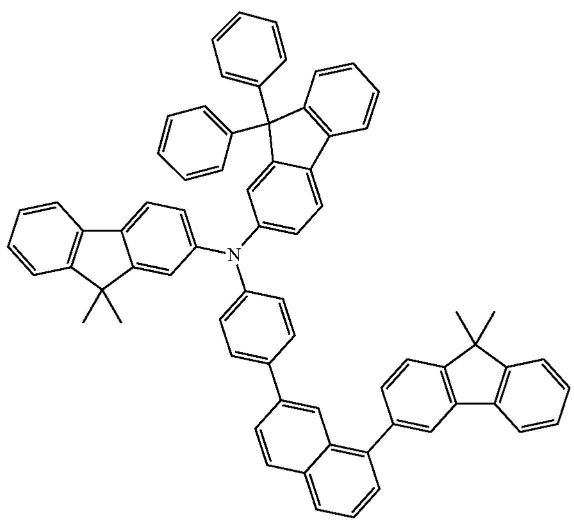
259
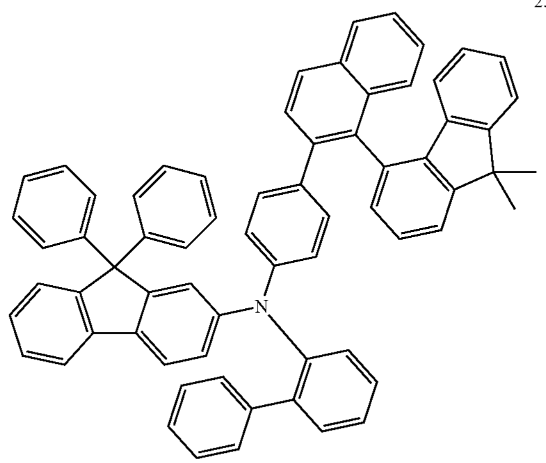
-continued
260
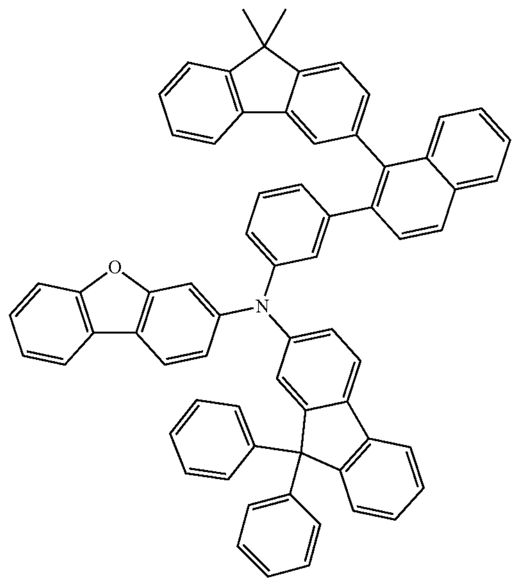
261
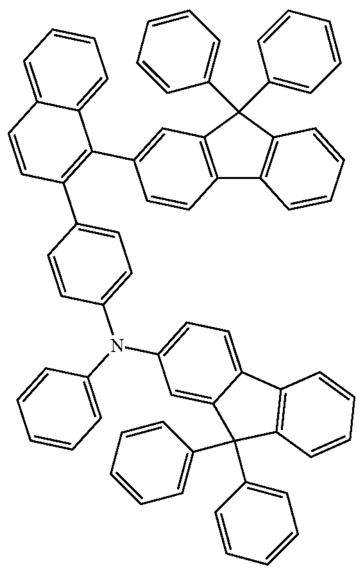
262
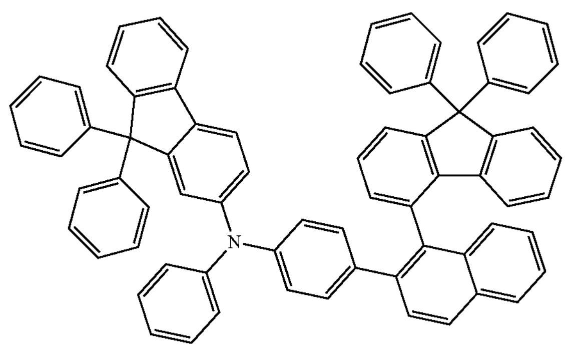

263
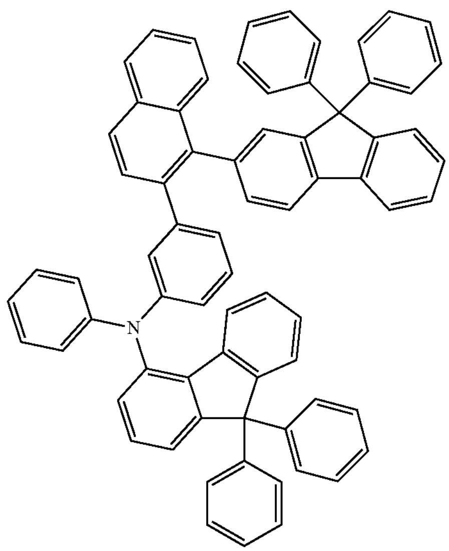
264
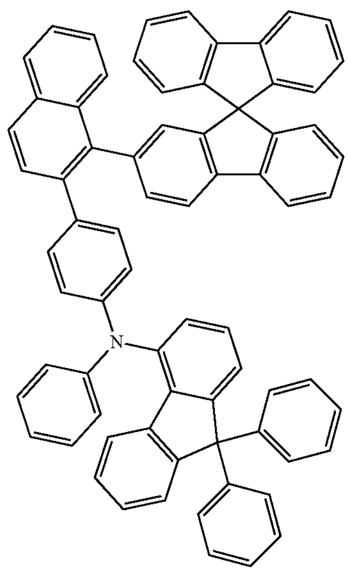
265
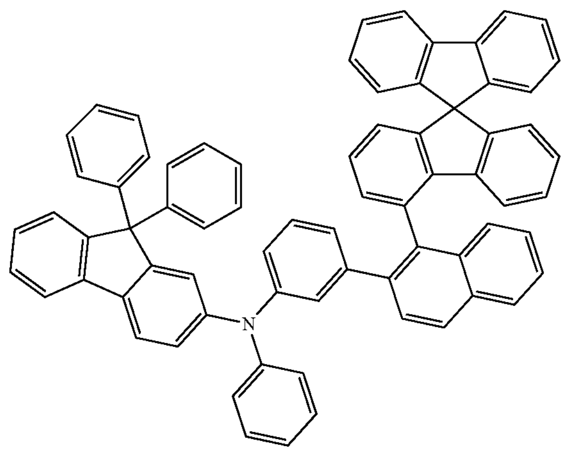
266
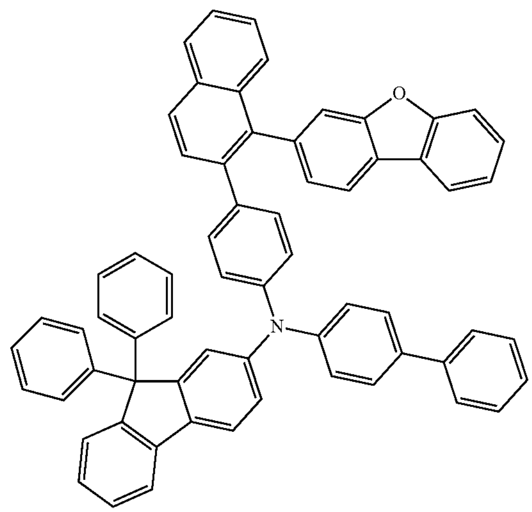
267
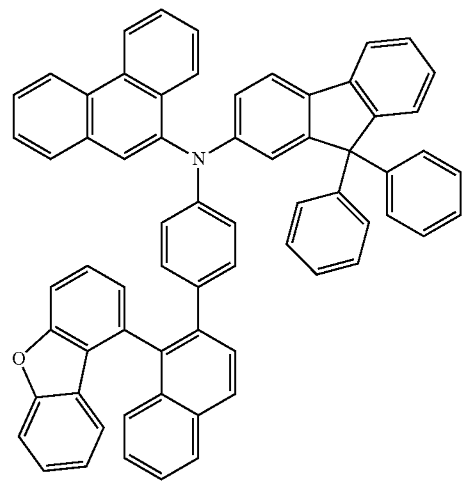
268
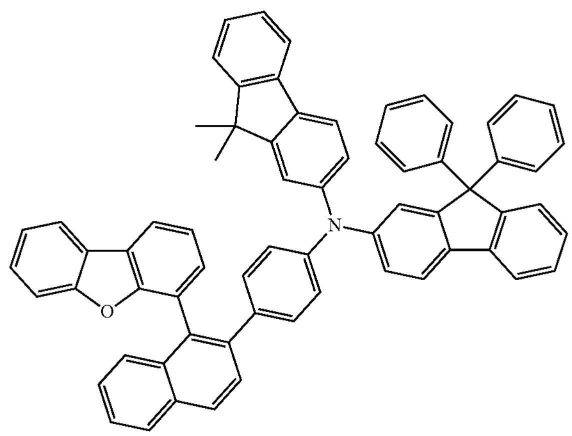

-continued
269
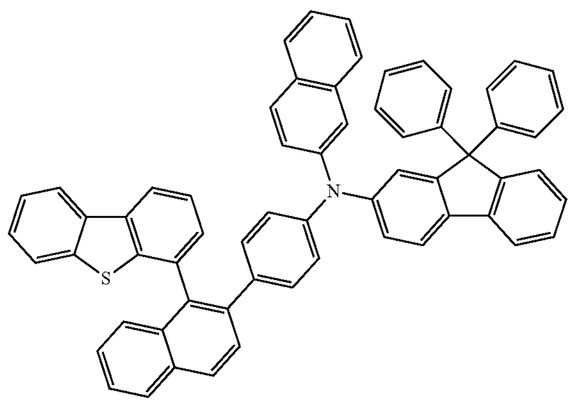
270
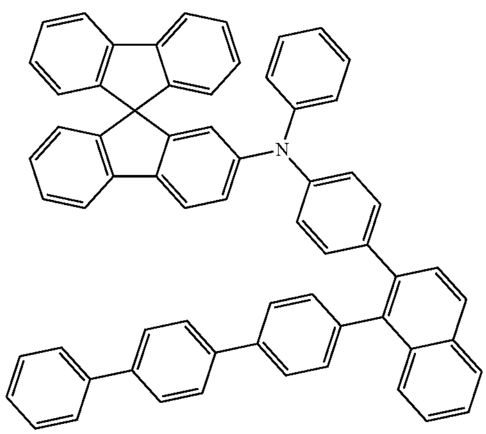
284
-continued
336
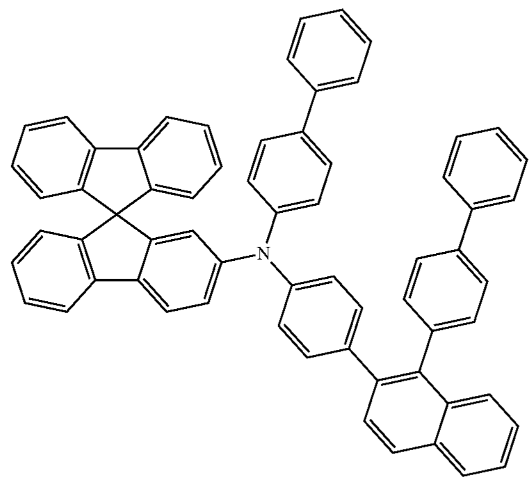
337
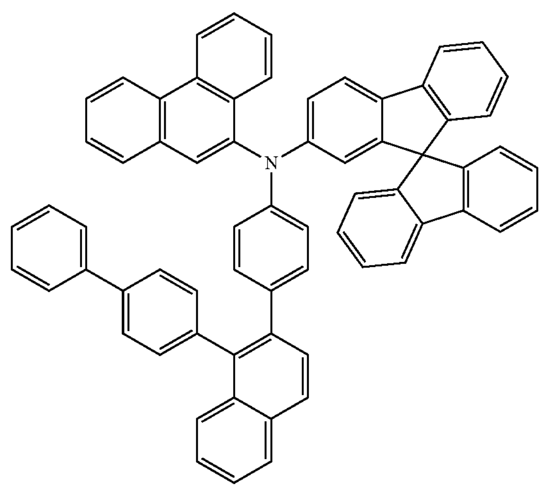
338
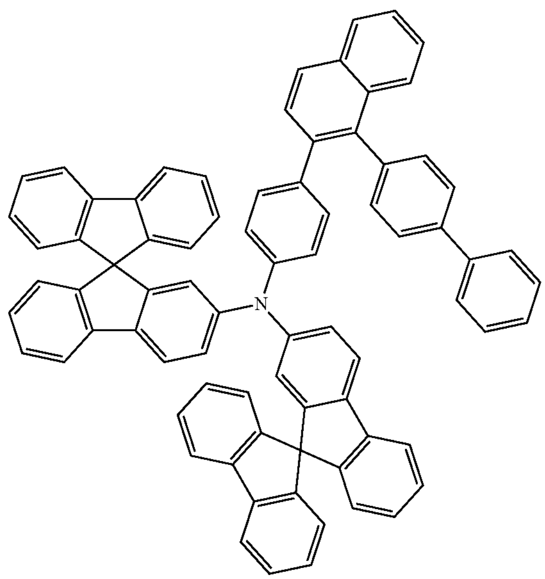

-continued
339
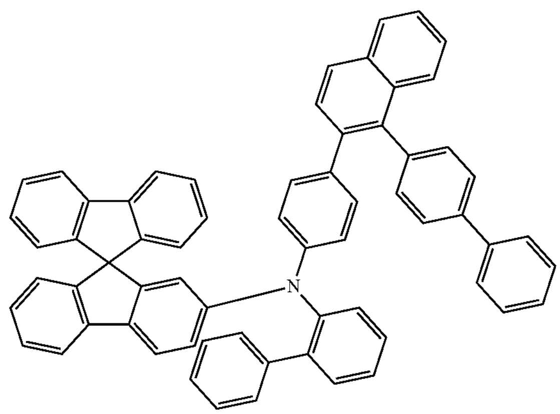
340
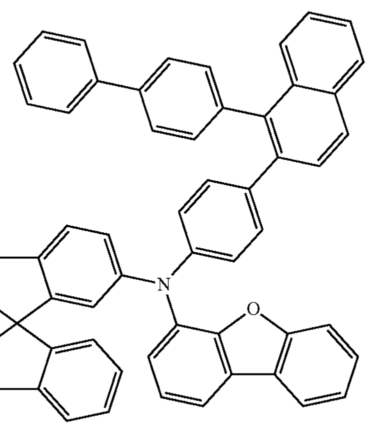
341
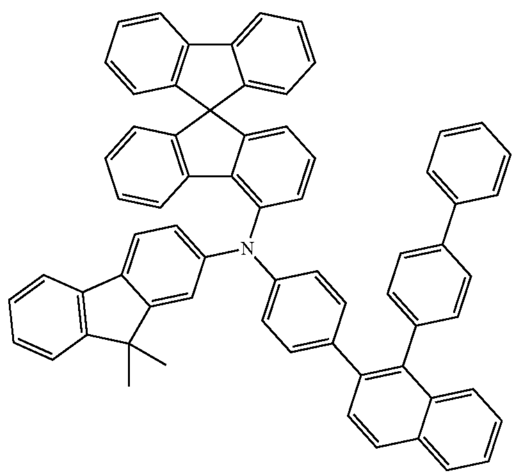
-continued
342
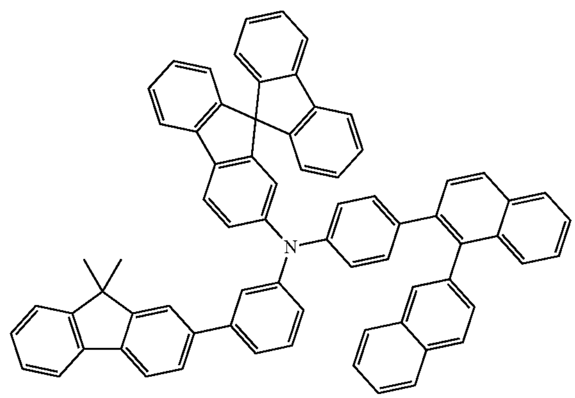
343
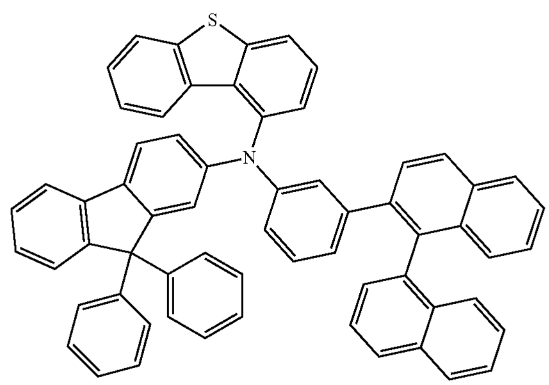
344
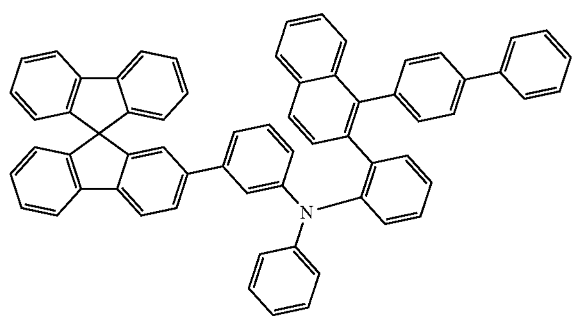
345
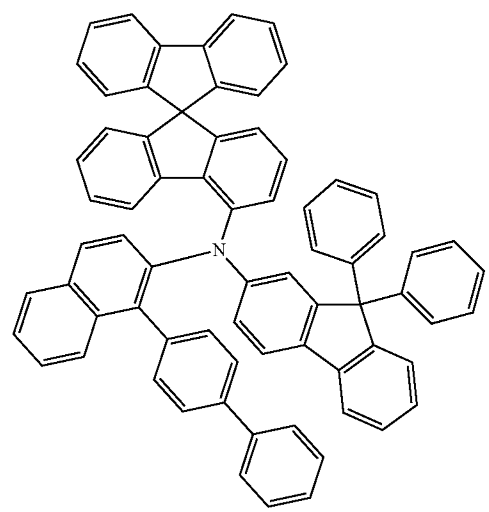

346
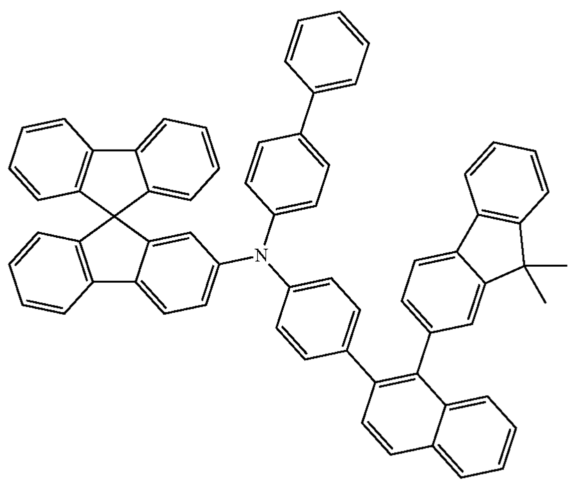
347
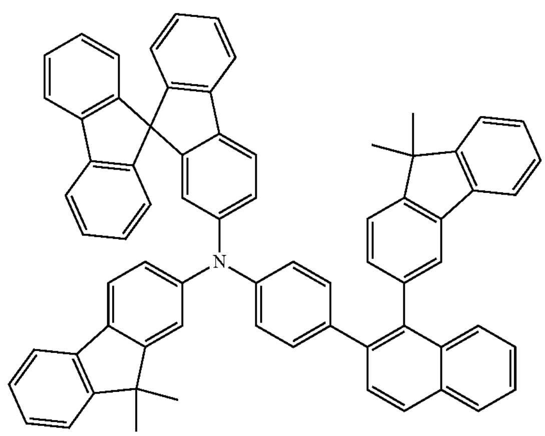
348
349
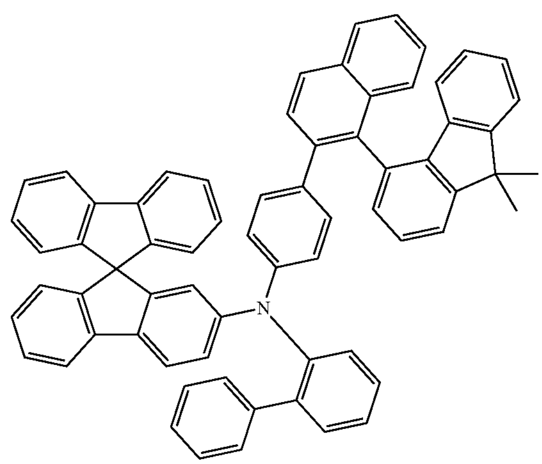
350
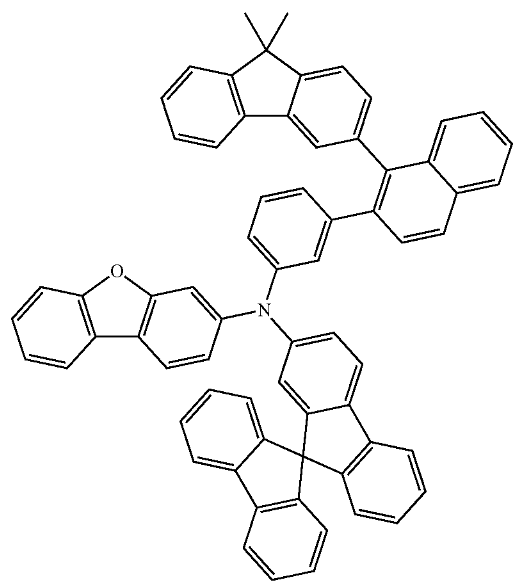
351
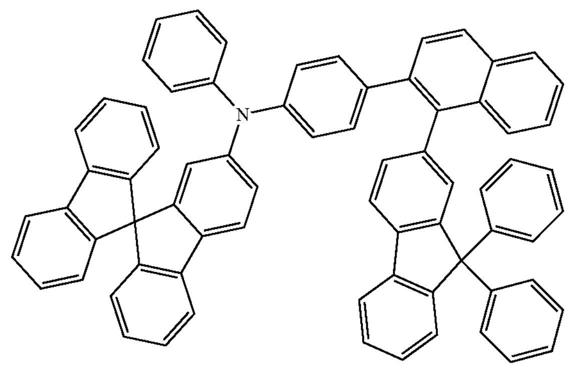

-continued
352
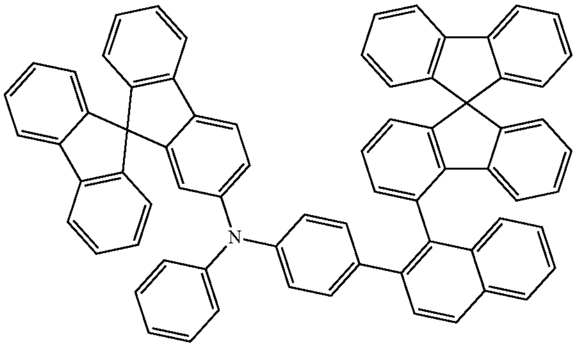
353
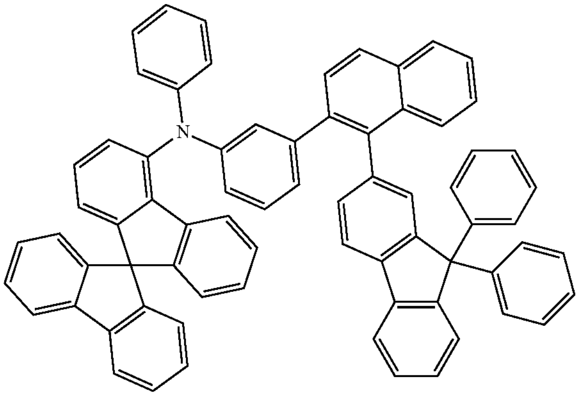
354
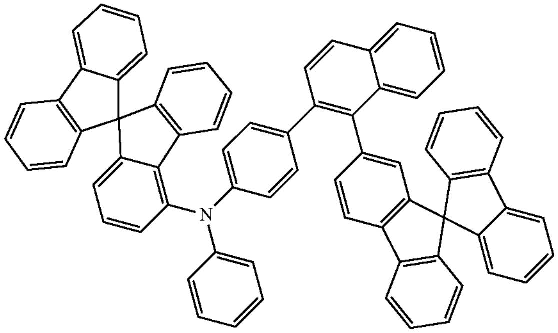
355
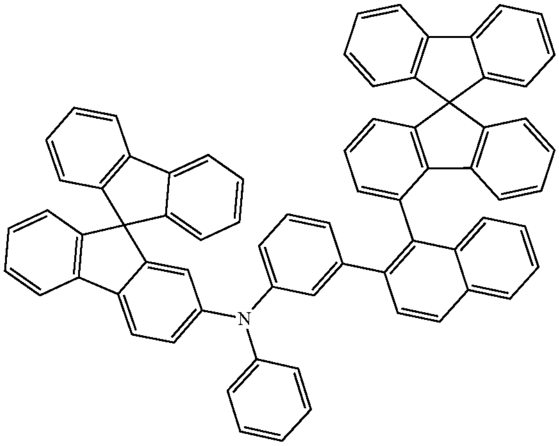
-continued
356
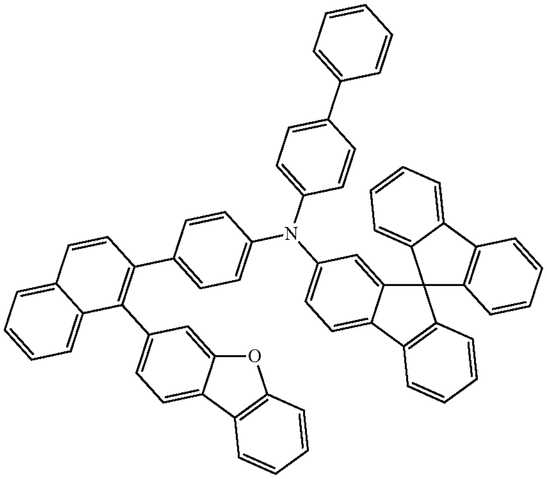
357
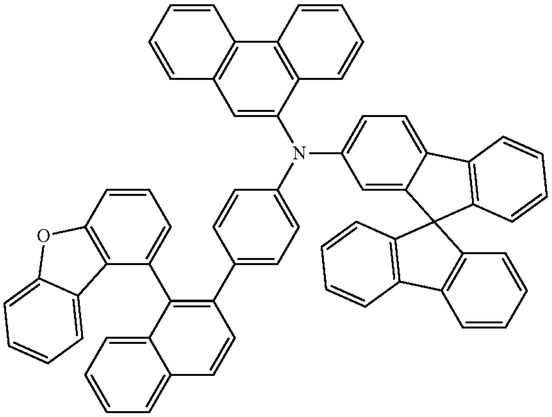
358
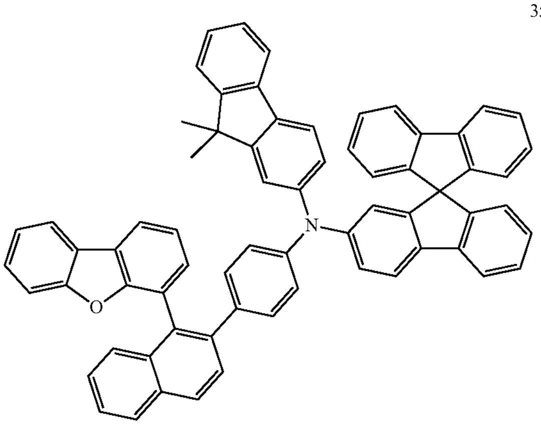

-continued

359

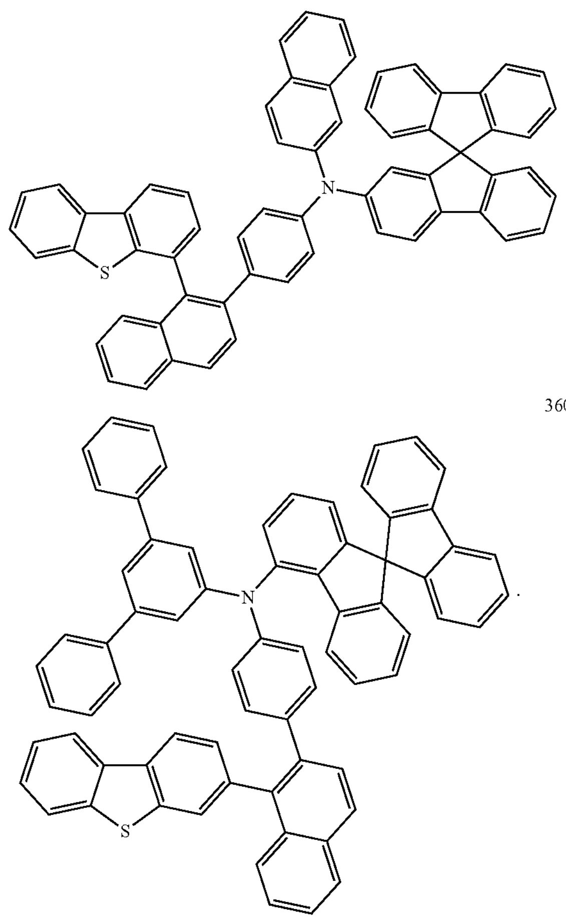

360

4. An organic light emitting device comprising:

a first electrode;

a second electrode; and one or more organic material layers provided between the first electrode and the second electrode, wherein one or more layers of the organic material layers include the heterocyclic compound of claim 1.

5. The organic light emitting device of claim 4, wherein the organic material layer includes a hole transfer layer, and the hole transfer layer includes the heterocyclic compound.

6. The organic light emitting device of claim 4, wherein the organic material layer includes one or more hole auxiliary layers, and the hole auxiliary layer includes the heterocyclic compound.

7. The organic light emitting device of claim 4, wherein the organic material layer includes a light emitting layer, and the light emitting layer includes the heterocyclic compound as a host material of a light emitting material.

8. The organic light emitting device of claim 7, wherein the light emitting layer includes two or more host materials, and at least one of the host materials includes the heterocyclic compound as a host material of a light emitting material.

9. The organic light emitting device of claim 4, comprising:

an anode;

a first stack provided on the anode and including a first light emitting layer;

a charge generation layer provided on the first stack;

a second stack provided on the charge generation layer and including a second light emitting layer; and a cathode provided on the second stack.

* * * * *